US007563573B2

(12) United States Patent
Fornace, Jr. et al.

(10) Patent No.: US 7,563,573 B2
(45) Date of Patent: Jul. 21, 2009

(54) METHOD FOR DETECTING RADIATION EXPOSURE

(75) Inventors: Albert J. Fornace, Jr., Bethesda, MD (US); Sally A. Amundson, Rockville, MD (US); Jeffrey M. Trent, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 343 days.

(21) Appl. No.: 11/370,079

(22) Filed: Mar. 6, 2006

(65) Prior Publication Data

US 2007/0166726 A1 Jul. 19, 2007

Related U.S. Application Data

(62) Division of application No. 09/913,171, filed as application No. PCT/US00/04897 on Feb. 25, 2000, now Pat. No. 7,008,768.

(60) Provisional application No. 60/121,756, filed on Feb. 26, 1999.

(51) Int. Cl.
*C12Q 1/68* (2006.01)
(52) U.S. Cl. .................. 435/6; 435/287.2; 536/24.3
(58) Field of Classification Search ................ None
See application file for complete search history.

(56) References Cited

U.S. PATENT DOCUMENTS

| | | | |
|---|---|---|---|
| 5,563,060 A | 10/1996 | Hozier | |
| 5,691,157 A | 11/1997 | Gong et al. | |
| 5,707,807 A | 1/1998 | Kato | |
| 5,744,305 A | 4/1998 | Fodor et al. | |
| 5,770,722 A | 6/1998 | Lockhart et al. | |
| 5,830,645 A | 11/1998 | Pinkel et al. | |
| 5,843,655 A | 12/1998 | McGall | |
| 5,866,330 A | 2/1999 | Kinzler et al. | |
| 5,877,215 A * | 3/1999 | McClay et al. | 514/573 |
| 5,910,309 A * | 6/1999 | Ullrich | 424/198.1 |
| 5,965,352 A * | 10/1999 | Stoughton et al. | 435/4 |
| 5,998,136 A * | 12/1999 | Kamb | 435/6 |
| 7,008,768 B1 * | 3/2006 | Fornace et al. | 435/6 |

FOREIGN PATENT DOCUMENTS

| | | | |
|---|---|---|---|
| WO | WO 97/30179 | | 8/1997 |
| WO | WO97/30179 | * | 8/1997 |
| WO | WO 98/18961 | | 5/1998 |
| WO | WO 98/56954 | | 12/1998 |
| WO | WO 99/55913 | | 11/1999 |

OTHER PUBLICATIONS

Amundson et al., "Identification of Gamma-Ray Responsive Genes by cDNA Array Hybridization," *Proceedings of the American Association for Cancer Research Annual Meeting* 39:454 (1998).
Amundson et al., "Induction of Stress Genes by Low Doses of Gamma Rays," *Radiat. Res.* 152:225-231 (1999).
Amundson et al., "Fluorescent cDNA Microarray Hybridization Reveals Complexity and Heterogeneity of Cellular Genotoxic Stress Responses," *Oncogene* 18:3666-3672 (1999).
Amundson et al., "Human In vivo Radiation-Induced Biomarkers: Gene Expression Changes in Radiotherapy Patients," *Cancer Res.* 64:6368-6371 (2004).
Carulli et al., "High Throughput Analysis of Differential Gene Expression," *J. Cell. Biochem.Suppl.* 30/31:286-296 (1998).
Derisi et al., "Use of a cDNA Microarray to Analyse Gene Expression Patterns in Human Cancer," *Nature Genetics* 14:457-460 (1996).
Fiscella et al., "Wip1, A Novel Human Protein Phosphatase that is Induced in Response to Ionizing Radiation in a p53-Dependent Manner," *Proc. Natl. Acad. Sci. USA* 94:6048-6053 (1997).
Fornace et al., "The Complexity of Radiation Stress Responses: Analysis by Informatics and Functional Genomics Approaches," *Gene Expr.* 7:387-400 (1999).
Goltry et al., "Induction of Serum Amyloid A Inflammatory Response Genes in Irradiated Bone Marrow Cells," *Radiat. Res.* 149:570-578 (1998).
Higuchi et al., "Search for Genes Involved in UV-Resistance in Human Cells by mRNA Differential Display: Increased Transcriptional Expression of Nucleophosmin and T-Plastin Genes in Association with the Resistance," *Biochem. Biophys. Res. Comm.* 248:597-602 (1998).
Iordanov et al., "Ultraviolet Radiation Triggers the Ribotoxic Stress Response in Mammalian Cells," *J. Biol.Chem.* 273:15794-15803 (1998).

(Continued)

*Primary Examiner*—Gary Benzion
*Assistant Examiner*—Stephanie K Mummert
(74) *Attorney, Agent, or Firm*—Klarquist Sparkman, LLP

(57) ABSTRACT

A method is disclosed for detecting exposure of organisms to biologically significant or hazardous amounts of ionizing radiation. The method uses nucleic acid microarray hybridization to evaluate biological effects, such as patterns of expression of genes after radiation exposure. Numerous genes are provided which have been found to be responsive to radiation exposure in a variety of cell lines. These genes are incorporated into probe sets, which are exposed to a labeled nucleic acid composition from a test cell, such as cDNA reverse transcribed from mRNA in the test cell, which specifically hybridizes to members of the probe set when the cell has been exposed to a biologically significant amount of ionizing radiation. Whether the nucleic acid composition hybridizes to the nucleic acid molecules representing genes that are differentially expressed is determined. The invention also includes methods for determining a dose response relationship between radiation exposure and differential expression of one or more genes, for example to determine a probable radiation dose in cells that have actually or potentially been exposed to the ionizing radiation. The invention also includes probe sets and microarrays used in this method.

52 Claims, 11 Drawing Sheets

OTHER PUBLICATIONS

Monks et al., "Feasibility of High-Flux Anticancer Drug Screen Using a Diverse Panel of Cultured Human Tumor Cell Lines," *J. Natl. Cancer Inst.* 83:757-766 (1991).

Myers et al., "A Protein Expression Database for the Molecular Pharmacology of Cancer," *Electrophoresis* 18:647-653 (1997).

Prasad et al., "Activation of Nuclear Factor kB in Human Lymphoblastoid Cells by Low Dose Ionizing Radiation," *Radiation Res.* 138:367-372 (1994).

Schena et al., "Quantitative Monitoring of Gene Expression Patterns with a Complementary DNA Microarray," *Science* 270:467-470 (1995).

Schena et al., "Parallel Human Genome Analysis: Microarray-Based Expression Monitoring of 1000 Genes," *Proc. Natl. Acad. Sci. USA* 93:10614-10619 (1996).

Weinstein et al., "An Information-Intensive Approach to the Molecular Pharmacology of Cancer," *Science* 275:343-349 (1997).

Zhang et al., "Differential Display of mRNA," *Mol. Biotech.* 10:155-165 (1998).

* cited by examiner

FIG. 5A

| | RCH1 | BCL3 | FRA1 | REL-B | ATF3 | IAP-1 | PC-1 | MBP-1 | SSAT | MDM2 | CIP1/WA | BAX |
|---|---|---|---|---|---|---|---|---|---|---|---|---|
| p53 wild type | | | | | | | | | | | | |
| ML-1 | 0.4 | 5.6 | 6.9 | 57.0 | 9.2 | 2.1 | 19.5 | 3.7 | 3.4 | 12.0 | 31.0 | 9.5 |
| Molt4 | 0.5 | 1.4 | 1.4 | 9.5 | 13.7 | 1.2 | 10.0 | 1.1 | 1.0 | 4.5 | 31.0 | 5.8 |
| SR | 0.5 | 0.9 | 1.7 | 5.6 | 6.1 | 2.9 | 3.1 | 2.0 | 1.2 | 8.9 | 8.7 | 1.9 |
| A549 | 0.6 | 1.1 | 1.1 | 1.4 | 1.7 | 1.2 | 1.8 | 0.8 | 1.1 | 4.8 | 22.4 | 2.9 |
| MCF7 | 0.4 | 1.8 | 9.5 | 4.4 | 4.6 | 1.0 | 0.6 | 1.1 | 1.1 | 2.5 | 7.5 | 0.5 |
| RKO | 0.7 | 2.2 | 0.7 | 3.4 | 5.3 | 3.0 | 3.5 | 1.7 | 1.4 | 2.5 | 4.0 | 1.7 |
| p53 mutant | | | | | | | | | | | | |
| CCRF-CEM | 0.5 | 3.8 | 10.7 | 13.4 | 10.7 | 4.3 | 11.9 | 1.7 | 0.7 | 1.0 | 0.8 | 0.7 |
| HL60 | 0.7 | 6.2 | 1.9 | 8.3 | 3.2 | 1.0 | 5.2 | 0.6 | 2.2 | 1.0 | 2.0 | 1.6 |
| K562 | 0.7 | 1.4 | 1.2 | 1.6 | 0.9 | 1.3 | 4.7 | 1.3 | 0.9 | 1.2 | 1.8 | 1.4 |
| H1299 | 0.2 | 3.1 | 0.5 | 7.2 | 1.0 | 1.4 | 3.8 | 1.1 | 0.9 | 1.0 | 2.0 | 1.6 |
| RKO-E6 | 0.7 | 1.8 | 0.7 | 2.1 | 0.9 | 1.4 | 1.3 | 1.6 | 1.1 | 1.0 | 1.5 | 0.9 |
| T47D | 0.7 | 1.8 | 0 | 4.8 | 1.5 | 1.6 | 1.9 | 2.0 | 0.9 | 0.8 | 2.2 | 0.7 |

FIG. 5B

|  |  | RCH1 | BCL3 | FRA1 | REL-B | ATF3 | IAP-1 | PC-1 | MBP-1 | SSAT | MDM2 | CIP1/WAF | BAX |
|---|---|---|---|---|---|---|---|---|---|---|---|---|---|
| p53 wild type | ML-1 MMS | 0.7 | 0.8 | 1.8 | 1.8 | 7.3 | 0.7 | 1.4 | 0.9 | 1.5 | 9.2 | 11.3 | 2.1 |
|  | Molt4 MMS | 1.4 | 1.0 | 1.1 | 1.6 | 32.0 | 1.3 | 1.6 | 0.6 | 1.2 | 1.1 | 12.5 | 0.9 |
|  | SR MMS | 1.2 | 1.5 | 0.5 | 0.5 | 10.3 | 0.2 | 0.4 | 0.5 | 1.5 | 2.3 | 6.3 | 0.9 |
|  | A549 MMS | 0.6 | 0.4 | 1.1 | 1.4 | 1.7 | 1.2 | 1.8 | 0.8 | 1.1 | 4.8 | 7.5 | 1.9 |
|  | UV | 0.8 | 0.6 | 0.6 | 1.6 | 4.4 | 0.6 | 1.5 | 0.5 | 1.4 | 3.2 | 5.7 | 0.8 |
|  | MCF7 MMS | 0.8 | 0.6 | 4.8 | 1.4 | 22.0 | 0.8 | 1.7 | 0.6 | 1.1 | 2.8 | 5.0 | 1.9 |
|  | UV | 0.9 | 1.1 | 24.7 | 1.5 | 39.0 | 1.4 | 1.2 | 0.9 | 1.0 | 2.3 | 9.8 | 0.7 |
|  | RKO MMS | 0.8 | 1.2 | 0.7 | 1.0 | 3.9 | 0.7 | 0.6 | 1.4 | 1.2 | 1.4 | 3.7 | 0.7 |
|  | UV | 0.8 | 1.2 | 0.9 | 0.9 | 4.6 | 1.1 | 1.1 | 1.1 | 1.0 | 1.4 | 2.7 | 1.0 |
| p53 mutant | CCRF-CEM MMS | 0.8 | 0.8 | 1.2 | 0.5 | 26.0 | 0.9 | 0.8 | 0.9 | 1.2 | 0.8 | 1.4 | 0.9 |
|  | HL60 MMS | 0.9 | 1.1 | 2.7 | 1.9 | 9.4 | 1.2 | 1.7 | 0.9 | 0.8 | 0.6 | 5.9 | 1.5 |
|  | K562 MMS | 1.0 | 1.7 | 1.2 | 0.8 | 37.0 | 0.9 | 0.8 | 0.6 | 0.7 | 0.7 | 1.8 | 0.7 |
|  | H1299 MMS | 0.9 | 0.7 | 0.6 | 1.0 | 21.0 | 0.5 | 0.5 | 0.8 | 0.8 | 0.6 | 6.3 | 0.6 |
|  | UV | 0.6 | 0.6 | 0.5 | 1.2 | 3.8 | 1.1 | 3.8 | 0.7 | 0.8 | 1.2 | 2.2 | 1.5 |
|  | RKO/E6 MMS | 0.5 | 1.5 | 0.7 | 0.8 | 42.0 | 0.5 | 0.6 | 1.3 | 0.8 | 3.6 | 2.3 | 0.7 |
|  | UV | 0.5 | 1.0 | 0.7 | 0.6 | 2.8 | 1.2 | 0.5 | 0.9 | 0.9 | 1.7 | 2.8 | 0.7 |
|  | T47D MMS | 0.8 | 0.8 | 0.6 | 0.6 | 38.0 | 0.5 | 0.6 | 0.7 | 1.2 | 0.9 | 3.9 | 0.8 |
|  | UV | 1.1 | 1.3 | 0.8 | 1.9 | 3.5 | 1.5 | 3.3 | 0.5 | 1.2 | 0.9 | 2.7 | 0.8 |

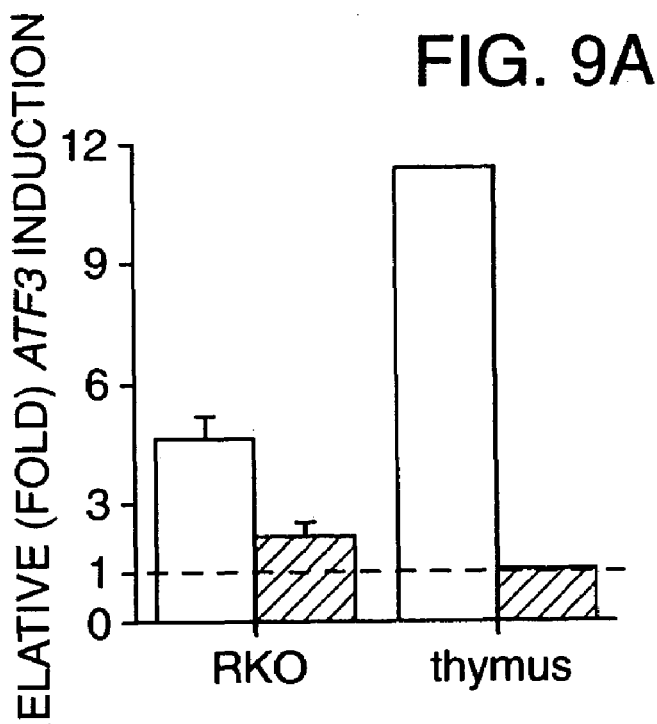
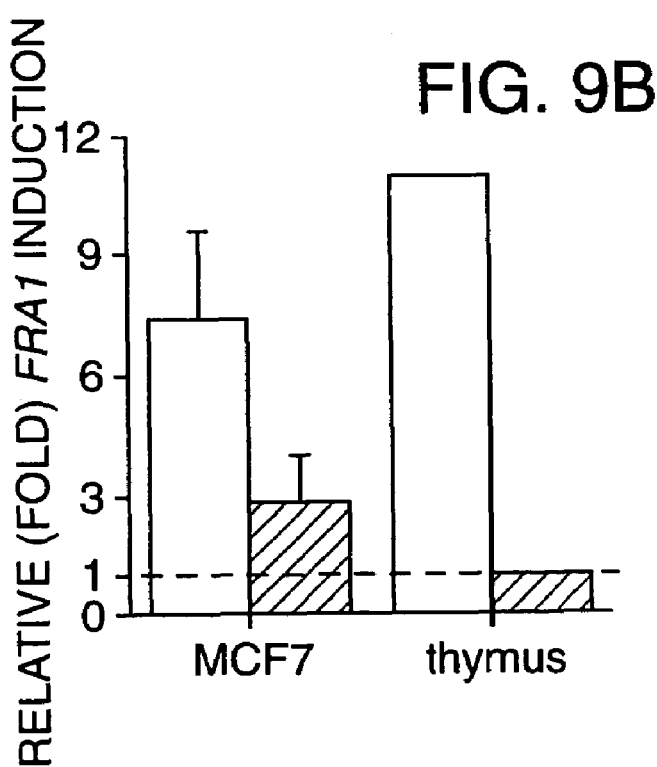

SEQUENCE LISTING

```
<160> NUMBER OF SEQ ID NOS: 28

<210> SEQ ID NO 1
<211> LENGTH: 495
<212> TYPE: DNA
<213> ORGANISM: Homo sapiens

<400> SEQUENCE: 1
atggcgacga aggccgtgtg cgtgctgaag ggcgacggcc cagtgcaggg catcatcaat      60
ttcgagcaga aggaaagtaa tggaccagtg aaggtgtggg gaagcattaa aggactgact     120
```

| | |
|---|---|
| gaaggcctgc atggattcca tgttcatgag tttggagata atacagcagg ctgtaccagt | 180 |
| gcaggtcctc actttaatcc tctatccaga aaacacggtg ggccaaagga tgaagagagg | 240 |
| catgttggag acttgggcaa tgtgactgct gacaaagatg gtgtggccga tgtgtctatt | 300 |
| gaagattctg tgatctcact ctcaggagac cattgcatca ttggccgcac actggtggtc | 360 |
| catgaaaaag cagatgactt gggcaaaggt ggaaatgaag aaagtacaaa gacaggaaac | 420 |
| gctggaagtc gtttggcttg tggtgtaatt gggatcgccc aataaacatt cccttggatg | 480 |
| tagtctgagg cccct | 495 |

<210> SEQ ID NO 2
<211> LENGTH: 4035
<212> TYPE: DNA
<213> ORGANISM: Homo sapiens

<400> SEQUENCE: 2

| | |
|---|---|
| tcccctggac ccgccgcaga gccagtgcag aatacagaaa ctgcagccat gaccacgcac | 60 |
| gtcaccctgg aagatgccct gtccaacgtg gacctgcttg aagagcttcc cctccccgac | 120 |
| cagcagccat gcatcgagcc tccaccttcc tccatcatgt accaggctaa ctttgacaca | 180 |
| aactttgagg acaggaatgc atttgtcacg ggcattgcaa ggtacattga gcaggctaca | 240 |
| gtccactcca gcatgaatga gatgctggag gaaggacatg agtatgcggt catgctgtac | 300 |
| acctggcgca gctgttcccg ggccattccc caggtgaaat gcaacgagca gcccaaccga | 360 |
| gtagagatct atgagaagac agtagaggtg ctggagccgg aggtcaccaa gctcatgaag | 420 |
| ttcatgtatt ttcagcgcaa ggccatcgag cggttctgca gcgaggtgaa gcggctgtgc | 480 |
| catgccgagc gcaggaagga ctttgtctct gaggcctacc tcctgaccct tggcaagttc | 540 |
| atcaacatgt ttgctgtcct ggatgagcta agaacatga agtgcagcgt caagaatgac | 600 |
| cactctgcct acaagagggc agcacagttc ctgcggaaga tggcagatcc ccagtctatc | 660 |
| caggagtcgc agaacctttc catgttcctg gccaaccaca caggatcac ccagtgtctc | 720 |
| caccagcaac ttgaagtgat cccaggctat gaggagctgc tggctgacat tgtcaacatc | 780 |
| tgtgtggatt actacgagaa caagatgtac ctgactccca gtgagaaaca tatgctcctc | 840 |
| aaggtgatgg ctttggcct ctacctaatg gatggaaatg tcagtaacat ttacaaactg | 900 |
| gatgccaaga agagaattaa tcttagcaaa attgataaat tctttaagca gctgcaggtg | 960 |
| gtgccccttt tcggcgacat gcagatagag ctggccagat acattaagac cagtgctcac | 1020 |
| tatgaagaga acaagtccaa gtggacgtgc acccagagca gcatcagccc ccagtacaat | 1080 |
| atctgcgagc agatggttca gatccgggat gaccacatcc gcttcatctc cgagctcgct | 1140 |
| cgctacagca cagtgaggt ggtgacgggc tcagggctgg acagccagaa gtcagacgag | 1200 |
| gagtatcgcg agctcttcga cctagccctg cggggtctgc agcttctatc caagtggagc | 1260 |
| gcccacgtca tggaggtgta ctcttggaag ctggttcatc ccacagacaa gttctgcaac | 1320 |
| aaggactgtc ctggcaccgc ggaggaatat gagagagcca cacgctacaa ttacaccagt | 1380 |
| gaggaaaaat ttgccttcgt tgaggtgatc gccatgatca aaggcctgca ggtgctcatg | 1440 |
| ggcaggatgg agagcgtctt caaccaggcc atcaggaaca ccatctacgc ggcattgcag | 1500 |
| gacttcgccc aggtgacgct gcgtgagccc tgcggcagg cggtacgaa gaagaagaat | 1560 |
| gtcctcatca gcgtcctaca ggcaattcga aagaccatct gtgactggga gggagggcga | 1620 |
| gagcccccta tgaccccatg cttgagaggg agaaggacc ccaaaggtgg atttgatatc | 1680 |
| aaggtgcccc ggcgtgctgt ggggccatcc agcacacagc tgtacatggt gcggaccatg | 1740 |

```
cttgaatcac tcattgcaga caaaagcggc tccaagaaga ccctgaggag cagcctggat   1800
ggacccattg tcctcgccat agaggacttt cacaaacagt ccttcttctt cacacatctg   1860
ctcaacatca gtgaagccct gcagcagtgt tgtgacctct cccagctctg gttccgagaa   1920
ttcttcctgg agttaaccat gggccgacga atccagttcc ccatcgagat gtccatgccc   1980
tggattctaa cggaccatat cctggaaacc aaagaacctt ccatgatgga gtatgtcctc   2040
taccctctgg atctgtacaa cgacagcgcc tactatgctc tgaccaagtt taaaaagcag   2100
ttcctgtacg atgagataga agctgaggtg aacctgtgtt ttgatcagtt tgtctacaag   2160
ctggcagacc agatctttgc ttactacaaa gccatggctg gcagtgtcct gttggataaa   2220
cgttttcgag ctgagtgtaa gaattatggc gtcatcattc cgtatccacc gtccaatcgc   2280
tatgaaacac tgctgaagca gagacacgtc cagctgttgg gtagatcaat tgacttgaac   2340
agactcatta cccagcgcat ctctgccgcc atgtataaat ccttggacca agctatcagc   2400
cgctttgaga gtgaggacct gacctccatt gtggagctgg agtggctgct ggagattaac   2460
cggctcacgc atcggctgct ctgtaagcat atgacgctgg acagcttcga tgccatgttc   2520
cgagaggcca atcacaatgt gtccgccccc tatggccgta tcaccctgca tgtcttctgg   2580
gaactgaact ttgactttct ccccaactac tgctacaatg ggtccactaa ccgtttttgtg   2640
cggactgcca ttcctttcac ccaagaacca caacgagaca aacctgccaa cgtccagcct   2700
tattacctct atggatccaa gcctctcaac attgcctaca gccacatcta cagctcctac   2760
aggaatttcg tggggccacc tcatttcaag actatctgca gactcctggg ttatcagggc   2820
atcgctgtgg tcatggagga actgctaaag attgtgaaga gcttgctcca aggaaccatt   2880
ctccagtatg tgaaaacact gatagaggtg atgcccaaga tatgccgctt gccccgacat   2940
gagtatggct ccccagggat cctggagttc ttccaccacc agctgaagga catcattgag   3000
tacgcagagc tcaaaacaga cgtgttccag agcctgaggg aagtgggcaa tgccatcctc   3060
ttctgcctcc tcatagagca agctctgtct caggaggagg tctgcgattt gctccatgcc   3120
gcacccttcc aaaacatctt gcctagagtc tacatcaaag aggggagcg cctggaggtc   3180
cggatgaaac gtctggaagc caagtatgcc ccgctccacc tggtccctct gatcgagcgg   3240
ctggggaccc ctcagcaaat cgccattgct cgcgagggtg acctcctgac caaggagcgg   3300
ctgtgctgtg gcctgtccat gttcgaggtc atcctgaccc gcattcggag ctacctgcag   3360
gaccccatct ggcggggccc accgcccacc aatggcgtca tgcacgtcga tgagtgtgtg   3420
gagttccacc ggctgtggag cgccatgcag ttcgtgtact gcatccctgt gggaaccaac   3480
gagttcacag ctgagcagtg tttcggcgat ggcttgaact gggctggttg ctccatcatt   3540
gtcctgctgg ccagcagcg tcgctttgac ctgttcgact tctgttacca cctgctaaaa   3600
gtgcagaggc aggacgggaa ggatgaaatc attaagaatg tgcccctgaa gaagatggcc   3660
gaccggatca ggaagtatca gatcttgaac aatgaggttt ttgccatcct gaacaaatac   3720
atgaagtccg tggagacaga cagttccact gtgggagcatg tgcgctgctt ccagccaccc   3780
atccaccagt ccttggccac cacttgctaa gcagaagatc ctgcagaccc ttatctggag   3840
gaggaagaga agcaggagag agaaagccac agccagcctg ccataggatc caactggaca   3900
acgtgtggga tggacctgga aacaagcacc tccccaaaca catcaccact ccctagggcg   3960
gggcctgtgc atgctctccc atgacatctc catgctggtt tctccatagc ataaatgaaa   4020
aaaaaaaaaa aaaaa                                                    4035
```

<210> SEQ ID NO 3
<211> LENGTH: 2392
<212> TYPE: DNA
<213> ORGANISM: Homo sapiens

<400> SEQUENCE: 3

```
agcggggcag cggctgcgcc ctgcgccggg gcggagccgg gggcgggccg gcggccggca        60 ggcggggct ggggcccgag gccgggagtg cctgagcgcc ggcggcgacg acggcagcgg       120
cggcccagcg ggctcggtgg ttgggtccgc ggcggctcgg ggtccgcccg cgggctgcgg       180
tgcgagcggg cggcccggct cccctcctcc cccgcccgcc gccgccgctg tgattgggtg       240
gaagatggcg ctggccggat ggaaatccta atgacagtct ccaaattcgc ctccatctgt       300
accatgggcg ccaatgcttc ggcattagag aaagagattg gtccagaaca gtttccggtc       360
aatgagcact attttggatt agtcaatttt gggaatacct gctactgcaa ttcagttctt       420
caagcacttt atttttgtcg tccatttcgg gaaaagttc ttgcgtataa gagtcaacct        480
aggaaaaagg agagccttct tacatgctta gcagatctct tccatagcat agccactcag       540
aagaaaaagg ttggagtaat accccctaag aagttcatca aagattacg aaagaaaat        600 gagcttttg acaactacat gcaacaagat gcccatgaat tcttaaatta cctactaaat       660
acaattgctg atattttaca agaagagaga agcaggaaa acaaaatgg tcgtttacct        720 aatggtaata ttgataatga aaataataac agcacaccag acccaacgtg ggttgatgag       780 attttttcagg gaacattaac taatgaaacc agatgtctta cttgtgaaac tataagcagc      840
aaagatgaag atttttttaga cctttctgtt gacgtggaac aaaatacatc aattactcac      900
tgcttaaggg gtttcagcaa cacagaaact ctgtgcagtg aatacaagta ttactgtgaa      960
gagtgtcgca gcaaacagga agcacacaaa cggatgaaag ttaaaaaact gcccatgatt      1020
ctagctctac acctgaagag atttaaatat atggatcaac ttcatcgata tacaaaactc      1080
tcttaccggg tagttttttcc tttagaactt cgtctgttta cacttcagg tgatgccacc      1140 aatccagaca gaatgtacga ccttgttgct gttgtggttc actgtggaag tggtcccaat      1200
cgaggccatt atattgcaat agttaagagt catgatttt ggttgttgtt tgatgacgac      1260
attgtagaaa aaatagatgc acaagctatt gaagaattct acgggttgac atcagatatc      1320
tcaaagaact ctgagtctgg ttacatcctt ttctatcagt ctcgggactg agagggaacc      1380
gtgatgaaga gacactttct gcctcatttc ttctctggtt attttggaaa ggatcaagca      1440 ctgattttc aagaaaagag aaatgcagga agctcagggg gcagtagcac actttgcaca      1500
cgataaagca aagacgatgg attgacaagc ccttccgatc atggtagttg atttatttgc      1560
tcaggtatca tgctgtctgt acagttccat acaacaagga ggtgaaatca gagataccag      1620
ctcctctttt aaaacagcct tccagtcatt ggcacgcatt ttctctttat taattgcacc      1680
aataatgctt tgaattcctt gggggtgcag tagaaagaat cggaatctgt gccgtattga      1740
taaggagatg atgttgaaca cactgcataa atttgcctgg ttcagtatgt atagaagcat      1800
attcagtggt cttttcaaga gtaaaccaga atactttttg ggcccaacac ttgcagttgc      1860
cttcctgatg taaaaactaa catgctagat aatccagtgt cgggaagaca aagatgtttt      1920
gcttctctga agaagcttat aataatatac agtatatgta tatgtaggga gcaattggtc      1980
aaaagtggct tttttgtttcc ccaaggggaa agactggctt tgtaattata attttttcct      2040
tatttatttt acttaaaact ggtagagtct aagtattata tgaagtgccc atgattctgt      2100
cagtaaattt gaacatattt ttattagtta atgtcagttt aagttgtcct tttgtttgtt      2160
```

```
tctatttta  aggtgaattt  taatttctat  ctgaaatcag  ttaagatacc  ttgagaaaaa    2220
ctgcagtgag  aggagataaa  tatcctttt   caggaggaac  tgatatctct  ggctaaatat    2280 ttgtccttt   attatggttt  ctaaatcagt  tattttcttc  agctttaatt  tcataaaatt    2340
aaaaaactat  tttaaaaaaa  aaaaaaaaaa  aaaaaaaaaa  aaaaaaaaaa  aa            2392

<210> SEQ ID NO 4
<211> LENGTH: 2207
<212> TYPE: DNA
<213> ORGANISM: Homo sapiens

<400> SEQUENCE: 4 cccttcctg   tggggttcat  tgggcatcc   cctttctgct  gcaggaacct  ctcatcagac      60
cgcctgaggg  aagcggcgcc  cggagacccg  ccccggcccg  gtccacattc  tccccaggaa     120
gccggactct  atggggcggg  accctggggg  agcctgagcc  gagcccggag  ccagcccga     180 accctgaac   ctccagccag  gggcgccccg  ggagcagcca  gccgtgggc   gagccgcccg     240 cccgccgagc  agccatgagc  gagacggtca  tctgttccag  ccgggccact  gtgatgcttt     300
atgatgatgg  caacaagcga  tggctccctg  ctggcacggg  tccccaggcc  ttcagccgcg     360
tccagatcta  ccacaacccc  acggccaatt  cctttcgcgt  cgtgggccgg  aagatgcagc     420
ccgaccagca  ggtggtcatc  aactgtgcca  tcgtccgggg  tgtcaagtat  aaccaggcca     480 ccccccaactt  ccatcagtgg  cgcgacgctc  gccaggtctg  gggcctcaac  ttcggcagca     540
aggaggatgc  ggcccagttt  gccgccggca  tggccagtgc  cctagaggcg  ttggaaggag     600
gtgggccccc  tccacccccca gcacttccca  cctggtcggt  cccgaacggc  cctcccggg     660 aggaggtgga  gcagcagaaa  aggcagcagc  ccggcccgtc  ggagcacata  gagcgccggg     720
tctccaatgc  aggaggccca  cctgctcccc  ccgctggggg  tccaccccca  ccaccaggac     780 ctcccccctcc  tccaggtccc  ccccacccc   caggttgcc   cccttcgggg  gtcccagctg     840
cagcgcacgg  agcaggggga  ggaccacccc  ctgcaccccc  tctcccggca  gcacagggcc     900
ctggtggtgg  gggagctggg  gccccaggcc  tggccgcagc  tattgctgga  gccaaactca     960
ggaaagtcag  caagcaggag  gaggcctcag  gggggcccac  agcccccaaa  gctgagagtg    1020
gtcgaagcgg  aggtgggga   ctcatggaag  agatgaacgc  catgctggcc  cggagaagga    1080
aagccacgca  agttggggag  aaaaccccca  aggatgaatc  tgccaatcag  gaggagccag    1140
aggccagagt  cccggcccag  agtgaatctg  tgcggagacc  ctgggagaag  aacagcacaa    1200
ccttgccaag  gatgaagtcg  tcttcttcgg  tgaccacttc  cgagacccaa  ccctgcacgc    1260
ccagctccag  tgattactcg  gacctacaga  gggtgaaaca  ggagcttctg  gaagaggtga    1320
agaaggaatt  gcagaaagtg  aaagaggaaa  tcattgaagc  cttcgtccag  gagctgagga    1380
agcggggttc  tccctgacca  cagggaccca  gaagacccgc  ttctcctttc  cgcacacccg    1440
gcctgtcacc  ctgctttccc  tgcctctact  tgacttggaa  ttggctgaag  acacaggaat    1500
gcatcgttcc  cactcccat   cccacttgga  aaactccaag  ggggtgtggc  ttccctgctc    1560
acacccacac  tggctgctga  ttggctgggg  aggccccgc   ccttttctcc  ctttggtcct    1620 tccctctgc   catcccttg   gggccggtcc  ctctgctggg  gatgcaccaa  tgaaccccac    1680 aggaagggg   aaggaaggag  ggaatttcac  attcccttgt  tctagattca  ctttaacgct    1740
taatgccttc  aaagttttgg  ttttttaag   aaaaaaaaat  atatatat    ttgggttttg    1800 ggggaaaagg  gaaattttt   tttctctttg  gttttgataa  aatgggatgt  gggagttttt    1860
```

| aaatgctata gccctgggct tgccccattt ggggcagcta tttaagggga ggggatgtct | 1920 |
| caccgggctg ggggtgagat atcccccac cccagggact ccccttccct ctggctcctt | 1980 |
| cccctttct atgaggaaat aagatgctgt aacttttgg aacctcagtt ttttgatttt | 2040 |
| ttatttgggt aggttttggg gtccaggcca ttttttttac cccttggagg aaataagatg | 2100 |
| agggagaaag gagaagggga ggaaacttct cccctcccac cttcacctt agcttcttga | 2160 |
| aaatgggccc ctgcagaata aatctgccag tttttataaa aaaaaaa | 2207 |

<210> SEQ ID NO 5
<211> LENGTH: 2189
<212> TYPE: DNA
<213> ORGANISM: Homo sapiens

<400> SEQUENCE: 5

| gcagagggag cgagcgggcg gccggctagg gtggaagagc cgggcgagca gagctgcgct | 60 |
| gcgggcgtcc tgggaaggga gatccggagc gaataggggg cttcgcctct ggcccagccc | 120 |
| tcccgctgat cccccagcca gcggtccgca acccttgccg catccacgaa actttgccca | 180 |
| tagcagcggg cgggcacttt gcactggaac ttacaacacc cgagcaagga cgcgactctc | 240 |
| ccgacgcggg gaggctattc tgcccatttg gggacacttc cccgccgctg ccaggacccg | 300 |
| cttctctgaa aggctctcct tgcagctgct tagacgctgg attttttcg ggtagtggaa | 360 |
| aaccagcagc ctcccgcgac gatgcccctc aacgttagct tcaccaacag gaactatgac | 420 |
| ctcgactacg actcggtgca gccgtatttc tactgcgacg aggaggagaa cttctaccag | 480 |
| cagcagcagc agagcgagct gcagccccg gcgcccagcg aggatatctg gaagaaattc | 540 |
| gagctgctgc ccaccccgcc cctgtcccct agccgccgct ccgggctctg ctcgccctcc | 600 |
| tacgttgcgg tcacacccct ctcccttcgg ggagacaacg acggcggtgg cgggagcttc | 660 |
| tccacggccg accagctgga gatggtgacc gagctgctgg gaggagacat ggtgaaccag | 720 |
| agtttcatct gcgacccgga cgacgagacc ttcatcaaaa acatcatcat ccaggactgt | 780 |
| atgtggagcg gcttctcggc cgccgccaag ctcgtctcag agaagctggc ctcctaccag | 840 |
| gctgcgcgca agacagcgg cagcccgaac ccgcccgcg gccacagcgt ctgctccacc | 900 |
| tccagcttgt acctgcagga tctgagcgcc gccgcctcag agtgcatcga cccctcggtg | 960 |
| gtcttcccct accctctcaa cgacagcagc tcgcccaagt cctgcgcctc gcaagactcc | 1020 |
| agcgccttct ctccgtcctc ggattctctg tctcctcga cggagtcctc cccgcagggc | 1080 |
| agccccgagc cctggtgct ccatgaggag acaccgccca ccaccagcag cgactctgag | 1140 |
| gaggaacaag aagatgagga agaaatcgat gttgttctg tggaaaagag gcaggctcct | 1200 |
| ggcaaaaggt cagagtctgg atcaccttct gctggaggcc acagcaaacc tcctcacagc | 1260 |
| ccactggtcc tcaagaggtg ccacgtctcc acacatcagc acaactacgc agcgcctccc | 1320 |
| tccactcgga aggactatcc tgctgccaag agggtcaagt tggacagtgt cagagtcctg | 1380 |
| agacagatca gcaacaaccg aaaatgcacc agcccaggt cctcggacac cgaggagaat | 1440 |
| gtcaagaggc gaacacacaa cgtcttggag cgccagagga ggaacgagct aaaacggagc | 1500 |
| ttttttgccc tgcgtgacca gatcccggag ttggaaaaca tgaaaagggc cccaaggta | 1560 |
| gttatcctta aaaagccac agcatacatc ctgtccgtcc aagcagagga gcaaaagctc | 1620 |
| atttctgaag aggacttgtt gcggaaacga cgagaacagt tgaaacacaa acttgaacag | 1680 |
| ctacggaact cttgtgcgta aggaaaagta aggaaaacga ttccttctaa cagaaatgtc | 1740 |
| ctgagcaatc acctatgaac ttgtttcaaa tgcatgatca aatgcaacct cacaaccttg | 1800 |

-continued

| | |
|---|---|
| gctgagtctt gagactgaaa gatttagcca taatgtaaac tgcctcaaat tggactttgg | 1860 |
| gcataaaaga acttttttat gcttaccatc tttttttttt ctttaacaga tttgtattta | 1920 |
| agaattgttt ttaaaaaatt ttaagattta cacaatgttt ctctgtaaat attgccatta | 1980 |
| aatgtaaata actttaataa aacgtttata gcagttacac agaatttcaa tcctagtata | 2040 |
| tagtacctag tattataggt actataaacc ctaattttt ttatttaagt acattttgct | 2100 |
| ttttaaagtt gatttttttc tattgttttt agaaaaaata aaataactgg caaatatatc | 2160 |
| attgagccaa aaaaaaaaaa aaaaaaaaa | 2189 |

<210> SEQ ID NO 6
<211> LENGTH: 3658
<212> TYPE: DNA
<213> ORGANISM: Homo sapiens

<400> SEQUENCE: 6

| | |
|---|---|
| gcccagacaa gcaacatggc tcggaaacgc gcggccggcg gggagccgcg gggacgcgaa | 60 |
| ctgcgcagcc agaaatccaa ggccaagagc aaggcccggc gtgaggagga ggaggaggat | 120 |
| gcctttgaag atgagaaacc cccaaagaag agccttctct ccaaagtttc acaaggaaag | 180 |
| aggaaaagag gctgcagtca tcctgggggt tcagcagatg gtccagcaaa aagaaagtg | 240 |
| gccaaggtga ctgttaaatc tgaaaacctc aaggttataa aggatgaagc cctcagcgat | 300 |
| ggggatgacc tcagggactt tccaagtgac ctcaagaagg cacaccatct gaagagaggg | 360 |
| gctaccatga atgaagacag caatgaagaa gaggaagaaa gtgaaaatga ttgggaagag | 420 |
| gttgaagaac ttagtgagcc tgtgctgggt gacgtgagag aaagtacagc cttctctcga | 480 |
| tctcttctgc ctgtgaagcc agtggagata gagattgaaa cgccagagca ggcgaagaca | 540 |
| agagaaagaa gtgaaaagat aaaactggag tttgagacat atcttcggag ggcgatgaaa | 600 |
| cgtttcaata aggggtcca tgaggacaca cacaaggttc accttctctg cctgctagca | 660 |
| aatggcttct atcgaaataa catctgcagc cagccagatc tgcatgctat tggcctgtcc | 720 |
| atcatcccag cccgctttac cagagtgctg cctcgagatg tggacaccta ctacctctca | 780 |
| aacctggtga agtggttcat tggaacattt acagttaatg cagaactttc agccagtgaa | 840 |
| caagataacc tgcagactac attggaaagg agatttgcta tttactctgc tcagatgat | 900 |
| gaggaattgg tccatatatt cttactgatt ctccgggctc tgcagctctt gacccggctg | 960 |
| gtattgtctc tacagccaat tcctctgaag tcagcaacag caaagggaaa gaaaccttcc | 1020 |
| aaggaaagat tgactgcgga tccaggaggc tcctcagaaa cttccagcca agttctagaa | 1080 |
| aaccacacca aaccaaagac cagcaaagga accaaacaag aggaaaccct tgctaagggc | 1140 |
| acctgcaggc caagtgccaa agggaagagg aacaagggag gcagaaagaa acggagcaag | 1200 |
| ccctcctcca gcgaggaaga tgagggccca ggagacaagc aggagaaggc aacccagcga | 1260 |
| cgtccgcatg gccgggagcg gcgggtggcc tccagggtgt cttataaaga ggagagtggg | 1320 |
| agtgatgagg ctggcagcgg ctctgatttt gagctctcca gtggagaagc ctctgatccc | 1380 |
| tctgatgagg attccgaacc tggccctcca aagcagagga agcccccgc tcctcagagg | 1440 |
| acaaaggctg gtccaagag tgcctccagg acccatcgtg ggagccatcg taaggaccca | 1500 |
| agcttgccag cggcatcctc aagctcttca agcagtaaaa gaggcaagaa atgtgcagc | 1560 |
| gatggtgaga aggcagaaaa aagaagcata gctggtatag accagtggct agaggtgttc | 1620 |
| tgtgagcagg aggaaaagtg ggtatgtgta gactgtgtgc acgtgtggt gggccagcct | 1680 |

```
ctgacctgtt acaagtacgc caccaagccc atgacctatg tggtgggcat tgacagtgac    1740
ggctgggtcc gagatgtcac acagaggtac gacccagtct ggatgacagt gacccgcaag    1800
tgccggggtg atgctgagtg gtgggccgag accttgagac cataccagag cccatttatg    1860
gacagggaga agaaagaaga cttggagttt caggcaaaac acatggacca gcctttgccc    1920
actgccattg gcttatataa gaaccaccct ctgtatgccc tgaagcggca tctcctgaaa    1980
tatgaggcca tctatcccga gacagctgcc atccttgggt attgtcgtgg agaagcggtc    2040
tactccaggg attgtgtgca cactctgcat tccagagaca cgtggctgaa gaaagcaaga    2100
gtggtgaggc ttggagaagt accctacaag atggtgaaag gcttttctaa ccgtgctcgg    2160
aaagcccgac ttgctgagcc ccagctgcgg gaagaaaatg acctgggcct gtttggctac    2220
tggcagacag aggagtatca gcccccagtg gccgtggacg ggaaggtgcc ccggaacgag    2280
tttgggaatg tgtacctctt cctgcccagc atgatgccta ttggctgtgt ccagctgaac    2340
ctgcccaatc tacaccgcgt ggcccgcaag ctggacatcg actgtgtcca ggccatcact    2400
ggctttgatt ccatggcgg ctactcccat cccgtgactg atggatacat cgtctgcgag    2460
gaattcaaag acgtgctcct gactgcctgg gaaaatgagc aggcagtcat tgaaaggaag    2520
gagaaggaga aaaaggagaa gcgggctcta gggaactgga agttgctggc caaaggtctg    2580
ctcatcaggg agaggctgaa gcgtcgctac gggcccaaga gtgaggcagc agctccccac    2640
acagatgcag gaggtggact ctcttctgat gaagaggagg ggaccagctc tcaagcagaa    2700
gcggccagga tactggctgc ctcctggcct caaaaccgag aagatgaaga aaagcagaag    2760
ctgaagggtg ggcccaagaa gaccaaaagg gaaaagaaag cagcagcttc ccacctgttc    2820
ccatttgaga agctgtgagc tgagcgccca ctagaggggc acccaccagt tgctgctgcc    2880
ccactacagg ccccacacct gccctgggca tgcccagccc ctggtggtgg gggcttctct    2940
gctgagaagg caaactgagg cagcatgcac ggaggcgggg tcaggggaga cgaggccaag    3000
ctgaggaggt gctgcaggtc ccgtctggct ccagcccttg tcagattcac ccagggtgaa    3060
gccttcaaag cttttttgcta ccaaagccca ctcacccttt gagctacaga acactttgct    3120
aggagatact cttctgcctc ctagacctgt tctttccatc tttagaaaca tcagtttttg    3180 tatgaagcc accgggagat ttctggatgg tggtgcatcc gtgaatgcgc tgatcgtttc     3240
ttccagttag agtcttcatc tgtccgacaa gttcactcgc ctcggttgcg gacctaggac    3300
catttctctg caggccactt accttcccct gagtcaggct tactaatgct gccctcactg    3360
cctctttgca gtaggggaga gagcagagaa gtacaggtca tctgctggga tctagttttc    3420
caagtaacat tttgtggtga cagaagccta aaaaaagcta aaatcaggaa agaaaaggaa    3480
aaatacgaat tgaaaattaa ggaaatgtta gtaaaataga tcagtgttaa actagattgt    3540
attcattact agataaaatg tataaagctc tctgtactaa ggagaaatga cttttataac    3600
attttgagaa aataataaag catttatcta aaaaaaaaa aaaaaaaaa aaaaaaa        3658

<210> SEQ ID NO 7
<211> LENGTH: 1704
<212> TYPE: DNA
<213> ORGANISM: Homo sapiens

<400> SEQUENCE: 7
ggcacgaggt acccctccac acggaggacg cgatggctcc caagaaacgc ccagaaaccc      60
agaagacctc cgagattgta ttacgcccca ggaacaagag gagcaggagt cccctggagc    120
tggagcccga ggccaagaag ctctgtgcga agggctccgg tcctagcaga agatgtgact    180
```

-continued

```
cagactgcct ctgggtgggg ctggctggcc cacagatcct gccaccatgc cgcagcatcg    240
tcaggaccct ccaccagcat aagctgggca gagcttcctg gccatctgtc cagcaggggc    300
tccagcagtc ctttttgcac actctggatt cttaccggat attacaaaag gctgccccct    360
ttgacaggag ggctacatcc ttggcgtggc acccaactca ccccagcacc gtggctgtgg    420
gttccaaagg gggagatatc atgctctgga attttggcat caaggacaaa cccaccttca    480
tcaaagggat tggagctgga gggagcatca ctgggctgaa gtttaaccct ctcaatacca    540
accagtttta cgcctcctca atggagggaa caactaggct gcaagacttt aaaggcaaca    600
ttctacgagt tttgccagc tcagacacca tcaacatctg gttttgtagc ctggatgtgt    660
ctgctagtag ccgaatggtg gtcacaggag acaacgtggg gaacgtgatc ctgctgaaca    720
tggacggcaa agagctttgg aatctcagaa tgcacaaaaa gaaagtgacg catgtggccc    780
tgaacccatg ctgtgattgg ttcctggcca cagcctccgt agatcaaaca gtgaaaattt    840
gggacctgcg ccaggttaga gggaaagcca gcttcctcta ctcgctgccg cacaggcatc    900
ctgtcaacgc agcttgtttc agtcccgatg gagcccggct cctgaccacg gaccagaaga    960
gcgagatccg agtttactct gcttcccagt gggactgccc cctgggcctg atcccgcacc   1020
ctcaccgtca cttccagcac ctcacaccta tcaaggcagc ctggcatcct cgctacaacc   1080
tcattgttgt gggccgatac ccagatccta atttcaaaag ttgtacccct tatgaattga   1140
ggacgatcga cgtgttcgat ggaaactcag ggaagatgat gtgtcagctc tatgacccag   1200
aatcttctgg catcagttcg cttaatgaat tcaatcccat gggggacacg ctggcctctg   1260
caatgggtta ccacattctc atctggagcc aggaggaagc caggacacgg aagtgagaga   1320
cactaaagaa ggtgtgggcc agacaaggcc ttggagccca cacatgggat caagtcctgc   1380
aagcagaggt ggcgatttgt taaagggcca aaagtatcca aggttagggt tggagcaggg   1440
gtgctgggac ctggggcact gtgggactgg gacactttta tgttaatgct ctggacttgc   1500
ctccagagac tgctccagag ttggtgacac agctgtccca agggcccctc tgtatctagc   1560
ctggaaccaa ggttatcttg gaactaaatg acttttctcc tctcagtggg tggtagcaga   1620
gggatcaagc agttatttga tttgtgctca cttttgatat ggccaataaa accataccga   1680
ctgaaaaaaa aaaaaaaaaa aaaa                                          1704
```

```

<210> SEQ ID NO 8
<211> LENGTH: 1578
<212> TYPE: DNA
<213> ORGANISM: Homo sapiens

<400> SEQUENCE: 8
gatcagggcc gagttgtctc ggcggcgctg ccgaggcctc cacccaggac agtccccctc     60
cccgggcctc tctcctcttg cctacgagtc ccctctcctc gtaggcctct cggatctgat    120
atcgtggggt gaggtgagca ggcccgggga gggtggttac cgctgaggag ctgcagtctc    180
tgtcaagatg atagaggtac tgacaacaac tgactctcag aaactgctac accagctgaa    240
tgccctgttg gaacaggagt ctagatgtca gccaaaggtc tgtggtttga gactaattga    300
gtctgcacac gataatggcc tcagaatgac tgcaagacta agggactttg aagtaaaaga    360
tcttcttagt ctaactcagt tctttggctt tgacacagag acattttctc tagctgtgaa    420
tttactggac agattcctgt ctaaaatgaa ggtacagccc aagcaccttg ggtgtgttgg    480
actgagctgc ttttatttgg ctgtaaaatc aatagaagag gaaaggaatg tcccattggc    540
```

```
aactgacttg atccgaataa gtcaatatag gtttacggtt tcagacttga tgagaatgga      600
aaagattgta ttggagaagg tgtgttggaa agtcaaagct actactgcct ttcaatttct      660
gcaactgtat tattcactcc ttcaagagaa cttgccactt gaaaggagaa atagcattaa      720
ttttgaaaga ctagaagctc aactgaaggc atgtcattgc aggatcatat tttctaaagc      780
aaagccttct gtgttggcat tgtctatcat tgcattagag atccaagcac agaagtgtgt      840
agagttaaca aaggaatag aatgtcttca gaaacattcc aagataaatg gcagagatct      900
gaccttctgg caagagcttg tatccaaatg tttaactgaa tattcatcaa ataagtgttc      960
caaaccaaat gttcagaagt tgaaatggat tgtttctggg cgtactgcac ggcaattgaa     1020
gcatagctac tacagaataa ctcaccttcc aacaattcct gaaatggtcc cttaactgga     1080
ttattacagc accaaaaaac ttctctgaag cctttctcca caaccttgtt ctatggattc     1140
cataatgtta caatggattt aagctatgaa gcctcaaaac atcacgagat aagcatgatg     1200
gtctcagact tgggaaaact gcctaatatt atgctgtagt ggaattatgt ttatgatttg     1260
aattcatctg tgaaggcatt caaatcaaag ctaaaagcct aaatgtgaaa tgctaatgac     1320
aagcctgaga aggtaaacta tgaatcttca tttctatcat tgatctaact ttagatattg     1380
gatcaatata tttaggtggt attgaaaatg ctattggagg agtcacacta atactatcaa     1440
ctatcagtct tcccacagct tcaatcactg tcattattct aatcctactc ctacttaaat     1500
tttaagttat gaggtttatg tcgaaagcaa catttcacaa atgtacttt aaggcataat      1560 aagggttaac attctagg                                                  1578

<210> SEQ ID NO 9
<211> LENGTH: 1776
<212> TYPE: DNA
<213> ORGANISM: Homo sapiens

<400> SEQUENCE: 9
tttcatttcc tcactgacta taaaagaata gagaaggaag ggcttcagtg accggctgcc       60
tggctgactt acagcagtca gactctgaca ggatcatggc tatgatggag gtccaggggg      120
gacccagcct gggacagacc tgcgtgctga tcgtgatctt cacagtgctc ctgcagtctc      180
tctgtgtggc tgtaacttac gtgtacttta ccaacgagct gaagcagatg caggacaagt      240
actccaaaag tggcattgct tgtttcttaa agaagatga cagttattgg gaccccaatg      300
acgaagagag tatgaacagc ccctgctggc aagtcaagtg caactccgt cagctcgtta      360 gaaagatgat tttgagaacc tctgaggaaa ccatttctac agttcaagaa aagcaacaaa      420
atatttctcc cctagtgaga gaaagaggtc ctcagagagt agcagctcac ataactggga      480
ccagaggaag aagcaacaca ttgtcttctc caaactccaa gaatgaaaag gctctgggcc      540
gcaaaataaa ctcctgggaa tcatcaagga gtgggcattc attcctgagc aacttgcact      600
tgaggaatgg tgaactggtc atccatgaaa aagggttta ctacatctat tcccaaacat      660
actttcgatt tcaggaggaa ataaaagaaa acacaaagaa cgacaaacaa atggtccaat      720
atatttacaa atacacaagt tatcctgacc ctatattgtt gatgaaaagt gctagaaata      780
gttgttggtc taaagatgca gaatatggac tctattccat ctatcaaggg ggaatatttg      840
agcttaagga aaatgacaga attttgtttt ctgtaacaaa tgagcacttg atagacatgg      900
accatgaagc cagttttttc ggggcctttt tagttggcta actgacctgg aaagaaaaag      960
caataacctc aaagtgacta ttcagttttc aggatgatac actatgaaga tgtttcaaaa     1020
aatctgacca aaacaaacaa acagaaaaca gaaaacaaaa aaacctctat gcaatctgag     1080
```

-continued

| | |
|---|---|
| tagagcagcc acaaccaaaa aattctacaa cacacactgt tctgaaagtg actcacttat | 1140 |
| cccaagagaa tgaaattgct gaaagatctt tcaggactct acctcatatc agtttgctag | 1200 |
| cagaaatcta gaagactgtc agcttccaaa cattaatgca atggttaaca tcttctgtct | 1260 |
| ttataatcta ctccttgtaa agactgtaga agaaagagca acaatccatc tctcaagtag | 1320 |
| tgtatcacag tagtagcctc caggtttcct taagggacaa catccttaag tcaaaagaga | 1380 |
| gaagaggcac cactaaaaga tcgcagtttg cctggtgcag tggctcacac ctgtaatccc | 1440 |
| aacattttgg gaacccaagg tgggtagatc acgagatcaa gagatcaaga ccatagtgac | 1500 |
| caacatagtg aaaccccatc tctactgaaa gtacaaaaat tagctgggtg tgttggcaca | 1560 |
| tgcctgtagt cccagctact tgagaggctg aggcaagaga attgtttgaa cccgggaggc | 1620 |
| agaggttgca gtgtggtgag atcatgccac tacactccag cctggcgaca gagcgagact | 1680 |
| tggtttcaaa aaaaaaaaaa aaaaaaactt cagtaagtac gtgttatttt tttcaataaa | 1740 |
| attctattac agtatgtcaa aaaaaaaaaa aaaaaa | 1776 |

<210> SEQ ID NO 10
<211> LENGTH: 1172
<212> TYPE: DNA
<213> ORGANISM: Homo sapiens

<400> SEQUENCE: 10

| | |
|---|---|
| gagacattcc tcaattgctt agacatattc tgagcctaca gcagaggaac ctccagtctc | 60 |
| agcaccatga atcaaactgc gattctgatt tgctgcctta tctttctgac tctaagtggc | 120 |
| attcaaggag tacctctctc tagaaccgta cgctgtacct gcatcagcat tagtaatcaa | 180 |
| cctgttaatc caaggtcttt agaaaaactt gaaattattc ctgcaagcca attttgtcca | 240 |
| cgtgttgaga tcattgctac aatgaaaaag aagggtgaga agagatgtct gaatccagaa | 300 |
| tcgaaggcca tcaagaattt actgaaagca gttagcaagg aaatgtctaa aagatctcct | 360 |
| taaaaccaga ggggagcaaa atcgatgcag tgcttccaag gatggaccac acagaggctg | 420 |
| cctctcccat cacttcccta catggagtat atgtcaagcc ataattgttc ttagtttgca | 480 |
| gttacactaa aaggtgacca atgatggtca ccaaatcagc tgctactact cctgtaggaa | 540 |
| ggttaatgtt catcatccta agctattcag taataactct accctggcac tataatgtaa | 600 |
| gctctactga ggtgctatgt tcttagtgga tgttctgacc ctgcttcaaa tatttccctc | 660 |
| acctttccca tcttccaagg gtactaagga atctttctgc tttggggttt atcagaattc | 720 |
| tcagaatctc aaataactaa aaggtatgca atcaaatctg cttttttaaag aatgctcttt | 780 |
| acttcatgga cttccactgc catcctccca aggggcccaa attctttcag tggctaccta | 840 |
| catacaattc caaacacata caggaaggta gaaatatctg aaaatgtatg tgtaagtatt | 900 |
| cttatttaat gaaagactgt acaaagtata agtcttagat gtatatattt cctatattgt | 960 |
| tttcagtgta catggaataa catgtaatta agtactatgt atcaatgagt aacaggaaaa | 1020 |
| ttttaaaaat acagatagat atatgctctg catgttacat aagataaatg tgctgaatgg | 1080 |
| ttttcaaata aaaatgaggt actctcctgg aaatattaag aaagactatc taaatgttga | 1140 |
| aagatcaaaa ggttaataaa gtaattataa ct | 1172 |

<210> SEQ ID NO 11
<211> LENGTH: 3302
<212> TYPE: DNA
<213> ORGANISM: Homo sapiens

<400> SEQUENCE: 11

```
ttgtttgatt actgtggctt ttctttacct acaacccaag cctgacgtcc ctcggtttta      60
aatagcaggg agaggggaat caatgtttga ttcaggtgtt tcgaagacca cgccacaggc     120
gatgagcaga actcttcatg ttgaaacggt tctgctacag tactagattg ctctcaggcg     180
atttggggtt gatacaggca agccggtgca aaactggaat actggatatg aagtgaaatg     240
tataaaagac ataaatgtca caaatagtt tgatcacaag tgttgatttt cctggtgagt      300
tggggctgcg tgtttccatg ttttctgaag gttcacataa acatgcagcc tgccaattct     360
ctgtacattt ttttttttca atgagtggta tttcggtttt cacgtttagt tgtaagacag     420
aaattggaga cttatatgta gctggagtgg atgacttctt tcttttgggg gaagaatgag     480
agatgcacat ttcgttagta aattgtgaac aacttgaaac aaacccaaat ccaattttga    540
atttaagaag tagagttaaa atgaaggta gccattcaaa tactatgcct tgctgccttc      600
acttattaag ttaggatttt cttcctttta gcccttagg gatacagtag tttaaaagag      660
cagtagccac atatgaaagg atcagattta gcttagaggg aattccttag accagccctg     720
ctgttaagac ttgacattca atattgtttg atcacattcc aaaatatagc ttagctaatg     780
gcaacatttg taaacatata aattgcaaaa gaagctttct tgtgtacata cattttaaa     840
agcttgaaat tgatgtgaac ttttaaaaac acgtaggatc tgtattacat tctacatctc     900
aaaacaaatt taattaaagt gaatatcatt ccagtatata caatatgcct aagacccaga     960
attggcacat tgatttacta gttgaaaata taacagtatt caccaaactt caatgtatac    1020
tttttggaga gaatgaaatt acagtatttc ttaatttact gtaatgtcat ctttgtaatt    1080
atgaactaac aattcaatga gaggagactt ggctgattaa attaatgctg gtcctacaca    1140
ttatatctaa aggatcttcg tatatgacta ctatcctctt ggattatttt aacagttaaa    1200
atatacaaag tggcccatta aaaacagagt tgacttttca ccattgctgt ttttctggtg    1260
agacatgtgg aaaggaagga caggtggact tttcaactaa ctagctctct gatttttaat    1320
aagatacctc agttcttttg gcctcagttt acttatctgt acaaagggta agtcatatgc    1380
ttaatcacta agatctgtta gatactgcag ttaagattct ttatcagcaa attactgaac    1440
tctagtgtta acatagctag aggtggaaaa gggagcaaga ccaggtgttg ggatgaataa    1500
ttaactaatc gagataacat cagttttcac cataggaaca agtaccatgg ttgctcttaa    1560
agtaagagat gtttcctatt ttatgtaatt ttactaaggg atagtgtttt cttttgtcac    1620
tgacttaaat gtacctggat gtttctcagc catttggcta agatcgaaca caagtaatac    1680
ctgggccttt tatatctaat ctaatgtaga ccagcctgtt aaaagagaaa gacaattggt    1740
taaactgctg atgtgttgct ttgtcttctc aaaagcttgt tctataatac aatatgtaaa    1800
aagttgttac agtgtagtaa ccgtagataa tcccttatg atttgtacct aatggcgaag     1860
accttttatt ttctgaaaat aacgtgtttg ttttcattac cgacattaga gccaatatt     1920
tattaatcta tttctcatcc tgacatttca gtcagactct taaaataatc ttgctgtgtt    1980
ttgatttaat gtgcttatca acttataata ttgaattaat gttaatagtg tcattttagg    2040
tgaactagac ttcattgaag gaggtgggag ccttatggag agagagtata tgattatctc    2100
tatttgtatt taattaccat ttcatctaac cattcagaac atatttcaag aataatttta    2160
attcaagttg tagataaaac ttactatacc attttcattt tgacgctttc caagaatgag    2220
atacacggta ttttaaagac aaagattgat cttacatgtt actattaaaa aaaacacgat    2280
aatttttgttc tacatttata cttttaattt ttctgtggat aataagaaat gccaagagtc    2340
```

```
gattgtgtcc atgctggcaa gtggcctaat aaattgtcct tttatttggt ggtcctcaga      2400
gtggcagtta acatcttgct attctgcctt gtggacttga ggtggaaagg ttcatggaat      2460
tatatccttg cttttggatg tgcaaactga ggctcagaga gtttaagaca catagtcact      2520
ttcaccaatt aaatgatgaa gctgccatgt aaacgtattt catcacactc ccgagacctt      2580
cttctccagt agtgttttca gcttttttga gcatgcagac actaccatca aaaaattatg      2640
tagagacata cttgagagtt acagtttaaa gaaaaaacaa ggtgtaatta tttggttatt      2700
agtagcattt acatatgctt gaaaacttct gctatatata cagtaagatt aatttattct      2760
aacaatgatc ttgataatcc ccctgattcc cagactcctt ggaatagctc cacagctatc      2820 agtggtctg ccacaggttc agagccttcc cagtactgcc ttcttatttg agaggtgtgc       2880
taagagctat aaagcagagg cttcaattgt acacagtttg gaagtttagg caaaagtcat      2940
ttcttcccta tattttgtca tgcttatctc ctgtctcttt ctgttttaca gattagcaat      3000
aaactcctta aaacccaaag gtttgggctt ctgttccttt cacttgcagt cagacatgga      3060
gttagtggta gaagaaacag aagggggtaac ctgcatggtg acagctactg aggggatgga     3120
taggaaagca ggctgagtcc ccggggccag tggttaccaa agccaaggag agagcaaggg     3180
gagcccagtg ggcctggcca tggactgctc tggaattccg agtgtgaact ttcagccaag     3240
aaggtagtgt gaaaatatta ctgtgaggtt ttaaaagtac acaataaca attgtttttt      3300 gt                                                                     3302

<210> SEQ ID NO 12
<211> LENGTH: 2943
<212> TYPE: DNA
<213> ORGANISM: Homo sapiens

<400> SEQUENCE: 12
tgagagaccg tgttgcaatg ttccgttcag cttggtgtca atggcctgtg tccacctggc        60
ttccaagata gaagaggccc caagacgcat acgggacgtc atcaatgtgt tcaccgcct        120 tcgacagctg agagacaaaa agaagcccgt gcctctacta ctggatcaag attatgttaa       180
tttaaagaac caaattataa aggcggaaag acgagttctc aaagagttgg gtttctgcgt       240
ccatgtgaag catcctcata agataatcgt tatgtacctt caggtgttag agtgtgagcg       300
taaccaacac ctggtccaga cctcatgggt agcctctgag ggtaagtgac taagacttct       360
cctctgctgt ccaagcgctt tggtgcaggg acagcggcat cttcagccaa tccagtgcag       420
gctctccacc gaaggctggc tctagactgg ttggcagcgg ctctgatgag cccgagaaga      480
ggcctgactc cttgggtgcg gagtctccct ccgcacgatg ctcccacgcg tccaacttgc       540
acccaagcgg gctttggtcc ctcttccaag tggactcctt caaggaagct gcagctcggt       600
cagcagagaa ggggcctgcc gccagcgccc tggaggaaga ggaagaggaa cccaagagga       660
tggcttgtct cccagcagcc acaccggctt tgtgctcagc cagttcattt gagtttgcat       720
gtttctctgc actatggatt ttgagcattt agatttcttt aatcaaaagc gttttagtga       780
ctccagtaga cattttcttt ctgaggcatc gtgctttgca tgagagcagg ccaaggttga       840
ggggaaaagt aaagttaaag tcggttctct ttcatagcaa cacgtattgt ctgacattca       900
gccagctttt ttttttttct aataaatttct gtgcctttct gtcctgtatt tactgtattt      960
agaaaaagca gctagaatat ttctccatta actcttgaga ttcacaggac tgtctagctc     1020
tgagtcctag caatagactc cttagaggag tagtacgttt atctagattt tctctagata     1080
```

-continued

```
atgcaggcgg aagacctggg ttcccgggtg gggcattgca gttcttcctg tgtttggctt    1140
ccaggaatta catgaacgac agccttcgca ccgacgtctt cgtgcggttc cagccagaga    1200
gcatcgcctg tgcctgcatt tatcttgctc cccggacgct ggagatccct ttgcccaatc    1260
gtccccattg gtttcttttg tttggagcaa ctgaagaaga aattcaggaa atctgcttaa    1320
agatcttgca gctttatgct cggaaaaagg ttgatctcac acacctggag ggtgaagtgg    1380 aaaaagaaa gcacgctatc gaagagcaag gcccaagccc ggggcctgtt gcctgggggc    1440
acacaggtgc tggatggtac ctcggggttc tcccatgtca gtggtctcaa tgtattgact    1500
ttgtgatcgc cctcctcggc gctatctggg atcactgcaa gctccgccta ccagattctg    1560
gtgattcttg tgcctcagcc tcccaagtag ctgggattgc aggcgccac caccacgctc     1620 agagtctcgc tgtgttgcca gtggaatccc ccaaagaagg taaagggagc aagccttccc    1680
cactgtctgt gaagaacacc aagaggaggc tggagggcgc caagaaagcc aaggcggaca    1740
gccccgtgaa cggcttgcca aagggcgag agagtcggag tcgagccgg agccgtgagc      1800 agagctactc gaggtcccca tcccgatcag cgtctcctaa gaggaggaaa agtgacagcg    1860
gctccacatc tggtgggtcc aagtcgcaga gccgctcccg gagcaggagt gactccccac    1920
cgagacaggc ccccgcagc gctccctaca aaggctctga gattcggggc tcccggaagt     1980
ccaaggactc caagtacccc cagaagccac acaagtctcg gagccggagt tcttcccgtt    2040
ctcgaagcag gtcacgggag cgggcggata tccgggaaaa atacaagaag aaaagtcatt    2100
actacagaga tcagcgacga gagcgctcga ggtcgtatga acgcacaggc cgtcgctatg    2160
agcgggacca ccctgggcac agcaggcatc ggaggtgagg cggggttgca gtgactggtg    2220
gccgcaagcc cttccctggg gagtacctga tggctgccct ttgacccccg gtggctgccc    2280 tttgacccccc gggtgtgctc tcagcgcaag tggtcctaga acaggattct ttttggaaat   2340
gtctgtcgac tggaccttgg tggatttgga aatggaactg agggaccggt gacacgtgct    2400
tcagaccggt ctggggtgcg cgcacacct gggccgtgc agggctcagc tcggcagcag      2460
ctctgaggga gctcaatga aaaagtgaat gcacacgccc ttgttggcgt ggcctggcat     2520
ggcctggtgc tatcggcagc cgctctccac tccccgactg atactcaatt acgtgaagcc    2580
aagaaagatg attttagaa cctttgccta tattaggttg tacttatgta catattttgc     2640
agtgtttcac aggagaaagt ggccttaact gccccttatt ctctctccac gttgtaaata    2700
aacatgtgtt taatacaagt taaagctatg tatgaaaact cagaacttga atcccgtcag    2760
cttaaaactt gtgtagggaa tcctgacttt taaaatgtga gggtatttgg atctgtgttg    2820
aaagtcgtat atttttatct gtgcggtgct gagtgcaggc caccagctcc taaatagagg    2880
ttccctatat gcgcgtatga catggtgaat aaacacaact ctctccacca aaaaaaaaa    2940 aaa                                                                  2943
```

<210> SEQ ID NO 13
<211> LENGTH: 397
<212> TYPE: DNA
<213> ORGANISM: Homo sapiens
<220> FEATURE:
<221> NAME/KEY: misc_feature
<222> LOCATION: (1)..(397)
<223> OTHER INFORMATION: n is a, c, t, or g.

<400> SEQUENCE: 13

```
aattaatata nnnntgaaac aatttggtaa tgcagactgg acaatgtca ctatacccac       60 tgaggtaact gagacatgag agctttccaa cccaaggtca gaaatcactg aaacagctta    120
```

```
tgaaaccctc actattttag tgttttaaat tcagaatgct gtattttct cttgggcaac        180 agataacctt cattttgac gtaaatgata atggtggctt cacatggccc agggcaaact        240
tcaaaacaaa actgtaggga ccacatttt ctaacctgga aaataagtca tataaggggt        300
ccaaataagg gtaaaatttg ggaatttaat tattcctggg gggaaaatat tgtgggggta      360
tccctggtat cctngggccc ggtaatcccg ggtttta                               397
```

```
<210> SEQ ID NO 14
<211> LENGTH: 323
<212> TYPE: DNA
<213> ORGANISM: Homo sapiens
<220> FEATURE:
<221> NAME/KEY: misc_feature
<222> LOCATION: (1)..(323)
<223> OTHER INFORMATION: n is a, c, t, or g.

<400> SEQUENCE: 14
```

```
gagtttaata ggccagacag aagggagaag gcagaaggaa gaagctcccc cgtacagaga       60
cagagggagg gaggctccaa agccaagaga agggatcccc aagtgcggtg gacaccagcc      120
aggtatatat gcagaggctg gagaaggtgg tnttcgattt gcatagggct ccggggattg      180
ggttgactag gcgcatcatt cacatagctc atgaaaaagc tggctcttcc accctgggnc      240
ttttaatatg caaatacatg ggcgccatga tgttctacgc tcgtcgggat tccnggggac      300
atgtaggggc aagggcaaga agg                                              323
```

```
<210> SEQ ID NO 15
<211> LENGTH: 497
<212> TYPE: DNA
<213> ORGANISM: Homo sapiens
<220> FEATURE:
<221> NAME/KEY: misc_feature
<222> LOCATION: (1)..(497)
<223> OTHER INFORMATION: n is a, c, t, or g.

<400> SEQUENCE: 15
```

```
gtgggcagaa gaaagtcata atttctgaag ataacaaatg cagcacagaa gtggaatagg       60
gccatgaata cctgaaaaca ctaacgttct ttttcctgt ggatttatgc atggagggct      120
tcgtataatg acttggtact accactgcta ttaggaacca ttggaattct gtgataattt     180
tggattgctt tttaattcac caagactact gtggatgatg tcagccacat tatggtgtga     240
gccctaaatt taaggtcaat atcatgtgct accttcatat ctggtgatac tagtattacc     300
tcaaatggtc tgagtacaaa tccccttcc cactctgctc ttttgtataa tgtgtcctag      360
cctaactacc ctttaaatca agaggactaa gcagagttnc ccgtttatta tttatttgta     420
ggcaagtttn gaatttcatt nctacacaca gagtttattt caaacaagcc gttacagctg     480
ggtgtgggtg tcgcaca                                                    497
```

```
<210> SEQ ID NO 16
<211> LENGTH: 317
<212> TYPE: DNA
<213> ORGANISM: Homo sapiens

<400> SEQUENCE: 16
```

```
ttaataggaa agtaaagagc actttcccca aacagcaaga acaaaatcgc tttctcttaa       60
cacattgatt tatttcattt gctaagcaca ggaaccatga aatgcttcat cccattagca      120
cattaaatat gtgcagaagt aaaattacag ctgaacagca ccttgtactt tgtactcatg      180
```

```
gtgtgtacat ttcagtaggc taggaggaaa aaacgaactg tagaaagata attttatggg      240
aattaaatta cctgttttgt attgctctga agctgtgcat gtaggctgtg ggatttcaga      300
gggacttgaa ctgttgc                                                    317
```

<210> SEQ ID NO 17
<211> LENGTH: 2596
<212> TYPE: DNA
<213> ORGANISM: Homo sapiens

<400> SEQUENCE: 17

```
ggcacgaggc cgggctcgcc gcgccgcgcc cgcgcgtcct tagcggggcc accgagcgat       60
gcccgccggg cgcccgcgaa agtttgtcgg ctcctgctga agggcagcgg cgccccgca      120 cccccgtgcc ccgctccggc caggagcctt cacgtaaatg ggtccagtca tgcctcccag     180
taagaagcca gaaagctcag gaattagtgt ctccagtgga ctgagtcagt gttacgggg     240 cagcggtttc tccaaggccc ttcaggaaga cgatgacctc gacttttctc tgcctgacat     300
ccgattagaa gaggggggcca tggaagatga agagctgacc aacctgaact ggctgcacga     360
gagcaagaac ttgctgaaga gctttgggga gtcggtcctc aggagtgtca gccccgtcca     420
ggacctggac gatgacaccc ccccatcccc tgcccactct gacatgccct acgatgccag     480 gcagaaccccc aactgcaaac ccccctactc cttcagctgc ctcatattta tggccatcga     540
ggactctcca accaagcgcc tgccagtgaa ggatatctac aactggatct tggaacattt     600
tccgtatttt gcaaatgcac ctactgggtg gaaaaactca gtgagacaca atttatcatt     660
gaataagtgt tttaagaaag tggacaaaga gaggagtcag agtattggga aagggtcgtt     720
gtggtgcata gacccagagt atagacaaaa tctaattcag gctttgaaaa agacaccttta    780 tcacccacac ccacacgtgt tcaatacacc tcccacctgt cctcaggcat atcaaagcac     840
atcaggtcca cccatctggc cgggcagtac cttcttcaag agaaatggag cccttctcca     900
agttcctcca ggagtgatcc aaaatggagc gcgggtcctg agccgagggc tgtttcctgg     960
cgtgcggccg ctgccaatca ctcccattgg ggtgacagcg ccatgagga atggcatcac    1020 cagctgccgg atgcggactg agagtgagcc atcttgtggc tccccagtgg tcagcggaga    1080
ccccaaggag gatcacaact acagcagtgc caagtcctcc aacgcccgga gcacctcgcc    1140
caccagcgac tccatctcct cctcctcctc ctcagccgac gaccactatg agtttgccac    1200
caaggggagc caggagggca gcgagggcag cgaggggagc ttccggagcc acgagagccc    1260
cagcgacacg gaagaggacg acaggaagca cagccagaag gagcccaagg attctctggg    1320
ggacagcggg tacgcatccc agcacaagaa gcgccagcac ttcgcaaagg ccaggaaggt    1380
ccccagcgac acactgcccc tcaaaaagag acgcaccgaa aagccccccg agagcgatga    1440
tgaggagatg aaagaagcgg cagggtccct cctgcactta gcagggatcc ggtcctgttt    1500
gaataacatc accaatcgga cggcaaaggg gcagaaagag caaaaggaaa ccacaaaaa    1560 ttaaaaacaa gtcactgatt tgttttgaac ttacgaccat ttggtttcag catgtcagga    1620
gatttctaat gatttgtggc aatatcagca atttttttc ttttttcttg ttttttggttt    1680 ggttttcttt cttttctttt cctttattt tgttttaatt tgcccccct ctctttgtttt     1740 ggacccttaa gaatttttatt tttaaggag attgaagcca tagaactcat attgacactc    1800
agctgtttta caaagctttt tcattatctg aagacaaaac cgaaaagcc aaaattacca    1860 ttgcttcctc cagcttgtca gaaacctgtg gctgaatccg cagggatgtc aacgtcaata    1920
tcacaggaac acacattcgg cacctagaag gcacgtgggc aaagtaatca tcgttcaggc    1980
```

| | |
|---|---:|
| ccaacccttta ggtttaaaaa gtcaggttgt ccatcccatt gggttcactg agtgaaggca | 2040 |
| cataaagcaa ttgaggagga ggaggaaccc ctcgtccccc taggagcaga cccaagcttg | 2100 |
| tggcaccagg catctgatgg tgccaggaaa gccactggaa ttgtcacacg gcgagcacag | 2160 |
| agggccggcc accagtcctc gatgcttctg aaccctgaag cccgatgaca tcttacgagg | 2220 |
| tggacgttgg actgttcatg cgcatcgggt gtcagtgact catggagaag aaatggggta | 2280 |
| aattttagt gatgttgcta atcattgaat tctgttctct attaaattaa gaaaatgttc | 2340 |
| caaaagccat aagcctgaag attggccctg tgcacgcacg cacacacaca cacacacaca | 2400 |
| cacacacaca cacacacaca cgaaggagag agagagaaaa ctgatgggga aaacaagctg | 2460 |
| tgtcttctta actgcccaag tgaaaagcaa ccaagtccag gaaattacaa tagctgttaa | 2520 |
| ggaaaggaaa taatggtaca gatctttttc tgtctatcaa aactatttga tccaagtgaa | 2580 |
| aaaaaaaaaa aaaaaa | 2596 |

<210> SEQ ID NO 18
<211> LENGTH: 2919
<212> TYPE: DNA
<213> ORGANISM: Homo sapiens

<400> SEQUENCE: 18

| | |
|---|---:|
| catccttgga tgatgaagga gatactcaaa acatagattc atggtttgag gagaaggcca | 60 |
| atttggagaa taagttactg gggaagaatg gaactggagg gcttttttcag ggcaaaactc | 120 |
| ctttgagaaa ggctaatctt cagcaagcta ttgtcacacc tttgaaacca gttgacaaca | 180 |
| cttactacaa agaggcagaa aaagaaaatc ttgtggaaca atccattccg tcaaatgctt | 240 |
| gttcttccct ggaagttgag gcagcccata tcaagaaaaac tccagcccag cctcagagaa | 300 |
| gatctcttag gctttctgct cagaaggatt tggaacagaa agaaaagcat catgtaaaaa | 360 |
| tgaaagccaa gagatgtgcc actcctgtaa tcatcgatga aattctaccc tctaagaaaa | 420 |
| tgaaagtttc taacaacaaa aagaagccag aggaagaagg cagtgctcat caagatactg | 480 |
| ctgaaaagaa tgcatcttcc ccagagaaag ccaagggtag acatactgtg ccttgtatgc | 540 |
| cacctgcaaa gcagaagttt ctaaaaagta ctgaggagca agagctggag aagagtatga | 600 |
| aaatgcagca agaggtggtg gagatgcgga aaaagaatga agaattcaag aaacttgctc | 660 |
| tggctggaat agggcaacct gtgaagaaat cagtgagcca ggtcaccaaa tcagttgact | 720 |
| tccacttccg cacagatgag cgaatcaaac aacatcctaa gaaccaggag gaatataagg | 780 |
| aagtgaactt tacatctgaa ctacgaaagc atccttcatc tcctgcccga gtgactaagg | 840 |
| gatgtaccat tgttaagcct ttcaacctgt cccaaggaaa gaaagaaca tttgatgaaa | 900 |
| cagtttctac atatgtgccc cttgcacagc aagttgaaga cttccataaa cgaaccccta | 960 |
| acagatatca tttgaggagc aagaaggatg atattaacct gttaccctcc aaatcttctg | 1020 |
| tgaccaagat ttgcagagac ccacagactc ctgtactgca aaccaaacac cgtgcacggg | 1080 |
| ctgtgacctg caaagtaca gcagagctgg aggctgagga gctcgagaaa ttgcaacaat | 1140 |
| acaaattcaa agcacgtgaa cttgatccca gaatacttga aggtgggccc atcttgccca | 1200 |
| agaaaccacc tgtgaaacca cccaccgagc ctattggctt tgatttggaa attgagaaaa | 1260 |
| gaatccagga gcgagaatca aagaagaaaa cagaggatga acactttgaa tttcattcca | 1320 |
| gaccttgccc tactaagatt ttggaagatg ttgtgggtgt tcctgaaaag aaggtacttc | 1380 |
| caatcaccgt ccccaagtca ccagcctttg cattgaagaa cagaattcga atgcccacca | 1440 |

-continued

```
aagaagatga ggaagaggac gaaccggtag tgataaaagc tcaacctgtg ccacattatg      1500
gggtgccttt taagccccaa atcccagagg caagaactgt ggaaatatgc cctttctcct      1560
ttgattctcg agacaaagaa cgtcagttac agaaggagaa gaaaataaaa gaactgcaga      1620
aaggggaggt gcccaagttc aaggcacttc ccttgcctca ttttgacacc attaacctgc      1680
cagagaagaa ggtaaagaat gtgacccaga ttgaaccttt ctgcttggag actgacagga      1740
gaggtgctct gaaggcacag acttggaagc accagctgga agaagaactg agacagcaga      1800
aagaagcagc ttgtttcaag gctcgtccaa acaccgtcat ctctcaggag ccctttgttc      1860
ccaagaaaga gaagaaatca gttgctgagg gcctttctgg ttctctagtt caggaacctt      1920
ttcagctggc tactgagaag agagccaaag agcggcagga gctggagaag agaatggctg      1980
aggtagaagc ccagaaagcc cagcagttgg aggaggccag actacaggag gaagagcaga      2040
aaaaagagga gctggccagg ctacggagag aactggtgca taaggcaaat ccaatacgca      2100
agtaccaggg tctggagata aagtcaagtg accagcctct gactgtgcct gtatctccca      2160
aattctccac tcgattccac tgctaaactc agctgtgagc tgcggatacc gcccggcaat      2220
gggacctgct cttaacctca aacctaggac cgtcttgctt tgtcattggg catggagaga      2280
acccatttct ccagactttt acctacccgt gcctgagaaa gcatacttga caactgtgga      2340
ctccagtttt gttgagaatt gttttcttac attactaagg ctaataatga gatgtaactc      2400
atgaatgtct cgattagact ccatgtagtt acttcctttta aaccatcagc cggccttta      2460 tatgggtctt cactctgact agaatttagt ctctgtgtca gcacagtgta atctctattg      2520
ctattgcccc ttacgactct cacctctcc ccacttttt taaaaatttt aaccagaaaa      2580
taaagatagt taaatcctaa gatagagatt aagtcatggt ttaaatgagg aacaatcagt      2640
aaatcagatt ctgtcctctt ctctgcatac cgtgaattta tagttaagga tccctttgct      2700
gtgagggtag aaaacctcac caactgcacc agtgaggaag aagactgcgt ggattcatgg      2760
ggagcctcac agcagccacg cagcaggctc tgggtggggc tgccgttaag gcacgttctt      2820
tccttactgg tgctgataac aacagggaac cgtgcagtgt gcattttaag acctggcctg      2880
gaataaatac gttttgtctt tccctcaaaa aaaaaaaa                            2919
```

<210> SEQ ID NO 19
<211> LENGTH: 3526
<212> TYPE: DNA
<213> ORGANISM: Homo sapiens

<400> SEQUENCE: 19

```
ccacgcgtcc ggacaggctt aagcatggcc aagaagcttg agagaagaaa aatttcagaa        60
aaattgtctc aatttgacta gaatatcaat gaaccaggaa aactgaagca ccttccctaa       120
agaaaacttg ggtatacaat tactccacag acagagctga gggtttttta cccaaatcag       180
tcactggatt ttgctgcctg atacgtgaat cttcttggaa ttttttctcat gtggatctaa       240 ggggaatgct ttattatggc tgctgttgtc caacagaacg acctagtatt tgaatttgct       300
agtaacgtca tggaggatga acgacagctt ggtgatccag ctattttcc tgccgtaatt       360 gtggaacatg ttcctggtgc tgatattctc aatagttatg ccggtctagc ctgtgtggaa       420
gagcccaatg acatgattac tgagagttca ctggatgttg ctgaagaaga aatcatagac       480
gatgatgatg atgacatcac ccttacagtt gaagcttctt gtcatgacgg ggatgaaaca       540
attgaaacta ttgaggctgc tgaggcactc ctcaatatgg attccctgg ccctatgctg       600 gatgaaaaac gaataaataa taatatattt agttcacctg aagatgacat ggttgttgcc       660
```

```
ccagtcaccc atgtgtccgt cacattagat gggattcctg aagtgatgga aacacagcag      720
gtgcaagaaa aatatgcaga ctcaccggga gcctcatcac cagaacagcc taagaggaaa      780
aaaggaagaa aaactaaacc accacgacca gattccccag ccactacgcc aaatatatct      840
gtgaagaaga aaacaaaga tggaaaggga aacacaattt atctttggga gttttactg       900 gcactgctcc aggacaaggc tacttgtcct aaatacatca agtggaccca gcgagagaaa      960 ggcatttta aattggtgga ttctaaagca gtgtccaggt tgtggggaa gcacaaaaac      1020 aaacctgata tgaattatga gaccatggga agagcactca ggtactatta ccaaagggt     1080 attctggcaa aagtggaagg tcagcgcttg gtgtatcagt ttaaagaaat gccaaaagat     1140
cttatatata taaatgatga ggatccaagt tccagcatag agtcttcaga tccatcacta     1200
tcttcatcag ccacttcaaa taggaatcaa accagccggt cgagagtatc ttcaagtcca     1260
ggggtaaaag gaggagccac tacagttcta aaaccaggga attctaaagc tgcaaaaccc     1320
aaagatcctg tggaagttgc acaaccatca gaagttttga ggacagtgca gcccacgcag     1380
tctccatatc ctacccagct cttccggact gttcatgtag tacagccagt acaggctgtc     1440
ccagagggag aagcagctag aaccagtacc atgcaggatg aaacattaaa ttcttccgtt     1500
cagagtatta ggactataca ggctccaacc caagttccag tggttgtgtc tcctaggaat     1560
cagcagttgc atacagtaac actccaaaca gtgccactca caacagttat agccagcaca     1620
gatccatcag caggtactgg atctcagaag tttattttac aagccattcc atcatcacag     1680
cccatgacag tactgaaaga aaatgtcatg ctgcagtcac aaaaggcggg ctctcctcct     1740
tcaattgtct ggggccctgc ccaggttcag caggtcctta ctagcaatgt tcagaccatt     1800
tgcaatggaa ccgtcagtgt ggcttcctct ccatccttca gtgctactgc acctgtggtg     1860 acctttctc ctcgcagttc acagctggtt gctcacccac ctggcactgt aatcacttca     1920
gttatcaaaa ctcaagaaac aaaaactctt acacaggaag tagagaaaaa ggaatctgaa     1980
gatcatttga aagagaacac tgagaaaacg gagcagcagc cacagcctta tgtgatggta     2040
gtgtccagtt ccaatggatt tacttctcag gtagctatga acaaaaacga actgctggaa     2100
cccaactctt tttagttaat ataccaaagc ttatgaataa ttgtttgtta attgaacatt     2160
ttcaattata tgcagactga ctgattctaa gataaattct aaggaggttt ctaattttgt     2220
aattgttaaa aatagagtta atttttgactt tgttagatga gggaggaaaa ctcaactgtt     2280
tctctttgtt atctaaatgt ttcagaattc aatcgtgaag gaacaggcat tttacactat     2340
gaagacattc ttttgagatt tttatttcag ttgctatatc ataagcattt ttaaagtttc     2400
ttttctaatt ttacattgta ttagattttc tgattctttt gtaaatacag aacttaaata     2460
gaaggcaaca ggaaatttat ataggaacta ttttcattcc acttgtgtaa gttaagtctt     2520
gactctttca aatgcaaaaa acctattta tgctttgtta aaattatggt gtcacttaga     2580
ttgactttag ttgactgcac tatataatat agaactatga atatgtagaa taacatgaaa     2640
aattggaggt gctggtggta tggctgaccc tgtttcagaa gcaggatagt ataaaagcat     2700
cagcctaaga atggcactcc cactaactag ctatgtaatc ttgacctctt tgggctttag     2760
ttcctctcat aaaaggaaga gatgtattgg attagactag attatcacca ctttctcttc     2820
tagttctaat ttttttaatt ctaataccta tattttcaag ttatgtcaat taaatcatta     2880
tcaggttatt tcctaatgta agaatagcta aaatgttgca gagaaataag tgacccaaca     2940
aaatttattc atctgttatg ggtaagatct gccataaatt cttcctaaat aatttgttta     3000
```

```
ctaactctttt aggccactgt gctttgcggt ccattagtaa acttgtgttg ctaagtgcta    3060
aacagaatac tgctatttg agagagtcaa gactctttct taagggccaa gaaagcaact     3120
tgagccttgg gctaatctgg ctgagtagtc agttataaaa gcataattgc tttatatttt    3180
ggatcatttt ttactggggg cggacttggg gggggttgca tacaaagata acatatatat    3240
ccaactttct gaaatgaaat gttttagat tacttttca actgtaaata atgtacattt      3300
aatgtcacaa gaaaaaatg tcttctgcaa attttctagt ataacagaaa ttttgtaga     3360 tgaaaaaaat cattatgttt agaggtctaa tgctatgttt tcatattaca gagtgaattt    3420
gtatttaaac aaaaatttaa attttggaat cctctaaaca tttttgtatc tttaattggt    3480
ttattattaa ataaatcata taaaaattct caaaaaaaaa aaaaaa                   3526

<210> SEQ ID NO 20
<211> LENGTH: 5441
<212> TYPE: DNA
<213> ORGANISM: Homo sapiens

<400> SEQUENCE: 20
ccacgcgtcc gcggacgcgt gggccgggag accctgacat atgcccaggc ccagcggatt      60
gtcgaggtag acattgatgg acgcctgcat cgtatcagca tctatgaccc actcaaaatc     120
attactgaag atgagctaac tgcccaggat atcaccgaat gcaatagtaa caaggaaaac     180
agtgaacagc ctcagttccc tggcaagtcc aagaaaccct catccaaggg caaaaagaag     240
gaatcctgct ccaagcatgc atctggtact tccttccacc tcccacagcc cagcttccgt     300
atggtggact caggcatcca gccagaagca cccccgctgc ctgctgccta ctaccgctac     360
attgagaagc cacctgaaga cctggatgca gaggtagagt atgacatgga tgaggaggac     420
cttgcctggc tggacatggt gaatgaaaaa cggcgagtag atgggcacag tttggtgtct     480
gcagatacct ttgagctgct ggtagaccgg cttgagaaag agtcatactt ggagagtcgc     540
agcagtgggg cccaacagtc actcatcgat gaagacgctt tctgctgtgt gtgcctggat     600
gatgaatgtc acaatagcaa tgttattctc ttctgtgaca tctgcaacct ggctgtacac     660
caggagtgct atggcgtccc atacatccct gagggccagt ggctatgccg ctgctgcctg     720
cagtctccct cccggcctgt ggattgcatc cttgccca ataagggtgg cgccttcaaa      780
cagaccagtg atgggcactg gcccatgtg tgtgtgcca tctggatccc tgaagtctgc      840
tttgctaaca ccgtgttctt ggaacctatt gagggcattg acaatatccc gcctgccgc     900 tggaaactaa cctgctatat ctgcaagcag aaagggctag gtgcagccat ccagtgccat     960
aaggtgaact gctacacagc attccatgtg acatgtgcac agcgggctgg gctcttcatg    1020
aagattgagc ccatgcgcga aaccagcctc aatggcacca tctttacagt gcgcaagact    1080
gcctactgtg aggcccactc gccaccaggt gcggccactg ctaggaggaa gggcgactcc    1140
cctagaagca tcagtgagac tggcgatgag gaagggctga ggagggtgga tggagaggag    1200
gaagaagagg aagaggtgga ggaagaagag caggaagctc aaggcggggt gagtggctcc    1260
ctcaagggag tgcccaagaa aagcaagatg agtttgaagc agaagatcaa gaaggagcca    1320
gaggaagcag gccaagacac accctccact ctccccatgc ttgctgtccc acagatacc     1380 tcttacaggt tgaacaagat ctgtagtggt ctctcctttc agaggaaaaa ccagtttatg    1440
cagcggcttc acaattattg gctgttgaag cggcaggcac ggaatggtgt ccctcttatc    1500
cggcgcttgc actcccatct gcagtcccaa gaaacgctg agcagcgaga gcaggatgag    1560
aagacaagtg cagtgaagga ggagctgaag tattggcaga agctccggca tgacttggag    1620
```

```
cgggcgcggc tgctgattga gctgattcgg aagagagaga agctcaaacg agagcaggtc    1680
aaagtccagc aggctgccat ggagctggag ctgatgccat tcaatgttct gttgaggaca    1740
acactggacc tgctgcagga gaaggatcct gcacacatct tcgcagaacc agtcaacttg    1800
agtgaggttt tatatgttta ggttccagat tacctggaat tcatatccaa gccaatggat    1860
ttttctacta tgaggcggaa gctggagtcc cacctgtacc gcaccttgga ggagtttgag    1920
gaggacttta accttatagt taccaactgc atgaagtata atgctaaaga cacaattttc    1980
caccgagcag ctgtccgcct gcgggacctg ggagggccca tcctacgca cgccggcgg      2040
caggcagaga acatcggcta tgaccccgag aggggcactc acctgcccga gtcacccaaa    2100
ttggaagact tttaccgctt ctcctgggaa gacgtggaca acatcctcat cccagagaac    2160
cgggcccatt tgtccccaga ggtgcagctg aaggagctgc tggagaaact ggacctggtg    2220
agcgccatgc ggtccagtgg ggcccgcacc cgtcgtgtcc gcctgctacg ccgggagatc    2280
aatgccttc ggcagaagct ggcacagcca ccaccaccac agccaccatc actcaacaag      2340
acagtatcca atggggagct gccagcaggg ccccagggg atgcagctgt gctggagcag      2400
gccttgcagg aggagccaga agacgatggg gacagagatg actccaaact gcctcctccg    2460
ccaaccctgg agcccactgg gcctgcacct tccttgtctg agcaagaatc cccccggag      2520
ccccctactc tgaaacccat taatgatagc aaacctccaa gcaggttcct aaagcccaga    2580
aaggtgaag aagatgagct cttggaaaaa tcaccactgc agctagggaa tgagcctttg       2640
caacgcttgc tcagtgacaa tggcatcaac agactatccc tcatgcccc tgacaccccg       2700
gccggtaccc cacttagtgg tgtgggtcgc cgcacatcag tcctcttcaa gaaggccaag    2760
aatgggtta gctacagag aagcccgac agggtcctgg agaatggcga ggaccatggt       2820
gtggcaggct ctcctgcctc tccagccagc atcgaggaag agcgccactc ccggaagcgg    2880
ccaaggagca ggagctgtag tgagagcgaa ggggagaggt ccccccagca ggaggaagag    2940
acaggcatga ccaacggctt tggaaaacac accgaaagcg ggtctgactc tgaatgtagt    3000
ttgggtctca gtggtggact ggcatttgaa gcttgcaggc agtggcttcc aagggacaaa    3060
gtcctgccct tgggtgtgga agacaccgtg gacaagctca agatgctgga aggccgcaag    3120
accagcatcc gcaagtcagt gcaggtggcc tatgaccgtg cgatgatcca cctgagcaga    3180
gtccggggc cccactcctt cgtcacttcc agctacctgt aagggcaggg ctgggcctgc    3240
atccgcttgc cctgcctcca tcccgcaggg cacagagaag cctcttctgc ccctgccaga    3300
tgtatggccg gcagcttccc cctctcatgg taggccaggg actgggcttt ctccccacta    3360
agggcaaggc cccagttttg accaatcgca tggttctcct ggcaggcctg ctctgtgcca    3420
aaaactccca cccaaggtcc ctcagggat atttcactga gaaccagtt agaagtagaa       3480
acagctgtgg ggcttgggcc cagcttagga gattgcccag atggcaagag gtcctgggct    3540
ccttcttgag gggctgcctg gccgctccca tcctactccc actaactaca cctcagggcg    3600
ggtgaggttc cgacactgat cccagagatg ccgtggatac gccagggtcc caggggaat     3660
ctccccaagc tcacactctc tcccgcttat cgcctattct cacacctctt ctcggtccca    3720
tcttctgcac ccattgccca gtcttgcttt ctctttccca tattccttt cttttctct        3780
tgtgccaaac tgacagaaac cgtcaccaca ctggtctttt tctttaatgt ctcattcccc    3840
ttgaggccag ctgctatgcc aggtggtgtc tctgccaggc tcctcaggcc cagacagagg    3900
ccagcccaca acctatgacc ccctccccca ggacaccacc tcccacccac agaccttccc    3960
```

```
tttagctgtt gacacaactt cccagctctg caagtgtgcc ccctggatca aggcgggtcc    4020
cctcttgttt ttttctttgc tgccacgagg tggtccaagc cttcagggtg ggctcctatc    4080
aggctgggtg tgcgagtgtc catctgtcca catggatgtc gagggtggtt tgtgtggagc    4140
tgtgctcgtc agctgggtct gccctcttcc ccttttctc cttcttctct cctcatggac    4200
tttttctgca attgcagtct taagcttcac tctccaccac ctggatggca tggcgcctgc    4260
caccaaacat cttcctggcc tgcgctctgc cctgccctgc ctagcctctg ctactcccac    4320
ttcccaactc cagggaatgc attacttta tttcaaaccc tctgcctcct tccttctttc    4380
tcttcaaccc cctccccacc ttcaccttct caaaaatgga aggaaaaaaa aactgtgaat    4440
ggggaatgct gactgacaaa ccaacacaac tttcagaggc ttcagtgtct gttctctgga    4500
catttctttt cacctcctga gcaccaaagt cgcaggccca gttgcaggcc gctgattgcc    4560
atgttgattt taacctgat attcttttta attgttttaa atttttcata ggggagtttt    4620
ggacaaaaca gtcactgggg agatcactgc cattttaca cacttgactt ttaaaaata    4680 caaccaacca accaccacaa cttcttatac atttgggaca tgagccagag tttaaaggg    4740 aaccaacaaa acactataac ttaaaaggat ggggttttgg attttgtata ataataaaa    4800 caatacagca tatggctagg aaggacatg gtgtatataa ttgtaaaata ctgttctaaa    4860
ttattcaggc ctatagtttc cattactgga gtcctccatt gtgtggccac acagtgtcgt    4920
tgatttaaag gagccagtgc ttcccctctc cccaggtagt tggtcagctg tggactctgt    4980
gacctttgtc taaacctgtg ttgtaagatc ttgggacttc ctctcttttct atgtctatct    5040 cttcccccca acactttctc ttcttagtct ctctctttat ttttcaatct ctgaatattt    5100
tagtctctct ctgagtctca tttttttaaaa tgctcttta gaacgggaaa cggctcagat    5160
cctgctgtgg cacggggcct atgtgtctct gtcgcgtctg ctgtgaagca catgatgctc    5220
tatttattgt agagagtgac tttatttgct ttctagaatt gtttataaca gatggtataa    5280
gagaggtaat aaacagagaa aaatctatgc ttgtaaagaa tacaaaagtt aattttacct    5340
actataatat gactgtctga aacttatttt ctctctgaga aataaatgtt ctaatgggca    5400
gtaaaaaaaa aaaaaaaaa aaaaaaaaa aaaaaaaaa a                          5441

<210> SEQ ID NO 21
<211> LENGTH: 1868
<212> TYPE: DNA
<213> ORGANISM: Homo sapiens

<400> SEQUENCE: 21
ccatttaaag aagatgctcg gccttaaagg aaatggcggt gcggttctgt ccatggccct     60
tccttttcag ccagagcaga gagattcaga ggatttattg aagaatttta attcagagtg    120
tgatacacac tgtggccttg atactgcacg acaagaatat ttgggtaact cattaagaca    180
ggaatcagac ttgaaaaaat ccacctcgtc agataattca agctctcatc atggtgaaaa    240
taaacaaaat ctgactgttg atccctgtga cattttgggt ggagttgata atcagcaaag    300
actgctacac attgtctggc ctcacaggtg ggagcatgat aaagatccag aaagcttttt    360
taaggtatta atgcatctta aagacttagg actcaatttc cacgtgtctg tacttggaga    420
aaccttcaca gatgtcccag atattttttc agaggccaaa aaggcattgg gatcttctgt    480
cttacactgg ggctacttac ccagcaaaga tgactacttc caagtactgt gcatggctga    540
tgttgtcatc tcaacagcta agcatgaatt ctttggagtg gcaatgttgg aagctgtgta    600
ctgtgggtgt acccactttt gtcctaaaga tttggtttat cccgaaatat ttccagctga    660
```

| | | |
|---|---|---|
| atatctgtat tctacacctg aacagctttc aaaaaggctc cagaatttct gcaagagacc | 720 |
| agatattata agaaaacatc tctataaggg tgaaatcgct ccgttttctt gggcagccct | 780 |
| acatggtaaa ttcaggtctc tgcttacaac agagcctagg gaagatttgt gacagatggg | 840 |
| gctaagtcac aaacttgcag cctaaggcag aatctgaaga actttccaga gtgtgcccat | 900 |
| atttacctga tcagagagaa aagaaaatct gcagaggaag ctgagcctgg ctgcttgtca | 960 |
| tagctgacac agagccatct gccacaaacc tgtggcggct tcagatctcc aatccctgcc | 1020 |
| accaccccaa ctcaaattaa atacagattc ctagagacgt tatgatggtt acacatgtcc | 1080 |
| tcggcatcac atgtaggaga ctgttcaaaa aaaatatgtg gcctgttgta taaccgcact | 1140 |
| catgtatccc atatgtggtg ccacattgaa tttccggttg aatccgtttt tatcctttgt | 1200 |
| actggatgac atggtgcctg aattctttct tttcgccgac acgatggcag ccaaactgca | 1260 |
| gcttcaaacg ctcacacttg gctgggtttc tacctaggtt gccaggttat catcggagcc | 1320 |
| ttcttgtgtc ctcaaagggc cacgaggcct gaaaggagga tcagaatgct ttgggattaa | 1380 |
| ttgggcagcc atcgcagaat tgtttgtggg caaagggctg ctttagcact tttcttttag | 1440 |
| caaattaatg actctcaggc acaggggtt ttaagtgaag gtattaataa gaggtctggc | 1500 |
| aggtattccc atgattcaca gagttacatt tgcatttaat taatcttaaa gttgcaagat | 1560 |
| aaacagctgt aattcggaca acatgacaa acacagtgaa gccaactatc ccataaaatg | 1620 |
| aacactgaca tacttgtttt aattttttc ccagcgtaaa aatagaaaaa tcaaaatact | 1680 |
| cctaacaaaa ccagtgattt tgatagaaat atttctccaa tatacttgca tccacctaca | 1740 |
| aatataaccct tttcaagata aatcgcttat gatttcaata gtcaaactgc tgtgtttgtt | 1800 |
| gatgtaaaga tgttttgaat ggctagatgg taaaataaat tcttaataaa gtacccactg | 1860 |
| caattttt | 1868 |

```
<210> SEQ ID NO 22
<211> LENGTH: 1322
<212> TYPE: DNA
<213> ORGANISM: Homo sapiens

<400> SEQUENCE: 22
```

| | | |
|---|---|---|
| taaaaatatc ctatcagtcc tttctaagaa gcctgaattg accaaaaaac atccccacca | 60 |
| ccactttata aagttgattc tgctttatcc tgcagtattg tttagccatc ttctgctctt | 120 |
| ggtaaggttg acatagtata tgtcaattta aaaaataaaa gtctgctttg taaatagtaa | 180 |
| ttttacccag tggtgcatgt ttgagcaaac aaaaatgatg atttaagcac actacttatt | 240 |
| gcatcaaata tgtaccacag taagtatagt ttgcaagctt tcaacaggta atatgatgta | 300 |
| attggttcca ttatagtttg aagctgtcac tgctgcatgt ttatcttgcc tatgctgctg | 360 |
| tatcttattc cttccactgt tcagaagtct aatatgggaa gccatatatc agtggtaaag | 420 |
| tgaagcaaat tgttctacca agacctcatt cttcatgtca ttaagcaata ggttgcagca | 480 |
| aacaaggaag agcttcttgc ttttattct tccaaccttta attgaacact caatgatgaa | 540 |
| aagcccgact gtacaaacat gttgcaagct gcttaaatct gtttaaaata tatggttaga | 600 |
| gttttctaag aaaatataaa tactgtaaaa agttcatttt attttatttt tcagcctttt | 660 |
| gtacgtaaaa tgagaaatta aaagtatctt caggtggatg tcacagtcac tattgttagt | 720 |
| ttctgttcct agcacttta aattgaagca cttcacaaaa taagaagcaa ggactaggat | 780 |
| gcagtgtagg tttctgcttt tttattagta ctgtaaactt gcacacattt caatgtgaaa | 840 |

```
caaatctcaa actgagttca atgtttattt gctttcaata gtaatgcctt atcattgaaa      900
gaggcttaaa gaaaaaaaaa atcagctgat actcttggca ttgcttgaat ccaatgtttc      960
cacctagtct ttttattcag taatcatcag tcttttccaa tgtttgttta cacagataga     1020
tcttattgac ccatatggca ctagaactgt atcagatata atatgggatc ccagcttttt     1080
ttcctctccc acaaaaccag gtagtgaagt tatattacca gttacagcaa atactttgt      1140 gtttcacaag caacaataaa tgtagattct ttatactgaa gctattgact tgtagtgtgt     1200
tggtgaaatg catgcaggaa aatgctgtta ccataaagaa cggtaaacca cattacaatc     1260
aagccaaaag aataaaggtt tcgcttttgt ttttgtattt aagaaaaaaa aaaaaaaaaa     1320
aa                                                                    1322

<210> SEQ ID NO 23
<211> LENGTH: 2608
<212> TYPE: DNA
<213> ORGANISM: Homo sapiens

<400> SEQUENCE: 23
ccgatgaccc ttctcctgtc ccgcatcccg agctgagctt ggctgaaagc ctgtggactt       60
ccaaaccacc acctctcttc catgaaggag caccttatcc tcccctttg tttatcaggg      120 acacatataa ccaatcaata cctcagccac ctcctcggaa aattaagcga cccaaacgaa      180
aaatgtacag ggaagaaccc acttcaataa tgaatgctat taaactacga cccaggcaag      240
ttctgtgtga taaatgtaaa aacagtgttg ttgctgaaaa aaaggaaatt agaaaaggta      300
gtagtgcaac tgactcttct aaatatgaag ataaaaaacg gagaaatgaa agtgtaacta      360
ctgtgaacaa aaaactgaaa actgaccata agtggatgg gaaaaaccaa aatgaaagcc      420
agaaaagaaa tgctgtggtt aaggtttcaa atattgctca cagcagaggc agagtagtaa      480
aagtttctgc tcaggcaaat acatcaaaag ctcagttaag tactaaaaaa gttctccaga      540
gtaagaacat ggatcatgcg aaagctcggg aagtgttaaa aattgccaaa gaaaaggcac      600
aaaagaagca aaatgaaacc tctacttcca aaaatgcaca ttcaaaagtc catttcacac      660
gtcgatatca gaatcctagc tcaggttccc ttccaccccg ggttcgttta aaaccacaga      720
ggtacaggaa tgaagaaaat gactcttctc tgaagacagg acttgagaaa atgcggagtg      780
gcaagatggc acccaagccc cagtctcgct gcacctctac ccgctcagca ggtgaggccc      840
cttcagaaaa tcagagtccc tcaaaaggcc ctgaagaggc cagcagtgag gttcaggaca      900
caaatgaagt gcatgtgcct ggtgatcagg atgaaccaca gacattgggc aaaaagggca      960
gcaaaaacaa tatctctgtt tatatgaccc taaatcaaaa gaaatctgac tcttccagtg     1020
cttcagtgtg tagcattgat agcacagatg atttgaaatc ttccaactct gagtgtagtt     1080
cttctgaaag ctttgatttt cctccaggca gtatgcatgc accttccacc tcctccactt     1140
cctcctcttc aaaggaagag aaaaagctca gtaattcctt gaaaatgaaa gtcttttcca     1200
aaaacgtctc taaatgcgtc acaccagatg gcaggaccat atgtgtaggg acattgttt      1260 gggccaagat atatggcttc ccttggtggc cagcccgtat tcttactata actgtgagcc     1320
ggaaagataa cggcctttta gtccgacagg aggcccgtat ttcatggttt gggtctccaa     1380
caacatcttt ccttgctctt tcacaactct cccccttttt agaaaacttc cagtcacgct     1440
ttaataagaa gagaaagggc ctgtatcgca aggctatcac agaggcagct aaggctgcca     1500
agcagctgac ccccgaagtg cgggcttgt tgacacagtt tgaaacgtga acatgggcag      1560
taaggtaggc aagaccattg gaagtcacca cagattttct agtctagtta ggaataattt     1620
```

```
ctacaaaata gcgtggccag attggagaga gaagttgcac tcagttggct ggcttttaa     1680 tacttacctt atagccattt ttagactgag agcttaaact gaacatataa tcaaattttg     1740
tgttaaggaa gtgagatttt agcagtattt ttcagttttg aagttcgaaa ccatcccaag     1800
gcataggagc catagcctca actgaaattg aattttgta gggactgtta attgccattt      1860
gtacctaata ctgtatatat acatatatat acgtgtgtgt gtatatatat atatatatat     1920
atatatatat atatatccgt gtatgtatat atacacacat atatatgtat atatacacat     1980
atatatatat gaaatacagc ctgtcactgt gtgacacaga ttgcatattt gggattgcaa     2040
taagggcttg gtgagctggg ggaatagtgg atatttaatg actacttgtt ttttaaataa     2100
tgaacactta gcctttctat gcgcataatg gtgtaaaagt tagatggtta ggtgtttgac     2160
aaacagatgg ttgcaattca gttacagact ggggaaatag cccagtgttt gggattaaaa     2220
ctgtcaagac tggataggtg ttagtcatca ctgtctttcg tccagtgggg atttaataaa     2280
tactttcaag cttctggttt gggagtttag ataggtttga ttttggattt gtaaatagtg     2340
attgctaaat ttggtcagat ttctcctgac tggctgttcc taaattctta ggatatgtcc     2400
cagtaaaatt atactttgtg aattaattgt catatgtgta attgttgcat tttggatgta     2460
cctaatttga taattaaaac aaaataattt ccgtttaagg tatctgtttg caggtcagaa     2520
aatgagaaaa tgtaattgtg taatgctctg aaatgtaaaa aaaaaaaaaa aaaccaaaaa     2580
aaagctgtaa ataaaatcaa ctaaatcc                                        2608

<210> SEQ ID NO 24
<211> LENGTH: 1567
<212> TYPE: DNA
<213> ORGANISM: Homo sapiens

<400> SEQUENCE: 24
gggtgaggag gaagaggagg aggaagagga ggaagaggat gacctgagtg agctgccacc       60
gctggaggac atgggacaac ccccggcgga ggaggctgag cagcctgggg ccctggcccg      120
agagttcctt gctgccatgg agcccgagcc cgccccagcc ccggcccag aagagtggct       180 ggacattctg gggaacgggc tgttgaggaa gaagacgctg gtcccagggc cgccaggttc      240
gagccgcccg gtcaagggcc agtggtcac cgtacatctg cagacgtcgc tggagaatgg      300
cacacgggtg caggaggagc cggagctggt gttcactctg ggtgactgtg acgtcatcca      360
ggccctggat ctcagtgtcc cactcatgga cgtgggggag acggccatgg tcactgctga     420
ctccaagtac tgctacggcc cccaaggcag caggagccca tacatccccc cgcacgcggc     480
cctgtgcctg gaggtgaccc tgaagacggc tgtggacggg cctgacctgg agatgctcac     540
ggggcaggag cgcgtggccc tggccaaccg gaagcgggag tgcggcaacg cccactacca     600
gcgggcggac ttcgtcctgg ccgccaactc ctacgacctc gccatcaagg ctatcacctc     660
cagcgccaaa gtggacatga cgttcgagga ggaggcacag ctcctgcagt tgaaggtgaa     720
gtgtctgaac aacctggcgg cctcgcagct gaagctcgac cactaccgcg cagccctgcg     780
ctcctgcagc cttgtgctgg agcaccagcc agacaacatc aaggctctct ccgcaaggg      840 caaggtgctg gcccagcagg gggagtacag tgaggccatc cccatcctga gggcagccct     900
gaagctggaa ccttccaaca agacgatcca cgcagagctc tcaaagctgg tgaagaagca     960
tgcggcgcag cggagcacgg agaccgcctt gtaccggaaa atgctgggca acccccagcc    1020
gctgcctgct aagtgccctg gcaagggtgc ctggtccatc ccatggaagt ggctgtttgg    1080
```

| | |
|---|---:|
| ggcgactgct gttgccttgg ggggtgtggc actctctgtg gtcatcgctg ccaggaactg | 1140 |
| accacctagg tggctgccac cccctctgca caccatggac cctgccctgc gctcccaac | 1200 |
| tcccccaggc tccctgtcca ctgccctccc tggtctggcc ccctcctccg ggttagggga | 1260 |
| gcaaggattg ggggtcgtgc agcccagcca gcaggaggga ctgaggccct ctaggaggaa | 1320 |
| agcccagagg gaggggcccc tcattccttc agacccagtt ttcccccacc ctccttaccc | 1380 |
| cgctgggcta ggtctccgcc agggctggcc tcagtttctc ctcaacaggc ctgggggcag | 1440 |
| cccttcccct gcctagtccc cgcctgagtg ccagccccc accccgcctg ccgcccctg | 1500 |
| tccaggttcc ctccccgcca cagtgaaata agcatccca ccctgcaaaa aaaaaaaaa | 1560 |
| aaaaaaa | 1567 |

<210> SEQ ID NO 25
<211> LENGTH: 2815
<212> TYPE: DNA
<213> ORGANISM: Homo sapiens
<400> SEQUENCE: 25

| | |
|---|---:|
| gaattcggca cgagctcttc tccctgatt caagactcct ctgctttgga ctgaagcact | 60 |
| gcaggagttt gtgaccaaga acttcaagag tcaagacaga aggaagccaa gggagcagtg | 120 |
| caatggattt ctcagtaaag gtagacatag agaaggaggt gacctgcccc atctgcctgg | 180 |
| agctcctgac agaacctctg agcctagatt gtggccacag cttctgccaa gcctgcatca | 240 |
| ctgcaaagat caaggagtca gtgatcatct caagagggga agcagctgt cctgtgtgtc | 300 |
| agaccagatt ccagcctggg aacctccgac ctaatcggca tctggccaac atagttgaga | 360 |
| gagtcaaaga ggtcaagatg agcccacagg aggggcagaa gagagatgtc tgtgagcacc | 420 |
| atggaaaaaa actccagatc ttctgtaagg aggatggaaa agtcatttgc tgggtttgtg | 480 |
| aactgtctca ggaacaccaa ggtcaccaaa cattccgcat aaacgaggtg gtcaaggaat | 540 |
| gtcaggaaaa gctgcaggta gccctgcaga ggctgataaa ggaggatcaa gaggctgaga | 600 |
| agctggaaga tgacatcaga caagagagaa ccgcctggaa gatcgagaga cagaagattc | 660 |
| tgaaagggtt caatgaaatg agagtcatct tggacaatga ggagcagaga gagctgcaaa | 720 |
| agctggagga aggtgaggtg aatgtgctgg acaacctggc agcagctaca gaccagctgg | 780 |
| tccagcagag gcaggatgcc agcacgctca tctcagatct ccagcggagg ttgacgggat | 840 |
| cgtcagtaga gatgctgcag gatgtgattg acgtcatgaa aaggagtgaa agctggacat | 900 |
| tgaagaagcc aaaatctgtt tccaagaaac taaagagtgt attccgagta ccagatctga | 960 |
| gtgggatgct gcaagttctt aaagagctga cagatgtcca gtactactgg gtggacgtga | 1020 |
| tgctgaatcc aggcagtgcc acttcgaatg ttgctatttc tgtggatcag agacaagtga | 1080 |
| aaactgtacg cacctgcaca tttaagaatt caaatccatg tgattttctc gcttttggtg | 1140 |
| tcttcggctg ccaatatttc tcttcgggga atattactg ggaagtagat gtgtctggaa | 1200 |
| agattgcctg gatcctgggc gtacacagta aaataagtag tctgaataaa aggaagagct | 1260 |
| ctgggttttgc ttttgatcca agtgtaaatt attcaaaagt ttactccaga tatagacctc | 1320 |
| aatatggcta ctgggttata ggattacaga atacatgtga atataatgct tttgaggact | 1380 |
| cctcctcttc tgatcccaag gttttgactc tctttatggc tgtgctccct gtcgtattgg | 1440 |
| ggttttccta gactatgagg caggcattgt ctcattttc aatgtcacaa accacggagc | 1500 |
| actcatctac aagttctctg gatgtcgctt ttctcgacct gcttatccgt atttcaatcc | 1560 |
| ttggaactgc ctagtcccca tgactgtgtg cccaccgagc tcctgagtgt tctcattcct | 1620 |

```
ttacccactt ctgcatagta gcccttgtgc tgagactcag attctgcacc tgagttcatc    1680
tctactgaga ccatctcttc ctttctttcc ccttcttta cttagaatgt ctttgtattc     1740
atttgctagg gcttccatag caaagcatca tagattgctg atttaaactg taattgtatt    1800
gccgtactgt gggctggaaa tcccaaatct agattccagc agagttggtt ctttctgagg    1860
tctgcaagga agggctctgt tccatgcctc tctccttggc ttgtagaagg catcttgtcc    1920
ctatgactct tcacattgtc tttatgtaca tctctgtgcc caagttttcc cttttatta    1980 agacaccagt catactggct cagggcccac cgctaatgcc ttaatgaaat cattttaaca    2040
ttatattctc tacaaagacc ttatttccaa ataagataat atttggaggt attgggaata    2100
aaatttgagg aaggcacgat ttcactcata acaatcttac cctttcttgc aagagatgct    2160
tgtacattat tttcctaata ccttggtttc actagtagta aacattatta tttttttat    2220 atttgcaaag gaaacatatc taatccttcc tatagaaaga acagtattgc tgtaattcct    2280
tttcttttct tcctcatttc ctctgcccct taaaagattg aagaaagaga aacttgtcaa    2340
ctcatatcca cgttatctag caaaagtcat aagaatctat cactaagtaa tgtatccttc    2400
agaatgtgtt ggtttaccag tgacacccca tattcatcac aaaattaaag caagaagtcc    2460
atagtaattt atttgctaat agtggatttt taatgctcag agtttctgag gtcaaatttt    2520
atcttttcac ttacaagctc tatgatctta aataatttac ttaatgtatt ttggtgtatt    2580
ttcctcaaat taatattggt gttcaagact atatctaatt cctctgatca ctttgagaaa    2640 caaacttta ttaaatgtaa ggcacttttc tatgaatttt aaatataaaa ataaatattg    2700
ttctgattat tactgaaaag atgtcagcca tttcaatgtc ttgggaaaca atttttgtt    2760 tttgttctgt tttcttttg cttcaataaa acaatagctg gctctaaaaa aaaaa          2815

<210> SEQ ID NO 26
<211> LENGTH: 1699
<212> TYPE: DNA
<213> ORGANISM: Homo sapiens

<400> SEQUENCE: 26
ggcacgaggg gcgccaccgc ggaggacagg ggcagctggc gggcagcggg tgaggggtg      60 gcggggacgc gagtggcggc cgcggggccc cggacaaggg tccgcagagc tgcagccttc    120
gagggccagc cctctccgag tccggggctg gtcccacca gtgacaaggc ggcagccccg    180
cgcacaccaa agagaaggcg gctgtggcgg cagcggcagc cccagccatg ctgtgttatg    240
tgacgaggcc ggacgcggtg ctgatggagg tggaggtgga ggcgaaagcc aacggcgagg    300
actgcctcaa ccaggtgtgc aggcgactgg gaatcataga agttgactat tttggactgc    360
agtttacggg tagcaaaggt gaaagtttat ggctaaacct gagaaaccgg atctcccagc    420
agatggatgg gctagcccct tacaggctta aacttagagt caagttcttc gtggagcctc    480
atctcatctt acaggagcag actaggcata tcttttctt gcacatcaag gaggccctct    540
tggcaggcca cctcttgtgt tccccagagc aggcagtgga actcagtgcc tcctggccc    600 agaccaagtt tggagactac aaccagaaca ctgccaagta taactatgag gagctctgtg    660
ccaaggagct ctcctctgcc accttgaaca gcattgttgc aaaacataag gagttggagg    720
ggaccagcca ggcttcagct gaataccaag ttttgcagat tgtgtcggca atggaaaact    780
atggcataga atggcattct gtgcgggata gcgaagggca gaaactgctc attggggttg    840
gacctgaagg aatctcaatt tgtaaagatg actttagccc aattaatagg atagcttatc    900
```

```
ctgtggtgca gatggccacc cagtcaggaa agaatgtata tttgacggtc accaaggaat      960
ctgggaacag catcgtgctc ttgttttaaaa tgatcagcac cagggcggcc agcgggctct    1020
accgagcgat aacagagacg cacgcattct acaggtgtga cacagtgacc agcgccgtga    1080
tgatgcagta tagccgtgac ttgaagggcc acttggcatc tctgtttctg aatgaaaaca    1140
ttaaccttgg caagaaatat gtctttgata ttaaaagaac atcaaaggag gtgtatgacc    1200
atgccaggag ggctctgtac aatgctgcg ttgtggacct cgtttcaaga aacaaccaga     1260
gcccttcaca ctcgcctctg aagtcctcag aaagcagcat gaactgcagc agctgcgagg    1320
gcctcagctg ccagcagacc cgggtgctgc aggagaagct acgcaagctg aaggaagcca    1380
tgctgtgcat ggtgtgctgc gaggaggaga tcaactccac cttctgtccc tgtggccaca    1440
ctgtgtgctg tgagagctgc gccgcccagc tacagtcatg tcccgtctgc aggtcgcgtg    1500
tggagcatgt ccagcacgtc tatctgccaa cgcacaccag tcttctcaat ctgactgtaa    1560
tctaatctgt tgtgcttttg ttggacttgg catgtttcca tgaactgcac tattataaac    1620
tattaaaatg atagattgtg gagaaagtaa ttattccaac acccatctgc catgcgatgt    1680
taaaaaaaaa aaaaaaaaa                                                  1699

<210> SEQ ID NO 27
<211> LENGTH: 1976
<212> TYPE: DNA
<213> ORGANISM: Homo sapiens

<400> SEQUENCE: 27
gccacacggt ctttgagctg agtcgaggtg gacccttga acgcagtcgc cctacagccg        60
ctgattcccc ccgcatcgcc tcccgtggaa gcccaggccc gcttcgcagc tttctccctt      120
tgtctcataa ccatgtccac caacgagaat gctaatacac cagctgcccg tcttcacaga      180
ttcaagaaca agggaaaaga cagtacgaaa atgaggcgtc gcagaataga ggtcaatgtg      240
gagctgagga aagctaagaa ggatgaccag atgctgaaga ggagaaatgt aagctcattt      300
cctgatgatg ctacttctcc gctgcaggaa aaccgcaaca accagggcac tgtaaattgg      360
tctgttgatg acattgtcaa aggcataaat agcagcaatg tggaaaatca gctccaagct      420
actcaagctg ccaggaaaact actttccaga gaaaaacagc cccccataga caacataatc      480
cgggctggtt tgattccgaa atttgtgtcc ttcttgggca gaactgattg tagtcccatt      540
cagtttgaat ctgcttgggc actcactaac attgcttctg gacatcaga acaaaccaag       600 gctgtggtag atggaggtgc catcccagca ttcatttctc tgttggcatc tccccatgct      660
cacatcagtg aacaagctgt ctgggctcta ggaaacattg caggtgatgg ctcagtgttc      720
cgagacttgg ttattaagta cggtgcagtt gacccactgt tggctctcct tgcagttcct      780
gatatgtcat ctttagcatg tggctactta cgtaatctta cctggacact ttctaatctt      840
tgccgcaaca agaatcctgc accccgata gatgctgttg agcagattct tcctacctta        900
gttcggctcc tgcatcatga tgatccagaa gtgttagcag atacctgctg ggctatttcc       960
taccttactg atggtccaaa tgaacgaatt ggcatggtgg tgaaaacagg agttgtgccc      1020
caacttgtga agcttctagg agcttctgaa ttgccaattg tgactcctgc cctaagagcc      1080
atagggaata ttgtcactgg tacagatgaa cagactcagg ttgtgattga tgcaggagca    1140
ctcgccgtct ttcccagcct gctcaccaac cccaaaacta acattcagaa ggaagctacg    1200
tggacaatgt caaacatcac agccggccgc caggaccaga tacagcaagt tgtgaatcat   1260
ggattagtcc cattccttgt cagtgttctc tctaaggcag attttaagac acaaaaggaa    1320
```

```
gctgtgtggg ccgtgaccaa ctataccagt ggtggaacag ttgaacagat tgtgtacctt   1380
gttcactgtg gcataataga accgttgatg aacctcttaa ctgcaaaaga taccaagatt   1440
attctggtta tcctggatgc catttcaaat atctttcagg ctgctgagaa actaggtgaa   1500
actgagaaac ttagtataat gattgaagaa tgtggaggct tagacaaaat tgaagctcta   1560
caaaaccatg aaaatgagtc tgtgtataag gcttcgttaa gcttaattga gaagtatttc   1620
tctgtagagg aagaggaaga tcaaaacgtt gtaccagaaa ctacctctga aggctacact   1680
ttccaagttc aggatggggc tcctgggacc tttaactttt agatcatgta gctgagacat   1740
aaatttgttg tgtactacgt ttggtatttt gtcttattgt ttctctacta agaactcttt   1800
cttaaatgtg gtttgttact gtagcacttt ttacactgaa actatacttg aacagttcca   1860
actgtacata catactgtat gaagcttgtc ctctgactag gtttctaatt tctatgtgga   1920
atttcctatc ttgcagcatc ctgtaaataa acattcaagt ccacccttaa aaaaaa       1976
```

<210> SEQ ID NO 28
<211> LENGTH: 2371
<212> TYPE: DNA
<213> ORGANISM: Homo sapiens

<400> SEQUENCE: 28

```
gacggggtgg ggggtggggg gacccccggtt gtgcagtttg atattgaggg agccccacc    60 tactcgctgg ggctgcgtaa tctgtacgct tccaaactga agcgaaggcg tcgggagact   120
aggcctcaga gaaccatggc tactgccaag ggaatcgcca taggcatcga cctgggcacc   180
acctactcct gtgtgggggt gttccagcac ggcaaggtgg agatcatcgc caacgaccag   240
ggcaaccgca ccaccccag ctacgtggcc ttcacagaca ccgagcggct cattggggat   300
gcggccaaga ccaggtagc aatgaatccc cagaacactg ttttttgatgc taaacgtctg   360 atcggcagga aatttaatga tcctgttgta caagcagata tgaaactttg gcctttttcaa   420 gtgattaatg aaggaggcaa gcccaaagtc cttgtgtcct acaaagggga gaataaagct   480
ttctaccctg aggaaatctc ttcgatggta ttgactaagt tgaaggagac tgctgaggcc   540
tttttgggcc accctgtcac caatgcagtg attaccgtgc cagcctattt caatgactct   600
caacgtcagg ctactaagga tgcaggtgtg attgctggac ttaatgtgct aagaatcatc   660
aatgagccca cggctgctgc cattgcctat ggtttagata aggaggtca aggagaacga   720 catgtcctga tttttgatct gggtggaggc acatttgatg tgtcaattct gaccatagat   780
gatgggattt ttgaggtaaa ggccactgct ggggacactc acctgggtgg ggaggacttt   840
gacaacaggc ttgtgagcca cttcgtggag gagttcaaga ggaaacacaa aaaggacatc   900
agccagaaca gcgagccgt gaggcggctg cgcaccgcct gcgagagggc caagaggacc   960
ctgtcgtcca gcacccaggc caacctagaa attgattcac tttatgaagg cattgacttc  1020
tatacatcca tcaccagagc tcgatttgaa gagttgtgtg cagacctgtt tagggggtacc  1080 ctggagcctg tagaaaaagc gcttcgggat gccaagatgg ataaggctaa atccatgac   1140 attgttttag taggggctc caccccgcatc cccaaggtgc agcggctgct tcaggactac  1200
ttcaatggac gtgatctcaa caagagcatc aaccctgatg aggccgtagc atatgggct   1260 gcggtacaag cagccatcct gatgggggac aagtctgaga aggtacagga cctgctgctg  1320
ctggacgtgg ctcccctgtc cctgggggctg gagacggctg ggggcgtgat gactgccctg  1380
ataaagcgca actccaccat ccccaccaag cagacacaga ttttcaccac ctactctgac  1440
```

-continued

```
aaccaacccg gggtgctgat ccaggtgtat gagggcgaga gggccatgac aaaggacaac    1500
aacctgctgg ggcggtttga cctgactgga atccctccag cacccagggg agttcctcag    1560
atcgaggtga cgtttgacat tgatgccaat ggtattctca atgtcacagc catggacaag    1620
agcaccggca aggtgaacaa gatcaccatc accaatgaca agggccgcct gagcaaggag    1680
gagattgagc gcatggttct ggatgctgag aaatataaag ctgaagatga ggtccagagg    1740
gagaaaattg ctgcaaagaa tgccttagaa tcctatgctt ttaacatgaa gagtgttgtg    1800
agtgatgaag gtttgaaggg caagattagt gagtctgata aaaataaaat attggataaa    1860
tgcaacgagc tcctttcgtg gctggaggtc aatcaactgg cagagaaaga tgagtttgat    1920
cataagagaa aggaattgga gcagatgtgt aaccctatca tcacaaaact ctaccaagga    1980
ggatgcactg ggcctgcctg cggaacaggg tatatgcctg gaaggcctgc cacaggcccc    2040
acaattgaag aagtagatta attcttttta gaactgaagc atcctaggat gcctctacat    2100
gtatttcatt cccctcatct tcaaacatca ttattattct tgaccagacc tgaatctaag    2160
ttaccatccc ttggaaattc tggagaagga gtctcatgca ccacctatca cactccctca    2220
catcctgttt ctgactttgg aatggactca ggaaaactag gcccctcttt aaaccgtgtg    2280
atgtatttga atgtctgtta tttccagcca ccctaacatt cttcttcctg tgtggatgct    2340
tatttgtcaa tcagtaaatt tgttcgtaaa g                                   2371
```

METHOD FOR DETECTING RADIATION EXPOSURE

PRIORITY

This is a divisional of U.S. application Ser. No. 09/913,171, filed Aug. 9, 2001, now U.S. Pat. No. 7,008,768 issued Mar. 7, 2006, which is a U.S. national stage § 371 application of PCT/US00/04897 filed Feb. 25, 2000, which was published in English under PCT Article 21(2), which claims the benefit of U.S. provisional application No. 60/121,756 filed Feb. 26, 1999.

FIELD

The present invention concerns gene expression, and is related to the detection of differential gene expression following exposure of cells to ionizing radiation.

BACKGROUND

Ionizing radiation has many medical, industrial and military uses. Although ionizing radiation can be used in the therapy of diseases such as cancer, exposure to biologically significant levels of such radiation can also cause genotoxic stress. Similarly, many industrial processes (such as the production of nuclear power) and military uses (such as nuclear weapons) can expose individuals to hazardous levels of ionizing radiation. Such radiation can elicit a variety of cellular responses, ranging from cell-cycle arrest to mutation, malignant transformation, or cell death. Many of the responses (such as genotoxicity) are often subtle, and exposed persons may be unaware or unsure if they have been exposed. Moreover, it may require years to evince an untoward effect (such as the development of a malignancy) caused by the exposure.

Many of the assumptions about low dose effects have been based on extrapolations from effects measured at high doses. Transcriptional responses to doses of ionizing radiation with relatively little effect on cell survival have not been as well investigated, although small variations in expression levels of several isolated genes have been detected. A dose of 50 cGy reportedly reduced expression of β- and γ-actin (Woloschak and Chang-Liu, *Int. J. Radiat. Biol.* 59:1173-83, 1991) and induced RB-1 and H4 histone (Woloschak and Chang-Liu, *Cancer Lett.* 97:169-75, 1995) in Syrian Hamster Embryo cells, while a decrease in c-myc and increase in c-jun was detected in these cells following a dose as low as 6 cGy (Woloschak and Chang-Liu, *Cancer Lett.* 97:169-75, 1995). In a transformed human lymphoblast cell line, activation of NF-κB has been reported with as little as 10 cGy of radiation (Prasad et al., *Radiat. Res.* 138:367-72, 1994), along with induction of c-FOS, c-JUN, c-MYC and c-Ha-RAS in the 25-200 cGy range (Prasad et al., *Radiat. Res.* 143:263-72, 1995). The induction by 25 cGy of PBP74, a member of the heat shock 70 gene family, has also been reported in two human cancer cell lines (Sadekova et al., *Int. J. Radiat. Biol.* 72:653-60, 1997).

SUMMARY

It would be advantageous to have a method for detecting exposure of organisms to biologically significant or hazardous amounts of ionizing radiation. Although small variations in expression levels of several isolated genes in cell lines have been detected at lower doses, none of these studies have demonstrated a dose-response relationship for gene induction at low radiation doses, and overall qualitative and/or quantitative patterns of differential expression have not been investigated. The present invention uses nucleic acid microarray hybridization to evaluate biological effects, such as patterns of expression of genes after radiation exposure. Using these methods, numerous genes have been found which are responsive to radiation exposure in a variety of cell lines, and microarrays have been constructed which are capable of detecting biological responses (such as patterns of expression) to radiation exposure with great sensitivity and specificity.

The present invention includes a method of identifying cells that have been exposed to radiation induced biological stress. The method further includes providing a probe set that includes nucleic acid molecules representing genes that are differentially expressed in cells that have been exposed to a biologically significant amount of ionizing radiation. The probe set is exposed to a labeled nucleic acid composition from a test cell which specifically hybridizes to members of the probe set when the cell has been exposed to a biologically significant amount of ionizing radiation. Whether the nucleic acid composition hybridizes to the nucleic acid molecules representing genes that are differentially expressed is determined.

The probe set may be nucleic acid molecules (such as cDNAs or oligonucleotides) bound in an array to a surface, wherein the nucleotides specifically hybridize to sequences in the nucleic acid composition from the test cell. In one example, the nucleic acid composition includes cDNA reverse transcribed from mRNA in the test cell, and labeled with a fluorophore that detects hybridization of the cDNA to the probe set. In another example, the method also includes exposing the probe set to a labeled nucleic acid composition from a control cell which has not been exposed to a biologically significant amount of ionizing radiation. Genes which are expressed in the absence of radiation exposure will therefore produce mRNA from which labeled cDNA is made that specifically hybridizes to some members of the probe set. The nucleic acids from the test cell and control cell can be labeled with different signals (such as red and green colors) to indicate differential (either increased or decreased) expression of genes in the test cell as compared to the control cell.

The probe set may include probes that specifically hybridize to the labeled nucleic acid composition from specimens obtained more than four hours after exposure to the biologically significant amount of ionizing radiation, and/or less than 24 hours after exposure. In another embodiment of the invention, the probe set includes probes that specifically hybridize to the labeled nucleic acid composition from specimens obtained more than 24 or 48 hours after exposure to the biologically significant amount of ionizing radiation. Probes which detect such late effect exposures may be used to screen for radiation exposure when such screening is not done until one or two days following potential radiation exposure, when a subject is examined in a medical or laboratory facility.

In yet other embodiments of the invention, the probe set includes probes that specifically hybridize to the labeled nucleic acid composition from specimens which have been exposed to less than about 25 cGy of ionizing radiation. The probe set may also include genes that are differentially expressed by at least 1.5-fold or 2-fold following exposure to a biologically significant amount of ionizing radiation. The probe set may include at least 10%, 30% 40%, 50%, 75%, 80%, 90%, 95%, or 99% of the probes identified in Tables 9, 10, 11, 12, 13 or 14 or the entire probe set shown in any of those Tables. The probe set may also include at least 10 or 20 of the probes identified in Tables 9, 10, 11, 12, 13 or 14. Examples of probes that represent such late effects include those listed in Tables 9-12. In another embodiment, the probe set includes nucleic acid sequences that are selected for having differential expression following exposure to a biologically significant amount of ionizing radiation. The probe set may be at least 50%, 75%, 80%, 90%, 95%, 99%, or consist essentially of nucleic acid sequences that are differentially expressed following exposure to a biologically significant amount of ionizing radiation. In yet another embodiment, the probe set includes nucleic acid sequences that are selected for having a differential expression of at least 1.5- or 2-fold following exposure to a biologically significant amount of ionizing radiation.

In yet other embodiments of the method, a plurality of nucleic acid probe elements are bound to a surface, for example in an array, wherein the nucleic acid represents a gene product (including a protein or a nucleic acid such as RNA) that is differentially expressed by a cell following radiation induced biological stress. The plurality of probe elements are contacted with a plurality of gene products from a test cell, under conditions that allow the gene products (such as the nucleic acid sequences) to specifically hybridize to one of more of the probe elements, and provide a signal which indicates differential expression of one or more genes in a test cell has been exposed to biologically significant levels of ionizing radiation, and detecting the presence or absence of the signal. The probe elements may be selected from a set of nucleic acids that specifically hybridize to nucleic acids obtained from cells exposed to ionizing radiation. For example, the target elements are nucleic acid sequences that are differentially expressed by a cell more than 4, 24 or even 48 hours after exposure to the ionizing radiation. The probe elements may also include, or be limited to, nucleic acid sequences that are differentially expressed by at least 1.5-fold or 2-fold following exposure to a biologically significant amount of ionizing radiation.

The target elements may be one or more of the clones listed in Tables 9, 10, 11, 12, 13, or 14, for example Image ID clones 39993, 47475, 109123, 120362, 136114, 195365, 202549, 209340, 221846, 232837, 241412, 244227, 251516, 260619, 280386, 297442, 308588, 549146, 753418, 841278, 51699, 417226 and 28116. The probe nucleic acids may be DNA, such as cDNA, and cDNA obtained from mRNA expressed by the test cell. When the probe is reverse transcribed from cellular RNA, it may average about 1000-2000 nucleotides in length, but may in some instances be as long as 10,000 nucleotides. The probe nucleic acids of the probe set may be about as short as 8 or 10 nucleotides in length, but may also be as long as about 1000 to 1,000,000 nucleotides in length.

The method can also include contacting the probe elements with a plurality of control nucleic acids obtained from mRNA (for example by reverse transcription) of a control cell that has not been exposed to biologically significant levels of ionizing radiation and determining whether the nucleic acids from mRNA of the control cells hybridize differentially to the probe elements than the nucleic acid composition from the test cell. The test nucleic acid sequences are labeled with a first label that detects hybridization of the test nucleic acid sequences to the probe sequences, and the control nucleic acid sequences are labeled with a second label that detects hybridization of the control nucleic acid sequences to the probe sequences. The first and second labels interact to indicate whether expression of a nucleic acid sequence in the test cell has increased or decreased, relative to a baseline level. The first and second labels may be fluorophores of different colors. The nucleic acids from the control cells may, for example, be labeled with a green fluorophore, and the nucleic acids from the test cells may be labeled with a red fluorophore. Hence target elements for which differential gene expression does not occur will appear yellow, while underexpressed (decreased) gene expression will be indicated by green and overexpression (increased expression) by red.

The test cells may be animal cells, such as human cells, for example human peripheral blood cells, for example peripheral blood mononuclear cells, such as lymphocytes. In addition, the cells may be microbial or plant cells, such as microbes or cells from plants in the vicinity of a suspected environmental exposure to ionizing radiation.

In view of the set of stress response genes which have been identified, and may be identified using the present methods, the invention also includes methods of making microarrays for identifying cells that have actually or potentially been exposed to a biologically significant amount of ionizing radiation, by identifying genes that are differentially expressed by a cell following exposure to biologically significant amounts of ionizing radiation. A probe set is then provided, each element of the set including a nucleic acid sequence from a gene that is identified as differentially expressed by a cell following radiation induced biological stress. The target nucleic acid sequence is capable of hybridizing to a nucleic acid sequence which is differentially expressed by the cell following exposure to the biologically significant amount of ionizing radiation. In other embodiments, the genes that are differentially expressed by a cell are identified by exposing the cell to a biologically significant amount of ionizing radiation, obtaining mRNA expressed by the cell, reverse transcribing the mRNA into cDNA, labeling the cDNA, and hybridizing the labeled cDNA to a probe set that represents potential genes that may be differentially expressed and identifying members of the probe set that hybridize with the labeled cDNA. Any high throughput genomic analysis may be used to analyze the differential expression of the stress response genes, as may more standard molecular biology techniques such as dot-blot hybridization. The genes may include p53 regulated genes.

In another embodiment, the method further includes determining a dose response relationship between radiation exposure and differential expression of one or more genes, for example to determine a probable radiation dose in cells that have actually or potentially been exposed to the ionizing radiation. In yet another embodiment, identifying genes that are differentially expressed, for making a microarray, includes identifying genes that are differentially expressed in a cell type that is to be obtained from a subject for testing. The microarray may be used to measure a biological response to potential radiation exposure in the subject, for example in a cell type. The invention also includes microarrays which are made by this method.

The cell type may be peripheral blood cells, for example peripheral blood mononuclear cells, such as lymphocytes. In addition, the cell type may be any microbial or plant cell.

The invention also includes a method of diagnosing biologically significant radiation exposure in a subject, by obtaining a biological specimen from the subject, synthesizing cDNA from mRNA expressed in one or more cells of the biological specimen, and labeling the mRNA with a detectable label. The labeled mRNA is exposed to a probe set which represents genes that are differentially expressed in the biological specimen following exposure to the radiation. A determination is then made whether the labeled mRNA selectively hybridizes to one or more probes of the probe set that are associated with the radiation exposure, or hybridizes in a pattern that is associated with radiation exposure. Particular patterns of hybridization can also be associated with specified exposure doses, or time periods following exposure. The probe set may be one or more of the probes listed in any of Tables 9, 10, 11, 12, 13 or 14, or a probe set that includes at least 10%, 30% 40%, 50%, 75%, 80%, 90%, 95%, or 99% of the probes listed in any of Tables 9, 10, 11, 12, 13 or 14. In another embodiment, the method detects patterns of differential expression associated with biologically significant radiation exposure.

The invention also includes use of the microarrays of the present invention for measuring a biological response to in a subject, by obtaining a biological sample from the subject, synthesizing cDNA from mRNA expressed in one or more cells of the biological sample, labeling the mRNA with a detectable label, and exposing the labeled mRNA to a probe set which represents genes that are differentially expressed in the biological sample following radiation exposure, and determining if the labeled mRNA selectively hybridizes to one or more probes of the probe set that are associated with radiation exposure. The subject may be undergoing radiotherapy (or a candidate for radiotherapy) for the treatment of cancer, and the microarray can used to monitor or predict the subject's biological response to the radiotherapy.

Also included in the invention are the probe sets that provide information about exposure to biologically significant doses of ionizing radiation, for example probe sets including the DNA probe sets shown in any of Tables 9, 10, 11, 12, 13 or 14, or subsets of the probe sets of Tables 13 or Table 14. Such subsets may include sets having at least 10%, 30% 40%, 50%, 75%, 80%, 90%, 95%, or 99% of the probes sets shown in any of Tables 9, 10, 11, 12, 13 or 14.

BRIEF DESCRIPTION OF THE FIGURES

FIGS. 5A and 5B are schematic diagrams illustrating increased or decreased expression of transcripts identified on a microarray. The expression was measured in a panel of human cancer cell lines listed along the left margin, where the cell lines are shown divided into p53 wild type cells and p53 mutant cells. Numbers shown in the diagram measure relative induction for each gene over levels in untreated controls four hours after treatment with a 20 Gy dose of (A) ionizing radiation or (B) following treatment with 100 μg/ml methyl methanesulfonate (MMS) or 14 J/m$^2$ ultraviolet (UV) radiation. A zero indicates no detectable expression in either control or treated cells. The results are coded: red (vertical lines) for >2-fold induction, green (horizontal lines) for >2-fold reduction, and yellow (horizontal and vertical lines) for <2-fold change from untreated control.

FIGS. 9A and 9B are bar graphs showing the induction of (A) ATF3 in p53 wild-type RKO cells (light bar), RKO/E6 cells (dark bar) and the thymus of p53 wild-type mouse (light bar), or p53−/− (dark bar); and (B) FRA-1 in p53 wild-type MCF7 cells (light bar), or in MCF7/E6 cells (dark bar) and in the thymus of p53 wild-type mouse (light bar), or p53−/− mouse (dark bar). The results shown for the RKO cell lines are the average of 4 independent experiments, and error bars are standard errors of the means. The results for the MCF7 cell lines are the average of 3 independent experiments.

SEQUENCE LISTING

Figure 1:
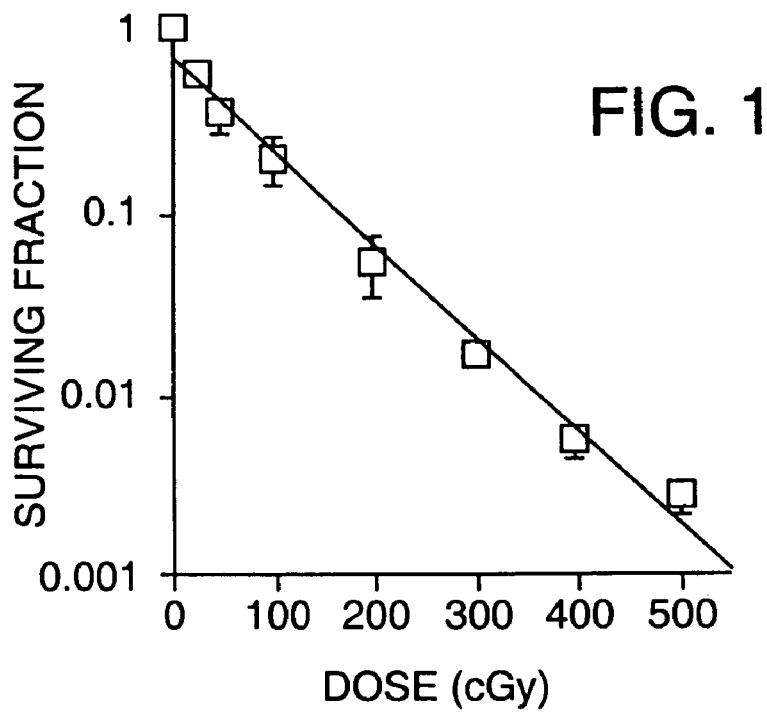
FIG. 1 is a graph showing the clonal survival of ML-1 cells exposed to $^{137}$CS γ-rays. Points are the average of five independent experiments, and error bars are standard errors. Linear regression of the data was used to fit the curve shown.

SEQ ID NO: 1 is the nucleic acid sequence of Image ID Number 26474.
SEQ ID NO: 2 is the nucleic acid sequence of Image ID Number 268652.
SEQ ID NO: 3 is the nucleic acid sequence of Image ID Number 34396.
SEQ ID NO: 4 is the nucleic acid sequence of Image ID Number 35318.
SEQ ID NO: 5 is the nucleic acid sequence of Image ID Number 50615.
SEQ ID NO: 6 is the nucleic acid sequence of Image ID Number 110589.
SEQ ID NO: 7 is the nucleic acid sequence of Image ID Number 203132.
SEQ ID NO: 8 is the nucleic acid sequence of Image ID Number 247483.
SEQ ID NO: 9 is the nucleic acid sequence of Image ID Number 251591.
SEQ ID NO: 10 is the nucleic acid sequence of Image ID Number 360778.
SEQ ID NO: 11 is the nucleic acid sequence of Image ID Number 415817.
SEQ ID NO: 12 is the nucleic acid sequence of Image ID Number 469954.
SEQ ID NO: 13 is the nucleic acid sequence of Image ID Number 489805.
SEQ ID NO: 14 is the nucleic acid sequence of Image ID Number 753447.
SEQ ID NO: 15 is the nucleic acid sequence of Image ID Number 884719.
SEQ ID NO: 16 is the nucleic acid sequence of Image ID Number 1493160.

DETAILED DESCRIPTION OF SEVERAL EMBODIMENTS

Abbreviations and Definitions

The following definitions and methods are provided to better define the present invention and to guide those of ordinary skill in the art in the practice of the present invention. It must be noted that as used herein and in the appended claims, the singular forms "a" or "an" or "the" include plural referents unless the context clearly dictates otherwise. Thus, for example, reference to "a protein" includes a plurality of such proteins and reference to "the array" includes reference to one or more arrays and equivalents thereof known to those skilled in the art, and so forth.

Unless defined otherwise, all technical and scientific terms used herein have the same meaning as commonly understood to one of ordinary skill in the art to which this invention belongs. Although methods and materials similar or equivalent to those described herein can be used in the practice or testing of the present invention, suitable methods and materials are described below. The materials, methods, and examples are illustrative only and are not intended to be limiting.

MMS: methanesulfonate

RT: room temperature

Animal Cells: Cells obtained from multicellular vertebrate organisms, a category which includes, for example: mammals, primates, rodents, veterinary subjects, and birds. The cells can be obtained from any source, for example peripheral blood, urine, saliva, tissue biopsy, surgical specimen, amniocentesis samples and autopsy material. From these cells, genomic DNA, cDNA, mRNA, RNA, or protein can be isolated.

Biologically significant radiation exposure: An amount of radiation exposure sufficient to cause differential expression of stress genes in cells after they are exposed to the radiation.

Biological Specimen/Sample: One or more cells obtained from an animal or plant.

Cancer: malignant neoplasm that has undergone characteristic anaplasia with loss of differentiation, increased rate of growth, invasion of surrounding tissue, and is capable of metastasis.

cDNA (complementary DNA): A piece of DNA lacking internal, non-coding segments (introns) and regulatory sequences which determine transcription. cDNA may be synthesized in the laboratory by reverse transcription from messenger RNA extracted from cells.

Control Cells: Cells which have not been exposed to biologically significant levels of ionizing radiation.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

DNA chip: A DNA array in which multiple DNA molecules (such as cDNAs) of known DNA sequences are arrayed on a substrate, usually in a microarray, so that the DNA molecules can hybridize with nucleic acids (such as cDNA or RNA) from a specimen of interest. DNA chips are further described in Ramsay (*Nature Biotech.* 16:40-44, 1998).

Differential expression of a gene: This refers to either an increased or decreased expression of a gene, or any other change from the normal expression of a gene.

EST (Expressed Sequence Tag): This refers to a partial DNA or cDNA sequence, typically of between 1000 and 2000 sequential nucleotides, obtained from a genomic or cDNA library, prepared from a selected cell, cell type, tissue or tissue type, organ or organism, which corresponds to an mRNA of a gene found in that library. An EST is generally a DNA molecule sequenced from and shorter than the cDNA from which it is obtained.

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy-3, FITC, and Oregon Green, are characterized by their emission at wavelengths generally in the range of 515-540 λ. Red fluorophores, for example Texas Red, Cy-5 and tetramethylrhodamine, are characterized by their emission at wavelengths generally in the range of 590-690 λ.

Examples of fluorophores that may be used in the present invention are provided in U.S. Pat. No. 5,866,366 to Nazarenko et al.: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include GFP, Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Gene expression microarrays: Microscopic arrays of cDNAs printed on a substrate, which serve as a high density hybridization target for mRNA probes, for example as described in Schena (*BioEssays* 18:427-431, 1996).

Genomic target sequence: A sequence of nucleotides located in a particular region in the human genome that corresponds to one or more specific loci.

High throughput genomics: This refers to application of genomic or genetic data or analysis techniques that use microarrays or other genomic technologies to rapidly identify large numbers of genes or proteins, or distinguish their structure, expression or function from normal or abnormal cells or tissues.

Human Cells: Cells obtained from *Homo sapiens*. The cells can be obtained from any source, for example peripheral blood, urine, saliva, tissue biopsy, surgical specimen, amniocentesis samples and autopsy material. From these cells, genomic DNA, cDNA, mRNA, RNA, or protein can be isolated.

Ionizing radiation (IR): An amount of radiation sufficient to separate orbiting electrons from an atomic nucleus. Ionizing radiation includes photons and accelerated particles. Photons (also called gamma rays) are given off in many types of nuclear decay. Ionizing rays (x-rays) occur when an electron is stopped in a dense material. Accelerated particles include protons from solar radiation, heavy nuclei in cosmic rays, and beta and alpha particles given up in nuclear decay.

Isolated: An "isolated" biological component (such as a nucleic acid, peptide, protein, or organelle) has been substantially separated, produced apart from, or purified away from other biological components in the cell of the organism in which the component naturally occurs, i.e., other chromosomal and extrachromosomal DNA and RNA, organelles, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Label: Detectable marker or reporter molecules, which can be attached to nucleic acids, for example probes. Typical labels include fluorophores, radioactive isotopes, ligands, chemiluminescent agents, and enzymes. Methods for labeling and guidance in the choice of labels appropriate for various purposes are discussed, e.g., in Sambrook et al., in Molecular Cloning: A Laboratory Manual, Cold Spring Harbor Laboratory Press (1989) and Ausubel et al., in Current Protocols in Molecular Biology, Greene Publishing Associates and Wiley-Intersciences (1987).

Malignant: cells which have the properties of anaplasia, invasion and metastasis.

Messenger RNA (mRNA): RNA that is translated into protein. cDNA can be reverse transcribed from mRNA using standard molecular biology methods.

Microarray: An array that is miniaturized so as to require microscopic examination for visual evaluation.

Microbes: Any microorganism. Includes for example, viruses and members of the Monera, Protista or Fungi Kingdoms, for example bacteria and parasites.

Neoplasm: abnormal growth of cells

Normal cells: Non-tumor, non-malignant cells.

Nucleic acid array: An arrangement of nucleic acids (such as DNA or RNA) in assigned locations on a matrix, such as that found in cDNA or CGH arrays.

Nucleic acid: A deoxyribonucleotide or ribonucleotide polymer in either single or double stranded form, including known analogs of natural nucleotides.

Nucleic acid molecules representing genes: Any nucleic acid, for example DNA, cDNA or RNA, of any length suitable for use as a probe that is informative about the genes.

Oligonucleotide: A linear single-stranded polynucleotide sequence ranging in length from 2 to about 1,000,000 bases, for example a polynucleotide (such as DNA or RNA) which is at least 6 nucleotides, for example at least 15, 50, 100, 200, 1,000, 10,000 or even 1,000,000 nucleotides long. Oligonucleotides are often synthetic but can also be produced from naturally occurring polynucleotides.

Plant Cells: Cells obtained from any member of the Plantae Kingdom, a category which includes, for example, trees, flowering and non flowering plants, grasses, and *Arabidopsis*. The cells can be obtained from any part of the plant, for example roots, leaves, stems, or any flower part. From these cells, nucleic acid or protein can be isolated.

Probes and primers: A probe is an oligonucleotide or isolated nucleic acid capable of binding to a target nucleic acid of complementary sequence through one or more types of chemical bonds, usually through complementary base pairing with hydrogen bond formation. Oligonucleotide probes are often 10-50 or 15-30 bases long, and can be as long as about 1,000,000 bases. An oligonucleotide probe may include natural (A, T, C, G) or modified bases (7-deazaguanosine, inosine, etc.). In addition, the bases in an oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages.

Detectable label or reporter molecules can be attached to probes. Typical labels include fluorophores, radioactive isotopes, ligands, chemiluminescent agents, and enzymes. Methods for labeling and guidance in the choice of labels appropriate for various purposes are discussed, e.g., in Sambrook et al., in Molecular Cloning: A Laboratory Manual, Cold Spring Harbor Laboratory Press (1989) and Ausubel et al., in Current Protocols in Molecular Biology, Greene Publishing Associates and Wiley-Intersciences (1987).

Primers are short nucleic acids, such as DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (Molecular Cloning: A Laboratory Manual, Cold Spring Harbor Laboratory Press, 1989), Ausubel et al., in Current Protocols in Molecular Biology, Greene Publishing Associates and Wiley-Intersciences (1987), and Innis et al., *PCR Protocols, A Guide to Methods and Applications,* 1990, Innis et al. (eds.), 21-27, Academic Press, Inc., San Diego, Calif. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a cDNA or gene will anneal to a target sequence contained within a cDNA or genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of a cDNA or gene sequence.

Thus isolated nucleic acid molecules that comprise specified lengths of a nucleic acid sequence can be used in the present invention. Such molecules may comprise at least 20, 40, 50, 100, 1000, 10,000, or even 1,000,000 or more consecutive nucleotides of a nucleic acid sequence and may be obtained from any region of a nucleic acid sequence.

Probe Element: A nucleic acid sequence from a gene which is represented in a probe set. For example, the gene may be differentially expressed by a cell following radiation induced biological stress. In addition, the gene may be unaffected in its expression following radiation induced biological stress, for example control genes.

Probe set: A population of two or more probes which represent genes that are differentially expressed in cells that have been exposed to a biologically significant amount of ionizing radiation. The probe set may be nucleic acids, for example RNA, cDNAs, and/or oligonucleotides that specifically hybridize to complementary sequences in a nucleic acid composition, for example from test cells which may have been exposed to ionizing radiation. For example, the probe set may contain any of the probes shown in Tables 4 or 5. In addition, the probe set can be bound in an array to a surface.

Purified: the term purified does not require absolute purity; rather, it is intended as a relative term. Thus, for example, a purified protein preparation is one in which the protein is more pure than the protein in its natural environment within a cell. In one embodiment, a preparation of a protein is purified such that the protein represents at least 50% of the total protein content of the preparation.

Radiation dose: Defined in terms of energy deposition. The basic unit is the gray (Gy), equal to 1 joule per kilogram.

Radiation induced biological stress: The induction of differential expression of stress genes in cells after they are exposed to radiation. Examples include, but are not limited to: CIP1/WAF1, GADD45, MDM2, BCL2, FOS, JUN, REL-B, ATF3, BAX.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of nucleic acid or amino acid sequences will possess a relatively high degree of sequence identity when aligned using standard methods. This homology will be more significant when the orthologous proteins or nucleic acids are derived from species which are more closely related (e.g., human and chimpanzee sequences), compared to species more distantly related (e.g., human and *C. elegans* sequences). Typically, orthologs are at least 50% identical at the nucleotide level and at least 50% identical at the amino acid level when comparing human orthologous sequences.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al. *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available at the NCBI website.

Homologs are typically characterized by possession of at least 60%, 70%, 75%, 80%, 90%, 95% or at least 98% sequence identity counted over the full length alignment with a sequence using the NCBI Blast 2.0, gapped blastp set to default parameters. Queries searched with the blastn program are filtered with DUST (Hancock, and Armstrong, 1994, *Comput. Appl. Biosci.* 10:67-70). Other programs use SEG.

One of ordinary skill in the art will appreciate that these sequence identity ranges are provided for guidance only; it is entirely possible that strongly significant homologs could be obtained that fall outside of the ranges provided. The present invention provides not only the peptide homologs described above, but also nucleic acid molecules that encode such homologs.

One indication that two nucleic acid sequences are substantially identical is that the polypeptide which the first nucleic acid encodes is immunologically cross reactive with the polypeptide encoded by the second nucleic acid.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that all encode substantially the same protein.

An alternative indication that two nucleic acid molecules are closely related is that the two molecules hybridize to each other under stringent conditions, as described under "specific hybridization."

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (In: Molecular Cloning: A Laboratory Manual, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (Molecular Cloning: A Laboratory Manual, Cold Spring Harbor, N.Y., 1989).

Hybridization with a target probe labeled with $[^{32}P]$-dCTP is generally carried out in a solution of high ionic strength such as 6×SSC at a temperature that is 20-25° C. below the melting temperature, $T_m$, described below. For such Southern hybridization experiments where the target DNA molecule on the Southern blot contains 10 ng of DNA or more, hybridization is typically carried out for 6-8 hours using 1-2 ng/ml radiolabeled probe (of specific activity equal to $10^9$ CPM/μg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at $T_m$ 50% of the probes are occupied at equilibrium. The $T_m$ of such a hybrid molecule may be estimated from the following equation (Bolton and McCarthy, *Proc. Natl. Acad. Sci. USA* 48:1390, 1962): $T_m=81.5°$ C.$-16.6(\log_{10}[Na^+])+0.41(\%$ G+C$)-0.63(\%$ formamide$)-(600/l)$; where l=the length of the hybrid in base pairs.

This equation is valid for concentrations of $Na^+$ in the range of 0.01 M to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (Molecular Cloning: A Laboratory Manual, Cold Spring Harbor, N.Y., 1989).

Thus, by way of example, for a 150 base pair DNA probe derived from a cDNA (with a hypothetical % GC=45%), a calculation of hybridization conditions required to give particular stringencies may be made as follows: For this example, it is assumed that the filter will be washed in 0.3× SSC solution following hybridization, thereby: $[Na^+]=0.045$ M; % GC=45%; Formamide concentration=0; l=150 base pairs; $T_m=81.5-16.6(\log_{10}[Na^+])+(0.41\times45)-(600/150)$; and so $T_m=74.4°$ C.

The $T_m$ of double-stranded DNA decreases by 1-1.5° C. with every 1% decrease in homology (Bonner et al., *J. Mol. Biol.* 81:123, 1973). Therefore, for this given example, washing the filter in 0.3×SSC at 59.4-64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target cDNA molecule will not hybridize. The above example is given entirely by way of theoretical illustration. One skilled in the art will appreciate that other hybridization techniques may be utilized and that variations in experimental conditions will necessitate alternative calculations for stringency.

In the present invention, stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe"

refers to probes whose sequence is deliberately selected not to be perfectly complementary to a particular target sequence.

Transcription levels can be quantitated absolutely or relatively. Absolute quantitation can be accomplished by inclusion of known concentrations of one or more target nucleic acids (for example control nucleic acids such as Bio B or with a known amount the target nucleic acids themselves) and referencing the hybridization intensity of unknowns with the known target nucleic acids (for example by generation of a standard curve).

Subject: Living multicellular vertebrate organisms, a category which includes, both human and veterinary subjects for example, mammals, birds and primates.

Test Cell: A cell which has been or may have been exposed to biologically significant levels of ionizing radiation. Using the method of the present invention, whether a test cell has been exposed to biologically significant levels of ionizing radiation can be determined. Test cells can be from any origin, including for example plant and animal cells. In particular examples, the test cells are peripheral blood cells.

Tumor: a neoplasm

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

EXAMPLE 1

Apoptosis of ML Cells after Irradiation

This example describes experiments in which the percent of cells undergoing apoptosis following different levels of irradiation was calculated.

ML-1 cells, a human myeloid leukemia cell line, were grown in RPMI 1640 medium supplemented with 10% heat-inactivated (56° C. for 45 minutes) fetal calf serum and 100 U/ml penicillin and 100 µg/ml streptomycin in a humidified, 5% $CO_2$ atmosphere in a 37° incubator. Cells were irradiated at approximately 5.1 cGy/minute to total doses between 2 and 2000 cGy using a Mark 1-68 $^{137}Cs$ source (J.L. Shepherd and Associates, Inc., San Fernando, Calif.) with lead attenuators in place. The dosimetry of the source was confirmed by exposing TLD monitors (Landauer Inc., Glenwood, Ill.) in the same configuration used for cellular irradiations to the range of doses used. Even at the lowest doses, the calculated absorbed dose (Landauer special dosimetry services) varied by less than 3% from the dose expected. Due to the nature of sparsely ionizing radiation such as γ-rays, it is highly unlikely that cells in the irradiated population will remain unexposed at even the lowest doses used.

To determine if cells underwent apoptosis following irradiation, the cells were irradiated and then incubated for 1, 2, or 3 days. The cells were subsequently fixed in methanol, and stained with DAPI solution (50 ng/ml final concentration). An Olympus fluorescent microscope was used to score nuclei exhibiting characteristic morphological features of apoptosis, and results were expressed as the number of apoptotic nuclei over the total number of nuclei counted. Flow cytometry was used to measure the effects of irradiation on the cell cycle. In this method, cells were fixed in 70% ethanol 0, 8, 10, 12 and 24 hours after irradiation, treated with RNase (100 ug/ml) at 37° C., then stained with propidium iodide. Samples were analyzed using a Becton-Dickenson FacScan and cell cycle distributions were fitted using the Cell Quest data analysis program.

ML-1 cells irradiated with $^{137}Cs$ γ-rays showed a survival response similar to that of other human cell lines of myeloid or lymphoid lineage (FIG. 1), which are typically more radiosensitive than cell lines derived from other tissue types. The survival curve had no apparent shoulder and predicted a $D_0$ of approximately 73 cGy. The changes in plating efficiency induced by doses of 2, 5, and 10 cGy were so low as not to be measurably different from fluctuations in the colony formation assay (p>0.1). In four independent experiments, the mean plating efficiency of untreated controls was 0.129+/−0.069 while the mean plating efficiency for all doses combined (2, 5 and 10 cGy) was 0.127+/−0.058.

Figure 2:
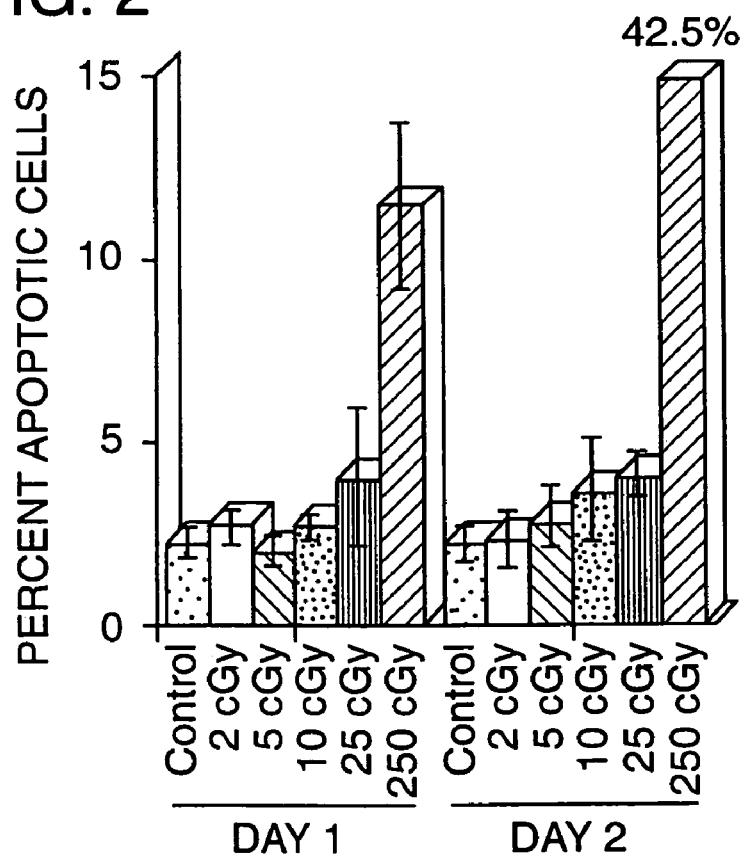
FIG. 2 is a bar graph showing the percent of apoptotic cells one or two days after radiation treatment. Results are the average of 3-4 independent experiments in which at least 250 cells were scored for each point. Error bars are standard errors.

Although previous studies demonstrated that high doses of ionizing radiation efficiently induce rapid apoptosis in ML-1 cells (Zhan et al. *Oncogene* 9:3743-51, 1994), at lower, relatively non-toxic doses (cells irradiated with 25 cGy or less), very little apoptosis was measurable. A more sensitive method for detecting apoptotic cells was achieved by scoring morphology of DAPI stained cells. As shown in FIG. 2, two days after irradiation, a trend of increasing apoptosis with increasing dose emerged between 2 and 25 cGy, although due to experimental fluctuations, this increase was only significant at the p<0.01 level (paired t-test) following the 25 cGy dose. In contrast, cultures treated with 250 cGy showed over 40% morphologically apoptotic cells two days after irradiation. No further increases in apoptotic fraction were observed at times later than two days following treatment for any of the doses tested.

Figure 3A:
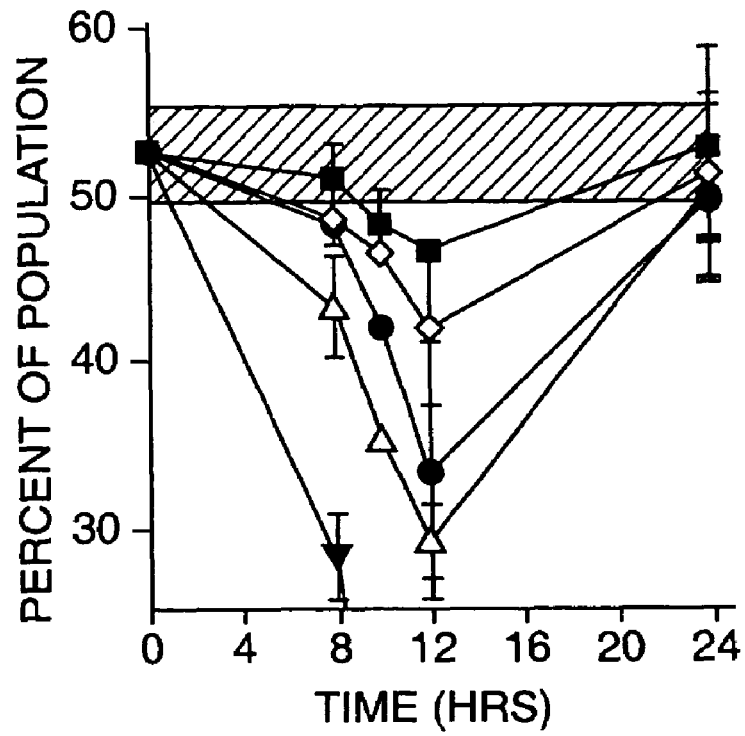
FIG. 3A is a graph showing the fraction of S-phase cells in the population at various times after irradiation of exponentially growing ML-1 cells with 2 cGy (■), 5 cGy (◇), 10 cGy (●), 25 cGy (Δ), or 250 cGy (▼) of $^{137}$Cs γ-rays. Points are the mean of three independent experiments, and error bars are standard deviations. The points for the 12 and 24 hour timepoints have been offset slightly to make the error bars more distinguishable. The shaded area represents the range of S-phase fractions in untreated control populations and is the mean plus and minus the standard deviation of the control measurements at all timepoints.
Figure 3B:
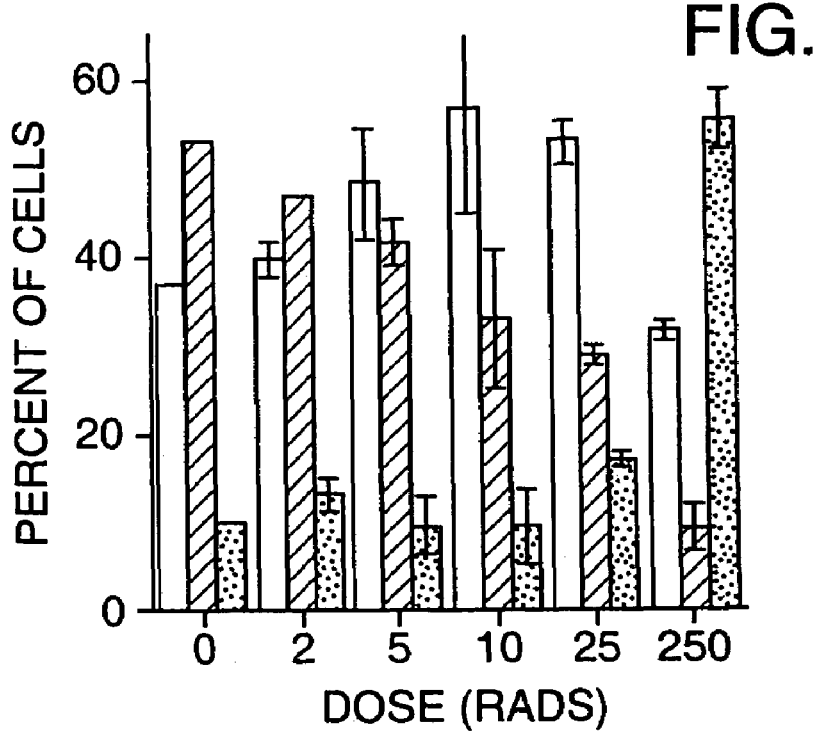
FIG. 3 B is a bar graph showing the cell cycle distribution at the time of maximum perturbation (12 hours) for the low dose treatments. For each dose, the percent of cells in G1 is represented by the open bar, cells in S by the grey bar, and cells in G2 by the black bar. The values shown are the mean of three independent experiments, and error bars are standard deviations. Where error bars are not visible the standard deviation was ≦0.76. An asterisk indicates a point not significantly different from the control at or below the p<0.005 level.

In contrast to their effect on apoptosis, doses below 25 cGy significantly and reproducibly perturbed cell cycle progression in a dose-dependent manner (FIGS. 3A and 3B). Even the lowest dose tested, 2 cGy, caused a transient reduction of the S-phase fraction. This effect was only significant at 12 hours after irradiation with 2 cGy, while increased doses resulted in larger and more rapid decreases in the S-phase fraction of the population (FIGS. 3A and 3B). By 24 hours post-irradiation, the populations treated with doses of 25 cGy or below had all recovered their normal cell cycle distributions, while cells treated with the higher dose of 250 cGy still showed a profoundly arrested profile with very few (6.6+/−1.9 percent) S-phase cells.

These results demonstrate that low-levels of non-toxic irradiation can be effectively administered, and that even at these low doses, progression of the cell cycle is perturbed.

EXAMPLE 2

Construction of cDNA Microarrays

This example describes experiments conducted to identify genes which are differentially expressed in cells exposed to radiation, such as low level radiation, which were used to construct cDNA microarrays. Before a probe set can be constructed which identifies differential expression of genes in radiation exposed cells, probes are selected for the set. This selection can be achieved by using cDNA arrays having a general sampling of ESTs, for example from human, mouse, or plant genes. The array of ESTs can be exposed to nucleic acid compositions from test cells that have been exposed to a dose of ionizing radiation sufficient to induce differential expression of stress genes in the test cells. The nucleic acids can then be labeled (for example by reverse transcription from cellular mRNA to labeled cDNA), and exposed to the array. Specific hybridization to an EST in the array, or differential hybridization by a cDNA from a cell that has been irradiated, identifies a potential probe for the probe set. Subsequent confirmation of differential expression can be achieved by northern blot analysis, or other techniques.

The microarray used in this example included a general sampling of human genes (622 ESTs) plus another set of genes (616 ESTs) which were chosen on the basis of their roles in cancer or lymphoid biology. The genes represented in the 1.2K array are shown in Table 1. The sequences are identified in Table 1 by Image Consortium Clone number (hereinafter "Image No."). This number can be searched on the ATCC Image Consortium Clones database at the ATCC (Manassas, Va.) website, with links to the ATCC accession number of clones from which the sequences can be obtained, and links to Genbank sequence listings which correspond to the Image Number. The array was constructed with ESTs informative for the exposure of interest, namely radiation exposure. A panel of housekeeping genes and other internal controls was also included on the array. The selection of this panel has been described (DeRisi et al., *Nat. Genet.* 14:457-460, 1996).

TABLE 1

Image ID Numbers of Genes Present in the 1.2K array.

21420; 22036; 29054; 33941; 34327; 38805; 42894; 43110; 47359; 471252; 486375; 80549;
161023; 51363; 310406; 470470; 485963; 298371; 62186; 41959; 25081; 25725; 32198; 36593;
36844; 40765; 44527; 44710; 49888; 51528; 51740; 31116; 253773; 266486; 364278; 51825;
193913; 363805; 344482; 360201; 21477; 22040; 29204; 34011; 34357; 38829; 42906; 43129;
47384; 471494; 486233; 81221; 162584; 51439; 310490; 470685; 486161; 298371; 80549; 135118;
25154; 25764; 32304; 36676; 36904; 40831; 44537; 44721; 49897; 51540; 51785; 32790; 253869;
267246; 364982; 52193; 196543; 364110; 344769; 361401; 21468; 22230; 29234; 34005; 34349;
38840; 42910; 43194; 47386; 471715; 486086; 82991; 162772; 51746; 310390; 470730; 486074;
299626; 110589; 136769; 25169; 25880; 32319; 36681; 36916; 40874; 44563; 44722; 49898;
51555; 51814; 32983; 257766; 267682; 364752; 52564; 199381; 364975; 345527; 361815; 21531;
22260; 29435; 34141; 34355; 38859; 42927; 43229; 47463; 472067; 486785; 82850; 48398; 51854;
310428; 470691; 486716; 300051; 113941; 154763; 25400; 26052; 32409; 36700; 36922; 40886;
44584; 45188; 49926; 51621; 51940; 33368; 258589; 268652; 364716; 178169; 200209; 366539;
347573; 366981; 21652; 28573; 29438; 34217; 38567; 38876; 42993; 47229; 47475; 484993;
62186; 84730; 49164; 307741; 322000; 471217; 296021; 301363; 121147; 25485; 31852; 32407;
36717; 40493; 40911; 44605; 49751; 49967; 51666; 27944; 34005; 260052; 362009; 365147;
178508; 361692; 366509; 347685; 21656; 28595; 29627; 34247; 38573; 38966; 43021; 47306;
47493; 485690; 77577; 85906; 49950; 309615; 322604; 471620; 296642; 303109; 129268; 25495;
31855; 32438; 36775; 40562; 40959; 44666; 49777; 49980; 51685; 28573; 35326; 261518; 362332;
365647; 182633; 361692; 366942; 357357; 22012; 28776; 29629; 34255; 38647; 38983; 43060;
47343; 47499; 486012; 79742; 86017; 50576; 309477; 323162; 471822; 297589; 306170; 26503;
25517; 31988; 32427; 36796; 40670; 40991; 44689; 49788; 50038; 51687; 28774; 35516; 262575;
362926; 366420; 183661; 362702; 375620; 358677; 21810; 28985; 29640; 34304; 38770; 39086;
43092; 47333; 47631; 486335; 80239; 23464; 50503; 310141; 323001; 471918; 298187; 307471;
26599; 25584; 32141; 32531; 36790; 40764; 41094; 44699; 49849; 50032; 51699; 30781; 36074;
264606; 363799; 366576; 191007; 363539; 375635; 358538; 22285; 22589; 30543; 34396; 34671;
39173; 43231; 43563; 47833; 486560; 488373; 110589; 52489; 193736; 323776; 486510; 489217;
321246; 162479; 231292; 26082; 26483; 32649; 36927; 37230; 41439; 45222; 45643; 50232;
51961; 52587; 43129; 268727; 279482; 375922; 205905; 236420; 377275; 375635; 417127; 22293;
22611; 30573; 34537; 34761; 39195; 43338; 43601; 47874; 486844; 488801; 110503; 52162;
190711; 324698; 487130; 489194; 321308; 50576; 247869; 26087; 26531; 32644; 36950; 37231;
41452; 45233; 45658; 50234; 52019; 52629; 131828; 270148; 279954; 376362; 209655; 239287;
377181; 375724; 418320; 22379; 22798; 30578; 34555; 34860; 39205; 43241; 43622; 47884;
487417; 488989; 112035; 52681; 200378; 324655; 487097; 510130; 322148; 52681; 252185;
26129; 26541; 32658; 36983; 37234; 41511; 45291; 45794; 50271; 52222; 52650; 132420; 270980;
281029; 376285; 213502; 241489; 377441; 375843; 428248; 22445; 22790; 30588; 34606; 34945;
39270; 43409; 43631; 48077; 487264; 489419; 114116; 179711; 201797; 324815; 487777; 510258;
322452; 190107; 256323; 26128; 26572; 32682; 36975; 37269; 41559; 45376; 45851; 50308;
52342; 52652; 133122; 271478; 281778; 376737; 219735; 242134; 415206; 376294; 470792;
22493; 29799; 30592; 34637; 39093; 39285; 43504; 47648; 48085; 487386; 108284; 114648;
180447; 323028; 325182; 487965; 308392; 323181; 192694; 26147; 32609; 32684; 37040; 41208;
41773; 45421; 50117; 50322; 52338; 36215; 135381; 271416; 366647; 376649; 231089; 376110;
415060; 376218; 22545; 30012; 30622; 34647; 39148; 39380; 43541; 47679; 48097; 487878;
108837; 115277; 183950; 323390; 327396; 488891; 320514; 323648; 193901; 26184; 32615;
32717; 37118; 41199; 41796; 45564; 50106; 50359; 52415; 36844; 137531; 271662; 366824;
380403; 231292; 376303; 415636; 376507; 22568; 30149; 30619; 34662; 39159; 39391; 43549;
47727; 48234; 488103; 110022; 115408; 187987; 323555; 328692; 489042; 320903; 324700;
209310; 26286; 32626; 32707; 37145; 41356; 41792; 45568; 50171; 50363; 52489; 39920; 137575;
272110; 366904; 415102; 231497; 376781; 415679; 380738; 22589; 30272; 30664; 34660; 39169;
39542; 43550; 47838; 48406; 488596; 109957; 115336; 192694; 323500; 340644; 489327; 321242;
328330; 222502; 26366; 32636; 32750; 37196; 41392; 41813; 45604; 50203; 50503; 52530; 41565;
138460; 278409; 375724; 415731; 232714; 376725; 416184; 381219; 23014; 23731; 30885; 34974;
35609; 39827; 43711; 44105; 48677; 489395; 510245; 121849; 201673; 221690; 343166; 510467;
112500; 343465; 257458; 282065; 26585; 27473; 32898; 37347; 37508; 42059; 45840; 46329;
50603; 52681; 53084; 140358; 283116; 293274; 417403; 243143; 262691; 427923; 471218;
488658; 23019; 23804; 30970; 35110; 35623; 39861; 43719; 44159; 48717; 509710; 512458;
123586; 203132; 221619; 343871; 512391; 120466; 343311; 260288; 286197; 26593; 27511;
33008; 37366; 37513; 42088; 45941; 46339; 50666; 52753; 53107; 140827; 284031; 293934;
417592; 253545; 264576; 427943; 471631; 488904; 23073; 23831; 30966; 35284; 35615; 39876;
43826; 44173; 48713; 509731; 512472; 123953; 203017; 223176; 344109; 198205; 124086;
343646; 264200; 288650; 26659; 27549; 33045; 37380; 37622; 42096; 46019; 46354; 50816;
52773; 53128; 143751; 284459; 295208; 417689; 254428; 264554; 427943; 471889; 509710;
23132; 23866; 30981; 35297; 35665; 39884; 43858; 44180; 48762; 509820; 512385; 124554;
204301; 230976; 345600; 322029; 26992; 345645; 271416; 290117; 26789; 27624; 33183; 37435;
37679; 42130; 46042; 46419; 50888; 52896; 53155; 144944; 288797; 298314; 418111; 254187;
268412; 427750; 485192; 509682; 23185; 30691; 31061; 35313; 39686; 39903; 43885; 48452;
48803; 510101; 116906; 125187; 204681; 340734; 345928; 60298; 328467; 345722; 272110;

TABLE 1-continued

Image ID Numbers of Genes Present in the 1.2K array.

26801; 32774; 33176; 37433; 41857; 42214; 46171; 50555; 50941; 52931; 138604; 144693;
289606; 417226; 418138; 258747; 417136; 427686; 486199; 23332; 30730; 31116; 35320; 39728;
39965; 43960; 48458; 49161; 510151; 116713; 125676; 205633; 341130; 346534; 72869; 340947;
346587; 279727; 26922; 32790; 33267; 37451; 41918; 42284; 46213; 50561; 50999; 53024;
138917; 145503; 291057; 417124; 427857; 258790; 417218; 428404; 486410; 23346; 30802;
31131; 35483; 39781; 39993; 44014; 48503; 49243; 510405; 116781; 126379; 209310; 340922;
357309; 73515; 341763; 346396; 280465; 27230; 32822; 33274; 37477; 42020; 42295; 46302;
50576; 51018; 53068; 139073; 145932; 291503; 417322; 428248; 259241; 418105; 428231;
487982; 23692; 30852; 31143; 35559; 39796; 40008; 44050; 48629; 49255; 510595; 120157;
126542; 213597; 340878; 357239; 23173; 342256; 346305; 280735; 27052; 32875; 33415; 37485;
42058; 42349; 46303; 50609; 51209; 53071; 138998; 147075; 291736; 417357; 429142; 259291;
418436; 429135; 488092; 24110; 24652; 31210; 35850; 36232; 40151; 44178; 44367; 49403;
512276; 26503; 231302; 244355; 358467; 36809; 43504; 357374; 291943; 309924; 27681; 28116;
33632; 37721; 38397; 42576; 46427; 47038; 51318; 53164; 53322; 153355; 299198; 306013;
430027; 271198; 290493; 469543; 509588; 203184; 24145; 24886; 31238; 35865; 36291; 40205;
44193; 44414; 49509; 512294; 26474; 233194; 248032; 358168; 146307; 47559; 358848; 293032;
320538; 27715; 28245; 33643; 37760; 38393; 42615; 46449; 47110; 51332; 53173; 53358; 154015;
299539; 306134; 469256; 280376; 290871; 470602; 509882; 241412; 24269; 24899; 31242; 35933;
36393; 40276; 44218; 44477; 49584; 512244; 26167; 234198; 248613; 359171; 151767; 49576;
359119; 295093; 322000; 27794; 28309; 33690; 37796; 38471; 42648; 46548; 47125; 51373;
53184; 154472; 300973; 307293; 469724; 280768; 290724; 470493; 510381; 248258; 24392;
24927; 31355; 36007; 36560; 40304; 44255; 44495; 49608; 512429; 26871; 234357; 249348
359051; 152762; 51686; 359077; 298314; 327111; 27815; 28410; 33692; 37797; 38500; 42677;
46574; 47202; 51418; 53185; 154441; 301723; 307342; 470185; 284546; 295389; 470635; 124927;
296476; 24588; 31155; 31454; 36060; 40026; 40360; 44266; 49277; 49665; 127089; 26811;
236338; 357435; 359412; 154420; 347032; 359466; 300071; 27818; 33438; 33794; 37892; 42352;
42700; 46711; 51219; 51432; 53238; 147744; 154536; 302394; 429057; 470196; 284669; 429539;
470610; 125555; 24609; 31154; 31456; 36109; 40117; 40450; 44302; 49318; 49666; 128100;
26599; 236422; 357442; 359769; 154420; 347751; 359465; 300960; 27848; 33477; 33803; 37904;
42363; 42777; 46777; 51241; 51454; 53227; 149910; 155717; 302157; 429368; 470251; 286249;
429861; 470817; 126519; 24638; 31169; 31687; 36191; 40110; 40440; 44307; 49322; 49691;
127821; 26599; 238577; 357909; 360531; 158970; 356890; 359793; 304947; 27927; 33525; 33831;
37962; 42380; 42844; 46920; 51302; 51461; 53292; 153025; 156103; 302490; 429926; 470062;
288733; 469272; 471096; 194384; 24642; 31164; 31863; 36202; 40111; 40442; 44311; 49383;
49725; 129632; 27899; 243159; 357807; 361381; 158970; 356964; 361728; 305455; 28089; 33620;
33943; 37964; 42532; 42888; 46936; 51293; 51504; 53316; 152844; 159833; 305455; 429976;
470621; 289428; 469731; 471174; 195889

The human myeloid leukemia cell line ML-1 is available from the National Cancer Institute's Anti-Neoplastic Drug Screen Panel (NCI-ADS). The members of this panel are listed in Table 2, and are described in many publications, including Monks et al. (*J. Nat. Cancer Institut.* 83:757-66, 1991), and on the NCI Web page. ML-1 was selected as the test cell in which radiation induced differential expression of genes would be measured. A characteristic of this cell that made it particularly useful for this purpose was that it contains endogenous wild-type p53, which is a cellular stress response mediator following exposure to ionizing radiation. ML-1 contains physiologic levels of p53, rather than the unnatural and often highly overexpressed levels often seen in artificially engineered systems. Moreover, ML-1 is a myeloid cell line, which is prone to undergo rapid apoptosis following genotoxic stress. This characteristic results in the induction of genes specifically associated with rapid apoptosis, such as BAX, MCLI, GADD34 and BCL-X (Zhan et al., *Oncogene* 9:3743-51, 1994 and *Oncogene* 14:1031-9, 1997). In addition to ML-1 cells, other cells that can be used to assess the induction of differential expression of genes in radiation exposed cells include other lymphoid cell lines, such as those with wild-type levels of p53, such as Molt4, WMN, TK6 or SR, which may induce genes not found to be regulated in ML-1. Cell lines derived from blood cells (such as these lines) are selected to provide responses more characteristic of peripheral blood responses than would cell lines from other sites, such as colon or breast cell lines (for example RKO or MCF7, respectively). Gene induction can also be measured directly in ex vivo irradiated human peripheral blood cells, as a particularly relevant model system, for methods in which peripheral blood specimens are analyzed to clinically screen for biologically significant radiation exposure (see EXAMPLE 9).

TABLE 2

The National Cancer Institute's Anti-Neoplastic Drug Screen Panel*

| Tissue Origin | Cell Line Names |
|---|---|
| Breast Cancer | BT-549; HS 578T; MCF7; MDA-MB-231; MDA-MB435; MDA-N; NCI-ADR; T-47D; NCI/ADR-RES; MAXF 401; MDA-MB-468; SK-BR-3 |
| CNS Cancer | SF-268; SF-295; SF-539; SNB-19; SNB-75; U251; SNB-78; TE671; XF 498 |
| Colon Cancer | COLO205; HCC-2998; HCT116; HCT15; HT29; KM12; RKO; SW-620; DLD-1; KM20L2 |
| Non Small Cell Lung Cancer | A549; EKVX; HOP-62; HOP-92; NCI-H226; NCI-H23; NCI-H322M; NCI-H460; NCI-H522; HOP-18; HOP-19; LXFL 529 |

TABLE 2-continued

The National Cancer Institute's Anti-Neoplastic Drug Screen Panel*

| Tissue Origin | Cell Line Names |
| --- | --- |
| Small Cell Lung Cancer | DMS 114; DMS 273; SHP-77 |
| Leukemia | CCRF-CEM; HL60; K562; MOLT4; RPMI-8226; SR; P388 P388/ADR |
| Melanoma | LOX-IVMI; M14; MALME-3M; SK-MEL-2; SK-MEL-28; SK-MEL-5; UACC-257; UACC-62; RPMI-7951; M19-MEL |
| Ovarian Cancer | IGROV-1; OVCAR-3; OVCAR-4; OVCAR-5; OVCAR-8; SK-OV-3 |
| Prostate Cancer | DU-145; PC-3 |
| Renal Cancer | 786-O; A498; ACHN; CAKI-1; RXF 393; SN12C; TK-10; UO-31; RXF-631; SN12K1 |

*Cells are available either from ATCC (Manassas, VA) or from the Frederick cancer research facility in Frederick, MD.

ML-1 cells were grown and irradiated at approximately 3.1 Gy/minute to total doses of 0.25, 2 or 20 Gy using a Mark 1-68 $^{137}$CS source, as described in EXAMPLE 1. EST targets identified in Table 1 were prepared by PCR amplification and arrayed on poly-L-lysine coated glass slides by high speed robotic printing as previously described (DeRisi et al., Nat. Genet. 14:457-460, 1996).

A complex cDNA probe was prepared from whole-cell RNA by a single round of reverse transcription using SuperscriptII (Gibco-BRL, Grand Island, N.Y.) for two hours at 42° C. according to the manufacturer's instructions in the presence of fluorescent dNTP (Cy3 dUTP or Cy5 dUTP, Amersham Pharmacia Biotech, Piscataway, N.J.). Probes were hybridized to the slides for 16 hours in 3×SSC (8.77 g/L NaCl, 4.41 g sodium citrate at pH 7.4) at 65° C. in the presence of blockers (8 µg Poly d A; 4 µg yeast tRNA; and 10 µg human Cot 1 per 10 µl hybridization). Hybridized slides were washed at room temperature (RT) in 0.5×SSC, 0.01% SDS, then in 0.06×SSC. The two fluorescent intensities (Cy3 and Cy5) were scanned separately using a laser confocal microscope, and the DeArray program was then used to identify target sites by image segmentation, calibrate relative ratios, and to develop confidence intervals for testing the significance of the ratios obtained (Chen et al., J. Biomed. Optics 2:364-374, 1997).

Local background was calculated for each target location. A normalization factor was estimated from a set of 88 internal control targets (De Risi et al., Nat. Genet, 14:457-60, 1996) with a theoretical ratio of 1.0, and the confidence interval for the array was estimated from the variance of these 88 control ratios from the expected value of 1.0. The ratios for all the targets on the array were then calibrated using the normalization factor, and ratios outside the 99% confidence interval (less than 0.54 or greater than 2.37) were determined to be significantly changed by the radiation treatment.

Figure 4:
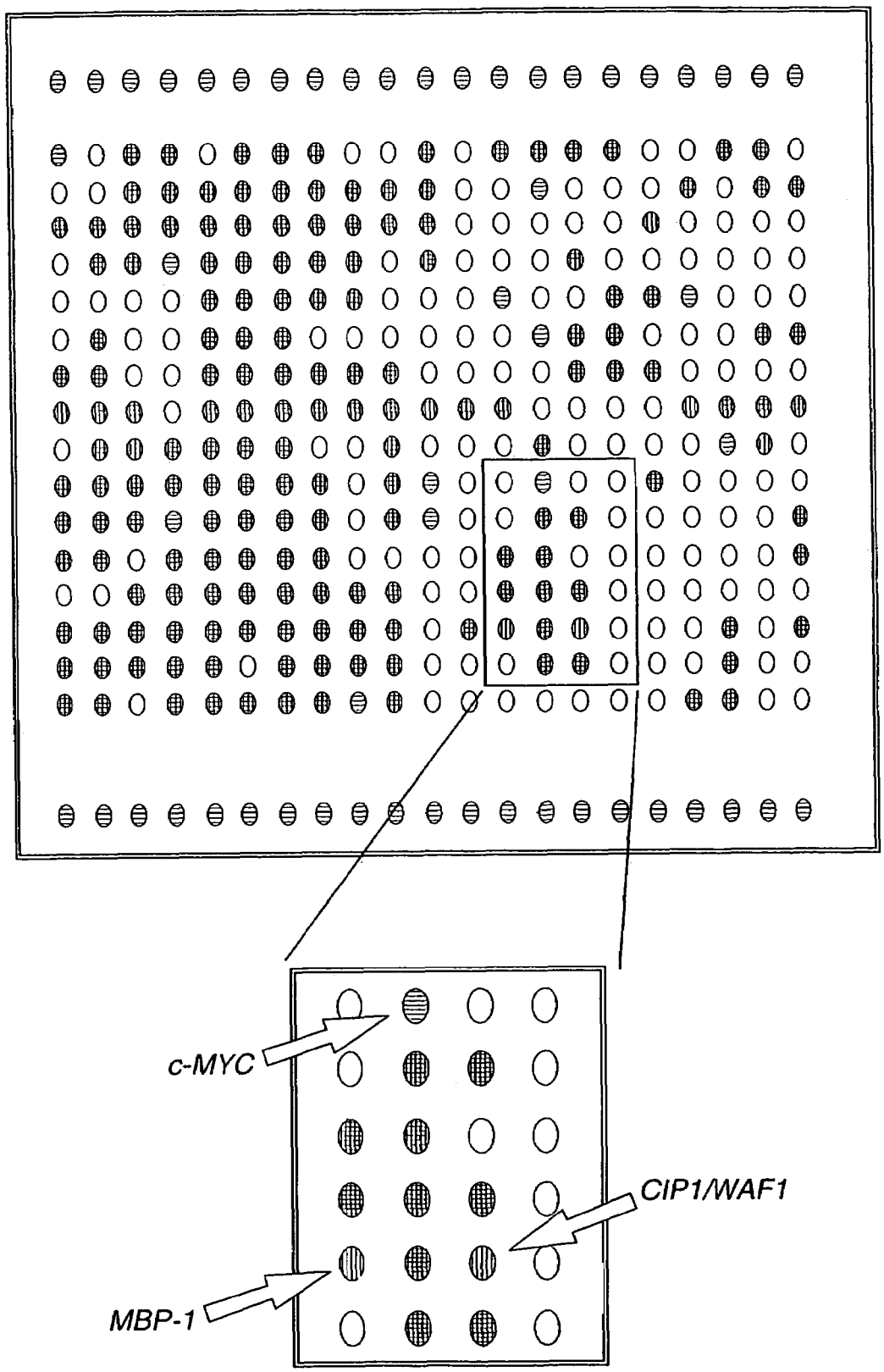
FIG. 4 is a schematic drawing of a quadrant of a microarray hybridized to RNA from untreated ML-1 cells (labeled with a green fluorophore, represented as circles containing horizontal lines) and ML-1 cells four hours after treatment with 20 Gy$^{137}$ (labeled with a red fluorophore, represented as circles containing vertical lines). Targets appearing as yellow spots (represented as circles containing horizontal and vertical lines) have equal representation of both fluorophores and indicate no change in expression by the irradiation. Red spots (circles containing vertical lines) are targets associated with increased expression following irradiation, and green spots (circles containing horizontal lines) are associated with decreased expression. Blank circles represent areas where no hybridization occurred. A horizontal row of green dots (circles containing horizontal lines) at the top and bottom of the schematic microarray represent DNA labeled prior to printing on the array, and serve as orientation markers for a computerized scanner.

In the hybridized microarray, induced transcripts hybridized with more of the probe from the IR-treated sample (labeled with a red fluorophore), resulting in red spots, such as that observed at the CIP1/WAF1 target. A transcript downregulated by IR, such as c-MYC, instead produced a green spot. Intermediate induction ratios result in a gradation of color, such as MBP-1. A schematic drawing showing the hybridized microarray is shown in FIG. 4, in which red spots are shown with vertical lines, green spots are shown with horizontal lines, and yellow spots (which have an equal representation of read an green label) are represented with both horizontal and vertical lines. One skilled in the art will appreciate that the color of the labels used is not critical, so long as the emission wavelength of the different fluorophores used can be resolved, and can be used to measure differential expression. Other fluorophores or labels can be used to practice the method of the present invention.

Transcripts significantly changed by radiation treatment are shown in Table 3 which also gives the mean intensities of hybridization to the unirradiated control on the microarray. This measure correlates with transcript abundance (Schena et al., Science 270:467-70, 1995; Schena et al., Proc. Natl. Acad. Sci. USA 93:10614-9, 1996), and demonstrates identification of IR modulated genes over three orders of magnitude of basal expression. Many of the stress regulated transcripts identified in Table 3 are known to be expressed at very low levels in ML-1 cells, consistent with their relative hybridization intensities on the array. For example, GADD45 and CIP1/WAF1 represent approximately $1/10^5$ transcripts in unirradiated cells.

TABLE 3

Stress gene responses in γ-irradiated human myeloid cells

| Transcript | Image ID | Microarray[a] | Mean Green Intensity[b] |
| --- | --- | --- | --- |
| CIP1/WAF1 | 268652 | 42.0[c] | 1121 |
| ATF3 | 428248 | 11.3[c] | 784 |
| FAS | 151767 | 9.5 | 1352 |
| IAP-1 | 129632 | 9.3[d] | 132 |
| .RELB | 52681 | 7.2[d] | 1027 |
| cyclin I | 512391 | 6.9 | 974 |
| RAB | 52530 | 6.4 | 1688 |
| GADD45 | 310141 | 5.8[d] | 2230 |
| FRA1 | 110503 | 4.8[c] | 672 |
| IL-8 | 328692 | 4.8 | 5307 |
| CSF-1 | 124554 | 4.7 | 356 |
| BCL3 | 236422 | 4.6[c] | 584 |
| MIP1α | 153355 | 4.3 | 475 |
| c-FOS | 26474 | 4.2 | 1314 |
| JUN-B | 309477 | 4.2 | 1892 |
| PC-1 | 52753 | 3.4[c] | 343 |
| CDC5 | 280376 | 3.4 | 1259 |
| MRC OX-2 | 51363 | 3.4[d] | 290 |
| ERR1 | 470602 | 3.2 | 490 |
| MDM2 | 147075 | 3.2[d] | 328 |
| Immunoglobulin J chain | 161023 | 3.1 | 331 |
| OX40 ligand | 35326 | 3.1 | 310 |
| DNA ligase III | 470062 | 3.0 | 636 |
| cytochrome p450 4A | 120466 | 3.0 | 218 |
| MEK1 | 486074 | 2.9 | 1885 |
| TPK receptor UFO | 112500 | 2.8 | 285 |
| Retinoic acid gamma-1 | 471252 | 2.8 | 288 |
| HPTP alpha | 487130 | 2.8 | 282 |
| MBP-1 | 291503 | 2.8[c] | 206 |
| SSAT | 41452 | 2.7[c] | 4160 |
| BAK | e | 2.7[c] | 341 |

TABLE 3-continued

Stress gene responses in γ-irradiated human myeloid cells

| Transcript | Image ID | Microarray[a] | Mean Green Intensity[b] |
|---|---|---|---|
| MBP-2 | 23464 | 2.5 | 462 |
| iL-TMP | 243143 | 2.5[d] | 383 |
| MIP1beta | 205633 | 2.5 | 352 |
| N-RAS | 284031 | 2.5 | 341 |
| nucleotide binding protein mRNA | 21420 | 2.5 | 394 |
| CAP-R | 48677 | 2.4 | 577 |
| BCL-XL | e | 2.3[c] | 313 |
| ch-TOG | 43060 | 0.53 | 9209 |
| ERK | 487417 | 0.51 | 9323 |
| CDC2 | 346534 | 0.47 | 19501 |
| SATB1 | 233194 | 0.46[c] | 30364 |
| SPI-B | 295093 | 0.45 | 3747 |
| ERF-1 | 48085 | 0.44 | 6935 |
| MADP2 homolog | 26541 | 0.43 | 20543 |
| neuron-specific protein gene | 28089 | 0.38 | 8098 |
| TOPO II | 248032 | 0.34[c] | 37173 |
| CDK RS2 | 359119 | 0.27 | 13935 |
| RCH-1 | 28116 | 0.23[c] | 24932 |
| c-MYC | 51699 | 0.12[c] | 17913 |

[a]Ratios of relative induction by γ-rays compared to basal levels in ML-1 cells.
[b]Fluorescence intensity of untreated control on the microarray.
[c]Microarray measurement confirmed by quantitative dot blot hybridization where expression varied by less than 2-fold.
[d]Quantitation varied by more than 2-fold.
[e]Inserts for BAK (Chittenden et al., Nature 374: 733-6, 1995) and BCL-XL (Boise et al., Cell 74: 597-608, 1993) from clones other than Image Consortium ESTs.

A subset of the IR-responsive genes indicated by the microarray with a range of relative ratios were chosen for further study. This subset of probes included the following: Image ID clones 268652, 428248, 129632, 52681, 52530, 310141, 110503, 236422, 153355, 52753, 51363, 147075, 291503, 41452, 243143, 233194, 248032, 28116, 51699. Probes were obtained from the same plasmids used as targets on the array, and γ-ray induction of these genes was confirmed in independent experiments by northern blot hybridization. Estimates of induction or repression as measured by the microarray were compared to quantitative hybridization with single labeled probes. As indicated in Table 3, estimated expression varied by less than 2-fold for many transcripts. However, all tested sequences that were identified on the microarray as induced showed an appreciable (>2-fold) induction by the quantitative hybridization approach, with the exception of MRC-OX, which showed only 1.5-fold induction. In the case of genes showing less than 2.4-fold induction by the microarray, useful data may still be obtainable. For example, MCL-1 showed 1.9-fold induction by the microarray and 2.5-fold induction by quantitative hybridization.

The time course of induction for nine of these genes was examined in ML-1 cells. The response over time of Rag cohort 1 (RCH1) (Cuomo et al., Proc. Natl. Acad. Sci. USA 91:6156-60, 1994), a newly recognized IR-down-regulated gene, was very similar to the response of TOPOII. Both repressed genes showed a similar rapid decrease of mRNA levels following irradiation, and remain maximally repressed 24 hours after treatment. The levels of most of the newly-identified IR-induced genes rose rapidly following treatment, peaked by four hours, and declined again to near the original levels by 24 hours after treatment, following the pattern of rapid response typical of many stress-induced immediate-early genes (Fornace, Ann. Rev. Genet. 26:507-26, 1992; Smith and Formace, Mutation Res. 340:109-24, 1996). By analogy, the genes described here appear to have roles in acute cellular responses to damage and may share some regulatory mechanisms with previously characterized IR-response genes.

Induction of nine of the newly-identified stress-response genes was next measured in a panel of human cancer cell lines to determine the scope of their IR-response, and to monitor for induction by exposure to two DNA-base-damaging agents, the alkylating agent methyl methanesulfonate (MMS) and ultraviolet (UV) radiation. The full list of cell lines from this panel is shown in Table 2.

The cell lines used in this comparison included six cell lines of myeloid-lymphoid lineage [ML-1 (myeloid), Molt4 (lymphoid), SR (lymphoid), CCRF-CEM (lymphoid), HL60 (myeloid) and K562 (myeloid)], two lung cancer lines (A549 and H1299), two breast carcinoma lines (MCF7 and T47D), and the colon cancer line RKO, along with its derivative transfected with E6 (RKO/E6) (Zhan et al., Mol. Cell. Biol. 13:4242-50, 1993). Relative induction of particular genes was measured four hours after treatment with a 20 Gy dose of ionizing radiation (FIG. 5A) or 100 μg/ml MMS or 14 J/m$^2$ UV radiation (FIG. 5B) as measured by quantitative dot-blot hybridization (Hollander and Fornace, Biotechniques 9:174-9, 1990), using the same conditions as described above. Differential expression of genes in tumor cells following radiation exposure can be used as a measure of therapeutic radiosensitivity, or to help study expression patterns that can be the subject of other therapeutic (e.g. drug) interventions.

A summary of the results of these induction experiments is shown in FIGS. 5A and 5B, in which induced genes are indicated by vertical lines, reduced expression is indicated by horizontal lines, and a combination of horizontal and vertical lines indicate substantially unchanged expression. Induction levels of the three p53-regulated genes MDM2, CIP1/WAF1 and BAX were also measured for comparison. CIP1/WAF1 is regulated by both p53-dependent and independent mechanisms, while BAX induction by IR appears to require p53 plus an "apoptosis-proficiency" factor frequently present in cells that undergo rapid apoptosis after IR. These three genes were more responsive in the p53 wildtype (wt) lines, with little or no IR-responsiveness in the p53 deficient lines. As reported previously, strong BAX induction was only seen in myeloid-lymphoid lines with weaker induction in MCF-7 cells. In the case of the SR leukemia line, constitutive BAX expression was approximately an order of magnitude greater than in the other lines, and appreciable induction was not seen. In contrast to these previously described genes, the ionizing radiation response of the newly characterized genes shows far more heterogeneity among different cell lines (FIG. 5A). Hence the present method can be used to select genes that are expressed in certain cells types (such as myeloid or other blood cells) that will be sampled in subjects who have been or have potentially been exposed to ionizing radiation.

While all of the newly-identified genes respond to IR in at least one cell line in addition to ML-1, two of the cell lines, K562 and A549, did not show γ-ray regulation of any of the newly-defined IR-responsive genes, and only ATF3 was induced by any stress agent tested in these two lines (FIG. 5B). Interestingly, K562 was the least responsive of any of the cell lines, and was the only line derived from a patient with chronic myelogenous leukemia. Of the nine genes screened, five: SSA T, c-Myc promoter binding protein (MBP-1, or PRDII-BF1), cellular inhibitor of apoptosis 1 (c-IAP1), RELB and BCL3 were primarily induced by IR in the 12 cell lines examined. Fos-related antigen-1 (FRA-1), RCH1, and prohormone convertase1 (PC1) or neuroendocrine convertase1 (NEC1), all showed regulation by the base-damaging agents MMS or UV radiation in some cell lines (FIG. 5B).

The most wide ranging response was seen for activating transcription factor 3 (ATF3), which was induced by both MMS and UV radiation in all cell lines tested. With such a strong and pervasive response, ATF3 was selected as playing an important role in generalized genotoxic stress responses. Such a strong and pervasive response is a factor that can be used in selecting a probe for the arrays of the present invention.

This example illustrates that a single cell type may provide a less optimal model for cellular response to genotoxic stress, such as IR. However, using the techniques in this example, genes can be chosen which are often or usually induced in response to a genotoxic stress, such as radiation exposure. Such identified genes can be incorporated into a probe set of a microarray.

In addition, particular cells to be sampled (such as peripheral blood lymphocytes, see EXAMPLE 9) can be studied to determine the genes that are differentially expressed in those cells in response to irradiation. Those genes identified as being differentially expressed in response to irradiation can be incorporated into a probe set of a microarray, which would be specific for the particular cell type to be tested. For example, a microarray can be developed which contains probes which are differentially expressed in a specific type of cell (for example peripheral blood mononuclear cells such as lymphocytes) in response to irradiation. Such a microarray can then be used to determine/monitor radiation exposure in that cell type.

The large number of probes in the probe set also overcomes the problem of using induction in a single cell line as evidence of radiation exposure induction. Hence a review of the results shown in FIGS. 5A and 5B illustrates that MDM2 and CIP1/WAF1 are suitable for incorporation into a probe set for detecting radiation induced stress in p53 wild type cells, because their expression is substantially induced in all or many of the cell lines tested. REL-B is also shown to be generally informative in both p53 mutants and wild type cells.

EXAMPLE 3

Dose Response Curves

This example describes methods used to generate a dose response curve which can be used to determine the time period during which a gene is differentially expressed following exposure to ionizing radiation. Such information is useful in determining which probes to incorporate into the probe set, particularly if the probe set is prepared for analysis of potential biological damage at a given time period after a known or suspected exposure. The genes studied in this example, CIP1/WAF1, GADD45, MDM2, ATF3 and BAX, were chosen since they were shown in the previous example to be differentially regulated in response to irradiation.

ML-1 cells were grown and exposed to various doses of radiation at approximately 5.1 cGy/min, to total doses of 2-50 cGy using the Mark I-68 $^{137}$Cs source as described in EXAMPLE 1. Gene induction was measured by incubating the irradiated cells at 37° C. for a predetermined number of hours (such as 1-4, or 24-48 hours following irradiation) followed by RNA extraction using a modified guanidine thiocyanate method (as detailed in Chomczynski and Sacchi, *Anal. Biochem.* 162:156-9, 1987). Gene expression was measured by quantitative dot-blot hybridization. Serial dilutions of RNA were immobilized on nylon membranes, hybridized with cDNA probes at 55° C. in a buffer containing 50% formamide (Hybrisol I, Oncor, Intergen, Purchase, NY), and washed under standard conditions. Hybridization is quantitated on a phosphorimager (Molecular Dynamics, Piscataway, N.J.), and relative signal levels, normalized to the polyA content of each sample, determined using the RNA-Think program. The values for relative RNA levels are directly proportional to RNA abundance, and differences of 1.5-fold or more can reliably be measured.

Figure 6A:
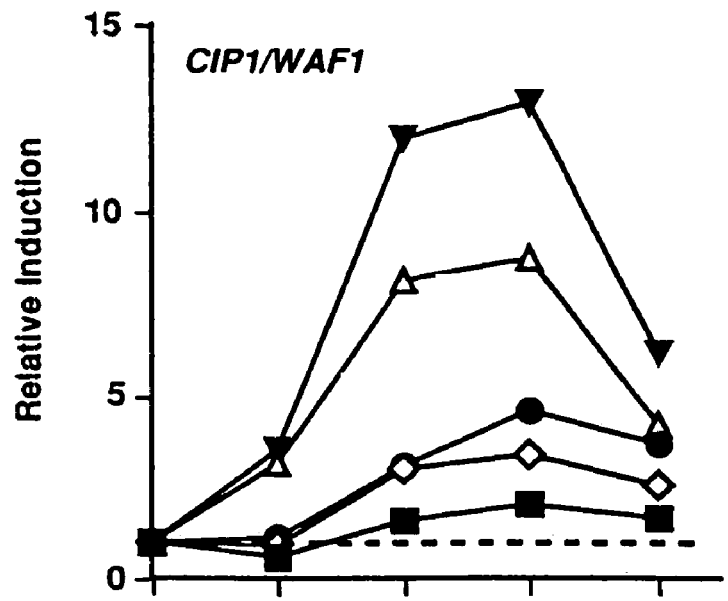
FIGS. 6A and 6B are graphical representations showing the time-course of induction of the (A) CIP1/WAF1 and (B) GADD45 genes following irradiation by 2 cGy (■), 5 cGy (◇), 10 cGy (●), 25 cGy (Δ), or 50 cGy (▼) of γ-rays. Data is shown from a representative experiment. The dashed line indicates the basal level in untreated controls.
Figure 6B:
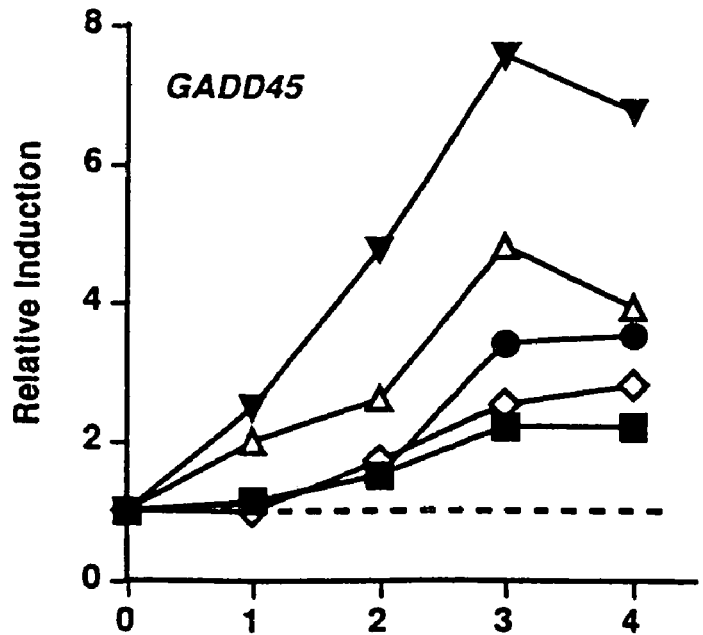

Following treatment with 20 Gy γ-rays, the CIP1/WAF1, GADD45, MDM2, ATF3 and BAX genes reached maximal induction four hours after irradiation, then declined rapidly until they reached basal levels by 24 hours. The induction of CIP1/WAF1 (FIG. 6A) and GADD45 (FIG. 6B) by lower doses of γ-rays was more rapid than the induction seen with supra-lethal doses, reaching maximum levels two to three hours post-irradiation, and in most cases beginning to decline after four hours.

Figure 7A:
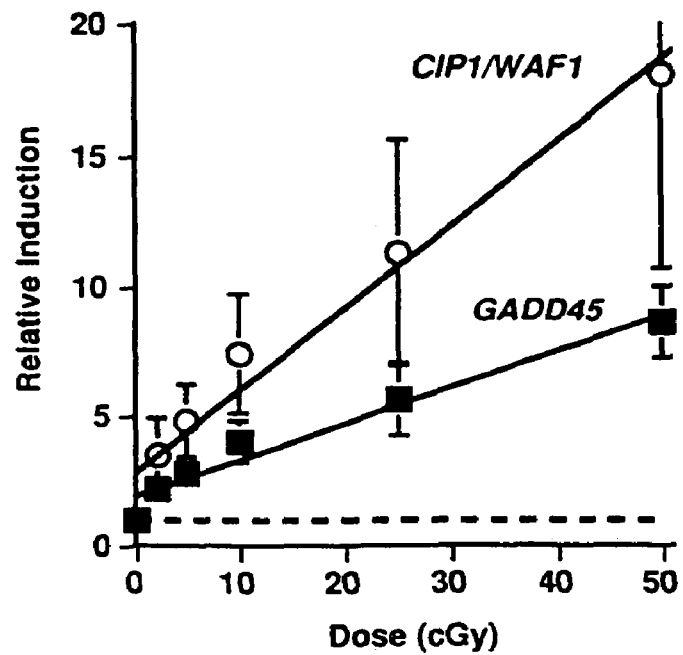
FIGS. 7A and 7B are graphical representations showing the maximal induction of (A) CIP1/WAF1 (○), GADD45 (■) and (B) MDM2 (■), ATF3 (○), and BAX (◆) by low doses of γ-rays. Points are the average of 4 independent experiments, and error bars are standard errors. The dashed line indicates the basal level in untreated controls, solid lines were fit by linear regression through the data.
Figure 7B:
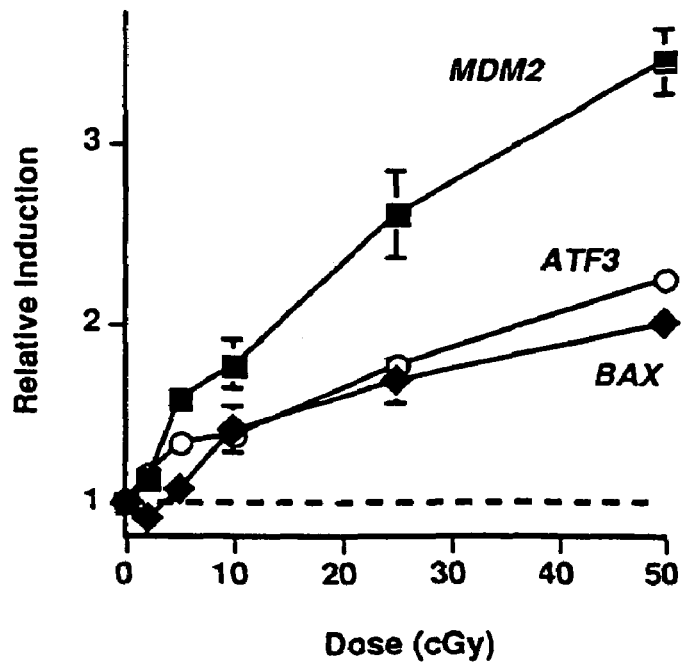

Relative induction of expression can be correlated to dosage, as shown in FIGS. 7A, 7B and 8 for several different genes. The maximal induction of CIP1/WAF1 and GADD45 was approximately linear between 2 and 50 cGy, and showed no indication of a threshold for gene induction (FIG. 7A). Significant induction over basal control levels was observed for both genes at all doses. A more gradual dose-dependent response was observed for the other genes tested (FIG. 7B). MDM2, BAX, and ATF3 were induced between two and three hours following low doses of IR, but 50 cGy only resulted in a 2-3 fold increase in the expression of these genes over control levels (FIG. 7B). The lower inducibility of these genes by low doses of radiation was consistent with their induction by high doses, which was considerably less than that of CIP1/WAF1 and GADD45 (Table 3). The maximal induction appeared linear between 5 and 50 cGy for MDM2, and between 10 and 50 cGy for the other genes. Below these doses, induction fell off sharply, dropping below the limit of accurate quantitation by this technique, previously shown to be approximately 1.5-fold.

Figure 8A:
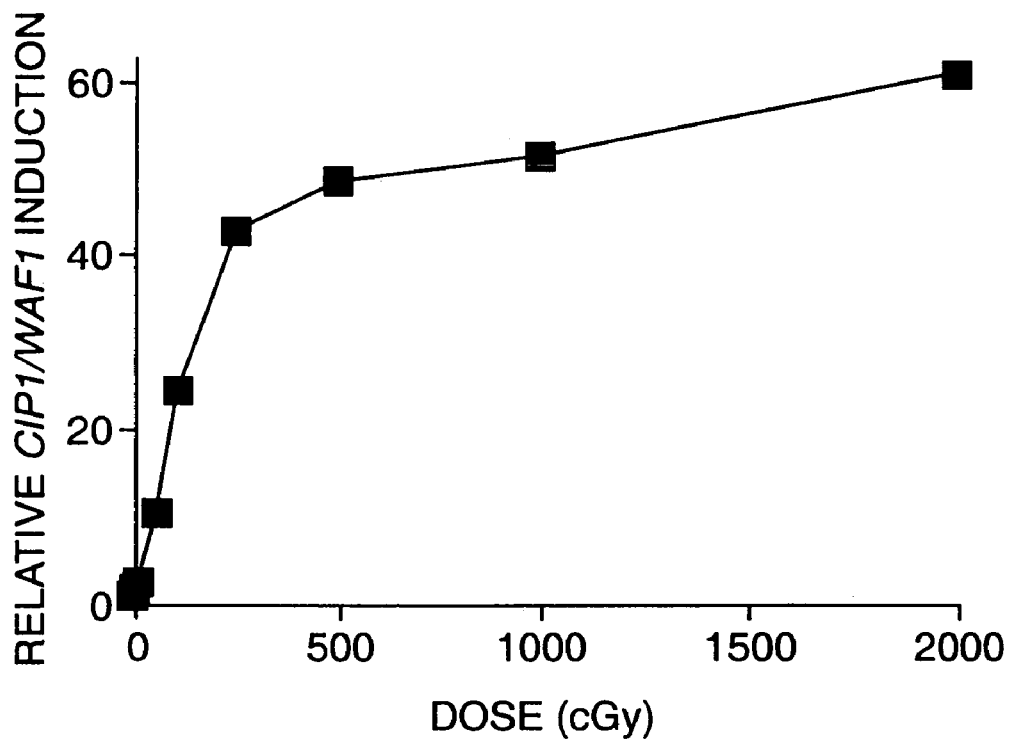
FIG. 8A is a graphical representation showing the dose response of maximal induction of CIP1/WAF1 across a broader range of doses. Data is shown from a representative experiment.

A broader dose range was next tested for the induction of CIP1/WAF1 to determine the point at which the induction response begins to saturate. Induction continued to increase in a dose-dependent manner up to approximately 250 cGy (FIG. 8A). Beyond this point, the dose-dependent increase in relative induction leveled off sharply, although a trend of increased induction appeared to continue up to 20 Gy, the highest dose tested.

The extrapolation of data gathered at high doses to predict effects at low doses can present difficulties. In particular, it cannot necessarily be assumed that the dose-response relationship observed at high doses applies to the entire dose spectrum. For example, very low doses of ionizing radiation may be more toxic per cGy than higher doses. Therefore, extrapolation from survival at high doses may not predict the low-dose hypersensitivity revealed by the more accurate methods. This response may reflect an induction of radio-resistance, perhaps through inducible DNA repair, which requires a certain threshold dose to be triggered in some cell lines. Understanding the mechanistic basis for such induced resistance could have broad implications in areas from risk assessment to cancer treatment.

Low-dose hypersensitivity and induced radio-resistance may be related to the adaptive response to ionizing radiation, another potentially important physiological effect of low dose exposures. Exposure to a "priming" or "adapting" dose, usually in the range of 1-25 cGy, reduces the effects of a subsequent higher "challenge" dose (Stecca and Gerber, Biochem. Pharmacol. 55:941-51, 1998).

The phenomena of low-dose hypersensitivity and radio-adaptation raise the question of the requirement for a minimum threshold dose to induce a transcriptional response. The threshold effect is a factor to be considered for modeling low dose effects from results gathered at high doses, as the existence of a threshold implies that a dose can be identified below which exposure carries no risk of response (at least for the endpoint under consideration). The experiments showing low dose hypersensitivity have been interpreted to indicate a threshold, usually in the neighborhood of 25-30 cGy, which is required to activate inducible repair. Doses below this threshold are proportionately more toxic than doses which trigger the putative repair system. Radio-adaptive protection against cytogenetic aberrations or cell killing, however, has been shown to occur following doses as low as 1-2 cGy, indicating a much lower or even absent threshold for induction of this effect, and perhaps a distinct mechanism of action for the two phenomena.

While the genes studied in this example have not been implicated in induced repair, changes in mRNA levels in response to radiation in the dose range relevant to these phenomena have been observed. The data reveal no indication of a threshold for the induction of the genes studied. CIP1/WAF1 and GADD45 were significantly induced by as little as 2 cGy with a linear dose-response through 50 cGy (FIG. 7A). For MDM2, ATF3 and BAX, however, the possibility of a threshold for induction could not be distinguished from the noise of the assay (FIG. 7B). An additional complication to the interpretation of this data is that it is currently unknown if a threshold exists for biological significance of relative gene expression levels. It is likely that no generalized answer to this question will apply to all genes in all cell lines or cell types.

Figure 8B:
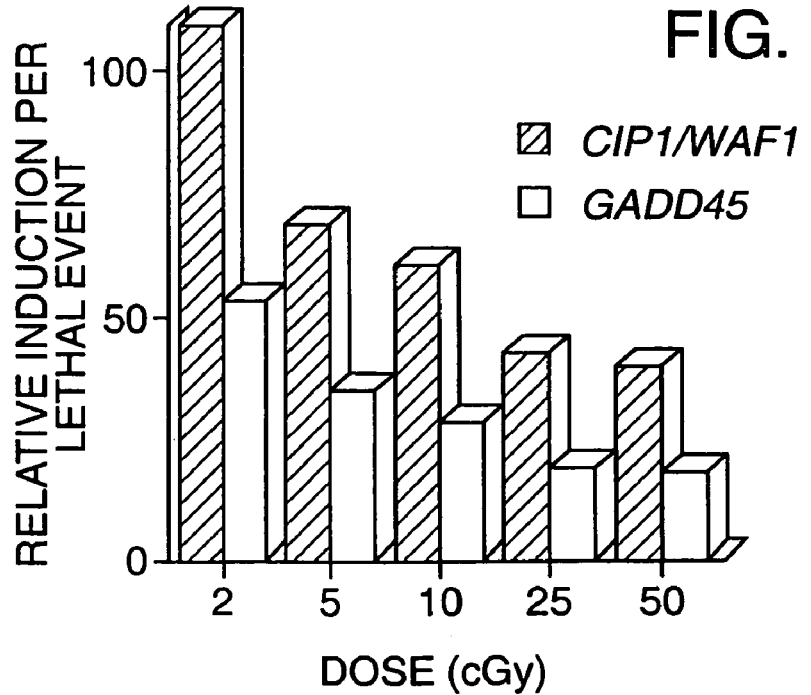
FIG. 8B is a bar graph showing the relative induction of CIP1/WAF1 and GADD45 which would be required per lethal event if the gene induction measured at low doses occurred only in lethally damaged cells. If only lethally damaged cells contributed to the observed gene induction, the induction per lethal event would be expected to be a constant for all doses. As this is not the case, it suggests surviving cells do contribute significantly to gene induction.

Although no evidence of a minimum threshold for induction of CIP1/WAF1 was observed, there was an upper limit to the linear increase in induction, as the induction by 50 cGy was about half that previously observed by 20 Gy (FIG. 7A). In experiments covering a wider range of doses from 10 cGy to 20 Gy, a saturation of induction of approximately 250 cGy was observed (FIG. 8A). At this dose, less than 5% of the cells retain mitotic viability. The coincidence of saturation for gene induction with nearly complete cell killing raises the issue of whether surviving cells contribute to the transcriptional response following even low doses of ionizing radiation, or if gene induction occurs only in lethally damaged cells. To address this question, the relative induction per lethally damaged cell which would be required to produce the inductions observed in the treated population as a whole, if the measured gene induction were due entirely to the response of lethally damaged, reproductively dead cells was calculated (FIG. 8B). For the doses where surviving fractions could not be measured directly, they were predicted from the survival curve (FIG. 1). In this model, each cell responding to 2 cGy would have to produce a relative induction of CIP1/WAF1 greater than 100-fold over the basal level to result in the observed induction of approximately 3.5-fold across the whole population. This relative induction per responding cell would then have to decrease with increasing dose through 50 cGy. Furthermore, as the proportion of the population suffering lethal damage increased further, the induction per responding cell would level out, then begin to increase again at doses above 5 Gy. A similar relationship was also calculated for the dose-response of GADD45 induction (FIG. 8B). If the measured gene induction were due entirely to the response of lethally damaged cells, the relative induction per lethal event would be expected to remain constant with changing dose and surviving fraction, so the relative induction of cell killing in an irradiated population would not appear to account for the observed increases in mRNA levels.

The contribution of cells which survive the treatment to the gene inductions measured at low doses would also be consistent with the disturbances in cell cycle progression observed at all doses tested. Even with 2 cGy, there was a transient decrease of S-phase cells in the population. This decrease corresponded to a larger proportion of the population than the predicted non-surviving fraction. A transient G1 delay following a consistent trend in both dose-response and temporal kinetics was observed (FIG. 3B). While the lowest dose used, 2 cGy, resulted in a brief accumulation of cells in G1, accumulation of cells in G2 appeared to require a higher dose. CIP1/WAF1, the transcript most strongly induced by low doses of γ-rays, is a major mediator of G1 arrest (Di Leonardo et al. *Genes Dev.* 8:2540-51, 1994; Waldman et al. *Cancer Res.* 55:5187-90, 1995). Thus, the observed G1 delay is consistent with this CIP1/WAF1 induction. A complete understanding of low-dose effects should not come solely from high dose experiments, but instead may require further careful studies in the low dose range.

Measurable differential gene expression effects were observed at relatively low, biologically relevant doses, such as 2 cGy. In radiotherapy the standard daily dose is about 2 Gy. Therefore, the results of these experiments indicate that the expression of many genes is altered at this dose. The probe sets of the present invention is capable of measuring exposure to relatively low doses of ionizing radiation (for example less than 2 Gy or 1 Gy) that may be considered non-toxic because of the absence of acute effects, but which may have short term effects that induce differential gene expression, and may have long term effects (such as carcinogenesis).

This example illustrates that probe sets that measure not only the fact of exposure to radiation, but also a probable dose of exposure to ionizing radiation, can be created by identifying genes that are differentially expressed at certain radiation doses. For example, probe sets can be designed which contain genes which are only differentially expressed at higher doses of irradiation (for example 20 Gy), or genes which are differentially expressed at lower doses of irradiation (for example 1-50 cGy). Furthermore, the methods for generating dose response curves described in this example can be used to select probes for the probe set, based on the probable time after radiation exposure occurred. Curves that show sustained or maximal expression 12, 24 or 48 hours after irradiation would identify probes that are useful for evaluation of genotoxic stress from exposure to ionizing radiation at times when clinical evaluations are likely to occur. In addition, patterns of probe set hybridization can also be associated with specified times following probable irradiation. After identifying the genes of interest, they can be incorporated into a probe set of a microarray.

EXAMPLE 4 p53-Associated Components of IR-Induction

This example demonstrates how to determine if the IR-induction of FRA-1 and ATF3 involve a p53 regulatory component. FRA-1 was induced by IR in some of the wt p53 lines, but was not induced in any of the p53 mutant lines studied (FIGS. 5A and 5B). In addition, the 5-fold IR-induction of ATF3 in RKO was attenuated in the RKO/E6 cell line, although some IR-induction was observed among the other p53 mutant cell lines. FIG. 9A shows the IR-induction of ATF3 in the p53 wild-type human carcinoma cell line RKO and in RKO/E6, in which p53 function has been abrogated by an E6 expression vector. RKO/E6 lacks appreciable functional p53. The disruption by E6 of ATF3 induction by IR supports a role for p53 in its induction.

To further examine the extent of dependence of ATF3 IR-induction on p53 status, in vivo induction was examined in wild-type and p53−/− (knockout) mice (Donehower et al., *Nature* 356:215-21, 1992) using 5 Gy whole-body γ-irradiation. While ATF3 was well induced by two hours after irradiation in the thymus of wild-type mice, there was no significant induction in the p53−/− mouse (FIG. 9A). ATF3 levels remained elevated at four and eight hours after irradiation in the thymus of wild-type mice, without any induction in the p53−/− mice. A similar trend was observed in the liver, where ATF3 was induced about 4-fold in the wild-type mouse, but showed no induction in the p53 knockout.

ATF3 is a member of the activating transcription factor/cAMP response element binding protein (ATF/CREB) family which homodimerizes to repress transcription from promoters with ATF sites. An alternatively spliced form of the ATF3 transcript, which lacks DNA binding activity, is also expressed in cells, but this form promotes transcription (Chen et al., *J. Biol. Chem.* 269:15819-26, 1994). The sizes of ATF3 transcripts hybridizing on the northern blot demonstrated that the smaller alternatively spliced form was the major transcript expressed in untreated ML-1 cells, whereas the IR-induced transcript was predominantly of the full length form.

The induction of ATF3 by the DNA-damaging agents MMS and UV radiation in all 12 cell lines examined (FIG. 5) extends the range of stress responses in which ATF3 is involved. Its wide-ranging responsiveness is similar to CIP1/WAF1 and GADD45, which are stress inducible by both p53-dependent and independent mechanisms, and highlights the complexity of ATF3 regulation.

Although FRA-1 was not IR-inducible in RKO cells, a similar comparison was possible using the MCF7 and MCF7/E6 cell lines. The human breast carcinoma cell line MCF7 has wild-type p53, while MCF7/E6 has lacked appreciable wild-type p53 function. The reduced IR-induction of FRA-1 in MCF7/E6 compared to MCF7 supports a role for p53 in the IR-induction of this gene (FIG. 9B). Furthermore, whole-body γ-irradiation of wild-type mice resulted in FRA-1 induction in the thymus, but no induction occurred in the thymus of the p53−/− (FIG. 9B). Such results can be used to select certain probes (for example FRA-1) for detection of whole-body radiation. FRA-1 is an immediate early gene induced by serum stimulation, the product of which shares several regions of amino acid homology with Fos. It is also down-regulated by UVB and upregulated by UVA. Because of its homology to Fos, and the involvement of p53 in its IR-induction, FRA-1 the use of the present assay can be taken to demonstrate a link between p53 and AP1 function and the MAPK pathway.

MBP-1 represented another potentially p53 regulated gene, showing a pattern similar to that seen for BAX or BCL-X, in that it was induced only in p53-wild-type cell lines of lymphoid or myeloid lineage. The induction of the murine homolog of MBP-1 in the tissues of wild-type and p53−/− mice was observed to have marginal to absent expression in liver and thymus, but strong expression in spleen. Treatment with ionizing radiation resulted in a 2-fold induction of this gene in the spleens of both p53 wild-type and p53−/− mice, suggesting that this gene does not require p53 function for its induction, but that its expression and induction are both limited to a subset of cell types. This would be consistent with a role for MBP-1 in tissue specific p53-independent stress responses.

The finding that only two of nine of these genes examined in this cell line panel showed a recognizable p53 component to their regulation belies the recent focus of stress-gene studies primarily on p53-regulated genes. In light of the loss of functional p53 in the majority of tumors, the non-p53-dependent stress response genes appears to also be an important consideration in cancer treatment.

An advantage o the present invention is its ability to examine both p53-regulated and non-p53 regulated genes, or other combinations of gene types (for example genes which are recognized oncogenes or genes which are not recognized oncogenes). Quantitative functional genomics approaches, such as cDNA microarray hybridization, can also be used in combination with the radiation sensor array to unravel the inter-relationships of the molecular response pathways involved. Although radioactive-probe hybridization to nylon filter arrays provides a useful method to screen for potential genes of interest which differ in expression levels between two samples, differential screening has its own limitations (Fargnoli et al., *Anal Biochem* 187:364-73, 1990) some of which are avoided by the use of probes labeled with different fluorochromes co-hybridized to the same microarray. Other methods for identification of differentially expressed mRNAs, such as differential display, subtractive library hybridization and serial analysis of gene expression (SAGE) (Velculescu et al., *Science* 270:484-7, 1995), can be biased toward detection of highly-expressed and/or strongly-induced transcripts.

With the microarray approach of the present invention, quantitative results over a wide dynamic range were obtained for many genes. The application and further refinement of quantitative fluorescent cDNA microarray hybridization have the potential to advance our understanding of the fields of stress gene response and radiation biology, and to extend this technology beyond simple pair-wise comparisons to applications such as tumor typing, pharmacological screening, biomonitoring, and rapid carcinogen screening.

This example combined with the results from EXAMPLE 2 illustrate that probe sets that measure differential expression in response to a biologically significant amount of radiation for specific tumors can be generated. Such probe sets can be used to monitor a subject who is undergoing radiotherapy for the treatment of a tumor. For example, probe sets can be designed which contain genes from a specific type of tumor, which are differentially expressed in response to irradiation of the tumor cells. This probe set would then be used to monitor a subject's response to the radiotherapy. Further details are provided in EXAMPLE 10. As an extension of this probe set, the present method can be used in "tumor profiling," wherein gene expression profiles are used to predict the most effective treatment for each individual subject. In this method, cells would be isolated from the tumor in a subject, and the differential expression of the genes in that tumor in response to irradiation measured as described in the examples herein. A pattern of differential expression found to be associated with a particular therapeutic response to radiation therapy can then be used as a factor when considering whether to include radiation therapy in the treatment of the tumor. For example, a pattern of differential expression associated with a good response to radiation therapy could be used to indicate that radiation therapy should be instituted.

EXAMPLE 5

New Radiation Responsive Sequences

Using the ML-1 cancer cell line and the cDNA microarray hybridization technology described in this specification, 30 sequences from ML-1 were identified that were not previously known to be radiation-responsive. These sequences are Image ID Nos. 428248, 129632, 52681, 52530, 110503, 236422, 153355, 52753, 51363, 161023, 35326, 487130, 291503, 41452, 23464, 243143, 205633, 21420, 48677, 43060, 233194, 295093, 48085, 26541, 28089, 359119, 28116, 80549, 485963, 24927. Arrays can be made that incorporate these sequences, or probe fragments thereof, along with controls and/or other sequences that are already known to be informative about radiation exposure, and/or dosage of radiation exposure.

EXAMPLE 6

Late Induced Genes

This example describes detection of differential gene expression in irradiated ML-1 cells using different microarrays. Although the specific example discloses expression in ML-1 cells, this method can be used to detect differential gene expression in any cell type.

ML-1 cells were grown and irradiated as described in EXAMPLE 1. Labeled cDNA subsequently prepared from the irradiated cells was exposed to various arrays as described in EXAMPLE 2. cDNA microarray hybridization studies were performed with the 1.2K chip described in EXAMPLE 2 which contained 1,200 probes in a probe set (Table 1), a 5K chip which contained 5,000 probes in a probe set, and a 7K chip which contained 7,000 probes in a probe set. The 5K and 7K chips contained representative verified expressed ESTs from the human genome, and were designed to permit as much as possible of the human genome to be screened using irradiated ML-1 cells. The arrays used represent the largest sequence verified clone sets available to print at the time of the experiments. As more clones become available, they are added to new prints to be screened. The 1.2K array was a smaller set of ESTs designed for the same purpose (see EXAMPLE 2).

Table 4 shows the clones used to make the 1.2K array along with data showing the relative expression detected at each position of the array. The clones used to make the 5K array are identified in Table 5 and for the 7K array in Table 6. Although these particular arrays were used in these experiments, other arrays may be used. For example, as additional arrays become available that include even more ESTs, additional biomarkers of radiation exposure can be found and added to the probe sets disclosed in Tables 9-13. Moreover, the 1.2K, 5K, and 7K arrays can also be used with different cells (such as human peripheral lymphocytes) to screen for other markers that would be even more informative when testing those cells.

TABLE 4

Results from the 1.2K microarray.

| Image ID or clone name | array ratio* |
|---|---|
| Waf1 | 42.02 |
| 268652 | 18.76 |
| 428248 | 14.53 |
| 428248 | 11.32 |
| 151767 | 9.48 |
| 129632 | 9.29 |
| 52681 | 7.17 |
| 512391 | 6.92 |
| 52530 | 6.37 |
| 110503 | 4.83 |
| 328692 | 4.82 |
| 124554 | 4.73 |

TABLE 4-continued

Results from the 1.2K microarray.

| Image ID or clone name | array ratio* |
|---|---|
| 236422 | 4.64 |
| 153355 | 4.32 |
| 26474 | 4.20 |
| 309477 | 4.17 |
| 52681 | 4.03 |
| 52753 | 3.40 |
| 280376 | 3.39 |
| 51363 | 3.38 |
| 470602 | 3.23 |
| 147075 | 3.17 |
| 161023 | 3.13 |
| 35326 | 3.12 |
| HIV F2 | 3.10 |
| 470062 | 3.03 |
| 120466 | 3.02 |
| CoT1 | 3.01 |
| 486074 | 2.93 |
| 112500 | 2.83 |
| 471252 | 2.81 |
| 487130 | 2.77 |
| 291503 | 2.76 |
| Mdm2 | 2.72 |
| 41452 | 2.65 |
| 52681 | 2.64 |
| Bak | 2.57 |
| 23464 | 2.53 |
| 243143 | 2.51 |
| 205633 | 2.51 |
| 284031 | 2.49 |
| 21420 | 2.47 |
| 48677 | 2.41 |
| 485963 | 2.34 |
| 162772 | 2.32 |
| Hu placental | 2.32 |
| 51439 | 2.30 |
| 126379 | 2.29 |
| 253545 | 2.27 |
| 80549 | 2.26 |
| Bcl-xl | 2.26 |
| 156103 | 2.25 |
| 489395 | 2.24 |
| 24927 | 2.23 |
| 27899 | 2.19 |
| 427923 | 2.17 |
| 286249 | 2.15 |
| 53164 | 2.14 |
| 470685 | 2.10 |
| 47679 | 2.09 |
| 116906 | 2.08 |
| HIV F8 | 2.07 |
| 21531 | 2.04 |
| 280768 | 2.04 |
| 178508 | 2.03 |
| 512472 | 2.03 |
| 121849 | 2.02 |
| 42906 | 2.01 |
| 52650 | 2.01 |
| 145503 | 2.01 |
| 110022 | 1.98 |
| 343311 | 1.98 |
| 149910 | 1.98 |
| 137531 | 1.97 |
| mouse c-kit | 1.97 |
| 231292 | 1.94 |
| mouseEDNRB | 1.94 |
| 290871 | 1.92 |
| 52193 | 1.91 |
| 26871 | 1.91 |
| 152844 | 1.91 |
| 23173 | 1.90 |
| 49164 | 1.89 |
| 512385 | 1.89 |
| 289606 | 1.89 |
| 108837 | 1.88 |

TABLE 4-continued

Results from the 1.2K microarray.

| Image ID or clone name | array ratio* |
|---|---|
| 283116 | 1.86 |
| 361381 | 1.86 |
| 51746 | 1.85 |
| 187987 | 1.85 |
| 132420 | 1.84 |
| 299198 | 1.84 |
| 154420 | 1.84 |
| 33941 | 1.83 |
| 376218 | 1.83 |
| 140358 | 1.83 |
| 116781 | 1.83 |
| 154420 | 1.83 |
| 359769 | 1.82 |
| 471494 | 1.81 |
| 486844 | 1.81 |
| 486716 | 1.80 |
| 308392 | 1.79 |
| empty | 1.79 |
| HIV F4 | 1.79 |
| 47229 | 1.78 |
| 39920 | 1.78 |
| 486785 | 1.77 |
| 203132 | 1.77 |
| 200209 | 1.76 |
| 123586 | 1.76 |
| 60298 | 1.76 |
| 296642 | 1.75 |
| 146307 | 1.74 |
| 429539 | 1.74 |
| 260288 | 1.73 |
| 73515 | 1.72 |
| 53173 | 1.72 |
| HIV F12 | 1.72 |
| 322604 | 1.71 |
| 125187 | 1.71 |
| 417357 | 1.71 |
| 77577 | 1.70 |
| 279954 | 1.70 |
| 417403 | 1.70 |
| 428231 | 1.69 |
| 120157 | 1.69 |
| 321242 | 1.68 |
| 264576 | 1.68 |
| 486199 | 1.68 |
| 158970 | 1.68 |
| 153025 | 1.68 |
| 41959 | 1.67 |
| 72869 | 1.67 |
| empty | 1.67 |
| HIV F5 | 1.66 |
| 53184 | 1.66 |
| 327111 | 1.66 |
| 307342 | 1.66 |
| 155717 | 1.66 |
| Alk | 1.65 |
| 135118 | 1.65 |
| 183661 | 1.65 |
| 34974 | 1.65 |
| 52162 | 1.64 |
| 22790 | 1.64 |
| mouse c-met | 1.64 |
| 154472 | 1.64 |
| 22036 | 1.63 |
| 35516 | 1.63 |
| 362702 | 1.63 |
| 417592 | 1.63 |
| 46427 | 1.63 |
| 360531 | 1.63 |
| 359793 | 1.63 |
| 298371 | 1.61 |
| 486161 | 1.61 |
| 310141 | 1.61 |
| 22589 | 1.61 |
| 418111 | 1.61 |
| 139073 | 1.61 |
| 31687 | 1.61 |
| 289428 | 1.61 |
| 366539 | 1.60 |
| 512276 | 1.60 |
| 127821 | 1.60 |
| mouse EDN3 | 1.59 |
| 377275 | 1.59 |
| 109957 | 1.59 |
| 147744 | 1.59 |
| 258589 | 1.58 |
| 29627 | 1.58 |
| 53358 | 1.58 |
| 306134 | 1.58 |
| 295389 | 1.58 |
| 21656 | 1.57 |
| 127089 | 1.57 |
| 30966 | 1.56 |
| mouse pme117 | 1.56 |
| 470730 | 1.55 |
| 471822 | 1.55 |
| 43231 | 1.55 |
| HIV F9 | 1.54 |
| 35665 | 1.54 |
| 154015 | 1.54 |
| 158970 | 1.54 |
| 363805 | 1.53 |
| 36676 | 1.53 |
| 47306 | 1.53 |
| 28774 | 1.53 |
| 209655 | 1.53 |
| 488103 | 1.53 |
| 50603 | 1.53 |
| 469543 | 1.53 |
| 143751 | 1.52 |
| 284546 | 1.52 |
| 51825 | 1.51 |
| 22012 | 1.51 |
| 509731 | 1.51 |
| 144693 | 1.51 |
| 138917 | 1.51 |
| 126542 | 1.51 |
| 38573 | 1.50 |
| 36927 | 1.50 |
| 236420 | 1.50 |
| 488801 | 1.50 |
| 137575 | 1.50 |
| 86017 | 1.49 |
| 31061 | 1.49 |
| 303109 | 1.48 |
| 22589 | 1.48 |
| 35865 | 1.48 |
| 359466 | 1.48 |
| 238577 | 1.48 |
| 302490 | 1.48 |
| 40442 | 1.48 |
| 36593 | 1.47 |
| 344482 | 1.47 |
| 471715 | 1.47 |
| 288650 | 1.47 |
| 470251 | 1.47 |
| 364110 | 1.46 |
| 154763 | 1.46 |
| 36809 | 1.46 |
| 36904 | 1.45 |
| 37797 | 1.45 |
| 298371 | 1.44 |
| 253869 | 1.44 |
| 21468 | 1.44 |
| 50503 | 1.44 |
| 270980 | 1.44 |
| 345928 | 1.44 |
| 35559 | 1.44 |
| mouse pdgfra | 1.43 |

TABLE 4-continued

Results from the 1.2K microarray.

| Image ID or clone name | array ratio* |
|---|---|
| 366420 | 1.43 |
| 205905 | 1.43 |
| 37347 | 1.43 |
| 288797 | 1.43 |
| 50941 | 1.43 |
| 37513 | 1.42 |
| 33415 | 1.42 |
| 221619 | 1.41 |
| 429976 | 1.41 |
| 136769 | 1.40 |
| 44180 | 1.40 |
| 254187 | 1.40 |
| 362009 | 1.39 |
| 30981 | 1.39 |
| 272110 | 1.39 |
| 51332 | 1.39 |
| 49725 | 1.39 |
| 472067 | 1.38 |
| 49967 | 1.38 |
| 36074 | 1.38 |
| 34396 | 1.38 |
| 418138 | 1.38 |
| 49509 | 1.38 |
| 154441 | 1.38 |
| 357807 | 1.38 |
| 281029 | 1.37 |
| syn cDNA 33 | 1.37 |
| 48803 | 1.37 |
| 46171 | 1.37 |
| 53155 | 1.36 |
| 429142 | 1.36 |
| 26811 | 1.36 |
| syn cDNA 33 | 1.36 |
| 32427 | 1.35 |
| 47874 | 1.35 |
| 270148 | 1.35 |
| 489419 | 1.35 |
| 266486 | 1.34 |
| 48398 | 1.34 |
| 34247 | 1.34 |
| 31855 | 1.34 |
| lambda | 1.34 |
| 162479 | 1.34 |
| 41439 | 1.34 |
| 193901 | 1.34 |
| 376303 | 1.34 |
| 254428 | 1.34 |
| 299539 | 1.34 |
| 510381 | 1.34 |
| 25880 | 1.33 |
| 364752 | 1.33 |
| 178169 | 1.33 |
| 25495 | 1.33 |
| 510258 | 1.33 |
| 39285 | 1.33 |
| 204301 | 1.33 |
| 26992 | 1.33 |
| 268412 | 1.33 |
| 26801 | 1.33 |
| 358168 | 1.33 |
| 44495 | 1.33 |
| 40117 | 1.33 |
| 182633 | 1.32 |
| mouse ece 1 | 1.32 |
| 264554 | 1.32 |
| 31210 | 1.32 |
| 49576 | 1.32 |
| 300973 | 1.32 |
| 44307 | 1.32 |
| 288733 | 1.32 |
| 323001 | 1.31 |
| 22379 | 1.31 |
| 487264 | 1.31 |
| 346396 | 1.31 |
| 44193 | 1.31 |
| 51293 | 1.31 |
| 82991 | 1.30 |
| 34217 | 1.30 |
| 27944 | 1.30 |
| 40562 | 1.30 |
| 363539 | 1.30 |
| 50503 | 1.30 |
| 264200 | 1.30 |
| 50816 | 1.30 |
| 417689 | 1.30 |
| 258790 | 1.30 |
| 417218 | 1.30 |
| 124927 | 1.30 |
| lambda | 1.29 |
| 35284 | 1.29 |
| 203017 | 1.29 |
| 213597 | 1.29 |
| 38393 | 1.29 |
| 509882 | 1.29 |
| 154536 | 1.29 |
| 128100 | 1.29 |
| 296021 | 1.28 |
| 52587 | 1.28 |
| 35609 | 1.28 |
| 359412 | 1.28 |
| 159833 | 1.28 |
| 33368 | 1.27 |
| 376781 | 1.27 |
| 512294 | 1.27 |
| 234198 | 1.27 |
| empty | 1.27 |
| 49666 | 1.27 |
| 162584 | 1.26 |
| 365147 | 1.26 |
| 268727 | 1.26 |
| 183950 | 1.26 |
| 489042 | 1.26 |
| 44722 | 1.25 |
| 486510 | 1.25 |
| 179711 | 1.25 |
| 41208 | 1.25 |
| 320903 | 1.25 |
| 23866 | 1.25 |
| 53024 | 1.25 |
| 47359 | 1.24 |
| 191007 | 1.24 |
| 48097 | 1.24 |
| 344109 | 1.24 |
| 198205 | 1.24 |
| 46019 | 1.24 |
| 27624 | 1.24 |
| HIV F11 | 1.24 |
| 236338 | 1.24 |
| 32304 | 1.23 |
| 322452 | 1.23 |
| syn cDNA 10 | 1.23 |
| 115277 | 1.23 |
| 201673 | 1.23 |
| mouse aim 1/2.2 | 1.23 |
| 46354 | 1.23 |
| 428404 | 1.23 |
| 471174 | 1.23 |
| 43229 | 1.22 |
| 306170 | 1.22 |
| 39148 | 1.22 |
| 249348 | 1.22 |
| 51686 | 1.22 |
| 253773 | 1.21 |
| 322000 | 1.21 |
| 25485 | 1.21 |
| 361692 | 1.21 |
| 47343 | 1.21 |

TABLE 4-continued

Results from the 1.2K microarray.

| Image ID or clone name | array ratio* |
|---|---|
| 510130 | 1.21 |
| 133122 | 1.21 |
| 37435 | 1.21 |
| 340947 | 1.21 |
| syn cDNA 31 | 1.21 |
| 209310 | 1.21 |
| 234357 | 1.21 |
| 298314 | 1.21 |
| 302394 | 1.21 |
| 360201 | 1.20 |
| 42927 | 1.20 |
| 47499 | 1.20 |
| 39086 | 1.20 |
| 487097 | 1.20 |
| 219735 | 1.20 |
| 488596 | 1.20 |
| 37962 | 1.20 |
| 49888 | 1.19 |
| 31988 | 1.19 |
| 51687 | 1.19 |
| 34761 | 1.19 |
| 34860 | 1.19 |
| 488989 | 1.19 |
| 377441 | 1.19 |
| 108284 | 1.19 |
| 36844 | 1.19 |
| 510467 | 1.19 |
| 290117 | 1.19 |
| 23185 | 1.19 |
| 241412 | 1.19 |
| 290724 | 1.19 |
| 40026 | 1.19 |
| 42363 | 1.19 |
| 356890 | 1.19 |
| 25081 | 1.18 |
| mouse tyrosinase | 1.18 |
| HIV F13 | 1.18 |
| 323162 | 1.18 |
| 363799 | 1.18 |
| 193736 | 1.18 |
| 48077 | 1.18 |
| 323555 | 1.18 |
| 37508 | 1.18 |
| 50666 | 1.18 |
| 44477 | 1.18 |
| 429926 | 1.18 |
| 45794 | 1.17 |
| CoT1 | 1.17 |
| 35110 | 1.17 |
| 509820 | 1.17 |
| 46042 | 1.17 |
| 509682 | 1.17 |
| 512244 | 1.17 |
| 42648 | 1.17 |
| 40304 | 1.17 |
| 359077 | 1.17 |
| 469731 | 1.17 |
| 364975 | 1.16 |
| 82850 | 1.16 |
| 488373 | 1.16 |
| 110589 | 1.16 |
| 37231 | 1.16 |
| 52629 | 1.16 |
| 231497 | 1.16 |
| 286197 | 1.16 |
| 144944 | 1.16 |
| 298314 | 1.16 |
| 48452 | 1.16 |
| 510101 | 1.16 |
| 342256 | 1.16 |
| 358467 | 1.16 |
| 305455 | 1.16 |
| 40831 | 1.15 |
| 47493 | 1.15 |
| 375922 | 1.15 |
| 252185 | 1.15 |
| 39542 | 1.15 |
| 37679 | 1.15 |
| 33176 | 1.15 |
| 36291 | 1.15 |
| 469256 | 1.15 |
| mouse slug | 1.15 |
| 27848 | 1.15 |
| 195889 | 1.15 |
| 80549 | 1.14 |
| 42910 | 1.14 |
| 365647 | 1.14 |
| 32531 | 1.14 |
| 247869 | 1.14 |
| 52019 | 1.14 |
| 324700 | 1.14 |
| 26585 | 1.14 |
| 262691 | 1.14 |
| 32774 | 1.14 |
| 33267 | 1.14 |
| 51318 | 1.14 |
| 36560 | 1.14 |
| 125555 | 1.14 |
| 37904 | 1.14 |
| 32319 | 1.13 |
| 36922 | 1.13 |
| 51666 | 1.13 |
| 260052 | 1.13 |
| 361692 | 1.13 |
| 36975 | 1.13 |
| 180447 | 1.13 |
| 30272 | 1.13 |
| 23692 | 1.13 |
| 44178 | 1.13 |
| 42576 | 1.13 |
| 36007 | 1.13 |
| empty | 1.13 |
| 44266 | 1.13 |
| syn cDNA 10 | 1.13 |
| 49318 | 1.13 |
| 34005 | 1.12 |
| 40670 | 1.12 |
| 324815 | 1.12 |
| 272110 | 1.12 |
| 427750 | 1.12 |
| 125676 | 1.12 |
| 49584 | 1.12 |
| 359171 | 1.12 |
| 470493 | 1.12 |
| 361728 | 1.12 |
| 42532 | 1.12 |
| 44710 | 1.11 |
| 51528 | 1.11 |
| 307471 | 1.11 |
| mouse mart1 | 1.11 |
| 241489 | 1.11 |
| 242134 | 1.11 |
| 487965 | 1.11 |
| 43858 | 1.11 |
| 259241 | 1.11 |
| 471096 | 1.11 |
| 49777 | 1.10 |
| 231292 | 1.10 |
| 43129 | 1.10 |
| 23731 | 1.10 |
| 53084 | 1.10 |
| 53107 | 1.10 |
| 271416 | 1.10 |
| syn cDNA 10 | 1.10 |
| 44218 | 1.10 |
| empty | 1.10 |
| 429368 | 1.10 |

TABLE 4-continued

Results from the 1.2K microarray.

| Image ID or clone name | array ratio* |
|---|---|
| 364278 | 1.09 |
| 22260 | 1.09 |
| 26052 | 1.09 |
| 84730 | 1.09 |
| 25517 | 1.09 |
| 50032 | 1.09 |
| 52489 | 1.09 |
| 30592 | 1.09 |
| 50117 | 1.09 |
| 135381 | 1.09 |
| 44105 | 1.09 |
| 427686 | 1.09 |
| 346587 | 1.09 |
| 24110 | 1.09 |
| 470185 | 1.09 |
| 49665 | 1.09 |
| 33477 | 1.09 |
| 40765 | 1.08 |
| 29204 | 1.08 |
| 47475 | 1.08 |
| 40493 | 1.08 |
| 79742 | 1.08 |
| 39195 | 1.08 |
| 271416 | 1.08 |
| 30885 | 1.08 |
| 43711 | 1.08 |
| 23073 | 1.08 |
| 52773 | 1.08 |
| syn cDNA 8 | 1.08 |
| 39796 | 1.08 |
| 36232 | 1.08 |
| 44367 | 1.08 |
| 231302 | 1.08 |
| 40205 | 1.08 |
| 44414 | 1.08 |
| 27715 | 1.08 |
| 33643 | 1.08 |
| 26599 | 1.08 |
| 347751 | 1.08 |
| 26599 | 1.08 |
| 33525 | 1.08 |
| 29054 | 1.07 |
| 31116 | 1.07 |
| 36950 | 1.07 |
| 320514 | 1.07 |
| 45564 | 1.07 |
| 488658 | 1.07 |
| 26593 | 1.07 |
| 488904 | 1.07 |
| 30730 | 1.07 |
| syn cDNA 30 | 1.07 |
| 418436 | 1.07 |
| 51373 | 1.07 |
| syn cDNA 31 | 1.07 |
| 470470 | 1.06 |
| 36700 | 1.06 |
| 38966 | 1.06 |
| syn cDNA 30 | 1.06 |
| syn cDNA 33 | 1.06 |
| 51961 | 1.06 |
| 34637 | 1.06 |
| 30622 | 1.06 |
| 39380 | 1.06 |
| 282065 | 1.06 |
| 46329 | 1.06 |
| 486410 | 1.06 |
| syn cDNA 38 | 1.06 |
| 40008 | 1.06 |
| 37721 | 1.06 |
| 47110 | 1.06 |
| 37892 | 1.06 |
| 33831 | 1.06 |
| 51940 | 1.05 |
| 41094 | 1.05 |
| 114116 | 1.05 |
| 271478 | 1.05 |
| 232714 | 1.05 |
| 43719 | 1.05 |
| 343871 | 1.05 |
| 26659 | 1.05 |
| 24652 | 1.05 |
| 306013 | 1.05 |
| 42677 | 1.05 |
| 47202 | 1.05 |
| 31852 | 1.04 |
| 362926 | 1.04 |
| 39173 | 1.04 |
| 52222 | 1.04 |
| 22545 | 1.04 |
| 26789 | 1.04 |
| 258747 | 1.04 |
| 53068 | 1.04 |
| 418105 | 1.04 |
| 30852 | 1.04 |
| 35850 | 1.04 |
| 33632 | 1.04 |
| 53238 | 1.04 |
| 364982 | 1.03 |
| 486086 | 1.03 |
| 43338 | 1.03 |
| HIV F6 | 1.03 |
| HIV F10 | 1.03 |
| 45840 | 1.03 |
| 23804 | 1.03 |
| 52896 | 1.03 |
| 417136 | 1.03 |
| empty | 1.03 |
| 40111 | 1.03 |
| 29629 | 1.02 |
| 34647 | 1.02 |
| 41565 | 1.02 |
| 23831 | 1.02 |
| 204681 | 1.02 |
| 44014 | 1.02 |
| 145932 | 1.02 |
| 32875 | 1.02 |
| 26503 | 1.02 |
| 357374 | 1.02 |
| 429057 | 1.02 |
| 32198 | 1.01 |
| 22040 | 1.01 |
| 36681 | 1.01 |
| 47333 | 1.01 |
| 50271 | 1.01 |
| 375843 | 1.01 |
| 376725 | 1.01 |
| 42059 | 1.01 |
| 39861 | 1.01 |
| 45941 | 1.01 |
| 33274 | 1.01 |
| 271198 | 1.01 |
| 24886 | 1.01 |
| 33690 | 1.01 |
| 33438 | 1.01 |
| 24609 | 1.01 |
| 470817 | 1.01 |
| 49691 | 1.01 |
| 110589 | 1.00 |
| 310428 | 1.00 |
| 25400 | 1.00 |
| syn cDNA 8 | 1.00 |
| 52338 | 1.00 |
| 32717 | 1.00 |
| 323500 | 1.00 |
| 27473 | 1.00 |
| 295208 | 1.00 |
| syn cDNA 25 | 1.00 |
| lambda | 1.00 |

TABLE 4-continued

Results from the 1.2K microarray.

| Image ID or clone name | array ratio* |
|---|---|
| 32822 | 1.00 |
| 46303 | 1.00 |
| 31242 | 1.00 |
| 42352 | 1.00 |
| 194384 | 1.00 |
| 36844 | 0.99 |
| 44537 | 0.99 |
| 347573 | 0.99 |
| 485690 | 0.99 |
| 486335 | 0.99 |
| 40764 | 0.99 |
| 30573 | 0.99 |
| 190711 | 0.99 |
| 50576 | 0.99 |
| 26087 | 0.99 |
| 41773 | 0.99 |
| syn cDNA 31 | 0.99 |
| 43549 | 0.99 |
| 50363 | 0.99 |
| 52489 | 0.99 |
| 39827 | 0.99 |
| 427943 | 0.99 |
| 53128 | 0.99 |
| 42130 | 0.99 |
| 52931 | 0.99 |
| 46302 | 0.99 |
| pUC18 | 0.99 |
| 50609 | 0.99 |
| 27681 | 0.99 |
| 35933 | 0.99 |
| empty | 0.99 |
| 53185 | 0.99 |
| 301723 | 0.99 |
| 31155 | 0.99 |
| 33803 | 0.99 |
| empty | 0.99 |
| 38829 | 0.98 |
| 34005 | 0.98 |
| 36916 | 0.98 |
| 44563 | 0.98 |
| 42993 | 0.98 |
| syn cDNA 31 | 0.98 |
| 36790 | 0.98 |
| 366576 | 0.98 |
| 418320 | 0.98 |
| 52342 | 0.98 |
| 487878 | 0.98 |
| 37196 | 0.98 |
| 39781 | 0.98 |
| 341763 | 0.98 |
| 37796 | 0.98 |
| 470635 | 0.98 |
| 31454 | 0.98 |
| 51432 | 0.98 |
| 36109 | 0.98 |
| 46777 | 0.98 |
| syn cDNA 38 | 0.98 |
| 305455 | 0.98 |
| 47384 | 0.97 |
| 300051 | 0.97 |
| 85906 | 0.97 |
| 29640 | 0.97 |
| Bcl-2 | 0.97 |
| 377181 | 0.97 |
| aim2/IFI16 | 0.97 |
| 209310 | 0.97 |
| 380738 | 0.97 |
| 415731 | 0.97 |
| 345600 | 0.97 |
| 40151 | 0.97 |
| 26167 | 0.97 |
| 28309 | 0.97 |
| 33692 | 0.97 |
| 429861 | 0.97 |
| 126519 | 0.97 |
| 357909 | 0.97 |
| 33620 | 0.97 |
| 25154 | 0.96 |
| 51785 | 0.96 |
| 51814 | 0.96 |
| 484993 | 0.96 |
| 25584 | 0.96 |
| 486560 | 0.96 |
| 50322 | 0.96 |
| 415679 | 0.96 |
| 343166 | 0.96 |
| 32898 | 0.96 |
| 471631 | 0.96 |
| 33183 | 0.96 |
| 31116 | 0.96 |
| 25169 | 0.95 |
| 366981 | 0.95 |
| 38567 | 0.95 |
| 44605 | 0.95 |
| 44666 | 0.95 |
| 239287 | 0.95 |
| 37234 | 0.95 |
| 45421 | 0.95 |
| 327396 | 0.95 |
| 35623 | 0.95 |
| 44159 | 0.95 |
| 48713 | 0.95 |
| 427943 | 0.95 |
| 35297 | 0.95 |
| 23332 | 0.95 |
| 37451 | 0.95 |
| 31131 | 0.95 |
| 42058 | 0.95 |
| 259291 | 0.95 |
| 46574 | 0.95 |
| 51241 | 0.95 |
| 486233 | 0.94 |
| 196543 | 0.94 |
| 49898 | 0.94 |
| 43601 | 0.94 |
| 200378 | 0.94 |
| syn cDNA 25 | 0.94 |
| 323648 | 0.94 |
| 48717 | 0.94 |
| 46339 | 0.94 |
| 30691 | 0.94 |
| 328467 | 0.94 |
| 39965 | 0.94 |
| 427857 | 0.94 |
| Gadd153 | 0.94 |
| 51418 | 0.94 |
| syn cDNA 25 | 0.94 |
| 361401 | 0.93 |
| 38876 | 0.93 |
| 49788 | 0.93 |
| 32609 | 0.93 |
| 32626 | 0.93 |
| 33008 | 0.93 |
| 39686 | 0.93 |
| 50555 | 0.93 |
| 23346 | 0.93 |
| 30802 | 0.93 |
| 47038 | 0.93 |
| 44302 | 0.93 |
| syn cDNA 30 | 0.93 |
| 36202 | 0.93 |
| 34327 | 0.92 |
| 267246 | 0.92 |
| 34141 | 0.92 |
| 307741 | 0.92 |
| 301363 | 0.92 |
| 26503 | 0.92 |
| 32649 | 0.92 |

TABLE 4-continued

Results from the 1.2K microarray.

| Image ID or clone name | array ratio* |
|---|---|
| 37230 | 0.92 |
| 45222 | 0.92 |
| 324698 | 0.92 |
| 37269 | 0.92 |
| 376737 | 0.92 |
| 29799 | 0.92 |
| 488891 | 0.92 |
| 41392 | 0.92 |
| 41813 | 0.92 |
| 23019 | 0.92 |
| 140827 | 0.92 |
| 37433 | 0.92 |
| HIV F7 | 0.92 |
| 46213 | 0.92 |
| 36393 | 0.92 |
| syn cDNA 8 | 0.92 |
| 44311 | 0.92 |
| 42888 | 0.92 |
| 53316 | 0.92 |
| 486375 | 0.91 |
| 49926 | 0.91 |
| 49950 | 0.91 |
| 40959 | 0.91 |
| 357357 | 0.91 |
| syn cDNA 38 | 0.91 |
| 323776 | 0.91 |
| 30588 | 0.91 |
| 35313 | 0.91 |
| 41857 | 0.91 |
| 53322 | 0.91 |
| 47125 | 0.91 |
| 357442 | 0.91 |
| 40440 | 0.91 |
| 38805 | 0.90 |
| 49897 | 0.90 |
| 51540 | 0.90 |
| TRP1 | 0.90 |
| syn cDNA 10 | 0.90 |
| 28985 | 0.90 |
| 26599 | 0.90 |
| 22293 | 0.90 |
| 26147 | 0.90 |
| 41199 | 0.90 |
| 415636 | 0.90 |
| 30664 | 0.90 |
| 46419 | 0.90 |
| 485192 | 0.90 |
| 39903 | 0.90 |
| 42615 | 0.90 |
| 512429 | 0.90 |
| 347032 | 0.90 |
| 359465 | 0.90 |
| 302157 | 0.90 |
| empty | 0.90 |
| 43110 | 0.89 |
| 361815 | 0.89 |
| 50576 | 0.89 |
| 40991 | 0.89 |
| 44699 | 0.89 |
| 321246 | 0.89 |
| 34537 | 0.89 |
| 43409 | 0.89 |
| 325182 | 0.89 |
| 36215 | 0.89 |
| syn cDNA 30 | 0.89 |
| 52415 | 0.89 |
| mouse mi/microphthalmia | 0.89 |
| 33045 | 0.89 |
| 37380 | 0.89 |
| 42096 | 0.89 |
| 471889 | 0.89 |
| 322029 | 0.89 |
| 42214 | 0.89 |
| 26922 | 0.89 |
| 35483 | 0.89 |
| 37485 | 0.89 |
| 138998 | 0.89 |
| 31238 | 0.89 |
| 40276 | 0.89 |
| 38471 | 0.89 |
| 27815 | 0.89 |
| 46711 | 0.89 |
| 49322 | 0.89 |
| 51461 | 0.89 |
| 53292 | 0.89 |
| 469272 | 0.89 |
| 33943 | 0.89 |
| 44527 | 0.88 |
| 34357 | 0.88 |
| 43129 | 0.88 |
| 32141 | 0.88 |
| 375724 | 0.88 |
| 30578 | 0.88 |
| 26572 | 0.88 |
| syn cDNA 8 | 0.88 |
| 43504 | 0.88 |
| 323028 | 0.88 |
| 340644 | 0.88 |
| 512458 | 0.88 |
| 39728 | 0.88 |
| 41918 | 0.88 |
| 42284 | 0.88 |
| 37477 | 0.88 |
| empty | 0.88 |
| 24899 | 0.88 |
| EDNRB | 0.88 |
| 121147 | 0.87 |
| 324655 | 0.87 |
| 34945 | 0.87 |
| 39270 | 0.87 |
| 376507 | 0.87 |
| 39159 | 0.87 |
| 222502 | 0.87 |
| 278409 | 0.87 |
| 343465 | 0.87 |
| 293934 | 0.87 |
| 43826 | 0.87 |
| 23132 | 0.87 |
| 49161 | 0.87 |
| 510405 | 0.87 |
| syn cDNA 33 | 0.87 |
| 340878 | 0.87 |
| 152762 | 0.87 |
| 296476 | 0.87 |
| 51854 | 0.86 |
| endothelin 1 | 0.86 |
| 32409 | 0.86 |
| syn cDNA 25 | 0.86 |
| 43021 | 0.86 |
| 51685 | 0.86 |
| 489194 | 0.86 |
| 321308 | 0.86 |
| 32644 | 0.86 |
| 487777 | 0.86 |
| 380403 | 0.86 |
| 39169 | 0.86 |
| 35615 | 0.86 |
| tyrosinase | 0.86 |
| 43885 | 0.86 |
| 32790 | 0.86 |
| 27794 | 0.86 |
| 24392 | 0.86 |
| 31154 | 0.86 |
| 37964 | 0.86 |
| 44721 | 0.85 |
| 199381 | 0.85 |

TABLE 4-continued

Results from the 1.2K microarray.

| Image ID or clone name | array ratio* |
|---|---|
| 38859 | 0.85 |
| 21652 | 0.85 |
| 49751 | 0.85 |
| 38647 | 0.85 |
| 486012 | 0.85 |
| 47631 | 0.85 |
| 34671 | 0.85 |
| 26082 | 0.85 |
| 22611 | 0.85 |
| 114648 | 0.85 |
| 50359 | 0.85 |
| syn cDNA 38 | 0.85 |
| 42088 | 0.85 |
| 343646 | 0.85 |
| 37622 | 0.85 |
| 43960 | 0.85 |
| 31143 | 0.85 |
| 42349 | 0.85 |
| 24145 | 0.85 |
| 293032 | 0.85 |
| 40450 | 0.85 |
| 51454 | 0.85 |
| 49383 | 0.85 |
| 36717 | 0.84 |
| 26483 | 0.84 |
| 213502 | 0.84 |
| 37040 | 0.84 |
| 30012 | 0.84 |
| 30619 | 0.84 |
| 43504 | 0.84 |
| 203184 | 0.84 |
| 38500 | 0.84 |
| 27818 | 0.84 |
| 42844 | 0.84 |
| 31863 | 0.84 |
| 81221 | 0.83 |
| 22230 | 0.83 |
| 50234 | 0.83 |
| 376362 | 0.83 |
| 43241 | 0.83 |
| 256323 | 0.83 |
| 323390 | 0.83 |
| 50203 | 0.83 |
| 23014 | 0.83 |
| 293274 | 0.83 |
| 44173 | 0.83 |
| 230976 | 0.83 |
| 50888 | 0.83 |
| 340734 | 0.83 |
| HIV F3 | 0.83 |
| 279727 | 0.83 |
| 42020 | 0.83 |
| 357435 | 0.83 |
| 33794 | 0.83 |
| 470621 | 0.83 |
| 25725 | 0.82 |
| 267682 | 0.82 |
| empty | 0.82 |
| 489217 | 0.82 |
| mouse TRP2 | 0.82 |
| mouse aim2/IFI16 | 0.82 |
| mouse TRP1 | 0.82 |
| 34606 | 0.82 |
| 487386 | 0.82 |
| 30149 | 0.82 |
| pUC18 | 0.82 |
| Gadd34 | 0.82 |
| 48458 | 0.82 |
| 291057 | 0.82 |
| CoT1 | 0.82 |
| 487982 | 0.82 |
| 42380 | 0.82 |
| 51302 | 0.82 |
| Hu placental | 0.82 |
| pUC18 | 0.82 |
| empty | 0.82 |
| empty | 0.82 |
| 51740 | 0.81 |
| 32790 | 0.81 |
| 310390 | 0.81 |
| 21810 | 0.81 |
| 49849 | 0.81 |
| 30781 | 0.81 |
| pUC18 | 0.81 |
| 30543 | 0.81 |
| 279482 | 0.81 |
| 52652 | 0.81 |
| 223176 | 0.81 |
| 345645 | 0.81 |
| 341130 | 0.81 |
| 50999 | 0.81 |
| 48503 | 0.81 |
| 280735 | 0.81 |
| 488092 | 0.81 |
| 38397 | 0.81 |
| 47559 | 0.81 |
| 358848 | 0.81 |
| 37760 | 0.81 |
| 36060 | 0.81 |
| 51219 | 0.81 |
| 470196 | 0.81 |
| 300960 | 0.81 |
| 310406 | 0.80 |
| 25764 | 0.80 |
| 344769 | 0.80 |
| 38840 | 0.80 |
| 47386 | 0.80 |
| 40874 | 0.80 |
| 28573 | 0.80 |
| 309615 | 0.80 |
| 362332 | 0.80 |
| 50232 | 0.80 |
| 39205 | 0.80 |
| 43622 | 0.80 |
| 470792 | 0.80 |
| 47838 | 0.80 |
| 26366 | 0.80 |
| 30970 | 0.80 |
| 510151 | 0.80 |
| 280465 | 0.80 |
| 50576 | 0.80 |
| 509588 | 0.80 |
| 34349 | 0.79 |
| 113941 | 0.79 |
| 471217 | 0.79 |
| 36775 | 0.79 |
| 28776 | 0.79 |
| 36796 | 0.79 |
| 38770 | 0.79 |
| 22445 | 0.79 |
| 45851 | 0.79 |
| 47648 | 0.79 |
| 41796 | 0.79 |
| 26286 | 0.79 |
| 45568 | 0.79 |
| 375724 | 0.79 |
| 49243 | 0.79 |
| 417322 | 0.79 |
| 291736 | 0.79 |
| 31456 | 0.79 |
| 42894 | 0.78 |
| 29438 | 0.78 |
| 32407 | 0.78 |
| 28595 | 0.78 |
| 45376 | 0.78 |
| 271662 | 0.78 |
| 47727 | 0.78 |

TABLE 4-continued

Results from the 1.2K microarray.

| Image ID or clone name | array ratio* |
|---|---|
| 50171 | 0.78 |
| ME491 | 0.78 |
| 39884 | 0.78 |
| 340922 | 0.78 |
| 24269 | 0.78 |
| 307293 | 0.78 |
| 49608 | 0.78 |
| 40360 | 0.78 |
| 284669 | 0.78 |
| 31164 | 0.78 |
| 43194 | 0.77 |
| 297589 | 0.77 |
| 80239 | 0.77 |
| 45643 | 0.77 |
| 281778 | 0.77 |
| 192694 | 0.77 |
| 43541 | 0.77 |
| 41356 | 0.77 |
| 123953 | 0.77 |
| 48629 | 0.77 |
| 290493 | 0.77 |
| 28245 | 0.77 |
| 46548 | 0.77 |
| 44255 | 0.77 |
| 21477 | 0.76 |
| 299626 | 0.76 |
| 43563 | 0.76 |
| 47833 | 0.76 |
| 112035 | 0.76 |
| 32682 | 0.76 |
| 489327 | 0.76 |
| 221690 | 0.76 |
| 257458 | 0.76 |
| 39876 | 0.76 |
| 39993 | 0.76 |
| 42295 | 0.76 |
| 27052 | 0.76 |
| 53071 | 0.76 |
| 248258 | 0.76 |
| 359051 | 0.76 |
| 24638 | 0.76 |
| 36191 | 0.76 |
| 34255 | 0.75 |
| 26128 | 0.75 |
| 26184 | 0.75 |
| 509710 | 0.75 |
| 27549 | 0.75 |
| 116713 | 0.75 |
| 44050 | 0.75 |
| 357239 | 0.75 |
| 31355 | 0.75 |
| 52564 | 0.74 |
| 345527 | 0.74 |
| 26129 | 0.74 |
| 43631 | 0.74 |
| 323181 | 0.74 |
| 32684 | 0.74 |
| 415060 | 0.74 |
| 32615 | 0.74 |
| 39391 | 0.74 |
| 45604 | 0.74 |
| 510245 | 0.74 |
| 27230 | 0.74 |
| 322000 | 0.74 |
| 470610 | 0.74 |
| 27927 | 0.74 |
| 46920 | 0.74 |
| 46936 | 0.74 |
| 44584 | 0.73 |
| 471620 | 0.73 |
| 129268 | 0.73 |
| 49980 | 0.73 |
| 261518 | 0.73 |
| 262575 | 0.73 |
| 375635 | 0.73 |
| 26531 | 0.73 |
| 366904 | 0.73 |
| 50561 | 0.73 |
| 346305 | 0.73 |
| 28410 | 0.73 |
| 24588 | 0.73 |
| 29234 | 0.72 |
| 366942 | 0.72 |
| 50038 | 0.72 |
| 375620 | 0.72 |
| 43092 | 0.72 |
| 45658 | 0.72 |
| 22798 | 0.72 |
| 41559 | 0.72 |
| 231089 | 0.72 |
| 32707 | 0.72 |
| 415102 | 0.72 |
| 32750 | 0.72 |
| 416184 | 0.72 |
| 284459 | 0.72 |
| 49403 | 0.72 |
| 50308 | 0.71 |
| 366647 | 0.71 |
| 376649 | 0.71 |
| 376110 | 0.71 |
| Hu placental | 0.71 |
| 37366 | 0.71 |
| 35320 | 0.71 |
| 417124 | 0.71 |
| 31169 | 0.71 |
| 304947 | 0.71 |
| 24642 | 0.71 |
| 34660 | 0.70 |
| 48406 | 0.70 |
| 192694 | 0.70 |
| 27511 | 0.70 |
| 48762 | 0.70 |
| 357309 | 0.70 |
| 429135 | 0.70 |
| 42700 | 0.70 |
| 53227 | 0.70 |
| 40110 | 0.70 |
| 51504 | 0.70 |
| 34011 | 0.69 |
| 32983 | 0.69 |
| 257766 | 0.69 |
| 34662 | 0.69 |
| 509710 | 0.69 |
| 244355 | 0.69 |
| 193913 | 0.68 |
| 310490 | 0.68 |
| 347685 | 0.68 |
| 471918 | 0.68 |
| 375635 | 0.68 |
| 358538 | 0.68 |
| 322148 | 0.68 |
| 36983 | 0.68 |
| 41511 | 0.68 |
| 39093 | 0.68 |
| 138604 | 0.68 |
| 51018 | 0.68 |
| 28573 | 0.67 |
| 32658 | 0.67 |
| pdgfr | 0.67 |
| 201797 | 0.67 |
| 50106 | 0.67 |
| 29435 | 0.66 |
| 40886 | 0.66 |
| CoT1 | 0.66 |
| 264606 | 0.66 |
| 22285 | 0.66 |
| 45291 | 0.66 |
| 190107 | 0.66 |

TABLE 4-continued

Results from the 1.2K microarray.

| Image ID or clone name | array ratio* |
|---|---|
| 49255 | 0.66 |
| 38983 | 0.65 |
| 298187 | 0.65 |
| 376294 | 0.65 |
| 48234 | 0.65 |
| 381219 | 0.65 |
| 471218 | 0.65 |
| 417127 | 0.64 |
| 47884 | 0.64 |
| 300071 | 0.64 |
| 356964 | 0.64 |
| 470691 | 0.63 |
| 51621 | 0.63 |
| 45233 | 0.63 |
| 131828 | 0.63 |
| 320538 | 0.63 |
| 46449 | 0.63 |
| HGF | 0.63 |
| 243159 | 0.63 |
| 45188 | 0.62 |
| 37118 | 0.62 |
| 364716 | 0.61 |
| 62186 | 0.61 |
| 40911 | 0.61 |
| 366824 | 0.61 |
| 115336 | 0.61 |
| 138460 | 0.61 |
| 124086 | 0.61 |
| 291943 | 0.61 |
| 62186 | 0.60 |
| 47463 | 0.60 |
| 366509 | 0.60 |
| Hu placental | 0.60 |
| 49277 | 0.60 |
| 34555 | 0.59 |
| 37145 | 0.59 |
| 41792 | 0.59 |
| 43550 | 0.59 |
| 510595 | 0.59 |
| 51209 | 0.59 |
| 44689 | 0.58 |
| 358677 | 0.58 |
| 34304 | 0.58 |
| 22493 | 0.58 |
| 115408 | 0.58 |
| 430027 | 0.58 |
| 51555 | 0.57 |
| 34355 | 0.57 |
| 328330 | 0.56 |
| 248613 | 0.56 |
| 469724 | 0.56 |
| lambda | 0.56 |
| 32636 | 0.55 |
| 32438 | 0.54 |
| 376285 | 0.54 |
| 22568 | 0.54 |
| 345722 | 0.54 |
| 309924 | 0.54 |
| 43060 | 0.53 |
| 415206 | 0.53 |
| 42777 | 0.53 |
| HIV F1 | 0.51 |
| 487417 | 0.51 |
| 346534 | 0.47 |
| 233194 | 0.46 |
| 295093 | 0.45 |
| 48085 | 0.44 |
| 26541 | 0.43 |
| empty | 0.41 |
| 28089 | 0.38 |
| 248032 | 0.34 |
| 359119 | 0.27 |
| 28116 | 0.23 |
| empty | 0.19 |
| empty | 0.18 |
| empty | 0.18 |
| empty | 0.15 |
| 417226 | 0.14 |
| 51699 | 0.12 |

*relative expression levels

TABLE 5

Image ID Numbers Present in the 5K microrray.

20115; 21652; 21738; 22012; 22040; 22074; 22260; 22293; 22411; 22493; 22711; 22731; 22918; 23019; 23073; 23132; 23173; 23185; 23282; 23431; 23772; 23776; 23804; 23831; 23878; 23932; 24004; 24032; 24085; 24145; 24415; 24642; 24884; 25499; 25584; 25588; 25679; 25725; 25755; 26021; 26162; 26184; 26314; 26366; 26418; 26566; 26566; 26578; 26616; 26617; 26711; 26811; 26910; 26922; 27104; 27548; 27549; 27624; 27787; 27848; 28012; 28098; 28218; 28309; 28410; 28422; 28469; 28475; 28823; 28985; 29054; 29063; 30093; 30170; 30272; 30502; 30664; 30885; 31072; 31093; 31143; 31169; 31210; 31251; 31842; 31866; 31873; 32231; 32472; 32609; 32684; 32875; 32898; 32996; 33045; 33049; 33051; 33051; 33182; 33299; 33327; 33478; 33525; 33632; 33690; 33826; 33941; 33949; 34106; 34255; 34302; 34315; 34355; 34357; 34396; 34439; 34616; 34671; 34689; 34773; 34778; 34795; 34849; 34852; 34888; 34945; 35077; 35105; 35185; 35191; 35191; 35236; 35271; 35483; 35828; 36374; 36387; 36393; 36493; 36607; 36775; 36950; 37196; 37234; 37366; 37449; 37451; 37491; 37904; 38465; 38471; 38763; 38763; 39093; 39127; 39159; 39173; 39274; 39285; 39593; 39796; 39798; 39808; 39884; 39884; 39993; 40017; 40026; 40042; 40056; 40299; 40304; 40360; 40365; 40562; 40567; 40580; 40643; 40699; 40704; 40721; 40751; 40751; 40781; 40844; 40887; 40946; 41199; 41356; 41452; 41511; 41541; 41565; 41591; 41650; 41658; 41672; 41898; 41929; 42059; 42076; 42076; 42096; 42118; 42214; 42258; 42313; 42313; 42352; 42373; 42558; 42576; 42706; 42739; 42880; 42993; 43021; 43129; 43198; 43207; 43231; 43241; 43338; 43550; 43563; 43622; 43743; 43771; 43826; 43833; 43878; 43884; 43977; 44164; 44180; 44255; 44255; 44307; 44351; 44477; 44505; 44537; 44563; 44692; 44975; 45099; 45138; 45231; 45233; 45272; 45291; 45525; 45525; 45542; 45544; 45556; 45632; 45641; 45921; 45941; 46054; 46154; 46154; 46171; 46182; 46284; 46356; 46518; 46786; 46897; 46916; 46916; 47043; 47110; 47142; 47202; 47475; 47510; 47542; 47559; 47647; 47681; 47833; 47853; 47853; 47900; 47908; 48136; 48182; 48283; 48285; 48398; 48530; 48614; 48631; 48799; 48886; 48906; 49117; 49164; 49260; 49344; 49352; 49404; 49464; 49509; 49518; 49591; 49630; 49665; 49710; 49860; 49873; 49888; 49920; 49970; 50043; 50117; 50182; 50188; 50214; 50359; 50413; 50506; 50614;

TABLE 5-continued

Image ID Numbers Present in the 5K microrray.

50666; 50680; 50754; 50765; 50794; 50941; 50990; 51041; 51263; 51293; 51328; 51362; 51408;
51447; 51448; 51450; 51463; 51532; 51543; 51640; 51666; 51666; 51702; 51737; 51740; 51746;
51814; 51865; 51899; 51916; 51974; 51981; 52079; 52228; 52327; 52419; 52430; 52431; 52629;
52629; 52646; 52933; 53099; 53099; 53316; 53341; 62277; 66316; 66317; 66322; 66327; 66329;
66333; 66335; 66336; 66341; 66352; 66354; 66369; 66377; 66390; 66391; 66400; 66406; 66407;
66420; 66423; 66428; 66430; 66443; 66454; 66467; 66474; 66475; 66497; 66507; 66532; 66533;
66534; 66535; 66540; 66550; 66552; 66555; 66556; 66560; 66562; 66564; 66574; 66582; 66584;
66594; 66596; 66606; 66608; 66609; 66630; 66663; 66685; 66686; 66686; 66694; 66697; 66711;
66714; 66718; 66721; 66728; 66731; 66753; 66774; 66792; 66815; 66829; 66864; 66894; 66895;
66898; 66902; 66903; 66910; 66919; 66931; 66937; 66944; 66946; 66952; 66953; 66972; 66975;
66977; 66982; 67006; 67009; 67016; 67033; 67036; 67037; 67055; 67069; 67070; 67074; 67075;
67654; 68103; 68225; 68977; 69672; 70002; 70349; 70489; 70692; 70827; 71101; 71116; 71432;
71434; 71545; 71606; 71622; 71626; 71672; 71727; 72050; 72391; 72778; 72869; 73268; 73381;
73531; 73782; 74119; 74566; 74593; 75009; 75254; 75415; 75923; 76362; 77133; 77391; 77533;
77577; 77577; 77636; 77728; 77805; 77897; 77915; 78217; 78294; 78869; 79022; 79229; 79254;
79353; 79502; 79520; 79520; 79624; 79629; 79688; 79710; 79712; 79828; 79898; 80095; 80109;
80109; 80146; 80374; 80384; 80399; 80410; 80500; 80504; 80549; 80708; 80772; 80910; 80915;
80924; 80946; 80948; 81129; 81289; 81315; 81331; 81336; 81394; 81417; 81427; 81518; 81599;
82710; 82734; 82871; 82879; 82976; 82991; 83083; 83120; 83129; 83210; 83210; 83231; 83363;
83605; 84295; 84750; 84820; 84955; 85093; 85128; 85202; 85259; 85394; 85394; 85497; 85509;
85561; 85624; 85634; 85678; 85682; 85690; 85805; 85840; 85979; 86220; 108177; 108197;
108208; 108208; 108265; 108316; 108330; 108351; 108395; 108422; 108425; 108471; 108651;
108658; 108667; 108716; 108730; 108763; 108783; 108797; 108801; 108815; 108836; 109049;
109089; 109108; 109123; 109153; 109179; 109200; 109221; 109265; 109269; 109271; 109277;
109279; 109304; 109309; 109314; 109316; 109466; 109483; 109488; 109523; 109708; 109811;
109888; 110094; 110198; 110281; 110282; 110307; 110347; 110417; 110436; 110467; 110503;
110503; 110507; 110519; 110578; 110582; 110585; 110653; 110703; 110741; 110746; 110772;
110788; 110791; 110893; 110904; 110912; 110980; 110987; 110996; 111004; 111006; 111054;
111070; 111101; 111122; 111136; 111150; 111200; 111204; 111264; 111266; 111389; 111391;
111413; 111492; 111510; 111516; 111549; 111571; 111634; 111693; 111705; 111714; 111721;
111722; 111750; 111755; 111765; 111825; 111844; 111884; 111981; 112131; 112158; 112371;
112409; 112440; 112494; 112525; 112530; 112541; 112576; 112577; 112629; 112865; 112896;
112906; 113048; 113206; 113281; 113283; 113284; 113298; 113300; 113308; 113394; 113399;
113431; 113488; 113538; 115111; 115143; 115155; 115223; 115230; 115281; 115292; 115307;
115337; 115414; 115447; 119384; 119530; 119882; 119914; 119914; 120015; 120097; 120106;
120113; 120124; 120138; 120153; 120162; 120173; 120189; 120297; 120306; 120309; 120318;
120343; 120362; 120375; 120383; 120413; 120516; 120533; 120544; 120551; 120561; 120572;
120598; 120631; 120634; 120681; 120695; 120701; 120773; 120823; 120863; 120881; 120964;
120973; 121018; 121072; 121133; 121159; 121184; 121206; 121214; 121218; 121220; 121239;
121251; 121252; 121270; 121275; 121316; 121341; 121355; 121365; 121412; 121415; 121420;
121458; 121459; 121462; 121475; 121500; 121501; 121521; 121530; 121533; 121543; 121546;
121558; 121559; 121564; 121577; 121600; 121611; 121615; 121616; 121621; 121625; 121628;
121661; 121662; 121687; 121715; 121722; 121727; 121736; 121756; 121770; 121776; 121792;
121798; 121803; 121808; 121828; 121877; 121880; 121898; 121954; 121977; 121981; 121994;
121997; 122019; 122063; 122077; 122091; 122126; 122150; 122159; 122159; 122161; 122170;
122178; 122194; 122237; 122274; 122295; 122345; 122354; 122359; 122364; 122397; 122428;
122443; 122636; 122684; 122702; 122762; 122787; 122796; 122822; 122875; 122889; 122899;
122906; 122913; 122915; 122946; 122955; 122963; 122982; 123061; 123065; 123067; 123074;
123079; 123087; 123112; 123117; 123196; 123222; 123229; 123255; 123262; 123331; 123354;
123400; 123405; 123408; 123425; 123433; 123436; 123439; 123441; 123448; 123459; 123474;
123506; 123561; 123578; 123579; 123604; 123614; 123627; 123627; 123646; 123649; 123666;
123699; 123700; 123720; 123724; 123729; 123730; 123755; 123788; 123790; 123802; 123805;
123815; 123817; 123858; 123926; 123932; 123952; 123980; 124009; 124014; 124020; 124042;
124043; 124052; 124059; 124070; 124071; 124077; 124079; 124087; 124090; 124091; 124116;
124126; 124127; 124128; 124132; 124137; 124138; 124143; 124155; 124168; 124179; 124203;
124232; 124241; 124261; 124271; 124277; 124286; 124320; 124405; 124502; 124505; 124530;
124578; 124597; 124605; 124629; 124637; 124719; 124730; 124753; 124781; 124788; 124795;
124808; 124822; 124824; 124853; 124891; 124909; 124922; 124965; 125040; 125092; 125134;
125148; 125183; 125308; 125548; 125589; 125608; 125665; 125666; 125685; 125709; 125722;
125737; 125739; 125741; 125767; 125769; 125788; 125799; 125809; 125822; 125828; 126219;
126221; 126225; 126229; 126230; 126234; 126237; 126243; 126320; 126321; 126338; 126341;
126355; 126368; 126371; 126390; 126393; 126401; 126406; 126412; 126413; 126419; 126438;
126450; 126453; 126459; 126465; 126466; 126470; 126497; 126508; 126509; 126519; 126522;
126544; 126568; 126581; 126638; 126650; 126670; 126702; 126722; 126788; 126792; 126795;
126858; 126882; 126883; 126884; 126887; 126988; 127054; 127076; 127096; 127099; 127119;
127120; 127147; 127173; 127182; 127185; 127193; 127194; 127197; 127199; 127216; 127243;
127272; 127354; 127400; 127408; 127409; 127415; 127462; 127473; 127486; 127509; 127514;
127519; 127542; 127610; 127625; 127636; 127646; 127665; 127666; 127677; 127682; 127710;
127729; 127766; 127769; 127821; 127841; 127843; 127881; 127925; 127928; 127943; 127970;
127974; 127983; 128054; 128118; 128126; 128143; 128150; 128159; 128193; 128204; 128208;
128243; 128245; 128248; 128260; 128274; 128290; 128297; 128301; 128302; 128322; 128346;
128351; 128426; 128457; 128460; 128503; 128509; 128518; 128530; 128561; 128602; 128617;
128627; 128632; 128679; 128690; 128695; 128735; 128737; 128738; 128775; 128783; 128785;
128795; 128833; 128875; 128905; 128947; 128954; 128970; 128973; 128985; 128993; 129000;
129071; 129112; 129146; 129177; 129293; 129331; 129332; 129342; 129355; 129392; 129407;
129442; 129446; 129477; 129502; 129506; 129514; 129516; 129541; 129563; 129567; 129569;
129585; 129600; 129610; 129616; 129624; 129644; 129721; 129725; 129748; 129770; 129817;

TABLE 5-continued

Image ID Numbers Present in the 5K microrray.

129840; 129853; 129865; 129922; 129925; 130004; 130005; 130008; 130027; 130028; 130043;
130044; 130053; 130054; 130057; 130100; 130107; 130116; 130120; 130153; 130156; 130233;
130243; 130276; 130280; 130294; 130334; 130342; 130358; 130371; 130421; 130541; 130572;
130582; 130610; 130617; 130656; 130677; 130716; 130747; 130756; 130758; 130773; 130777;
130781; 130788; 130791; 130801; 130820; 130824; 130826; 130835; 130843; 130857; 130868;
130876; 130884; 130892; 130895; 130916; 130972; 130977; 131010; 131016; 131029; 131050;
131104; 131238; 131239; 131307; 131316; 131318; 131362; 131365; 131370; 131388; 131446;
131563; 131595; 131653; 131668; 131764; 131824; 131839; 131867; 131877; 131886; 131887;
132012; 132017; 132019; 132066; 132111; 132122; 132140; 132142; 132159; 132215; 132285;
132304; 132323; 132358; 132373; 132381; 132464; 132524; 132527; 132549; 132569; 132623;
132630; 132631; 132690; 132708; 132748; 132789; 132828; 132835; 132848; 132871; 132899;
132911; 133084; 133096; 133114; 133130; 133158; 133178; 133180; 133197; 133213; 133225;
133236; 133273; 133303; 133331; 133333; 133519; 133534; 133613; 133820; 133964; 133972;
134120; 134172; 134192; 134229; 134235; 134256; 134269; 134270; 134312; 134322; 134368;
134394; 134422; 134439; 134476; 134482; 134495; 134520; 134523; 134525; 134537; 134544;
134643; 134712; 134719; 134748; 134753; 134783; 134829; 134856; 134948; 135010; 135058;
135083; 135083; 135094; 135203; 135212; 135219; 135220; 135221; 135240; 135247; 135273;
135303; 135426; 135431; 135449; 135450; 135454; 135527; 135538; 135561; 135608; 135653;
135654; 135673; 135676; 135688; 135692; 135710; 135713; 135721; 135766; 135773; 135777;
135789; 135791; 135853; 135892; 135901; 135910; 135922; 135941; 135999; 136064; 136073;
136114; 136117; 136180; 136188; 136218; 136223; 136235; 136286; 136301; 136303; 136317;
136382; 136409; 136449; 136536; 136557; 136560; 136571; 136598; 136632; 136706; 136730;
136744; 136772; 136775; 136780; 136801; 136802; 136814; 136821; 136855; 136856; 136874;
136909; 136919; 136933; 136954; 136984; 137016; 137017; 137020; 137063; 137096; 137139;
137158; 137178; 137182; 137208; 137209; 137236; 137254; 137349; 137353; 137387; 137396;
137417; 137456; 137506; 137531; 137535; 137581; 137638; 137647; 137653; 137663; 137736;
137760; 137793; 137794; 137797; 137836; 137853; 137862; 137884; 137885; 137918; 137931;
137940; 137971; 137981; 137989; 138021; 138059; 138104; 138116; 138139; 138141; 138165;
138168; 138189; 138210; 138234; 138239; 138304; 138337; 138374; 138444; 138455; 138477;
138496; 138507; 138533; 138550; 138579; 138589; 138592; 138601; 138672; 138706; 138737;
138745; 138752; 138775; 138837; 138861; 138865; 138917; 138929; 138936; 138974; 138978;
138991; 138999; 139009; 139009; 139051; 139062; 139113; 139138; 139189; 139199; 139217;
139226; 139250; 139268; 139278; 139331; 139354; 139365; 139376; 139462; 139490; 139540;
139558; 139573; 139593; 139641; 139656; 139660; 139680; 139689; 139705; 139708; 139764;
139766; 139818; 139835; 139837; 139872; 139883; 139957; 139962; 140000; 140057; 140100;
140103; 140131; 140171; 140197; 140210; 140252; 140289; 140301; 140304; 140328; 140334;
140337; 140354; 140422; 140455; 140515; 140635; 140655; 140716; 140732; 140759; 140761;
140792; 140806; 140811; 140830; 140852; 140921; 140966; 141106; 141123; 141169; 141171;
141192; 141209; 141230; 141298; 141314; 141316; 141361; 141366; 141453; 141522; 141562;
141589; 141623; 141627; 141675; 141677; 141684; 141723; 141763; 141765; 141768; 141818;
141845; 141854; 141931; 141959; 141966; 142067; 142076; 142087; 142090; 142120; 142122;
142134; 142139; 142259; 142326; 142385; 142395; 142397; 142442; 142499; 142532; 142551;
142556; 142586; 142647; 142689; 142733; 142788; 142851; 142927; 142944; 142984; 143039;
143054; 143115; 143169; 143208; 143209; 143227; 143287; 143306; 143310; 143322; 143443;
143454; 143519; 143523; 143654; 143661; 143748; 143756; 143759; 143846; 143887; 143910;
143919; 143962; 143966; 143995; 144029; 144042; 144675; 144740; 144747; 144762; 144777;
144786; 144791; 144793; 144797; 144802; 144816; 144834; 144852; 144855; 144861; 144867;
144870; 144878; 144880; 144881; 144885; 144893; 144894; 144902; 144905; 144915; 144916;
144924; 144926; 144930; 144932; 144951; 144956; 144977; 145001; 145132; 145284; 145503;
145513; 146081; 146123; 146577; 146605; 146726; 147414; 147630; 148021; 148379; 148421;
148743; 149013; 149373; 149737; 149742; 149910; 150221; 150314; 150466; 150466; 150623;
150702; 151251; 151261; 151418; 151662; 151896; 153006; 153025; 153340; 153411; 153473;
153743; 153779; 154015; 154093; 154138; 154214; 154289; 154312; 154323; 154465; 154477;
154482; 154608; 154616; 154654; 154707; 154749; 154789; 154795; 154999; 155064; 155072;
155128; 155201; 155287; 155434; 155575; 155583; 155716; 156023; 156045; 156211; 156270;
156386; 156473; 156551; 156874; 157856; 159118; 159166; 159455; 159608; 159725; 159935;
160126; 160485; 160488; 160573; 160616; 160628; 160656; 160664; 160723; 160730; 160793;
160838; 161195; 161456; 161484; 161583; 161950; 161992; 161993; 162161; 162208; 162211;
162365; 162722; 162775; 162778; 163174; 163528; 163579; 165818; 165818; 165857; 165878;
165921; 166004; 166195; 166199; 166236; 166934; 167032; 167076; 167280; 171936; 172440;
172440; 172721; 172765; 172783; 173228; 173309; 173674; 173878; 175103; 175123; 175140;
175528; 175727; 176606; 177621; 177737; 178463; 178468; 178779; 178818; 179232; 179256;
179276; 179283; 179334; 179336; 179403; 179426; 179500; 179534; 179804; 179890; 180195;
180244; 180298; 180520; 180803; 180864; 180885; 180902; 181831; 182661; 182977; 183120;
183194; 183200; 183337; 183462; 183476; 184038; 184175; 184240; 184365; 186132; 186918;
187147; 187266; 187616; 188036; 188232; 188388; 188390; 190468; 190491; 190732; 190887;
191497; 191508; 191516; 191569; 191572; 191599; 191603; 191648; 191664; 191882; 191978;
192481; 192694; 193067; 193106; 193122; 193139; 193182; 193200; 193381; 193383; 193394;
193481; 193533; 193546; 193586; 193617; 193690; 193713; 193724; 193742; 193790; 193811;
193892; 193913; 193913; 193923; 193937; 193938; 193987; 193990; 194005; 194006; 194031;
194061; 194131; 194136; 194155; 194161; 194182; 194182; 194214; 194282; 194297; 194307;
194342; 194351; 194364; 194384; 194395; 194399; 194401; 194468; 194587; 194600; 194656;
194670; 194704; 194804; 194872; 194906; 194921; 194949; 194965; 194972; 194985; 194986;
195037; 195051; 195052; 195091; 195117; 195127; 195132; 195138; 195139; 195200; 195232;
195314; 195340; 195346; 195358; 195365; 195381; 195387; 195429; 195458; 195487; 195513;
195524; 195546; 195553; 195555; 195668; 195712; 195720; 195753; 195772; 195784; 195820;
195821; 195852; 195853; 195875; 195903; 195911; 195947; 195974; 195995; 196005; 196038;

TABLE 5-continued

Image ID Numbers Present in the 5K microarray.

196047; 196109; 196115; 196125; 196148; 196185; 196189; 196214; 196222; 196282; 196303;
196345; 196348; 196350; 196387; 196433; 196444; 196501; 196522; 196539; 196612; 196636;
196640; 196650; 196837; 196849; 196860; 196866; 196992; 197051; 197054; 197093; 197128;
197176; 197300; 197323; 197343; 197404; 197413; 197414; 197474; 197500; 197525; 197637;
197676; 197720; 197736; 197765; 197775; 197776; 197791; 197843; 197855; 197856; 197868;
197888; 197907; 197933; 197975; 198011; 198026; 198033; 198104; 198169; 198190; 198312;
198339; 198372; 198451; 198509; 198578; 198580; 198582; 198593; 198605; 198647; 198694;
198807; 198815; 198874; 198904; 198917; 198960; 198961; 199143; 199158; 199180; 199205;
199220; 199228; 199229; 199239; 199243; 199251; 199258; 199272; 199286; 199327; 199403;
199558; 199571; 199602; 199610; 199623; 199624; 199627; 199628; 199641; 199645; 199663;
199709; 199945; 199995; 200015; 200031; 200136; 200174; 200302; 200307; 200395; 200402;
200418; 200545; 200595; 200599; 200604; 200608; 200773; 200780; 200814; 200838; 200840;
200847; 200855; 200863; 200873; 200934; 200937; 200969; 201006; 201030; 201168; 201173;
201192; 201203; 201207; 201229; 201241; 201264; 201274; 201288; 201301; 201309; 201314;
201317; 201322; 201334; 201383; 201393; 201483; 201517; 201519; 201525; 201562; 201586;
201628; 201650; 201651; 201687; 201727; 201757; 201784; 201818; 201819; 201890; 201902;
201961; 201981; 201986; 202034; 202066; 202168; 202209; 202213; 202243; 202315; 202320;
202339; 202348; 202353; 202357; 202414; 202485; 202492; 202514; 202535; 202549; 202553;
202559; 202577; 202607; 202612; 202621; 202682; 202692; 202703; 202704; 202706; 202722;
202740; 202769; 202795; 202802; 202901; 202904; 202919; 202921; 202931; 202990; 203038;
203122; 203132; 203227; 203240; 203275; 203287; 203302; 203347; 203348; 203350; 203351;
203388; 203390; 203400; 203434; 203469; 203514; 203544; 203547; 203551; 203721; 203772;
203791; 203805; 203850; 203905; 203910; 203918; 203931; 203956; 204083; 204098; 204111;
204122; 204148; 204179; 204208; 204211; 204214; 204251; 204299; 204300; 204301; 204312;
204335; 204356; 204360; 204406; 204444; 204489; 204539; 204541; 204545; 204558; 204614;
204614; 204624; 204638; 204684; 204688; 204735; 204737; 204755; 204814; 204897; 205049;
205085; 205090; 205185; 205303; 205417; 205445; 205490; 205633; 205715; 205745; 205913;
205993; 206094; 206217; 206544; 206565; 206651; 206683; 206781; 206786; 206794; 206816;
206831; 206841; 206849; 206867; 206882; 206895; 206907; 206937; 206949; 206986; 206992;
206994; 207006; 207016; 207029; 207082; 207087; 207098; 207107; 207248; 207255; 207288;
207293; 207358; 207370; 207379; 207421; 207448; 207618; 207618; 207649; 207665; 207771;
207778; 207794; 207813; 207850; 207869; 207881; 207920; 207952; 207968; 207989; 207990;
208001; 208001; 208161; 208161; 208210; 208319; 208375; 208383; 208407; 208413; 208434;
208524; 208531; 208570; 208663; 208699; 208718; 208741; 208769; 208790; 208798; 208904;
208940; 208984; 208993; 209014; 209137; 209167; 209224; 209246; 209264; 209277; 209296;
209340; 209381; 209468; 209518; 209583; 209624; 209655; 209683; 209841; 210317; 210343;
210348; 210368; 210405; 210415; 210431; 210494; 210501; 210522; 210523; 210525; 210548;
210565; 210575; 210610; 210622; 210646; 210687; 210688; 210698; 210710; 210717; 210744;
210862; 210873; 210887; 210887; 210919; 210923; 211024; 211202; 211206; 211216; 211319;
211351; 211361; 211548; 211557; 211747; 211758; 211780; 211800; 211813; 211859; 211878;
211940; 211951; 212021; 212078; 212098; 212165; 212180; 212198; 212236; 212252; 212325;
212398; 212406; 212429; 212496; 212542; 212620; 212634; 212640; 212649; 212703; 212704;
212712; 212772; 212787; 212815; 213118; 213136; 213280; 213496; 213509; 213527; 213535;
213577; 213698; 213754; 213871; 213875; 213890; 213969; 214043; 214068; 214077; 214133;
214136; 214162; 214165; 214205; 214331; 214441; 214448; 214537; 214565; 214572; 214577;
214614; 214658; 214731; 214744; 214816; 214823; 214826; 214848; 214858; 214906; 214916;
214981; 214990; 219976; 220096; 221092; 221172; 221808; 221826; 221846; 222181; 223098;
223483; 223661; 229290; 229330; 229365; 229467; 229537; 229579; 229580; 229617; 229651;
229692; 229701; 229702; 229723; 229915; 229997; 230013; 230090; 230100; 230116; 230170;
230180; 230191; 230196; 230202; 230205; 230218; 230224; 230235; 230240; 230247; 230251;
230260; 230261; 230267; 230271; 230274; 230341; 230359; 230360; 230370; 230385; 230509;
230560; 230562; 230613; 230637; 231355; 231574; 231675; 232586; 232612; 232624; 232628;
232658; 232670; 232714; 232723; 232772; 232789; 232826; 232837; 232899; 232908; 232933;
232946; 232950; 232965; 232973; 233071; 233074; 233078; 233179; 233183; 233199; 233214;
233274; 233289; 233299; 233308; 233318; 233347; 233349; 233365; 233399; 233419; 233446;
233457; 233547; 233550; 233579; 233581; 233583; 233645; 233688; 233719; 233721; 233734;
233783; 233802; 233852; 233909; 233927; 233939; 234011; 234036; 234080; 234150; 234170;
234191; 234201; 234237; 234318; 234320; 234331; 234376; 234380; 234398; 234419; 234425;
234468; 234469; 234484; 234527; 234537; 234539; 234559; 234562; 234617; 234647; 234664;
234736; 234856; 234907; 234975; 235008; 235026; 235040; 235055; 235056; 235070; 235102;
235149; 235155; 235164; 235173; 235924; 235934; 236055; 236129; 236305; 236305; 236333;
236355; 239524; 239692; 239708; 239711; 239712; 239835; 239874; 239877; 239958; 240022;
240033; 240050; 240062; 240099; 240138; 240151; 240199; 240208; 240249; 240318; 240353;
240357; 240367; 240406; 240430; 240480; 240500; 240505; 240506; 240518; 240586; 240589;
240634; 240637; 240648; 240674; 240694; 240702; 240748; 240766; 240769; 240843; 240914;
240937; 240938; 240945; 240961; 240977; 240992; 241003; 241038; 241066; 241070; 241097;
241113; 241160; 241171; 241179; 241258; 241274; 241288; 241346; 241348; 241350; 241355;
241365; 241392; 241412; 241474; 241475; 241482; 241497; 241507; 241530; 241539; 241587;
241658; 241677; 241788; 241794; 241824; 241826; 241874; 241880; 241900; 241932; 241982;
241985; 241988; 242010; 242011; 242037; 242062; 242070; 242084; 242087; 242578; 242642;
242644; 242687; 242698; 242700; 242706; 242778; 242779; 242780; 242790; 242797; 242820;
242823; 242955; 242985; 243088; 243100; 243113; 243149; 243151; 243154; 243155; 243186;
243194; 243199; 243202; 243230; 243245; 243260; 243291; 243294; 243312; 243317; 243321;
243343; 243350; 243358; 243360; 243370; 243385; 243399; 243403; 243405; 243414; 243428;
243460; 243524; 243537; 243546; 243549; 243580; 243614; 243638; 243641; 243648; 243652;
243653; 243656; 243659; 243675; 243700; 243741; 243770; 243784; 243808; 243816; 243817;
243878; 243887; 243980; 243989; 244055; 244058; 244062; 244063; 244077; 244079; 244086;

TABLE 5-continued

Image ID Numbers Present in the 5K microrray.

244100; 244147; 244154; 244189; 244201; 244202; 244205; 244227; 244243; 244267; 244277;
244299; 244307; 244310; 244313; 244329; 244343; 244350; 244355; 244386; 244387; 244391;
244618; 244637; 244646; 244652; 244654; 244684; 244686; 244703; 244722; 244764; 244767;
244781; 244784; 244801; 244806; 244815; 244846; 244847; 244879; 244911; 244955; 244974;
245000; 245015; 245062; 245099; 245136; 245147; 245195; 245198; 245217; 245219; 245235;
245242; 245247; 245273; 245296; 245299; 245319; 245330; 245330; 245386; 245388; 245401;
245409; 245413; 245422; 245426; 245442; 245444; 245457; 245479; 245484; 245485; 245489;
245517; 245531; 245534; 245549; 245556; 245570; 245585; 245586; 245624; 245742; 245745;
245764; 245765; 245769; 245774; 245806; 245853; 245860; 245881; 245885; 245894; 245899;
245920; 245936; 245964; 245970; 245986; 246035; 246041; 246073; 246074; 246079; 246116;
246117; 246119; 246120; 246143; 246144; 246194; 246246; 246276; 246292; 246300; 246304;
246377; 246449; 246478; 246522; 246524; 246537; 246541; 246543; 246546; 246549; 246598;
246619; 246620; 246652; 246661; 246680; 246684; 246686; 246703; 246705; 246722; 246749;
246765; 246766; 246786; 246789; 246792; 246808; 246824; 246869; 247081; 247082; 247117;
247125; 247159; 247194; 247216; 247233; 247281; 247367; 247466; 247482; 247546; 247587;
247614; 247616; 247635; 247655; 247660; 247710; 247783; 247803; 247816; 247818; 247833;
247859; 247863; 247901; 247925; 247967; 247986; 248009; 248020; 248039; 248071; 248092;
248095; 248112; 248143; 248256; 248261; 248288; 248306; 248371; 248454; 248478; 248481;
248485; 248504; 248531; 248535; 248545; 248594; 248599; 248601; 248624; 248649; 248688;
248698; 248856; 249688; 249705; 249856; 250519; 250667; 250673; 251019; 251135; 251250;
251461; 251516; 251685; 251875; 252185; 254321; 254625; 256260; 256664; 257011; 258589;
258589; 258790; 260200; 260303; 260325; 260619; 261204; 261494; 261519; 261587; 261828;
261971; 262231; 262920; 262932; 262996; 263040; 263097; 263200; 264117; 265060; 265494;
265680; 265874; 266361; 267431; 267634; 267634; 268412; 269806; 271985; 273435; 274529;
274578; 274638; 274932; 274979; 275173; 275176; 275180; 275612; 275634; 275738; 275802;
275871; 275871; 275950; 276091; 276286; 276449; 276547; 277015; 277274; 277305; 278501;
278808; 278808; 279329; 280122; 280236; 280386; 280666; 280750; 280752; 280837; 280882;
280882; 281114; 281125; 281465; 281467; 281843; 281904; 281978; 282051; 282310; 282378;
282501; 282587; 282980; 283023; 283301; 283398; 283715; 283897; 283954; 284341; 284592;
284620; 284734; 284882; 285226; 287300; 288658; 288896; 289143; 289288; 289337; 289502;
289551; 289615; 289666; 289818; 289923; 289978; 290039; 290054; 290124; 290230; 290308;
290422; 292171; 292201; 292207; 292212; 292213; 292217; 292219; 292222; 292230; 292232;
292236; 292244; 292270; 292272; 292292; 292306; 292308; 292312; 292314; 292332; 292357;
292362; 292364; 292388; 292388; 292391; 292392; 292416; 292424; 292452; 292463; 292471;
292475; 292482; 292496; 292501; 292512; 292515; 292519; 292522; 292528; 292542; 292553;
292559; 292567; 292568; 292612; 292613; 292624; 292628; 292633; 292654; 292679; 292690;
292719; 292726; 292731; 292749; 292770; 292806; 292812; 292833; 292834; 292882; 292908;
292920; 292933; 292938; 292939; 292964; 292966; 292996; 293005; 293045; 293078; 293104;
293128; 293157; 293177; 293178; 293191; 293222; 293257; 293306; 293325; 293328; 293331;
293336; 293356; 293358; 293366; 293380; 293403; 293417; 293421; 293431; 293436; 293437;
293457; 293471; 293500; 293503; 293510; 293539; 293557; 293564; 293569; 293576; 293579;
293599; 293606; 293632; 293637; 293664; 293675; 293676; 293683; 293696; 293715; 293727;
293736; 293755; 293763; 293785; 293820; 293835; 293845; 293847; 293858; 293859; 293901;
293916; 293921; 293932; 293940; 293940; 293977; 293990; 294014; 294018; 294040; 294127;
294133; 294150; 294167; 294221; 294255; 294259; 294304; 294310; 294311; 294444; 294445;
294457; 294483; 294485; 294487; 294496; 294512; 294647; 294682; 294740; 294873; 294881;
294892; 294916; 294942; 294951; 294968; 294973; 294995; 295044; 295106; 295137; 295140;
295206; 295229; 295255; 295283; 295303; 295321; 295324; 295376; 295386; 295389; 295410;
295483; 295492; 295497; 295501; 295514; 295527; 295545; 295577; 295583; 295590; 295594;
295599; 295600; 295604; 295630; 295710; 295723; 295729; 295741; 295781; 295798; 295831;
295866; 295873; 295889; 295916; 295923; 295939; 295973; 295974; 295982; 295985; 295992;
295997; 296010; 296030; 296041; 296072; 296094; 296102; 296132; 296136; 296140; 296141;
296149; 296155; 296162; 296168; 296170; 296177; 296180; 296181; 296184; 296188; 296189;
296190; 296198; 296199; 296330; 296334; 296375; 296393; 296444; 296454; 296472; 296476;
296483; 296498; 296508; 296529; 296549; 296552; 296559; 296562; 296568; 296587; 296597;
296602; 296616; 296623; 296640; 296679; 296683; 296702; 296741; 296749; 296752; 296754;
296757; 296773; 296793; 296795; 296797; 296805; 296838; 296857; 296880; 296883; 296901;
296998; 297050; 297061; 297063; 297084; 297086; 297102; 297107; 297110; 297136; 297148;
297155; 297178; 297212; 297305; 297392; 297403; 297405; 297411; 297421; 297437; 297439;
297442; 297919; 298118; 298155; 298833; 298963; 299085; 299093; 299154; 299388; 299442;
299600; 299630; 299663; 299679; 299737; 299815; 300103; 300237; 300474; 300482; 300590;
300632; 300866; 300972; 301018; 301061; 301082; 301122; 301380; 301504; 301678; 301752;
301849; 301976; 302031; 302190; 302292; 302310; 302369; 302549; 302591; 303035; 303048;
303196; 305227; 305336; 305606; 305606; 306013; 306380; 306412; 306484; 306771; 306806;
306813; 306901; 307231; 307255; 307532; 307553; 307843; 307882; 308041; 308163; 308231;
308281; 308415; 308437; 308478; 308588; 308633; 308682; 308989; 309032; 309039; 309045;
309092; 309161; 309316; 309583; 309685; 309776; 309864; 309894; 309993; 310034; 310105;
310356; 310493; 310519; 320606; 320630; 320763; 320834; 320903; 321189; 321189; 321247;
321354; 321386; 321455; 321529; 321580; 321605; 321661; 321706; 321708; 321723; 322051;
322561; 322617; 322617; 322723; 322759; 322786; 322794; 323404; 323506; 323506; 324210;
324255; 324342; 324745; 324815; 324861; 324901; 325062; 325070; 325102; 325160; 325365;
325365; 325370; 325375; 327094; 327150; 327304; 327350; 327506; 327676; 328591; 328802;
340558; 340630; 340644; 340712; 340722; 340734; 340745; 340840; 341137; 341246; 341269;
341310; 341317; 341328; 341336; 341706; 341805; 341821; 341942; 342069; 342378; 342543;
342593; 342640; 342721; 342994; 343072; 343167; 343320; 343352; 343443; 343646; 343646;
343661; 343737; 344133; 344141; 344251; 344282; 344352; 344672; 344757; 344820; 345047;
345055; 345090; 345128; 345208; 345342; 345348; 345423; 345430; 345559; 345586; 345670;

TABLE 5-continued

Image ID Numbers Present in the 5K microrray.

345751; 345839; 345858; 346117; 346134; 346299; 346484; 346545; 346552; 346995; 347036;
347224; 347373; 347434; 347615; 347687; 347687; 356665; 356707; 356800; 356992; 357031;
357046; 357091; 357120; 357220; 357344; 357970; 358162; 358162; 358333; 358344; 358456;
358457; 358468; 358531; 358531; 358543; 358549; 358609; 358673; 358675; 358736; 358850;
358885; 358984; 359184; 359247; 359395; 359411; 359713; 359747; 359764; 359781; 359835;
359982; 360047; 360079; 360168; 360213; 360245; 360478; 360885; 361048; 361097; 361097;
361171; 361204; 361485; 361565; 361639; 361656; 361943; 361974; 362624; 362694; 362729;
362742; 362853; 363058; 363086; 363103; 363144; 363146; 363377; 363569; 363569; 363575;
363590; 363597; 364329; 364469; 364840; 364873; 364921; 365060; 365098; 365539; 365641;
365755; 365930; 365945; 366085; 366154; 366156; 366341; 366389; 366511; 366526; 366558;
366570; 366580; 366585; 366728; 366834; 366893; 366966; 376290; 376515; 376516; 376875;
377152; 377191; 377320; 380057; 380245; 380263; 380394; 380620; 380737; 380797; 380851;
381067; 381166; 381287; 381812; 381866; 381931; 382195; 382654; 382693; 382773; 382787;
383016; 383089; 413633; 415698; 416280; 416803; 416833; 416833; 416959; 417226; 417385;
417403; 417508; 417509; 418126; 418126; 418422; 427812; 428231; 429182; 429574; 430318;
448190; 469281; 469345; 469412; 469685; 469686; 469704; 469762; 469924; 469952; 469954;
469981; 470061; 470175; 470179; 470216; 470232; 470348; 470368; 470379; 470379; 470393;
470846; 470861; 470930; 471196; 471200; 471266; 471372; 471498; 484535; 484641; 485195;
485744; 485854; 485858; 485989; 486208; 486279; 486544; 487118; 488019; 488019; 488413;
489079; 490306; 490368; 491066; 491232; 501994; 502067; 502369; 502909; 503097; 503617;
504226; 504236; 504544; 504763; 504774; 504877; 505059; 509484; 509495; 509588; 509731;
509760; 509823; 510032; 510396; 510542; 510679; 510702; 510760; 511012; 511066; 511428;
511521; 511521; 511586; 511814; 511816; 511832; 512133; 525518; 525566; 526184; 526282;
526657; 529861; 530662; 530814; 530820; 530875; 531028; 531739; 544639; 544664; 545189;
546600; 547058; 547247; 548693; 548957; 549016; 549073; 549101; 549146; 549728; 550353;
550355; 562867; 562927; 562983; 563201; 563403; 563444; 563451; 563465; 563574;
563598; 563621; 563673; 563701; 564050; 564621; 564803; 564846; 564962; 565235; 565379;
565493; 566760; 566887; 566887; 567265; 567414; 586698; 587010; 587525; 587847; 588500;
589115; 589362; 589433; 589751; 591266; 591281; 591465; 591653; 591683; 591864; 591907;
592243; 592359; 592498; 592540; 592801; 594540; 594743; 595009; 609332; 609663; 610012;
611956; 612274; 612616; 613126; 625923; 626502; 627114; 627541; 627542; 627939; 628295;
628336; 628357; 628418; 628418; 628529; 628955; 630013; 632074; 632137; 665658; 665774;
666128; 666218; 666377; 666377; 666425; 666639; 666658; 666829; 666879; 667482; 667598;
667883; 668007; 668182; 668442; 668685; 668851; 669419; 669435; 669443; 669471; 681906;
681948; 682522; 682528; 682555; 684634; 684661; 684940; 684940; 685371; 685912; 686164;
686172; 687270; 687397; 687820; 687875; 687990; 700302; 700527; 700699; 700792; 701112;
701231; 701481; 701532; 701751; 703479; 703581; 703739; 703846; 703964; 704020; 704290;
704299; 704459; 704532; 704697; 704760; 704905; 704992; 705110; 705188; 705265; 705265;
705274; 711450; 711552; 711680; 711768; 711826; 711826; 711857; 711918; 711959; 711961;
712023; 712049; 712341; 712378; 712577; 712604; 712641; 712641; 712668; 712683; 712840;
712840; 712848; 713080; 713145; 713382; 713469; 713647; 713653; 713660; 713685; 713782;
713839; 713862; 713886; 713922; 714106; 714210; 714426; 714453; 723972; 723986; 724052;
724112; 724378; 724387; 724588; 724615; 724652; 724892; 725223; 725266; 725274; 725454;
725473; 725503; 725677; 725680; 726086; 726147; 726236; 726637; 726678; 726779; 727026;
727192; 727210; 727229; 727251; 727292; 727390; 727526; 727551; 727792; 729942; 730149;
730410; 730410; 738899; 739126; 739183; 739625; 739625; 739901; 739983; 739990; 739993;
740027; 740122; 740130; 740344; 740457; 740476; 740554; 740554; 740914; 740914; 740925;
741067; 741139; 741379; 741429; 741474; 741497; 741769; 741815; 741841; 741841; 742007;
742082; 742101; 742125; 742143; 745347; 746321; 752557; 752631; 752652; 752732; 753069;
753104; 753184; 753211; 753215; 753234; 753285; 753301; 753313; 753321; 753346; 753381;
753381; 753418; 753420; 753430; 753446; 753447; 753457; 753467; 753587; 753587; 753610;
753620; 753692; 753700; 753770; 753775; 753862; 753897; 753914; 753917; 753923; 753987;
754031; 754046; 754080; 754085; 754093; 754275; 754355; 754358; 754436; 754436; 754479;
754490; 754490; 754509; 754538; 754538; 754600; 754601; 754998; 755037; 755054; 755093;
755145; 755239; 755416; 755506; 755663; 755752; 755821; 755891; 755975; 756163; 756211;
756272; 756372; 756373; 756452; 756480; 756488; 756657; 756666; 756769; 756847;
756898; 756968; 757381; 757961; 758037; 758148; 758222; 758266; 758329; 758365; 758366;
758468; 758662; 759164; 759865; 759873; 759948; 760148; 760224; 760231; 760282; 760298;
760299; 760344; 767034; 767049; 767069; 767183; 767202; 767345; 767638; 767753; 767765;
767769; 767784; 767798; 767817; 767828; 767851; 767994; 768031; 768168; 768205; 768246;
768272; 768296; 768299; 768316; 768324; 768357; 768370; 768443; 768453; 768496; 768497;
768561; 768562; 768638; 768644; 769028; 769513; 769645; 769657; 769676; 769846; 769921;
770012; 770014; 770027; 770066; 770080; 770192; 770212; 770216; 770355; 770377; 770377;
770391; 770452; 770462; 770570; 770593; 770670; 770794; 770858; 770859; 770868; 770884;
770884; 770901; 770910; 770957; 770992; 771000; 771084; 771173; 771196; 771206; 771220;
771236; 771258; 771308; 771323; 772111; 772220; 772261; 772455; 772481; 772878; 772951;
773170; 773188; 773192; 773215; 773217; 773233; 773236; 773246; 773254; 773301; 773305;
773319; 773332; 773344; 773599; 773618; 773724; 773771; 773922; 774036; 774071; 774082;
774082; 774409; 774471; 774502; 774751; 774754; 780937; 781014; 781018; 781019; 781050;
781097; 781222; 781341; 781362; 781510; 781704; 781738; 781766; 782047; 782199; 782315;
782339; 782449; 782488; 782497; 782513; 782513; 782543; 782587; 782594; 782618; 782692;
782760; 782789; 782797; 782800; 782811; 783629; 783645; 783681; 783696; 783697; 783698;
783721; 783729; 783836; 783849; 784104; 784124; 784126; 784224; 784278; 784319; 784337;
784360; 784504; 784593; 784744; 784772; 784777; 784830; 784841; 784876; 784910; 784959;
785148; 785293; 785334; 785371; 785415; 785459; 785574; 785575; 785595; 785605; 785616;
785744; 785745; 785793; 785816; 785816; 785845; 785933; 785963; 785975; 786048; 786048;
786067; 786083; 786084; 786155; 786202; 786213; 786607; 786672; 786674; 786675; 787857;

TABLE 5-continued

Image ID Numbers Present in the 5K microrray.

787861; 787938; 788107; 788136; 788141; 788185; 788190; 788203; 788247; 788285; 788286;
788334; 788421; 788444; 788472; 788486; 788493; 788511; 788518; 788566; 788574; 788645;
788647; 788654; 788695; 788721; 788745; 788832; 789011; 789012; 789014; 789049; 789049;
789069; 789069; 789091; 789147; 789152; 789182; 789204; 789232; 789253; 789318; 789357;
789369; 789376; 789382; 795173; 795178; 795241; 795288; 795296; 795330; 795498; 795543;
795738; 795771; 795805; 795827; 795830; 795840; 795847; 795888; 795936; 795965; 795989;
796000; 796137; 796147; 796181; 796198; 796198; 796253; 796258; 796268; 796341; 796398;
796542; 796646; 796680; 796757; 796904; 796984; 796994; 796996; 797016; 797059; 809353;
809394; 809454; 809464; 809464; 809494; 809523; 809530; 809535; 809541; 809557; 809578;
809588; 809598; 809598; 809627; 809639; 809648; 809696; 809776; 809779; 809784; 809838;
809892; 809901; 809916; 809938; 809939; 809944; 809981; 809992; 810010; 810017; 810019;
810039; 810040; 810053; 810057; 810063; 810092; 810117; 810124; 810131; 810156; 810213;
810242; 810282; 810316; 810321; 810325; 810331; 810358; 810372; 810391; 810408; 810420;
810444; 810445; 810452; 810485; 810504; 810506; 810512; 810521; 810551; 810552; 810600;
810612; 810617; 810625; 810632; 810671; 810703; 810724; 810725; 810729; 810734; 810743;
810761; 810787; 810791; 810802; 810813; 810854; 810859; 810873; 810891; 810899; 810934;
810942; 810974; 810986; 811012; 811029; 811044; 811088; 811096; 811108; 811108; 811162;
811600; 811740; 811771; 811792; 811827; 811842; 811843; 811870; 811890; 811899; 811900;
811911; 811920; 811930; 811942; 811999; 812042; 812048; 812083; 812105; 812126; 812126;
812144; 812155; 812167; 812196; 812227; 812246; 812251; 812266; 812266; 812276; 812965;
812968; 812975; 813149; 813158; 813166; 813171; 813179; 813184; 813254; 813256; 813266;
813279; 813280; 813387; 813402; 813410; 813410; 813419; 813426; 813444; 813459; 813460;
813462; 813520; 813533; 813536; 813552; 813591; 813614; 813630; 813635; 813648; 813651;
813673; 813675; 813678; 813707; 813711; 813712; 813714; 813742; 813751; 813757; 813818;
813823; 813827; 813828; 813830; 813841; 813854; 814014; 814054; 814095; 814101; 814117;
814119; 814119; 814214; 814246; 814260; 814270; 814270; 814306; 814319; 814357; 814378;
814381; 814409; 814460; 814465; 814478; 814508; 814526; 814526; 814546; 814576; 814595;
814615; 814636; 814640; 814696; 814701; 814731; 814765; 814776; 814792; 815235; 815239;
815245; 815285; 815287; 815294; 815501; 815503; 815507; 815526; 815529; 815530; 815534;
815539; 815542; 815555; 815564; 815774; 815781; 815816; 823562; 823590; 823590; 823598;
823614; 823663; 823679; 823691; 823696; 823715; 823756; 823775; 823779; 823794; 823819;
823851; 823851; 823859; 823864; 823871; 823876; 823886; 823900; 823901; 823928; 823930;
823940; 823943; 824024; 824031; 824041; 824044; 824044; 824068; 824070; 824074; 824117;
824340; 824352; 824382; 824393; 824426; 824511; 824527; 824531; 824547; 824568; 824591;
824602; 824704; 824753; 824895; 824906; 824922; 825013; 825060; 825080; 825085; 825214;
825224; 825265; 825271; 825293; 825295; 825296; 825323; 825335; 825369; 825399; 825433;
825442; 825451; 825470; 825470; 825478; 825577; 825583; 825585; 825677; 825842; 826077;
826135; 826137; 826138; 826166; 826173; 826204; 826211; 826217; 826254; 826350; 826405;
826459; 826622; 826668; 827013; 827120; 827132; 827144; 827156; 837870; 837905; 838359;
838373; 838389; 838568; 838676; 838716; 838802; 838856; 839094; 839101; 839516; 839552;
839594; 839623; 839682; 839682; 839736; 839890; 839991; 840158; 840158; 840325; 840333;
840364; 840384; 840404; 840404; 840486; 840493; 840511; 840517; 840524; 840567; 840600;
840606; 840620; 840636; 840654; 840658; 840683; 840687; 840691; 840702; 840768; 840776;
840788; 840818; 840821; 840865; 840878; 840882; 840889; 840894; 840940; 840942; 840944;
840978; 840990; 841008; 841044; 841059; 841093; 841149; 841203; 841261; 841263; 841278;
841282; 841292; 841308; 841331; 841332; 841334; 841340; 841352; 841357; 841370; 841384;
841470; 841478; 841498; 841501; 841507; 841617; 841620; 841641; 841664; 841669; 841679;
841689; 841691; 841691; 841695; 841698; 841703; 842784; 842785; 842802; 842806; 842818;
842820; 842836; 842846; 842849; 842860; 842863; 842894; 842906; 842928; 842939; 842980;
842980; 842989; 843016; 843028; 843049; 843067; 843069; 843070; 843076; 843094; 843110;
843121; 843133; 843134; 843139; 843140; 843159; 843174; 843248; 843249; 843287; 843312;
843319; 843321; 843352; 843426; 859359; 877613; 877644; 877651; 897497; 897531;
897544; 897563; 897567; 897570; 897594; 897596; 897619; 897626; 897632; 897636; 897642;
897646; 897652; 897655; 897667; 897669; 897670; 897673; 897690; 897751; 897770; 897774;
897781; 897788; 897806; 897814; 897822; 897835; 897840; 897880; 897901; 897901; 897906;
897910; 897952; 897956; 897963; 897971; 897982; 897983; 897987; 897997; 898032; 898035;
898062; 898073; 898092; 898095; 898096; 898108; 898109; 898122; 898123; 898138; 898148;
898198; 898218; 898219; 898221; 898237; 898242; 898253; 898258; 898262; 898265; 898281;
898286; 898305; 898312; 898317; 898328; 949914; 949928; 949932; 949934; 949938; 949940;
950092; 950096; 950356; 950367; 950369; 950430; 950445; 950445; 950482; 950489; 950574;
950578; 950607; 950680; 950682; 950689; 950690; 950710; 951117; 951233; 1035182; 1046522;

TABLE 6

Image ID Numbers Present in the 7K microrray.

502055; 809578; 171936; 897646; 810632; 530139; 377252; 731257; 49464; 120881; 755416;
950574; 712341; 783697; 434833; 258606; 743804; 39313; 144924; 209014; 126401; 135450;
243638; 244310; 245489; 126219; 111634; 309515; 340974; 1493527; 362624; 131839; 740554;
214816; 855521; 971372; 195330; 44351; 232772; 134476; 123666; 826459; 214858; 85541;
266318; 878468; 788109; 307255; 341706; 127473; 139217; 195381; 203227; 296754; 200402;
293471; 243603; 809383; 322561; 292463; 725677; 839991; 428412; 796323; 399049; 289978;
550355; 347373; 843067; 700792; 232826; 365973; 490778; 24918; 786677; 121252; 121239;
126465; 135203; 193923; 234469; 247986; 232670; 22074; 782439; 782783; 1455566; 666218;

TABLE 6-continued

Image ID Numbers Present in the 7K microrray.

46182; 108815; 366341; 869375; 300051; 214006; 795498; 810934; 809353; 950092; 787861;
246869; 179753; 430218; 433162; 812955; 36607; 115307; 127542; 137208; 195553; 194307;
295723; 141171; 324861; 770887; 782503; 503841; 810617; 149737; 783696; 323474; 884655;
192569; 432194; 66686; 813166; 207794; 725274; 824068; 52096; 309591; 504791; 79592;
767475; 416833; 121355; 126453; 207098; 548693; 244391; 244806; 281843; 141768; 427692;
21652; 1472150; 713839; 727251; 79520; 877827; 549933; 285780; 240651; 769657; 46518;
525518; 759873; 625923; 137535; 756931; 266106; 767471; 66467; 127185; 127943; 136954;
242011; 292522; 292230; 141675; 343320; 321739; 39993; 280371; 249856; 246619; 703739;
66965; 810999; 811927; 436106; 141818; 365930; 360213; 841689; 897910; 824659; 45284;
345626; 415388; 813513; 293632; 121365; 126508; 199571; 199641; 234419; 245217; 292559;
35236; 1031045; 22260; 1492147; 40643; 208001; 826077; 491403; 310406; 1475659; 243181;
68977; 345586; 243741; 79624; 773724; 1031045; 773637; 278650; 609087; 813738; 246117;
120318; 127666; 136919; 295386; 207665; 295599; 211800; 358531; 269815; 40304; 430614;
147414; 194949; 712683; 809507; 256907; 42906; 436155; 50754; 48136; 127928; 825451;
815534; 415089; 344139; 82225; 767419; 139766; 121415; 241003; 139835; 194587; 195555;
244879; 132871; 149373; 323371; 22493; 1493160; 66982; 813552; 740476; 611532; 757440;
1475797; 154600; 197176; 768496; 547058; 767994; 823871; 269354; 611407; 854645; 345833;
665373; 207813; 126234; 130358; 136933; 195668; 208383; 294167; 212180; 413633; 365841;
41199; 489506; 292475; 823562; 840384; 323603; 489839; 785572; 450152; 181831; 756488;
177737; 773188; 796181; 310138; 194236; 770000; 81475; 768347; 230196; 121159; 292171;
142984; 200031; 246119; 244646; 247466; 42706; 501430; 23132; 1461664; 813841; 148021;
753620; 855749; 153505; 1476181; 156033; 210887; 769921; 84750; 80910; 711918; 109310;
430465; 120600; 625584; 66329; 244063; 127173; 142326; 137663; 295600; 208524; 297437;
247635; 417226; 502506; 41511; 857603; 771323; 214572; 814260; 269878; 486787; 28774;
448514; 811108; 810506; 810724; 825224; 773170; 324494; 289706; 203130; 23514; 138021;
108177; 121206; 151896; 138999; 292966; 213698; 296623; 248545; 160664; 343073; 25584;
859478; 813630; 770858; 427812; 884641; 770880; 1323539; 878564; 755054; 28098; 183337;
49630; 66718; 810059; 811024; 882484; 838434; 66352; 113399; 134525; 130716; 300632;
201519; 208790; 295324; 140422; 429574; 795809; 42096; 969568; 813823; 122159; 898281;
810753; 882548; 42864; 815861; 377320; 810092; 194182; 814409; 83129; 810264; 725335;
757489; 45645; 202901; 212236; 196214; 138374; 138837; 196837; 214823; 296773; 293564;
503737; 416305; 26184; 684626; 204897; 898262; 789369; 489519; 295843; 1456120; 878798;
810452; 293820; 261519; 841308; 85840; 119133; 740672; 882439; 298303; 66369; 297439;
122019; 130756; 140210; 200418; 229290; 239712; 140655; 504794; 487929; 42352; 971199;
292306; 36387; 784224; 884842; 123264; 488964; 824552; 767638; 26021; 41591; 77728; 784772;
429721; 487115; 971212; 855872; 66898; 233349; 123817; 138304; 248535; 196849; 213875;
296857; 197413; 298384; 502818; 815284; 742082; 271985; 843287; 756600; 415817; 1493383;
878681; 41658; 209137; 123926; 68225; 951233; 782578; 429349; 432042; 897865; 66390;
247710; 357970; 130791; 141106; 293128; 240050; 243460; 241113; 325155; 810083; 1409509;
359747; 307231; 840889; 502690; 428103; 1473304; 825418; 810600; 46897; 77897; 48631;
504774; 488645; 323500; 773568; 511909; 123255; 137182; 123858; 134192; 144956; 243652;
295140; 296141; 297919; 324225; 771197; 815110; 85509; 841149; 842894; 289447; 344997;
461516; 1055753; 144816; 196115; 211548; 785793; 781050; 590544; 377275; 773511; 66540;
111884; 122126; 130747; 141169; 201586; 292308; 293356; 144878; 296095; 112565; 213607;
214068; 166199; 788647; 247103; 455121; 1486082; 825606; 48614; 41356; 112629; 564803;
814526; 263836; 854668; 868332; 280740; 159166; 129177; 124730; 131877; 262920; 196636;
121727; 296170; 142927; 359933; 488707; 712460; 23831; 841703; 898092; 452374; 757873;
487297; 45636; 23772; 247281; 201628; 839516; 758365; 856354; 141852; 1031747; 270136;
66533; 121072; 123065; 134829; 140759; 206781; 240318; 144885; 825842; 795735; 810923;
725746; 221092; 124127; 297392; 858204; 854760; 123916; 825740; 172765; 293104; 827144;
841093; 814119; 878744; 757222; 255333; 324715; 151261; 123112; 244062; 132285; 244299;
201006; 300972; 296188; 130773; 809517; 299274; 815535; 809598; 843159; 85497; 769890;
855624; 471725; 1358393; 70002; 308588; 86220; 839094; 788421; 174627; 856174; 511459;
293191; 123788; 122237; 134368; 140966; 204098; 240586; 310034; 110347; 566474; 810096;
292996; 469412; 812083; 758222; 502832; 179603; 110226; 826352; 80146; 347434; 85678;
144777; 137638; 755751; 897107; 866882; 593183; 66475; 120309; 124788; 132358; 151418;
201030; 243808; 132464; 108330; 376767; 365177; 40704; 150702; 842846; 898122; 731648;
588829; 489553; 511814; 823851; 155583; 897670; 815235; 428231; 770444; 251936; 148225;
416643; 111492; 121133; 126221; 134856; 141230; 203791; 240674; 292633; 111054; 324313;
810229; 341328; 308437; 81417; 275180; 590727; 82131; 193087; 45556; 190468; 124781;
897952; 826350; 293403; 489664; 430928; 745214; 784109; 240977; 111136; 127462; 133130;
292496; 201902; 308231; 136855; 132066; 430153; 795277; 66731; 812246; 430318; 85634;
878835; 241489; 1404841; 753430; 229723; 43207; 897982; 795543; 448190; 205239; 471598;
586895; 784253; 277274; 121462; 126371; 138550; 194704; 203805; 241350; 195911; 111264;
487819; 795439; 24085; 681948; 809394; 66534; 460487; 949939; 162533; 207082; 213890;
27548; 258790; 796147; 356707; 382564; 745007; 755228; 788420; 142076; 110507; 127881
137653; 195387; 202066; 243385; 292812; 135220; 488386; 429799; 49553; 159118; 44563;
701481; 83605; 166245; 49318; 1391682; 357031; 136744; 813714; 839552; 71101; 809694;
433567; 853809; 971382; 726791; 34302; 198647; 126650; 136301; 234380; 205490; 245484;
308163; 194155; 269354; 366848; 1412398; 810512; 34849; 897788; 360885; 145112; 287125;
183602; 813444; 823876; 137794; 51974; 897971; 143306; 244951; 239446; 49560; 796475;
66902; 161195; 128193; 132748; 211319; 202485; 309685; 299442; 230116; 810762; 324699;
32493; 30093; 36374; 840865; 773301; 33643; 825170; 450949; 768370; 160793; 139573; 824041;
786155; 488303; 431908; 383175; 271045; 233308; 121214; 126702; 135853; 206949; 205085;
245556; 139558; 80384; 291974; 811028; 1412412; 795178; 241474; 774502; 160664; 754406;
796287; 220851; 770452; 345858; 194214; 713469; 824393; 470061; 344243; 781047; 252663;
785707; 293177; 111006; 194136; 140337; 194972; 202348; 293005; 246546; 485195; 810741;

TABLE 6-continued

Image ID Numbers Present in the 7K microrray.

268152; 246748; 127841; 28475; 628336; 307138; 855586; 266312; 451098; 724588; 741067;
243580; 813266; 75254; 811168; 744917; 264646; 796759; 767236; 197676; 120297; 214744;
139051; 242010; 292628; 245765; 130892; 172440; 376802; 26922; 1412503; 770014; 668851;
772455; 853368; 755402; 85514; 221828; 299388; 130153; 365060; 949928; 897626; 66714;
263229; 198982; 869538; 767312; 232658; 234398; 128460; 193381; 195127; 210494; 292690;
232628; 586698; 249949; 42993; 430297; 756452; 240518; 260200; 302286; 469306; 25988;
450777; 754085; 293325; 130820; 613126; 78217; 809456; 161998; 855684; 796134; 244847;
247216; 126883; 137981; 195720; 232965; 245936; 135910; 180902; 66437; 27624; 1416782;
768296; 194384; 609663; 345553; 68049; 1325605; 362278; 725473; 119384; 234237; 504877;
897901; 810272; 415086; 51064; 869187; 768464; 248624; 233347; 128973; 470232; 195117;
210501; 293500; 130777; 755093; 811097; 43129; 884743; 160723; 202682; 685371; 301735;
878406; 503717; 451907; 305336; 261828; 340558; 842820; 783629; 344091; 447365; 1031552;
67759; 110893; 130276; 301752; 138507; 193200; 235026; 245986; 296041; 187616; 66373;
28309; 1473289; 47142; 132373; 382195; 884766; 435953; 1455976; 395708; 809776; 753069;
812251; 713782; 810942; 298231; 121551; 773381; 755581; 681917; 127970; 203469; 130826;
154312; 212815; 210525; 293664; 132549; 782594; 502496; 43338; 773367; 179500; 809639;
704290; 324437; 724932; 488956; 452780; 341942; 726637; 810986; 726236; 788107; 782853;
781139; 41345; 129516; 121501; 128617; 138579; 245413; 244784; 246537; 296162; 196282;
323623; 28985; 1474337; 140806; 153473; 758037; 280735; 68950; 811088; 110467; 204539;
781510; 784744; 417855; 739511; 1056200; 611075; 66582; 144902; 206544; 130857; 138141;
206849; 210343; 293675; 274578; 136780; 795442; 43550; 755474; 469345; 809901; 71672;
488276; 193736; 247483; 453107; 240367; 567265; 50506; 810703; 70489; 809526; 491565;
739109; 70245; 295376; 110094; 121803; 322786; 138672; 197093; 293990; 296199; 796198;
219976; 504300; 30272; 592592; 128143; 682528; 487118; 80186; 436062; 1472336; 757500;
771236; 549073; 125092; 897563; 842939; 795730; 490763; 882488; 302632; 66596; 128204;
296883; 130972; 138189; 359411; 210565; 120701; 753381; 155072; 809596; 43622; 267420;
810325; 810358; 843140; 782193; 740801; 82297; 897720; 234736; 240062; 144834; 786084;
826173; 320509; 262251; 67769; 280837; 110198; 123805; 128690; 138752; 197776; 214848;
296334; 121420; 259587; 810992; 31143; 263716; 754600; 842802; 897690; 525926; 868652;
1472698; 1472753; 146123; 754538; 810444; 789204; 785744; 810502; 343871; 773137; 838149;
66608; 247660; 122354; 130572; 140252; 201173; 234170; 132789; 293510; 327221; 343343;
44255; 322079; 823696; 298155; 725503; 745343; 797048; 432050; 897978; 725680; 131653;
323506; 52629; 760224; 770614; 510002; 306444; 842861; 292232; 125828; 124132; 207649;
139189; 197736; 230180; 295501; 172721; 810395; 470144; 183556; 72869; 758266; 236305;
868484; 756556; 1456937; 1474684; 362853; 727210; 701112; 713886; 594743; 490556; 756596;
1142132; 840766; 66630; 210923; 122359; 130582; 471372; 207016; 241475; 193937; 143756;
341588; 279399; 346009; 811044; 51448; 815555; 971276; 25517; 395711; 279378; 124138;
770192; 245920; 79022; 66564; 488157; 969854; 505491; 842918; 211813; 128503; 124143;
294483; 288658; 292568; 243405; 295206; 244055; 365665; 809488; 878652; 129506; 796000;
782811; 769716; 878280; 1048985; 34184; 841357; 782800; 825433; 146577; 756709; 252515;
129387; 843098; 66910; 111549; 122684; 130977; 138337; 201334; 241587; 230274; 120306;
366009; 291623; 379920; 811162; 628357; 784777; 461804; 756533; 769552; 756708; 471200;
123730; 134748; 739126; 40017; 471859; 49963; 135085; 810801; 234036; 110578; 123932;
132848; 293755; 198026; 243887; 295321; 123229; 810664; 810389; 741880; 327350; 148421;
796984; 83444; 491692; 1309620; 1032405; 345348; 813675; 784124; 788745; 632137; 257523;
770394; 362910; 299559; 66903; 295985; 122796; 135058; 137760; 206882; 240992; 366526;
128795; 280286; 66965; 448619; 809464; 127821; 244147; 431296; 869466; 263894; 814080;
26314; 299679; 80549; 815285; 898258; 435551; 23012; 625683; 66977; 200863; 233688; 132524;
470348; 194297; 485858; 297411; 811890; 810510; 491157; 502518; 296587; 71727; 795830;
756502; 896962; 1343468; 700721; 119530; 754355; 81599; 73381; 207358; 291448; 77539;
51826; 610097; 546600; 111714; 122397; 135777; 137862; 204638; 241258; 345342; 130610;
795499; 810989; 366893; 767851; 43826; 307532; 284001; 484874; 280252; 265102; 178463;
123980; 81518; 814465; 121776; 857661; 50519; 345957; 839888; 274529; 110912; 124126;
132623; 160616; 197500; 296180; 129600; 129514; 488359; 795529; 810802; 124824; 504763;
774754; 462953; 70332; 1343971; 144867; 811920; 135692; 843248; 47908; 429466; 155768;
740604; 855890; 753794; 209624; 111722; 126581; 136117; 137885; 204814; 241070; 296030;
149742; 810038; 282907; 823864; 236355; 773215; 51640; 781233; 235135; 271744; 151662;
246304; 37491; 788472; 712848; 130100; 290091; 562811; 745503; 505225; 208798; 140171;
127729; 133197; 162161; 295527; 197843; 244637; 213754; 810864; 505062; 204299; 753215;
839623; 795840; 433553; 823982; 1375309; 210687; 45542; 198917; 785933; 841679; 491121;
884438; 1031799; 450307; 627039; 294133; 111755; 126544; 135922; 194656; 204444; 241932;
128457; 208699; 323474; 795803; 240766; 665774; 703581; 548693; 260035; 269381; 257135;
345430; 246522; 752732; 810859; 740914; 299630; 854696; 725721; 530185; 812967; 309092;
203918; 128118; 133303; 209583; 202243; 243878; 109049; 130120; 195813; 343562; 853570;
126470; 361639; 48886; 713145; 279790; 67221; 868838; 143443; 360168; 309316; 815774;
628418; 782824; 293925; 784257; 192271; 295410; 248288; 125608; 136730; 193533; 204312;
247159; 297063; 233579; 109310; 66676; 1486260; 810873; 35828; 837870; 504452; 415145;
366945; 132144; 240634; 292933; 754046; 842836; 77533; 309092; 358643; 268188; 815303;
811848; 121521; 120153; 128954; 134120; 210622; 202612; 296181; 299093; 120516; 357626;
505289; 843398; 132911; 143523; 840942; 193913; 365515; 309288; 454333; 742143; 145001;
153411; 75415; 563574; 344039; 742798; 590615; 361239; 204545; 214165; 297442; 136632;
233289; 207248; 247859; 136560; 232714; 259462; 132248; 127709; 115143; 204541; 826211;
291255; 281145; 72663; 810959; 768316; 130280; 154749; 85202; 74566; 233547; 277906;
268736; 51950; 43733; 66552; 120631; 129442; 233547; 195513; 202769; 296752; 142134;
175528; 429555; 504783; 665674; 811012; 244387; 80109; 427750; 868380; 461327; 49591;
46356; 66317; 786083; 626502; 488435; 377692; 857652; 79782; 236129; 206565; 125822;
140057; 295866; 207293; 248092; 112371; 258589; 809490; 31210; 248631; 123579; 179890;

TABLE 6-continued

Image ID Numbers Present in the 7K microrray.

789253; 840708; 756490; 33294; 267725; 44255; 753587; 813158; 784126; 840606; 563621;
121406; 769901; 884822; 53039; 38465; 120162; 129407; 197054; 195524; 293178; 296901;
139278; 202921; 491559; 44537; 754649; 71622; 245853; 789069; 795309; 68557; 505881;
471742; 45544; 44505; 669443; 824527; 796253; 284701; 78353; 852829; 246430; 247803;
295492; 126988; 141298; 193713; 230560; 246824; 115414; 267431; 249895; 32898; 392622;
813279; 246765; 361974; 295093; 343867; 1472743; 259579; 223483; 188036; 770216; 810729;
591281; 306921; 306575; 755612; 82903; 786673; 115155; 120533; 129567; 154789; 195232;
229702; 297136; 294127; 234664; 344648; 45941; 812033; 340644; 124605; 82734; 308746;
845419; 857681; 486076; 180864; 293859; 898218; 75009; 782385; 854284; 69184; 742576;
124891; 121687; 129840; 141366; 193790; 233734; 248688; 344352; 268412; 284479; 33632;
280507; 36493; 242062; 841352; 856796; 279970; 1492104; 289677; 809784; 52933; 471266;
52079; 773192; 782688; 588598; 450386; 1032004; 767277; 109108; 120823; 131316; 140852;
195820; 211361; 294485; 203302; 295873; 811150; 47110; 796388; 343072; 283023; 825060;
324383; 884867; 248295; 487761; 361171; 23173; 203721; 774036; 212165; 502333; 51817;
295857; 627273; 109279; 121543; 358543; 139656; 198578; 240406; 248601; 358673; 273435;
795151; 34357; 1342650; 365755; 769513; 41650; 364510; 432651; 1492304; 306358; 484641;
33049; 612274; 784830; 814460; 267390; 33096; 179163; 769942; 66944; 128150; 120173;
131388; 202514; 206937; 292424; 294942; 204208; 233927; 810411; 47833; 450745; 811740;
127974; 666425; 377731; 298268; 858293; 489535; 346552; 292388; 753467; 684661; 687875;
257422; 433481; 151449; 845363; 136223; 108730; 121898; 296177; 139689; 198582; 233719;
130916; 134422; 278501; 782306; 34396; 307873; 738899; 666879; 504544; 139840; 264640;
1326920; 814961; 682522; 24642; 841334; 758662; 62277; 283751; 586685; 148968; 366132;
67016; 109277; 122443; 131370; 160628; 200855; 229915; 356800; 241179; 136814; 503335;
50117; 453641; 811096; 222181; 51666; 297731; 724831; 293924; 855391; 28469; 138917;
214990; 784910; 838568; 223274; 241481; 30175; 629896; 292528; 294973; 293380; 144791;
139705; 198169; 294150; 122963; 563701; 260707; 795677; 35483; 42070; 154707; 950489;
781341; 53092; 322148; 1461138; 825411; 293696; 548957; 726086; 841617; 841282; 377166;
525799; 297895; 950709; 67006; 109309; 240199; 131050; 138455; 233852; 230013; 275950;
211859; 782161; 795647; 50666; 486110; 813179; 23804; 842849; 138788; 360778; 741988;
277537; 547247; 809494; 813757; 293940; 51814; 430471; 502161; 724893; 950568; 246598;
126882; 124241; 341805; 188390; 199205; 230090; 123448; 130835; 366238; 811035; 782406;
809557; 784337; 786213; 586839; 854338; 1468310; 502141; 198372; 46284; 724652; 825085;
502369; 428338; 51320; 212115; 758343; 67009; 239692; 123405; 132159; 141453; 200840;
242084; 292624; 235149; 782462; 144801; 487704; 180803; 289923; 838373; 725285; 183440;
288796; 704690; 207920; 754479; 143519; 772261; 505059; 460114; 745138; 203003; 780977;
132527; 110703; 127354; 198190; 162722; 199229; 123755; 128290; 125685; 290893; 809397;
838366; 308041; 359781; 840600; 759163; 223350; 1393018; 685801; 770080; 813184; 80915;
321386; 859359; 154720; 773617; 869233; 795254; 67069; 111844; 122906; 132019; 141765;
200937; 230251; 251516; 144870; 220077; 503083; 506369; 156473; 788141; 753862; 415828;
432210; 290378; 713129; 767049; 165878; 809939; 741841; 310519; 856135; 857640; 882483;
796946; 203350; 110741; 124530; 134520; 209167; 199220; 293858; 132111; 133972; 415948;
795256; 129988; 296757; 785574; 785975; 45600; 809720; 244146; 704254; 768562; 810974;
840691; 687397; 589751; 145383; 726658; 1049330; 244194; 154999; 129293; 214577; 135901;
142385; 201393; 242780; 486279; 194872; 179419; 771133; 878578; 124597; 841203; 278501;
454822; 121454; 1405689; 825287; 210405; 47475; 949914; 814478; 271899; 773478; 884355;
842973; 66474; 110996; 124277; 325375; 309039; 210710; 280386; 139818; 134712; 325150;
770838; 71626; 248261; 74119; 897531; 784589; 856650; 896949; 713047; 261204; 35077;
843076; 711959; 214162; 435434; 133637; 283436; 531862; 201981; 246143; 123222; 136286;
142532; 294018; 242797; 200302; 160573; 259169; 809552; 126858; 49665; 49164; 324861;
780947; 897485; 379771; 284799; 33949; 243358; 786067; 897814; 42258; 358433; 757404;
768292; 594322; 138592; 110791; 124014; 143208; 191508; 202553; 243641; 126229; 139680;
265350; 505199; 137531; 811792; 898242; 704459; 770454; 814353; 1393834; 771220; 155716;
813707; 310105; 814378; 782462; 788256; 417424; 884539; 265645; 121577; 109811; 125548;
136571; 155128; 248481; 243088; 360885; 205417; 811126; 810133; 128875; 26418; 843134;
809603; 781506; 431397; 741497; 130884; 839594; 380737; 321723; 877782; 586725; 841179;
509943; 293078; 112525; 128301; 134753; 191569; 202704; 243656; 206986; 141684; 415700;
810483; 240099; 713922; 898219; 490368; 447509; 85643; 1161775; 592243; 810063; 293916;
51746; 788190; 417251; 878413; 287749; 470261; 73609; 138059; 129563; 129721; 234150;
193586; 204251; 243154; 133236; 233074; 67002; 809719; 320763; 22411; 363569; 251351;
155717; 786194; 417783; 41565; 301504; 21738; 897567; 416833; 66711; 590640; 744047;
487373; 788196; 53099; 111510; 200608; 133964; 195995; 202802; 243659; 203547; 243546;
126284; 283375; 681997; 713685; 35185; 839594; 950710; 725321; 431803; 120108; 214133;
363597; 108667; 897956; 814508; 344825; 344134; 770579; 454908; 143227; 242070; 127199;
137096; 197343; 208319; 292244; 124578; 296797; 269930; 359539; 378565; 82871; 741769;
773771; 272183; 162491; 884480; 1240116; 233583; 756373; 363144; 80708; 381067; 108330;
270626; 202897; 773479; 796513; 247818; 120681; 130054; 134394; 244781; 203390; 294951;
206992; 295916; 121731; 504575; 1411726; 31072; 771196; 774471; 773305; 781017; 730124;
489631; 810521; 301122; 45272; 781362; 795936; 810762; 472095; 366105; 868400; 120561;
121977; 143759; 136856; 207990; 213118; 292364; 125739; 279329; 263846; 809513; 1389018;
186132; 755506; 843174; 323577; 795526; 627306; 344272; 120106; 470179; 809992; 897570;
825577; 840683; 855864; 344432; 731308; 786078; 112577; 120695; 129332; 121546; 243360;
203434; 295106; 202549; 135791; 359119; 418299; 1475595; 412048; 243202; 592540; 884790;
796197; 295551; 502582; 280752; 307553; 179283; 785415; 704299; 491559; 221076; 857319;
25922; 139138; 121558; 127766; 140000; 241171; 211351; 292654; 839682; 285226; 810403;
36950; 1358229; 753184; 810625; 383089; 460398; 745116; 813654; 345787; 346117; 50413;
184365; 841620; 811870; 273435; 772425; 739090; 897823; 1046484; 283897; 126355; 299737;
193139; 196350; 212398; 296094; 233550; 138444; 244044; 51293; 1323328; 143287; 122091;

TABLE 6-continued

Image ID Numbers Present in the 7K microrray.

714453; 755373; 742115; 611027; 506032; 230261; 128783; 234011; 782797; 785459; 309515;
429448; 341978; 841070; 123408; 127625; 230224; 139883; 194965; 235040; 292964; 233071;
293715; 810861; 37366; 1292073; 754509; 201650; 842784; 282956; 502622; 1466844; 378955;
126413; 204755; 302591; 796757; 788334; 491418; 882515; 178792; 52076; 785847; 109271;
294881; 293683; 154138; 293431; 212252; 297050; 232789; 159725; 290753; 51740; 1323157;
240151; 51865; 488019; 486623; 343987; 767495; 506658; 250667; 159455; 589433; 825323;
530814; 855843; 450854; 856585; 80338; 108836; 121736; 296155; 139365; 195037; 239874;
293257; 774082; 305606; 810059; 37904; 1344137; 200814; 753346; 788654; 878836; 40773;
1412245; 379309; 753917; 183462; 241880; 712023; 813520; 487773; 725533; 34102; 509800;
42123; 122889; 120863; 131668; 198451; 290054; 295497; 296568; 214981; 131239; 810878;
1456160; 740925; 549728; 813830; 503338; 123971; 823574; 1292432; 324210; 752557; 811999;
842806; 753700; 296032; 461759; 840474; 837904; 108425; 121770; 130116; 246292; 199272;
240637; 293331; 115337; 309864; 282404; 39093; 1160732; 470393; 70827; 840990; 250654;
415102; 1412344; 379708; 754093; 40946; 491066; 824117; 898253; 489805; 502682; 22883;
884272; 66443; 121270; 120973; 131446; 366966; 200545; 245764; 296597; 233419; 154323;
809850; 878689; 292219; 545189; 83231; 1020315; 714213; 35318; 1033708; 813419; 142395;
138936; 843139; 843049; 855786; 487988; 270505; 950507; 246703; 108763; 139113; 364873;
139268; 197868; 295992; 208904; 470846; 322617; 32444; 39173; 324901; 196612; 195903;
700527; 377441; 377461; 1412502; 713236; 221808; 66946; 79502; 788832; 609332; 782725;
433573; 796689; 770675; 31251; 109488; 244686; 136772; 140328; 241658; 244077; 129569;
245534; 232826; 418394; 1161155; 810331; 77133; 782760; 769600; 786680; 1469234; 810550;
280666; 292272; 33826; 814214; 795827; 153355; 80633; 471664; 276237; 203544; 275802;
124071; 130294; 140103; 213969; 241507; 244343; 129071; 366933; 327250; 39796; 755145;
178468; 610012; 51702; 853151; 845355; 1434948; 746232; 50614; 727792; 784593; 842863;
42076; 346947; 770424; 755526; 843234; 154654; 243770; 128297; 143322; 142689; 201229;
244267; 233802; 245774; 782203; 504516; 1384851; 665658; 815526; 795296; 586803; 853687;
1470333; 815575; 289666; 770910; 809916; 827013; 840486; 884425; 502486; 51406; 897575;
233183; 246116; 123646; 292939; 191648; 245299; 230509; 292471; 130421; 306216; 266531;
34778; 82879; 711961; 72395; 377314; 1435003; 814086; 31873; 361048; 773599; 824426;
782339; 809453; 140574; 249603; 60605; 173878; 120097; 122875; 136317; 241482; 201314;
243230; 233274; 247616; 203474; 795572; 1460110; 756666; 897642; 950690; 454475; 82195;
434768; 511850; 187147; 144932; 810039; 814306; 730410; 971399; 857874; 203732; 610113;
324255; 240353; 245549; 131764; 242700; 199623; 244243; 201651; 247081; 758332; 770866;
812965; 276449; 897667; 81289; 853906; 745402; 625011; 814240; 33327; 202535; 785148;
950578; 38763; 853988; 135630; 293792; 277339; 196038; 229701; 122946; 233318; 157856;
202353; 245401; 275173; 241794; 809489; 782719; 1474174; 23776; 714106; 839736; 502499;
491727; 1390584; 774446; 47647; 248371; 179403; 897594; 242578; 809946; 769571; 731273;
509570; 201483; 297107; 240357; 135273; 470368; 199624; 284341; 202414; 126225; 271378;
809685; 810420; 768246; 773246; 258589; 345232; 80221; 969914; 814410; 753285; 33941;
840940; 897806; 838359; 298417; 755385; 773290; 897641; 242706; 112494; 122955; 234617;
160730; 246792; 243312; 200307; 243414; 771023; 33616; 1486109; 196992; 841292; 281476;
897177; 814798; 450574; 37553; 812196; 246524; 488413; 897636; 897880; 460673; 854581;
588822; 951022; 111721; 113281; 124795; 234376; 243294; 297084; 244722; 243428; 136180;
272063; 810519; 78294; 741474; 32684; 267634; 868169; 286378; 1155071; 814773; 193067;
811899; 712049; 119882; 289496; 235938; 725176; 782275; 29063; 112541; 123441; 142090;
144905; 296132; 230260; 122787; 113300; 810609; 504207; 813614; 125722; 898138; 243603;
361840; 595175; 452588; 768644; 810612; 770462; 71434; 809648; 194600; 250069; 295412;
769911; 593251; 297102; 127272; 124909; 135654; 295229; 203038; 245062; 246686; 142067;
126277; 503214; 753923; 127509; 840493; 785845; 855910; 108377; 1408710; 292613; 194364;
49860; 796268; 627939; 249687; 287687; 432581; 364934; 774420; 120413; 245742; 127096;
137016; 143995; 207968; 234320; 301082; 143661; 308497; 810402; 205633; 510679; 85979;
415700; 289857; 838611; 454896; 811900; 823940; 470930; 898221; 785334; 310034; 146868;
214985; 80659; 271670; 201264; 243614; 130044; 135676; 208570; 203122; 243700; 295389;
144880; 415406; 322695; 134544; 681906; 814095; 109179; 471642; 490947; 810806; 39798;
823663; 295729; 510396; 840517; 771089; 755578; 433307; 490805; 727147; 138929; 123724;
127147; 143654; 242687; 198807; 362694; 121798; 240208; 297043; 66576; 49970; 753447;
898123; 357626; 252259; 626206; 1390860; 42558; 343443; 341246; 843094; 814640; 301082;
238821; 742767; 148469; 785886; 135561; 244618; 130004; 135094; 195852; 244086; 246766;
197855; 135688; 366971; 306726; 503724; 51981; 363103; 192694; 284882; 122394; 772304;
757165; 212021; 361565; 281978; 824531; 897632; 240961; 280970; 854576; 288695; 811813;
132569; 121475; 126459; 135454; 197300; 203956; 247967; 485854; 201517; 771272; 770785;
1325751; 209655; 197525; 509484; 788285; 429557; 628602; 195751; 34773; 122915; 40056;
897646; 788286; 300474; 755299; 293950; 469369; 665356; 246041; 245000; 127514; 132708;
195772; 194061; 294014; 223661; 229580; 344825; 293094; 504682; 365945; 196189; 796646;
714426; 487071; 363055; 399456; 51328; 325062; 42118; 366728; 781019; 768344; 365973;
897271; 49351; 53384; 295982; 294892; 126450; 135426; 295973; 204558; 248009; 309583;
110503; 321163; 795832; 1471829; 212429; 810899; 704905; 566760; 502355; 757375; 239611;
770027; 755975; 212078; 80399; 772951; 209224; 153694; 131988; 345063; 813611; 142944;
207869; 293736; 234425; 195546; 109123; 296010; 299815; 342069; 195723; 320712; 23353;
549101; 195712; 789357; 263846; 743077; 81604; 435219; 25499; 509588; 377152; 898109;
782692; 810104; 855390; 365326; 624634; 768406; 296483; 121341; 126497; 358549; 242778;
204624; 244815; 244277; 33051; 206632; 22012; 1472689; 756272; 771258; 824024; 852520;
840460; 223176; 202958; 509495; 249705; 138116; 700302; 843319; 261494; 296123; 269292;
266146; 34837; 66711; 293336; 127983; 340745; 195784; 292357; 292332; 814270; 343646;
487087; 40026; 283034; 223098; 85561; 784278; 782835; 263014; 36491; 399532; 241530;
241985; 78869; 838676; 773220; 471641; 739155; 52996; 813168; 209277; 121412; 126509;
139764; 194600; 358984; 245219; 212620; 38763; 323577; 22293; 1492412; 121218; 125134;

TABLE 6-continued

Image ID Numbers Present in the 7K microrray.

80374; 298062; 289606; 1475746; 247241; 142556; 24032; 810791; 416959; 814765; 323371; 487429; 844725; 726768; 111516; 295583; 127710; 137349; 196047; 208375; 292501; 247783; 380620; 262053; 40360; 435597; 591864; 810321; 33045; 415084; 41195; 785930; 447167; 23282; 723972; 813591; 842818; 814731; 272327; 744052; 530545; 50491; 754582; 127769; 207379; 156023; 139490; 245517; 229997; 244350; 246194; 42076; 429323; 23019; 1493175; 810017; 66322; 773332; 740620; 491763; 1476065; 179617; 810331; 229579; 199663; 138139; 842928; 810558; 811046; 47665; 627251; 796448; 234318; 124853; 135766; 137647; 293637; 208407; 293222; 139376; 416280; 782841; 41452; 878815; 687270; 126795; 773236; 502977; 878838; 768377; 448386; 183194; 26910; 742101; 796680; 49260; 272690; 436135; 588559; 80162; 785760; 125666; 121184; 179426; 138978; 294444; 213509; 245457; 248698; 48283; 280527; 24145; 1467195; 244307; 243816; 79712; 868212; 759200; 1323448; 161172; 345559; 767798; 73782; 713660; 877613; 284479; 436029; 268946; 151595; 66333; 113394; 246074; 130656; 137506; 200773; 293847; 293358; 138865; 428231; 810868; 42059; 844816; 289615; 249688; 376875; 258120; 730002; 786537; 449058; 51543; 50680; 511066; 81394; 796341; 323989; 243159; 49311; 47037; 290308; 108197; 125769; 127486; 139062; 248020; 213535; 296741; 292770; 77577; 490755; 25725; 1468820; 809981; 241365; 703964; 293032; 128493; 1456424; 878545; 47681; 309032; 768357; 47510; 843121; 811150; 50888; 85313; 416316; 66341; 113431; 121994; 130677; 293599; 200395; 208663; 233214; 141192; 448190; 809645; 42214; 970271; 770012; 771308; 789012; 782545; 325182; 501939; 725340; 188232; 360047; 470175; 815539; 703479; 346360; 503579; 153541; 796806; 66420; 193122; 123506; 196860; 138974; 245235; 214136; 296838; 293835; 782718; 811066; 26366; 1032431; 51916; 208161; 214441; 454083; 128753; 1435300; 878676; 141562; 563598; 265874; 490306; 951117; 503083; 49548; 435561; 131626; 66377; 113538; 240937; 130758; 140792; 245386; 233783; 230341; 138234; 299197; 279407; 42576; 1408407; 153025; 813711; 80410; 970590; 431655; 490244; 824728; 45138; 243321; 770868; 814014; 795173; 505538; 853938; 530282; 122150; 108471; 211024; 321580; 563621; 196222; 232624; 296136; 294740; 1030929; 810852; 83011; 550353; 24415; 712840; 230882; 46166; 1493390; 896921; 242037; 823614; 770212; 774071; 797059; 282907; 884783; 595604; 66555; 290230; 296444; 130801; 141123; 201525; 280750; 244386; 143910; 127860; 795798; 120468; 126390; 247117; 80500; 624627; 789314; 1474149; 825604; 288896; 48182; 755037; 781018; 789318; 358752; 450661; 1031076; 324122; 261587; 245745; 123578; 292236; 143887; 296508; 260619; 296168; 840404; 321271; 309803; 686081; 245422; 486208; 949940; 39920; 130242; 462113; 50887; 380797; 45231; 262231; 40299; 83363; 742064; 161373; 502753; 838744; 66550; 128561; 122170; 130824; 140732; 243194; 469981; 297405; 244202; 504979; 364555; 399318; 126368; 813280; 789147; 360854; 949971; 1474955; 825726; 810743; 26578; 33690; 898317; 841698; 361899; 470279; 248463; 855620; 740554; 109523; 198874; 137918; 154477; 159935; 282980; 296184; 143169; 810154; 310894; 713193; 293859; 81427; 418422; 51373; 455128; 487348; 49389; 810551; 300482; 274638; 40562; 233581; 214982; 455115; 435036; 278101; 66562; 198605; 123067; 134229; 140811; 206831; 240843; 126393; 129541; 771215; 795382; 769542; 260325; 128243; 115281; 755689; 789383; 110168; 826256; 292212; 124753; 773254; 704532; 796542; 590692; 230971; 251591; 951142; 67037; 121880; 244058; 133331; 322759; 296498; 309045; 296189; 344133; 809995; 356835; 826984; 289337; 526657; 83210; 884301; 854879; 1404396; 1470060; 302549; 813827; 758366; 840404; 239877; 856489; 432072; 725501; 950473; 383016; 110436; 294255; 134439; 140921; 203910; 240648; 292222; 112896; 771255; 810843; 190491; 133213; 243100; 66560; 487777; 594120; 211275; 788269; 203240; 27787; 897619; 814117; 165921; 502669; 280356; 743041; 626531; 132215; 111101; 124808; 138737; 197975; 296149; 292270; 132690; 131887; 810575; 771233; 149013; 897497; 795330; 85624; 845415; 346604; 1350468; 51408; 813460; 361097; 814696; 789232; 429574; 214884; 470122; 200018; 626716; 195051; 111200; 126237; 143919; 140304; 211557; 292834; 230360; 109483; 271357; 282320; 723986; 669419; 841384; 208413; 361323; 564492; 248583; 510032; 134269; 244703; 814246; 785745; 812144; 491486; 857002; 26568; 593023; 66406; 111413; 142087; 133158; 274979; 247194; 366085; 128260; 121251; 809422; 277003; 283954; 212649; 322051; 85128; 755750; 562813; 1367900; 810445; 40887; 209841; 843249; 839890; 755093; 755301; 376785; 852913; 108801; 111705; 128322; 135212; 194395; 203850; 241355; 130334; 126438; 357681; 191743; 530875; 146605; 827132; 280882; 1035889; 233479; 395440; 770670; 298963; 234562; 79629; 841332; 283715; 346696; 856434; 769579; 26884; 51450; 245885; 132835; 132323; 195358; 207778; 295997; 248143; 769846; 191826; 502405; 588911; 770391; 195340; 815542; 841059; 49987; 897950; 1376827; 668007; 44975; 127193; 898265; 429182; 344274; 1031203; 745433; 460106; 768329; 142139; 111825; 126670; 136382; 293328; 234647; 245479; 357120; 156874; 502421; 811095; 1412238; 205185; 49509; 51041; 137158; 469969; 745496; 190666; 162775; 823598; 49518; 842989; 796996; 246722; 769948; 278242; 486113; 38642; 154616; 130243; 128346; 134482; 194921; 202315; 293436; 126341; 194031; 323117; 811607; 148231; 245296; 220096; 824070; 950096; 362409; 384078; 450983; 136821; 358457; 811842; 39593; 949932; 810395; 491544; 769712; 845663; 726846; 50214; 137793; 126722; 136909; 294647; 204489; 245570; 325365; 163579; 810558; 810846; 1412481; 246300; 756163; 759164; 269806; 377671; 626358; 172751; 308281; 292806; 823930; 704760; 824922; 838856; 882506; 324891; 856535; 785967; 83210; 293569; 128737; 154214; 195052; 202357; 293045; 121997; 491232; 795604; 795750; 309970; 340630; 42373; 68103; 811585; 586888; 52741; 450711; 376290; 160838; 262996; 825013; 713080; 127860; 139681; 731339; 51083; 306806; 121220; 126884; 137931; 297061; 207370; 245894; 212406; 175727; 1048810; 27549; 1412504; 812276; 753301; 950445; 754034; 22895; 586990; 360392; 809627; 756769; 469686; 814701; 843070; 194161; 472186; 303109; 811000; 842968; 40751; 121877; 142647; 154289; 195091; 210431; 292908; 125308; 730410; 343744; 43021; 488873; 813742; 247816; 740457; 327635; 288663; 25807; 451855; 813459; 296529; 203351; 824602; 739993; 321734; 178825; 264895; 84713; 108265; 123439; 126887; 137989; 193481; 232723; 245964; 109200; 1035182; 66491; 27848; 1435862; 810372; 768168; 897669; 1030769; 296448; 1325816; 141221; 627114; 221846; 511428; 289818; 826135; 504207; 261580; 243882; 838612; 813499; 200969; 841691; 128993; 138104; 195139; 210523; 293503; 292542; 770593; 256515; 43231; 725076; 32609;

TABLE 6-continued

Image ID Numbers Present in the 7K microrray.

246246; 840687; 281003; 842825; 489485; 453005; 35105; 356665; 202904; 814546; 789011;
809621; 470128; 199833; 108316; 121500; 138589; 143454; 193546; 235102; 246144; 297178;
193913; 66950; 28410; 1435029; 133273; 201727; 711826; 784179; 756405; 1455641; 236263;
810242; 265680; 727292; 843321; 782488; 810567; 220655; 285544; 856961; 767188; 293417;
296393; 137456; 138168; 195974; 210348; 293676; 193938; 783697; 322537; 43241; 897158;
213280; 301061; 774409; 428756; 433253; 197657; 452963; 127677; 25588; 509760; 789091;
711768; 782679; 859807; 884719; 86160; 108351; 121808; 128627; 141209; 197051; 293845;
246684; 295514; 207618; 365423; 29054; 1486083; 594540; 753897; 826204; 844680; 624754;
1456900; 725672; 166934; 510702; 767753; 877651; 825214; 279146; 152453; 770588; 884500;
66584; 251461; 123720; 130876; 138165; 200780; 209340; 293727; 343737; 148743; 123546;
43563; 269606; 50182; 134783; 840944; 365826; 770835; 783998; 453183; 43771; 562983;
768299; 949934; 328802; 284160; 502151; 586854; 40608; 66919; 274932; 121828; 128679;
138706; 230637; 214826; 296330; 301678; 230370; 345177; 30664; 108378; 134322; 295137;
687397; 435330; 83549; 1472643; 1456118; 342378; 813426; 811942; 824511; 358531; 809390;
486678; 1032796; 526945; 66606; 246680; 122295; 133180; 138210; 230191; 233939; 234468;
199258; 144930; 257823; 44180; 284220; 244355; 140131; 950367; 342008; 344430; 282977;
897767; 727192; 179804; 296998; 71545; 810787; 268876; 455025; 770337; 85320; 144894;
110282; 124128; 128695; 138745; 197720; 232950; 296454; 323404; 810509; 277044; 31169;
430314; 509823; 485744; 727390; 433474; 460470; 1472719; 1473788; 42739; 327150; 563673;
814636; 627542; 491460; 342647; 755302; 509887; 66609; 234975; 122364; 130617; 140301;
234484; 234201; 345751; 201383; 809456; 782766; 44307; 324492; 727551; 309993; 815564;
383188; 41208; 436121; 771303; 198815; 752652; 71606; 825677; 767817; 795522; 252953;
433666; 731051; 363146; 294221; 124137; 129624; 139250; 198593; 296795; 295545; 235008;
201641; 810571; 813997; 813387; 712641; 416803; 773330; 713974; 1472735; 1049030; 197128;
771206; 783729; 796258; 203132; 490995; 45578; 884692; 742977; 66685; 124020; 122702;
144893; 138239; 201309; 241497; 209381; 193811; 135752; 809961; 378461; 754080; 26617;
705274; 162199; 788764; 392390; 347560; 46786; 129865; 197888; 795738; 753862; 810697;
177772; 757248; 123262; 296549; 124179; 129817; 295577; 198339; 243524; 295303; 344141;
795229; 795399; 859858; 23185; 789376; 840158; 154790; 769959; 1321598; 684655; 754031;
564962; 841340; 773344; 235155; 362718; 141815; 384081; 266085; 66895; 111571; 212634;
144802; 137736; 296640; 240506; 343661; 124271; 249618; 133735; 436094; 752631; 366511;
950680; 773567; 154472; 725649; 814251; 50188; 306771; 768443; 685912; 142788; 868368;
487338; 869450; 510856; 240033; 110582; 123952; 132899; 175140; 198033; 243980; 297212;
840683; 809603; 258454; 814780; 767828; 52327; 724615; 436554; 433155; 1320746; 687054;
592359; 51737; 840567; 815245; 841695; 263727; 855745; 131091; 784065; 66931; 111693;
123331; 135721; 137797; 206895; 240769; 359247; 129770; 195129; 39874; 450060; 360478;
48799; 141314; 362926; 741977; 266720; 814123; 753914; 236333; 82991; 814101; 825335;
236059; 345525; 724888; 773383; 245485; 110904; 123699; 132631; 160485; 242644; 130027;
300866; 132304; 811168; 809969; 809421; 811827; 787857; 898286; 611255; 868304; 1343768;
814989; 234559; 204214; 757961; 841261; 787938; 731029; 745019; 259842; 773579; 66400;
144852; 124087; 136114; 137884; 292292; 241274; 197414; 131238; 321734; 770935; 755821;
66728; 687820; 80095; 845477; 290234; 271102; 814316; 730149; 179534; 784876; 591907;
144881; 432564; 769603; 854401; 545403; 66574; 139354; 124168; 133096; 248306; 235924;
347036; 247614; 128632; 325380; 809815; 26616; 563444; 841669; 839101; 359661; 322914;
1343980; 526282; 204148; 145503; 231355; 756968; 811006; 811015; 32565; 41648; 772938;
247655; 111750; 126522; 136409; 137853; 204688; 241677; 230240; 136874; 810809; 67067;
130788; 135449; 22731; 682555; 855800; 141972; 291756; 49920; 246120; 129146; 774751;
843312; 308682; 51022; 725395; 307471; 837923; 126466; 110987; 198961; 133225; 197775;
202990; 243350; 128985; 129748; 415215; 809504; 214537; 178779; 784959; 711552; 784296;
756549; 1391644; 509731; 810282; 771084; 417508; 79688; 300137; 743188; 249606; 277186;
771295; 52419; 247125; 126568; 135999; 214658; 209468; 246276; 248599; 140761; 782635;
782335; 179334; 209296; 612616; 292222; 130201; 855523; 1435638; 194804; 810725; 132012;
814615; 788247; 302310; 770837; 743038; 586706; 785778; 201301; 123079; 297403; 133333;
194670; 202320; 243989; 111122; 131307; 415022; 201056; 882522; 321661; 381812; 824704;
783836; 502367; 49410; 844768; 36393; 234191; 724112; 825080; 824591; 782217; 138369;
248412; 179776; 244079; 124286; 125665; 136598; 211758; 200683; 247833; 130895; 229330;
289638; 416042; 121659; 812227; 770957; 789182; 284619; 259591; 66315; 756401; 243549;
813673; 810040; 898237; 39274; 126221; 141731; 382457; 66599; 768515; 51640; 120634;
345670; 135240; 196522; 245247; 296683; 213496; 347224; 291097; 502062; 897768; 359184;
229692; 71432; 343646; 855755; 41607; 460806; 823886; 143846; 256664; 712577; 811771;
415264; 222025; 83279; 291478; 113048; 121459; 125799; 247082; 193617; 242790; 248071;
111070; 244652; 281901; 244896; 245979; 190732; 813635; 838802; 416567; 448032; 27516;
811161; 813256; 210522; 813751; 754436; 758329; 144905; 811145; 430968; 111460; 42313;
120113; 294259; 207850; 203772; 202795; 296805; 143310; 196640; 279195; 758301; 753157;
342543; 813254; 824547; 782427; 307660; 86160; 415978; 47542; 39127; 767183; 826217;
786607; 356783; 590759; 742862; 49303; 196650; 121616; 125809; 139331; 193690; 204356;
248112; 115223; 1046522; 809858; 32875; 1435339; 153006; 740130; 855395; 755881; 502706;
291216; 544664; 233909; 299154; 381287; 773217; 262920; 884718; 461727; 135338; 767422;
123604; 124320; 129477; 205715; 294968; 229651; 295483; 202559; 240480; 322961; 45233;
768064; 167032; 564050; 842785; 809619; 530359; 744940; 486607; 161456; 810316; 212640;
815239; 897987; 416099; 204257; 141495; 743230; 129000; 121662; 127054; 141316; 193742;
233179; 292201; 143115; 267634; 795877; 33525; 278570; 300103; 809523; 67654; 729964;
45464; 1472775; 259973; 340734; 179276; 251019; 843110; 782449; 502891; 770059; 418138;
592802; 811956; 109089; 120773; 129922; 154795; 195314; 296140; 294445; 209683; 295604;
323917; 46171; 823718; 342721; 363058; 725266; 321470; 39722; 868308; 486186; 756372;
769028; 823901; 796137; 781014; 198093; 366100; 745360; 68605; 108651; 295594; 129853;
141361; 193724; 233446; 248594; 235055; 269806; 488155; 34255; 1387760; 810671; 178818;

TABLE 6-continued

Image ID Numbers Present in the 7K microrray.

511586; 362483; 156437; 1492230; 298612; 199403; 204335; 755239; 772220; 587525; 810167;
32664; 1020212; 743278; 813698; 124965; 120598; 131318; 240938; 195821; 211940; 294512;
204360; 161583; 119133; 47202; 796613; 154015; 296198; 591683; 811166; 884894; 627533;
487296; 110281; 131595; 52228; 713647; 40580; 429494; 742792; 278483; 624360; 108716;
121564; 321706; 139660; 198580; 240500; 194282; 257011; 277305; 487444; 34355; 1388395;
50043; 810117; 85690; 433350; 344759; 1473274; 324885; 41898; 376516; 788695; 843352;
714210; 271662; 743229; 590500; 840803; 66937; 293606; 125767; 131010; 210919; 293932;
229617; 294873; 322723; 240961; 809587; 49888; 454048; 770859; 727526; 630013; 810711;
755923; 971367; 491001; 811843; 282310; 173228; 811600; 841470; 811023; 531957; 854899;
770704; 321723; 200595; 121954; 125040; 139708; 275634; 294457; 112409; 131016; 278808;
376058; 34945; 41074; 136188; 49352; 85259; 177967; 366541; 1461104; 824025; 52431; 667598;
71116; 843028; 294487; 795191; 866694; 796297; 1049033; 66975; 109304; 130028; 131029;
248504; 200873; 247863; 121615; 210744; 143054; 809788; 50359; 454339; 233721; 813712;
365641; 745003; 342181; 809910; 586650; 120015; 245330; 230218; 785595; 840894; 725968;
1031940; 26249; 725188; 200599; 127610; 124502; 346484; 139957; 234527; 296749; 125737;
140635; 342522; 811582; 36775; 549139; 131362; 797016; 486175; 46367; 1468263; 826142;
230385; 213136; 840788; 840524; 788185; 810496; 845453; 223128; 593114; 67036; 206651;
124042; 143209; 138477; 200838; 211747; 204406; 128426; 811609; 810939; 50941; 489489;
66428; 704992; 841478; 741960; 206795; 511303; 684879; 31866; 768497; 306901; 841691;
789049; 215000; 246872; 295986; 377048; 203931; 124077; 245442; 137971; 162365; 199228;
230170; 123729; 247367; 505344; 795216; 85171; 261971; 897822; 841008; 731054; 472008;
1461737; 685808; 511832; 175123; 841507; 897652; 745347; 366859; 299360; 856427; 564756;
67070; 109269; 200174; 132017; 141723; 200847; 242087; 135219; 235173; 811059; 343079;
502177; 276091; 824074; 257162; 841221; 289645; 280934; 729942; 357344; 741429; 824382;
77805; 257445; 302933; 741958; 626555; 241066; 110746; 124505; 294496; 162778; 199239;
239708; 128248; 144029; 247582; 809729; 626967; 812126; 76362; 221826; 291880; 366067;
878129; 701625; 328591; 37234; 282501; 81315; 48285; 611443; 884462; 131268; 488207; 66423;
296472; 122913; 137178; 142397; 247482; 244100; 193182; 281467; 795371; 810613; 878178;
823943; 815816; 842860; 325641; 50480; 1359579; 824081; 246549; 207288; 813678; 669435;
897655; 21899; 471799; 611586; 595109; 357091; 111004; 124203; 133613; 202740; 199243;
213871; 142120; 144855; 268960; 376652; 753234; 45632; 950482; 357046; 969748; 859586;
1160723; 712401; 813149; 193990; 950607; 810854; 785293; 273546; 82738; 429368; 769926;
66430; 111765; 123196; 140830; 142442; 203551; 242779; 591653; 172783; 251028; 809413;
878259; 366834; 840511; 309864; 897233; 279172; 378502; 825648; 810124; 810391; 485989;
162208; 42880; 435858; 109863; 40692; 252382; 282378; 128602; 124637; 134643; 201562;
202492; 275176; 155201; 135247; 270997; 811010; 50794; 136235; 785616; 725454; 590264;
825312; 1160558; 713230; 566887; 510542; 840702; 760299; 83083; 447568; 510381; 490819;
345103; 144797; 121661; 195346; 136064; 155064; 207421; 242698; 110307; 198104; 490751;
809569; 809535; 66532; 840768; 666169; 435470; 773392; 431376; 809998; 754601; 359395;
49710; 810552; 122150; 744800; 277229; 28510; 897595; 345047; 245860; 124009; 134719;
191497; 204122; 243648; 125709; 127400; 377587; 325090; 229365; 823928; 950430; 739183;
854444; 740907; 1161013; 163174; 769645; 531028; 838389; 795771; 324618; 266094; 756687;
328745; 206816; 111391; 341821; 136557; 240748; 207771; 243113; 469952; 232586; 129530;
795582; 359835; 66507; 824568; 341588; 361122; 417920; 399604; 753457; 357220; 129644;
897544; 897774; 244955; 725308; 531319; 809876; 594633; 144042; 206841; 128518; 133534;
191599; 202703; 243653; 324342; 137158; 505573; 341654; 770901; 137940; 796994; 504226;
810142; 236034; 868575; 382787; 248531; 138991; 47853; 788566; 268727; 857264; 855385;
741885; 47481; 241988; 244154; 125589; 136706; 200015; 204300; 243199; 111150; 234539;
67031; 66457; 205303; 753104; 382654; 323777; 362795; 300012; 433544; 196348; 176606;
72050; 825295; 827120; 66574; 41406; 770074; 845519; 813384; 47853; 341336; 128905; 133519;
199327; 202931; 195487; 295889; 308415; 345523; 428773; 1410444; 753211; 815501; 128302;
47359; 840753; 878112; 263097; 241160; 668442; 898328; 898073; 415022; 51582; 770388;
759173; 281114; 235070; 127216; 136801; 197323; 210548; 292312; 126230; 305227; 271952;
341901; 384851; 149910; 276547; 897673; 357681; 725877; 75644; 148444; 810213; 184240;
70349; 77391; 825478; 769846; 769537; 755952; 81203; 1046542; 243817; 196109; 130053;
134495; 196125; 203400; 295044; 296562; 284592; 213660; 502762; 1475633; 235934; 109708;
897781; 809828; 884546; 489677; 755663; 211216; 813854; 484535; 841331; 343744; 486591;
773286; 856447; 244955; 121981; 243403; 138496; 197637; 208940; 292391; 128245; 280882;
809758; 810463; 461425; 666829; 208718; 950682; 429323; 970591; 73527; 345077; 40781;
123802; 166236; 825585; 898312; 135247; 50930; 345935; 840466; 42627; 292749; 120375;
243291; 296552; 196303; 207448; 295590; 214331; 138533; 417694; 140267; 1476053; 245242;
264117; 772878; 453147; 384015; 882510; 431501; 813402; 345208; 564621; 898062; 565235;
417694; 878833; 745188; 859422; 204735; 121600; 210688; 139593; 194906; 208434; 293421;
129616; 292726; 360075; 37196; 1358266; 770794; 240249; 788136; 343736; 264556; 788205;
377468; 47900; 196501; 210317; 760298; 825296; 293715; 855438; 124575; 725630; 27544;
245195; 207006; 129342; 292392; 196345; 211951; 296102; 214043; 144861; 343990; 51666;
1323432; 130541; 241348; 489079; 562115; 361688; 738900; 506548; 47559; 811911; 813536;
686164; 815287; 782439; 884673; 725877; 594517; 108783; 121715; 127409; 144793; 194985;
240138; 294311; 134312; 302369; 809824; 37451; 1404995; 296880; 44164; 788518; 196543;
290724; 1468461; 378488; 668685; 183476; 549146; 782315; 503617; 490232; 415870; 884993;
839374; 30850; 132630; 120383; 203514; 138601; 243784; 212098; 296559; 214614; 246377;
115443; 53316; 1323203; 275738; 84295; 236282; 271006; 813637; 745249; 292213; 768205;
210862; 705110; 840821; 490772; 45376; 841287; 877835; 201241; 121756; 130057; 139962;
195365; 137396; 293306; 136984; 309776; 771172; 38471; 1376853; 809938; 813651; 587847;
236155; 361807; 1412300; 385003; 296476; 767034; 810813; 824352; 488888; 148028; 502565;
813815; 109466; 120964; 131104; 167076; 280122; 234080; 296602; 230613; 135713; 365536;
1456419; 39884; 511521; 40017; 486221; 291985; 823665; 878130; 823590; 741815; 241412;

TABLE 6-continued

Image ID Numbers Present in the 7K microrray.

34439; 840776; 151501; 415554; 1031185; 511091; 200934; 121792; 130107; 140334; 197856;
241097; 293785; 210610; 321189; 795453; 39159; 1161797; 22040; 823775; 82710; 562729;
858292; 1416502; 385017; 246786; 320606; 713382; 724387; 814381; 810960; 340657; 175536;
328207; 66497; 112530; 121018; 134235; 195429; 200604; 233399; 297110; 239711; 203348;
771016; 32257; 141966; 810408; 739901; 855061; 856454; 1469230; 878182; 809892; 31093;
184175; 785575; 840978; 454440; 435611; 460403; 741831; 66407; 129331; 343352; 139837;
139462; 197907; 239835; 191572; 293457; 324815; 44310; 39285; 210575; 589115; 154608;
841370; 756595; 345538; 1473131; 713263; 22918; 144675; 759948; 45099; 196387; 884436;
624429; 342349; 40721; 206794; 123074; 131563; 214205; 201192; 212712; 137139; 134537;
233645; 782578; 1374571; 810019; 417403; 949938; 250883; 454672; 1469292; 811013; 813533;
767765; 810053; 705188; 306013; 769686; 868630; 60565; 77244; 193987; 241539; 124091;
130342; 140455; 198011; 230359; 195132; 233299; 415178; 782537; 39884; 753418; 212496;
897906; 382693; 857243; 897164; 1434905; 813983; 206217; 127519; 773319; 897751; 127925;
428223; 32304; 743701; 530035; 214906; 111389; 209264; 131886; 142733; 201961; 212787;
240914; 127646; 307314; 428582; 1471841; 361943; 795847; 841641; 725284; 74537; 1470048;
214965; 34888; 380394; 810057; 785371; 305606; 377560; 287745; 435855; 30473; 294040;
292482; 124079; 135892; 191516; 232837; 244201; 246652; 281125; 205152; 144862; 782789;
667482; 773618; 28218; 855547; 854138; 1388373; 814124; 173674; 768272; 898148; 73531;
38763; 505005; 435076; 489823; 267865; 293901; 230247; 122899; 196185; 156270; 201317;
243186; 126321; 132140; 161988; 321330; 1473300; 77636; 81336; 701751; 272529; 795321;
448432; 774078; 321529; 823691; 301976; 711450; 85805; 969877; 241736; 487425; 877664;
136073; 111266; 128785; 130233; 204179; 199602; 245806; 201203; 161993; 214583; 771058;
260303; 753775; 840364; 783849; 293925; 744417; 858469; 814287; 190887; 812105; 712378;
72778; 33051; 586796; 291057; 39843; 626822; 111981; 112440; 127120; 131824; 141522;
201784; 243245; 109314; 241038; 417305; 782283; 1475730; 813648; 760344; 795965; 283315;
307069; 450375; 207274; 28823; 823679; 44692; 767345; 156386; 46938; 624617; 796278;
773203; 345090; 113284; 127415; 135303; 135789; 199709; 245899; 248478; 206867; 209182;
66656; 809454; 122636; 788511; 322617; 344589; 26295; 1422723; 814444; 769676; 756847;
898198; 781097; 77577; 755599; 795729; 882511; 321389; 340840; 123433; 123436; 682555;
183120; 201818; 243317; 194131; 234537; 269680; 810272; 151104; 810156; 826254; 491113;
489626; 856519; 451706; 154651; 726779; 243343; 726147; 668182; 154093; 855487; 80649;
378813; 611150; 139199; 113283; 124822; 134256; 188388; 245586; 244846; 294995; 141931;
268951; 241847; 124261; 471498; 166195; 760148; 854701; 277660; 1155191; 815794; 809588;
156045; 825442; 796904; 246035; 742132; 866874; 858153; 1031748; 66391; 199627; 123459;
136775; 143748; 207881; 242642; 124232; 208210; 195370; 810448; 486544; 45291; 950356;
269815; 322160; 610362; 453689; 302190; 31842; 137836; 80948; 781704; 297061; 866702;
741891; 51363; 839882; 234331; 113308; 160488; 135653; 194401; 204684; 244313; 139226;
142851; 195034; 810299; 469954; 51362; 80946; 191664; 362059; 611581; 187614; 182661;
341310; 810761; 814595; 109888; 307933; 588915; 415529; 877832; 82556; 125741; 202209;
127099; 137020; 143962; 207952; 244227; 121611; 813410; 132217; 810754; 768561; 128126;
70692; 505573; 882459; 814266; 462595; 51447; 230100; 128530; 75923; 824906; 139278;
285460; 416390; 781075; 839980; 133820; 110417; 130043; 135710; 295741; 203287; 246478;
194399; 212542; 115408; 501674; 529861; 823859; 767202; 897596; 884644; 856167; 271748;
135221; 289551; 740027; 759865; 789014; 487172; 415899; 755630; 34140; 768260; 366156;
115230; 127182; 144762; 202621; 208984; 245409; 296616; 142586; 415741; 346447; 754998;
26811; 503097; 429555; 309893; 298965; 462645; 810504; 810010; 254321; 795288; 840818;
233071; 204686; 32299; 841396; 754378; 144747; 128054; 130005; 135010; 195853; 203388;
245273; 206786; 240430; 272183; 503033

The disclosed microarrays can be constructed using the Image ID number provided in these tables, and other available information. In particular, the Image ID number can be searched on the ATCC website, with hypertext links available to ATCC deposit numbers for deposited clones corresponding to the Image ID numbers. Hypertext links are also available to Genbank entries, which disclose sequence information about the nucleic acid at each array site corresponding to Image ID numbers.

Tables 7 and 8 summarize the results for exposure of cells to ionizing radiation using the 1.2K, 5K and 7K microarrays. Table 7 shows the results of different radiation doses (2 and 20 Gy), and hypoxia (which triggers p53 induction) using the 1.2K and 5K microarrays. As shown in Table 7, a very large fraction of the genes tested showed altered expression. As shown in the last two rows of Table 7, a substantial number of genes responded both acutely (3 hours) and at a later time (24 hours) after irradiation. The genes which showed expression at 24 hours were considered particularly suitable for a clinical biodetector that would detect the effects of radiation exposure during a time period when laboratory investigations of potential radiation exposure are likely to occur. However the genes which respond acutely (at three hours) could also be placed in an array to measure even more immediate exposures. Other arrays that include both acute (e.g. three hours) and later (e.g. 24 hours) response can be included in a single array. Differences between response of these two subsets can be used to help determine a probable time of radiation exposure. For example, if the three hour responders are positive but the 24 hours responders are not, then the time of exposure would have been at least three but less than 24 hours before the test. The results shown in Table 8 focus on lower doses and longer timepoints than the studies shown in Table 7.

TABLE 7

Summary of results for microarray analysis of stress responses[1]

| Array[2] | Targets | Treatment | Induced[3] | Reduced[4] | 99% Conf.[5] |
|---|---|---|---|---|---|
| 1.2K Chip | 1238 | 20 Gy + 4 hr | 38 | 11 | 0.63-2.37 |
| | 1238 | 6 hr hypoxia | 135 | 19 | 0.51-2.47 |
| | 1238 | 24 hr hypoxia | 202 | 8 | 0.55-2.38 |

TABLE 7-continued

Summary of results for microarray analysis of stress responses[1]

| Array[2] | Targets | Treatment | Induced[3] | Reduced[4] | 99% Conf.[5] |
|---|---|---|---|---|---|
| 5K Chip | 5408 | 2 Gy + 3 hr | 67 | 21 | 0.68-2.31 |
|  | 5408 | 2 Gy + 24 hr | 161 | 26 | 0.69-1.89 |

[1]Results are summarized for microarray hybridizations conducted in ML-1 cells. Many of the results for row 1 and 3 have been verified by quantitative single-probe hybridization.
[2]Two different microarrays (chips) used contained only limited overlap in the genes represented.
[3]The number induced refers to cDNA clones showing significant induction (>99% confidence).
[4]For cDNA clones showing a significant reduction, values are shown for those having at least a 2-fold reduction in expression compared to untreated cells; all these values exceeded 99% confidence.
[5]Values represent range of relative expression of irradiated sample compared to untreated control; e.g. only targets showing an increase in the relative mRNA level of 2.37-fold or more were scored as induced in the first row.

TABLE 8

Summary of γ-ray Experiments with 7K Microarrays

| Cell Line | Dose | Time | # Up[a] | # Down[b] | 99% Conf. | C.V. |
|---|---|---|---|---|---|---|
| ML-1 | 10 Gy | 4 hr | 86 | 23 | .38-3.00 | .16 |
| ML-1 | 2 Gy | 4 hr | 32 | 3 | .51-4.38 | .27 |
| ML-1 | 2.5 Gy | 24 hr | 62 | 8 | .93-7.08 | .23 |
| ML-1 | 2.5 Gy | 48 hr | 60 | 17 | .60-4.85 | .24 |
| ML-1 | 0.2 Gy | 3 hr | 86 | 29 | .74-2.43 | .15 |
| ML-1 | 0.2 Gy | 24 hr | 114 | 11 | .83-3.42 | .18 |
| ML-1 | 0.02 Gy | 3 hr | 68 | 40 | 1.16-9.18 | .24 |
| ML-1 | 0.02 Gy | 24 hr | 55 | 6 | .78-5.92 | .23 |
| HL60 | 0.25 Gy | 3 hr | 77 | 2 | .63-4.95 | .24 |

[a]Number of Image ID clones that were upregulated in response the irradiation.
[b]Number of Image ID clones that were downregulated in response the irradiation.

Tables 9-12 lists the clones (by Image ID number) for which there was 99.9% confidence that the genes were differentially expressed in ML-1 cells with the 7K array at: 24 hours after 200 cGy of irradiation (Table 9); 24 hours after 20 cGy of irradiation (Table 10); 24 hours after 2 cGy of irradiation (Table 11) and; 48 hours after 200 cGy of irradiation (Table 12). Late responding genes were found by using RNA harvested at the timepoint of interest, for example 24 or 48 hours after exposure to ionizing radiation. A more detailed timecourse of expression (such as that disclosed in EXAMPLE 3) can be used to determine if expression peaks at the time of identification (24 or 48 hours), or if there is a sustained elevation of expression. To identify genes for other timepoints post-exposure, or for different exposures, the cells would be treated with the agent/dose of interest, and the RNA would be harvested at the appropriate time.

TABLE 9

Image ID numbers of genes differentially expressed after 200 cGy and 24 hours.

280386; 753418; 308588; 241412; 109123; 47475; 549146; 841278; 221846; 159455; 251516; 345839; 240249; 136114; 703846; 66972; 153025; 713145; 366558; 209340; 242780; 293325; 843312; 240843; 35828; 810391; 264117; 293940; 244227; 262231; 180520; 294487; 562927; 160793; 72391; 120362; 346995; 232837; 297442; 295939; 810372; 120572; 666658; 550355; 48398; 469954; 110653; 211548; 260619; 128290; 210522; 241788; 122091; 140921; 120881; 755416; 504226; 738899; 346552; 248256; 66728; 122159; 232612; 753447; 813591; 245585; 325375; 289551; 366341; 36950; 236355; 125092; 204814; 196387; 843287; 34773; 120695; 287300; 234376; 813179; 293557; 712840; 244703; 24415; 138579; 229723; 206816; 108658; 157856; 308041; 727026; 292217; 231675; 135240; 194965; 246661; 812196; 135538; 41452; 123474; 49710; 823928; 141818; 823940; 327094; 141854; 282051; 195720; 813675; 795543; 128530; 124071; 810156; 293727; 768638; 773332; 121159; 724892; 295710; 809588; 121251; 139835; 781341; 815534; 770355; 841703; 293306; 202549; 39993; 195365

TABLE 10

Image ID numbers of genes differentially expressed after 20 cGy and 24 hours.

854401; 854701; 131887; 112896; 296149; 725501; 41648; 66400; 132690; 415022; 770866; 292222; 323917; 83210; 772220; 288896; 110436; 248306; 743278; 826984; 760148; 322160; 234527; 969748; 291985; 795877; 430968; 487172; 198815; 343646; 204814; 562115; 491692; 274638; 244227; 111571; 242780; 279195; 509887; 343744; 769603; 264117; 771295; 322961; 825295; 141768; 753418; 686164; 383016; 109123; 80649; 841282; 450375; 66898; 111693; 210317; 627251; 24415; 740027; 685801; 448619; 773567; 768272; 854576; 510381; 66457; 298963; 611443; 243100; 771023; 884500; 221846; 200031; 843312; 839516; 120695; 195129; 266094; 234562; 127709; 704690; 768443; 796278; 242087; 47475; 195346; 123441; 140921; 214165; 34255; 549146; 626555; 713193; 142087; 811015; 815816; 126453; 123408; 46786; 359395; 269381; 122443; 1408710; 825442; 111765; 241412; 490763; 739183; 30272; 152453; 108801; 82556; 204148

TABLE 11

Image ID numbers of genes differentially expressed
after 2 cGy and 24 hours.

703846; 84820; 745347; 274638; 24415; 841278; 66975; 221846; 712840;
308041; 562927; 359184; 135538; 308588; 282051; 738899; 109123;
Bcl-x; 359793; 246661; 204814; 755416; 897781; 773332; 813591;
52681; 810142;

TABLE 12

Image ID numbers of genes differentially expressed after 200
cGy and 48 hours.

264117; 240430; 811015; 262231; 308588; 159455; 549933; 323474;
840944; 432194; 109123; 321739; 366945; 843287; 240249; 111765;
48182; 130541; 771295; 624627; 294487; 812126; 345559; 382654;
755037; 203130; 193087; 843312; 214133; 811000; 3084437; 431655;
448619; 823940; 41356; 612616; 725746; 47475; 549146; 162775;
35828; 46284; 120881; 770935; 208161; 745188; 843139; 377671;
838373; 809639; 686164; 206816; 770394; 179617; 809394; 591281;
294496; 124795; 782760; 767828; 308041; 731308;

Genes with sustained elevated expression (for example 24-48 hours following the exposure) may be suitable for inclusion in probe sets for clinical tests which would not be performed for several days after potential exposure to ionizing radiation. Using dose response information, different probe sets can be designed for different clinical situations, tailored to detection of exposure a certain number of hours following potential exposure.

Probe sets can also be designed that detect certain subsets of genes that are differentially expressed at a particular post-exposure time and level of expression. The levels of differential expression can be correlated to the dose of ionizing radiation to which the subject was exposed, such that the probe set can also be informative about the dose of exposure. This information can provide helpful prognositc information, such as the likelihood of carcinogenesis brought about by the exposure. Alternatively, levels of differential expression can be used to determine a subjects' response to radiation therapy for a tumor, as described in EXAMPLE 10.

EXAMPLE 7

Nucleic Acid Probe Sets

Nucleic acid hybridization technologies may be used to survey gene expression patterns in organisms or cells that have been exposed to ionizing radiation. Such technologies are not necessarily limited to nucleic acid arrays. By way of example, northern blot and/or dot blot techniques (see EXAMPLE 3) may also be used to determine the quantitative and qualitative expression patterns of some or all of the disclosed radiation responsive sequences.

While more conventional nucleic acid hybridization techniques (such as northern and dot blots) have been used for many years, nucleic acid array technology is now widely used for monitoring and analyzing gene expression patterns. This array technology may be used in a number of forms, including microarrays. Microarrays typically comprise a large number of nucleic acid probes spotted at high density onto a surface. Descriptions of nucleic acid array and microarray technology may be found in the scientific literature, including, for example, in Chee et al., *Science* 274:610-4 (1996); Lockhart et al., *Nature Biotechnol.* 14:1675-80 (1996); Lipshutz et al. *Biotechniques* 19:4427 (1995); Southern et al., *Trends Genetics* 12:110-5 (1996); Soares et al., *Curr. Op. in Biotech.* 8:542-6 (1997); Ramsay et al., *Nature Biotech.* 16:40-4 (1997); Schena et al., *Science* 270:467-70 (1995); Schena et al., *BioEssays* 18:427-31 (1996); DeRisi et al., *Science* 278:680 (1998), and Iyer et al., *Science* 283:83-7 (1999). Detailed technical descriptions of various forms of this technology can also be found in the patent literature, including in the following patent documents:

U.S. Pat. No. 5,744,305 ("Arrays of materials attached to a substrate");

U.S. Pat. No. 5,807,522 ("Methods for fabricating microarrays of biological samples");

U.S. Pat. No. 5,545,531 ("Methods for making a device for concurrently processing multiple biological chip assays");

U.S. Pat. No. 5,593,839 ("Computer-aided engineering system for design of sequence arrays and lithographic masks");

U.S. Pat. No. 5,837,832 ("Arrays of nucleic acid probes on biological chips");

WIPO publication number WO 9710365 ("Expression monitoring by hybridization to high density oligonucleotide arrays").

cDNA arrays can be formed on non-porous surfaces (such as glass) by in situ synthesis of oligodeoxynucleotides on a chemically sensitized glass surface (as in WO 92/10588 and WO 95/11995), or by robotic micropipetting of nanoliter quantities of DNA to predetermined positions on a non-porous glass surface (as in Schema et al., *Science* 270:467-470, 1995, and WO 95/35505). DNA may be coupled to the solid support by electrostatic interactions with a coating film of a polycationic polymer such as poly-L-lysine (WO 95/35505), or covalently bound to the solid support.

Nucleic acid arrays employ conventional nucleic acid hybridization methods that have been used for decades to identify and quantify nucleic acids in biological samples (such conventional methods include southern and northern blots, colony hybridizations and dot blots). However, whereas such conventional techniques typically employ one or two hybridization probes to obtain information on the expression patterns of one or a few genes, array techniques typically employ very large probe sets (for example at least 100, 1000 or even 5000 or 10,000 probes) to obtain data on the expression of a vast number of genes simultaneously.

The basic principle underlying the array technology is the hybridization of a sample nucleic acid composition with a defined set of nucleic acid probes, followed by detection of specific hybridization of the sample to one of more of these probes. The hybridization pattern obtained is then analyzed and compared to hybridization patterns obtained with control nucleic acid samples.

Most arrays comprise a defined set of nucleic acid probes immobilized on a fixed surface in an ordered and known sequence, forming an array of discrete spots of nucleic acid material. A number of substrates may be used to form the fixed surface, including silica-based chips, nylon membranes, microtiter plates and glass slides. Each probe within the set is typically produced by polymerase chain reaction amplification (alternative methods include purification from cloning vectors and, for oligonucleotide probes, chemical synthesis). Each amplification product (probe) is then typically spotted onto the fixed surface using a mechanized means (such as a robotic arm) to form the array. The sample nucleic acid composition (for example, labeled cDNA produced by RT-PCR from mRNA extracted from a tissue sample) is labeled with a detectable marker (e.g., a fluorescent label) prior to hybridization to the array to permit detection of specific hybridization of the sample to a particular probe. Following hybridization, the hybridization pattern is detected and an image of the array is produced for analysis of gene expression. The use of multiple different fluorescent labels to label the samples permits multiple different samples to be hybridized to a single array. Typically however, no more than two samples are hybridized to a single array.

Alternatively, the arrangement may be reversed. The fixed array may include a number of nucleic acid test samples and the probes may be hybridized to a number of duplicates of the array. In this situation, a large number of test sample nucleic acid compositions are attached to the surface to form the array. Subsets of the nucleic acid probe set are subsequently hybridized to duplicates of the array, and hybridization of the probes to individual spots of the array is detected. The use of multiple different fluorophores to label the probes permits multiple different probes from the probe set to be hybridized to a single array.

By way of illustration, a microarray may be produced and employed using the following techniques:

Each probe in the microarray probe set is produced by PCR amplification. This may be achieved by using primers that are specific for the sequence of the differentially expressed gene (as disclosed herein) in conjunction with genomic DNA or cDNA as a template. The amplified PCR products are purified to remove excess primer and template, for example by column chromatography, or by simple sodium acetate or ammonium acetate precipitation, followed by either isopropanol or ethanol washing, and drying. In certain instances, the probe may be used without purification. Following purification, the PCR-amplified probes are resuspended in 10 µl of a salt solution (3×SSC) and transferred into 96-well or 384-well microtiter plates (if they were not already in a microtiter plate from previous steps). The samples are mechanically spotted onto coated glass slides, using a robotic arm containing pins that transfer an amount of each probe from the microtiter plate onto the coated glass slide. Several hundred or several thousand probe spots are spotted onto the array such that each probe is represented by a discrete spot with a center to center distance between spots of about 250 µm to about 500 µm. The glass slides are then processed to cross-link the probe set onto the glass surface.

The nucleic acid sample to be hybridized to the array is typically cDNA obtained by RT-PCR of mRNA extracted from a biological sample (e.g., plant or animal cells) (see EXAMPLE 2). The detectable label (e.g., the fluorophore) may be incorporated during the RT-PCR amplification step. Typical experiments involve either single-color fluorescence hybridization to measure the absolute levels of gene expression in a single sample, or two-color fluorescence hybridization to examine the relative expression of genes in two different samples.

For single-color fluorescence hybridization experiments, mRNA is isolated from a sample of interest and used as a template to produce cDNA. The cDNA is labeled, for example using a fluorescent dye such as Cy-3 or Cy-5 (Amersham Pharmacia Biotech, Piscataway, N.J.), or any other fluorophore or label. The label can be incorporated directly during the reverse transcription step. The sample is then hybridized to the array. Following washing to remove non-specifically bound sample, the array is scanned for fluorescent emission following laser excitation, and the intensity of each fluorescing spot is measured. The intensity of each spot is approximately proportional to the expression of the gene (corresponding to the probe) in the sample examined. This data provides an indication of the expression of a particular gene in the tissues from which the sample nucleic acid was prepared.

For two-color fluorescence hybridization experiments, RNA is isolated from two samples of interest and labeled as described above, except that each sample is labeled with a different fluorescent label, each of which fluoresces at a different wavelength (for example, one sample may be labeled with Cy-3 and the other with Cy-5). After the two sample preparations are labeled, they are mixed together and hybridized to a single microarray. After washing, the microarray slide is scanned in two fluorescence channels. Because the two fluorescent labels are selected such that their emission spectra do not overlap, the signal of each of the two fluors can measured for each of the probes of the array. The absolute levels of intensity for each probe in an array is approximately proportional to the expression of the gene in the sample examined, and the ratio of the two fluor intensities indicates the relative expression of a gene in the two different samples.

Each probe includes at least one copy (and more typically many copies) of an isolated nucleic acid molecule. Typically, the nucleic acid molecule is in substantially pure form, i.e., while there may be small amounts of other nucleic acid molecules in the probe preparation (such as degradation products), the selected nucleic acid molecule will be the predominant nucleic acid molecule present. In addition, a probe is generally of known sequence. A "probe set" comprises a collection of two or more such probes (the individual probes within the probe set not being co-mingled). A probe set will include probes selected for a particular purpose (such as detection of acute or semi-acute exposure to ionizing radiation), but may also include controls or other probes for different purposes. In some examples, at least 10% of the probes in the probe set are selected for the particular purpose of determining an actual or potential biological response to an actual or potential radiation exposure. In other examples, at least 5, 10 25, or 50 of the probes of an array are selected for this purpose.

A hybridization probe for use in an array produced according to the present invention may be referred to as a sequence "representing" a particular gene product. A sequence "representing" a particular gene product is one that will specifically hybridize to a nucleic acid molecule encoding that gene product, thereby permitting identification of that gene product. A sequence representing a particular gene product may comprise an entire cDNA sequence (or the corresponding genomic gene sequence) or less than an entire cDNA sequence. For example, the probe may comprise an oligonucleotide comprising a minimum specified number of consecutive bases of a selected gene that is differentially expressed following irradiation. Oligonucleotides as short as 8-10 consecutive bases of a cDNA will be effective to produce meaningful gene expression data using microarray technology. For example, a nine base oligonucleotide can distinguish 262, 144 transcripts ($4^9$). However, for enhanced specificity of hybridization, longer oligonucleotides may be employed, such as at least 10, 15, 20, 25, 30, 50, 50 or more consecutive bases of a cDNA. Furthermore, a probe "representing" a particular gene product need not be a complete match. While probes that share 100% sequence identity over their entire length to the corresponding cDNA sequence will typically provide enhanced specificity of hybridization, probes that share less than 100% sequence identity may also be useful in such microarray applications. Typically, such probes will share at least 70% sequence identity with the corresponding cDNA, but probes sharing at least 75%, 80%, 85%, 90%, 95%, 97%, 98%, and 99% sequence identity may be utilized to achieve enhanced specificity.

EXAMPLE 8

Examples of Arrays for Detecting Genotoxic Stress

An examples of a probe sets that has been used to make a cDNA array that detects differential expression of genes following irradiation is shown in Tables 13. The clones on this chips include all the positive hits from studies with larger arrays (5K and 7K), in addition to probes for other genes that have been reported in the literature as being stress-induced.

TABLE 13

Image ID Numbers of Genes Differentially Expressed in Response to Irradiation.

21652; 23132; 753430; 78294; 127193; 155287; 825080; 703846; 121877; 128785; 549933; 781139; 811927; 884500; 381287; 700792; 196185; 133225; 739183; 502832; 40692; 626531; 840511; 39993; 41511; 812196; 346995; 123926; 240249; 504226; 510760; 160573; 324861; 81203; 85195; Bcl-x; 784179; 66428; 125741; 134537; 795877; 46284; 134476; 377587; 141763; 22260; 25584; 753418; 141818; 129506; 547058; 814701; 686172; 121159; 297442; 289606; 78353; 34184; 785847; 760299; 788185; 134235; 143208; 323474; 433253; 950507; 754378; 126858; 40304; 42096; 727026; 229723; 51448; 191664; 203132; 769846; 240961; 49410; 80162; GADD153; 322160; 77636; 241539; 136984; 856961; 41356; 511066; 323577; 25588; 22493; 26184; 345839; 130788; 120572; 549146; 772220; 77728; 247216; 143209; 756405; 624617; 878676; 12637; 41074; 33051; 131886; 138496; 811166; 757873; 509887; 108801; 810372; 41199; 42352; 140716; 550335; 125092; 788141; 297392; 294487; 160664; 795893; 147050; 22428; GADD34; 293925; 80946; 201241; 77087; 22293; 740027; 840691; 770935; 26922; 28985; 36393; 214537; 50506; 562927; 72391; 843312; 135240; 138579; 45578; 243882; 504745; CR6; 297061; 257445; 137020; 234527; 431655; 366945; 120383; 138477; 772878; 42993; 43550; 160793; 221846; 714106; 841703; 859339; 841278; 272183; 504372; 28985; 291985; 279172; 206651; 111004; 31169; 50794; 773319; 686164; 245774; 27624; 30272; 813614; 359184; 308041; 66728; 774036; 826166 136114; 140921; 266094; 882484; BAX; GADD45; 300137; 151501; 139462; 198011; 856519; 247483; 131010; 204179; 824352; 43129; 43622; 289551; 135538; 95036; 842802; 214162; 122822; 487819; 502977; 36950; 53164; 384015; 454672; 230247; 113284; 489506; 550353; 843249; 815245; 120306; 28309; 31143; 204299; 813841; 823928; 306901; 293940; 781019; 154214; 157856; 235938; 745116; c-Myc; MDM2; 490232; 769686; 197720; 230191; 756549; 487348; 133331; 296189; 66975; 43338; 44255; 666658; 261828; 24415; 841334; 292217; 245444; 119133; 41452; 110589; 223350; 1388373; 112530; 111693; 489489; 727551; 231355; 796904; 590544; 31210; 34357; 128143; 589115; 156473; 753104; 739625; 587847; 194965; 240843; 884719; 781017; RelB; 417694; 204686; 744047; 204122; 229617; 179617; 814123; 244386; 132304; 855521; 44537; 47833; 159455; 145503; 785574; 192694; 205049; 282051; 323185; 491403; 35516; 193901; 878182; HsKg21F11; 296393; 123436; 767828; 49509; 74566; 856489; 85195; 32898; 34396; 34773; 153025; 809939; 770957; 781341; 23073; 232837; 242780; 810999; 128493; V(D)J (RAG2); 270626; 340657; 1031185; 208940; 295497; 432194; 214133; 193182; 135713; 253009; 45941; 50117; 308588; 175123; 789182; 768638; 295939; 50765; 282978; 884425; 234357; 280507; 1049030; 754601; 207006; 124168; 45632; 810408; 235155; 21899; 85906; 33632; 35483; 738899; 327676; 232612; 753447; 48398; 231675; 204814; 260619; 251591; 436062; HbclW8; 44495; 148028; 435855; 233939; 230359; 713236; 240634; 132140; 321271; 949971; 47110; 50666; 813675; 202535; 70692; 786067; 245585; 66972; 280893; 590544; 773367; 774078; 234559; 121715; 124091; 308437; 49352; 429574; 50888; 44495; 36950; 39093; 813179; 725680; 741769; 42373; 760224; 841641; 280386; 139226; 724888; 360778; 510130; H36; 840466; 784065; 241097; 299815; 810331; 592359; 377587; CIP1/WAF1; 51293; 26578; 810391; 725266; 789369; 34689; 66430; 487777; 586839; 626358; 31093; 759948; 130053; 139837; 712641; 51041; 280356; 852829; 37366; 39173; 810485; 729942; 195712; 264117; 630013; 204301; 293727; 296030; 193736; 740907; 433551; 52753; 839374; 82556; 295303; 112371; 190887; 361097; 323577; GADD45; 51740; 244703; 128530; 592540; 287300; 246722; 546600; 780947; 145383; 269606; 35318; 812105; 825295; 128695; 137456; 166195; 796994; 866874; 85313; 37904; 39796; 810600; 42739; 249688; 122091; 842849; 841470; 345751; 172721; 755923; 378813; 52681; 51699; 252382; 27544; 246652; 121798; 28823; 51737; 770935; 145503; 129865; 207794; 772878; 712840; 295710; 108351; 462953; 855521; 73527; 489485; 40056; 484535; 130057; 130617; 809394; 842860; 857002; 854899; 22012; 24145; 755145; 124261; 293916; 823901; 898062; 84820; 120695; 125589; 310406; 377692; 220851; 951142; 795771; 305606; 131824; 134643; 307532; 845415; 743230; 785778; 36393; 40026; 42059; 823940; 244767; 211548; 122159; 713145; 358531; 121251; 417226; 125187; 85195; CIP1/WAF1; 236155; 233721; 66574; 295514; 428582; 35077; 241880; 161988; 325062; 22293; 25725; 812965; 666218; 124824; 752732; 843321; 815539; 123439; 130043; 491763; 345525; 825740; 124143; 814117; 196387; 131563; 134256; 810711; 271006; 416316; 242706; 214537; 40360; 42214; 141763; 120881; 274638; 701112; 172440; 199180; 123229; 268727; 309288; 26997; GADD45; 755750; 141966; 292482; 262053; 121611; 129146; 770212; 310894; 159455; 23019; 26366; 180520; 205185; 669443; 177737; 824352; 613126; 124071; 325375; 487820; 845363; 488596; 549139; 194600; 132708; 137016; 361323; 858292; 811000; 125767; 223483; 41452; 42576; 110653; 325062; 811942; 840511; 85840; 745347; 232714; 269815; 83999; 50615; 429555; 854701; 28218; 200934; 427692; 30664; 234562; 898198; 810448; 70692; 27549; 29054; 126858; 245296; 323506; 197525; 71545; 416833; 234376; 139957; 133637; 745433; 814476; GADD153; 233071; 377560; 195429; 197907; 841221; 197657; 123067; 262920; 712840; 43021; 43563; 809588; 210522; 898138; 825470; 48285; 133114; 782712; 34005; 47359; 714213; 109271; 128602; 40360; 340630; 773254; 843139; 172721; 27848; 30664; 26616; 469954; 136235; 236355; 724892; 897690; 144762; 137853; 770424; 384081; Bcl-x; Killer/DR5; 487172; 454440; 195853; 200780; 322914; 1472735; 137918; 212712; 613126; 43231; 44180; 769921; 293325; 208161; 612274; 196387; 141627; 810059; 782545; 39993; 85906; 361688; 1473274; 109466; 113283; 450745; 810017; 757961; 73531; 769846; 28410; 31169; 203275; 810372; 137940; 241788; 795543; 815534; 139835; 195720; 266106; 253009; CIP1/WAF1; MyD118; 215000; 755599; 198593; 234484; 856167; 1320746; 139490; 300866; 345751; 43241; 44307; 292806; 25588; 841149; 726086; 366341; 108658; 809585; 489805; 26474; 26295; 1416502; 110582; 296472; 814780; 178779; 684661; 787861;

TABLE 13-continued

Image ID Numbers of Genes Differentially Expressed in Response to Irradiation.

845477; 32875; 34355; 770670; 223483; 137017; 35828; 85259; 376875; 195365; 240648; 796278;
26568; V(D)J (RAG-1); 347586; 46938; 755630; 245586; 212098; 385003; 163174; 359247;
141931; 491763; 45233; 49888; 823614; 212198; 74119; 82991; 120362; 293557; 324494; 289428;
49950; 288650; 687054; 173674; 196109; 123459; 812126; 665774; 591281; 447568; 80162;
3352; 34945; 162775; 770355; 241412; 810156; 135083; 840944; 109123; 244227; 263014;
415817; Bak; 43021; 415870; 460403; 208984; 214826; 1472753; 753457; 194131; 809995;
251591; 46171; 50359; 727210; 248454; 361974; 796646; 141854; 248256; 342008; 364510;
486074; 768064; 824081; 230100; 121600; 124822; 35185; 51865; 122150; 435858; 878676;
34255; 36775; 22040; 122428; 22411; 26811; 39274; 950680; 209340; 293858; 39722; 491692;
GADD34; 45794; 32304; 192271; 230013; 244201; 825726; 380797; 109483; 810154; 85195;
47202; 50941; 135692; 135527; 77915; 49710; 246661; 129585; 204569; 624627; 359793;
1467195; 1493160; 341310 244686; 126568; 49509; 43826; 429494; 773637; Bcl-x; 37196;
39159; 240151; 346552; 292463; 771196; 666425; 839736; 293306; 202549; 949971; 66599;
503724; 133637; 297061; 773579; 239835; 194399; 511832; 767765; 161988; GADD153; 51666;
123474; 823691; 897781; 843287; 205993; 111981; 845477; 810142; 120468; 882510; 213136;
485989; 129332; 130342; 950430; 503097; 770394; 268946; 37451; 39285; 126243; 210887;
85561; 245388; 51666; 898286; 128290; 245774; 788764; 245990; 592485; 264937; 594633;
626822; 123729; 50188; 204214; 310894; GADD34; 53316; 131653; 755416; 810131; 897570;
327094; 206816; 756502; 1035889; 454339; 82297; 236333; 80948; 135892; 130876; 841384;
705274; 415529; 505491; 38471; 39884; 127677; 232772; 28475; 179403; 838373; 725454;
251516; 120306; 342181; 757350; B1; 280386; 771295; 136188; 297405; 296616; 31842; 51737;
810448; 47475; 813591; 773332; 366728; 66975; 110746; 359661; 586796; 75644; 858293;
810813; 759865; 130107; 131668; 612616; 724615; 376785; 856535

A microarray was assembled which contained each clone in Table 13 printed only once on the array. However the arrays can routinely include duplicates of each position as the stress-array, to provide an additional degree of certainty for positive "hits." In addition, internal controls of the type known in the art can be used on each array.

The probe set for a cDNA array can be made using a probe set comprising nucleic acid molecules representing a portion of the cDNAs disclosed in Tables 9-13. Alternatively, such probe sets may be used to analyze gene expression patterns using other hybridization techniques, such as northern and dot blots (see EXAMPLE 3). However, useful information may also be obtained using arrays or other techniques that employ probe sets representing less than all of the disclosed cDNAs in the array of Tables 9-13. For example, arrays that employ probe sets representing between 10% and 99% of the disclosed cDNA sequences may be employed. Thus, arrays employing probe sets representing at least 25%, 50%, 80% or 90% of the disclosed cDNAs depicted in any of Tables 9-13 may be employed. Alternatively the probe set may represent at least 5, 10, 25, or 50 of the disclosed cDNAs depicted in any of Tables 9-13. Each probe can "represent" the cDNA by having sufficient contiguous nucleotide (or variant thereof) that hybridizes to a target nucleic acid of interest. Alternatively, an array can be made using probes that detect differential expression of genes within a certain time period. An example would be an array consisting of the probes of any of Tables 9-12 or combinations thereof.

The sets of disclosed probes may also be used in nucleic acid hybridization techniques. Such probe sets are particularly useful for assessing differential gene expression in cells that have been exposed to radiation. The probe sets comprise nucleic acid probes representing specified percentages of the differentially expressed cDNAs disclosed herein. These probe sets may be used with any nucleic acid hybridization technique that can be used to analyze patterns of gene expression, including but not limited to: northern blotting, dot blotting, arrays and microarrays.

In addition, the invention also provides methods for analyzing expression of multiple genes in a biological sample. A biological sample is provided which includes nucleic acids, and the biological sample is hybridized to a nucleic acid probe set arrayed on a surface. Typically, the nucleic acids of the biological sample are labeled with a detectable label such as a fluorescent label, to permit easy detection of hybridization between the sample and a probe. The nucleic acid probe set arrayed on the surface includes nucleic acid probes representing, for example at least 2%, 5%, 10%, 25%, 50% or more of the radiation induced cDNA sequences disclosed in any of Tables 9-13, such as subsets of probes for genes that have sustained expression at 24 or 48 hours, or expression at a level that corresponds to clinical exposure to a certain dose of ionizing radiation.

The present invention also includes providing a plurality of duplicate arrays of test sample nucleic acid compositions (such as samples taken from one or more subjects) immobilized on a fixed surface. These arrays are then hybridized with a nucleic acid probe set (typically labeled with a detectable label). Hybridization using the complete set of probes is typically achieved by hybridizing a small subset of the probes (typically 2-5 probes) to one of the array duplicates, and then repeating the procedure by hybridizing additional subsets of the probe set to additional duplicates of the array. To facilitate detection of hybridization, each of the probes within a particular subset is typically conjugated to a different detectable label. The probe set used in this method comprises nucleic acid probes representing at least 2%, 5%, 10%, 25%, 50% or more of the cDNA sequences disclosed in any of Tables 9-13, or the complete probe sets disclosed in those Tables, other subsets thereof (such as at least 5, 10, 25, or 50 of the disclosed sequences), or probe sets that are larger than any of these sets and include additional informative markers that have been or are discovered.

Arrays of polynucleotide DNA probes immobilized on solid supports have been used to study the composition of complex mixtures of DNA by hybridization techniques. For example, a complex mixture of labeled cDNA is hybridized to the DNA array under conditions of appropriate stringency, and unbound material is washed away. The array is then scanned using a detector, such as a scanning fluorescent microscope, capable of sensing the remaining bound labeled cDNA. The intensity of the detected signal at any given element is a measure of the concentration of the corresponding cDNA in the original complex mixture. See Schema et al., *Science* 270:467-470, 1995 and WO 96/17958.

EXAMPLE 9

Analysis of Biological Specimens

This example demonstrates that cDNA microarrays can be used to assess the effects on gene expression of irradiating isolated human peripheral blood lymphocytes or alternatively can detect altered gene expression to assess potential radiation exposure. Peripheral blood lymphocytes provide an easily accessible source of radiation sensitive tissue from a subject who has potentially been exposed to ionizing radiation. To determine whether the subject has experienced a biologically significant radiation exposure, approximately 30 ml may be obtained by conventional phlebotomy. This amount of blood provides sufficient mRNA for hybridization to a large array (such as a 5K array or 7K array), or several smaller arrays (such as 1.2K arrays), during efforts to determine which genes are differentially expressed. However, much smaller probe sets can be used diagnostically, with corresponding smaller amounts of blood required.

Although this example describes methods which were used to analyze peripheral blood lymphocytes, one skilled in the art will recognize that similar methods can be used to analyze any biological specimen. Biological specimens can be obtained from subjects who have potentially been, or are known to have been, exposed to ionizing radiation. A variety of biological specimens can be used in the present invention. Examples include, but are not limited to: peripheral blood, urine, saliva, tissue biopsy, surgical specimen, amniocentesis samples and autopsy material.

Blood may be drawn from potentially exposed individuals, RNA extracted immediately, and tested against an established baseline to determine relative levels of a number of genes, then compared to profiles for various qualities or quantities of radiation, or other environmental agents, to determine likelihood of exposure. Approximate dose and time since exposure can also be determined.

Human blood from normal healthy donors were obtained from the NIH blood bank (Department of Transfusion Medicine) and within 30-60 minutes of drawing, the components were separated by centrifugation on a Lymphoprep (Nycomed, Oslo, Norway) density gradient according to the manufacturer's instructions. The buffy coat layers were recovered, washed in phosphate buffered saline and resuspended at a density of $0.5\text{-}1\times10^6$ cells per ml in RPMI 1640 medium supplemented with 10% heat-inactivated (56° C. for 45 minutes) fetal calf serum and 100 U/ml penicillin and 100 μg/ml streptomycin at 37° C. in a humidified, 5% $CO_2$ atmosphere. Peripheral blood lymphocytes (PBLs) were allowed to equilibrate to culture conditions for 45-60 minutes, then irradiated at approximately 60 cGy/min. to total doses of 20-200 cGy using a Mark I-68 $^{137}Cs$ source (J.L. Shepherd and Associates, Inc., San Fernando, Calif.) with lead attenuators in place.

RNA was harvested at 0, (unirradiated) 4, 24, 48 or 72 hours after irradiation using an acid guanidinium thiocyanate-phenol-chloroform mixture, as described by Chomczynski et al. (*Anal. Biochem.* 162:156-9, 1987). RNA harvested 24 hours after irradiation was hybridized to the 7K microarray (Table 6) and to the array shown in Table 13 and analyzed as described in EXAMPLE 2.

The results shown in Table 14 show the Image ID of PBL genes which were differentially expressed 24 hours following 2 Gy of irradiation. These results indicate that cDNA microarrays, such as the 7K microarray shown in Table 6, can be used to identify genes which are differentially expressed in response to irradiation. Such information can be used to identify genes to include in a probe set (such as those shown in Table 14) which will be useful for assessing potential radiation exposure in a cell from an animal or plant subject.

TABLE 14

Image ID Numbers of Differentially Expressed PBL Genes by 2 Gy.

Figure 10:
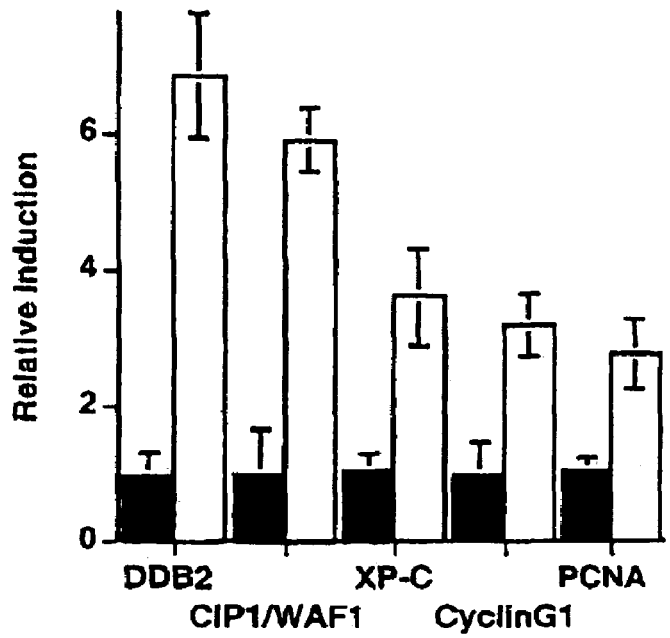
FIG. 10 is a bar graphic representation of a section of a microarray hybridized to RNA from unirradiated (filled bars, normalized to the levels in the first donor) and 2 Gy gamma-irradiated (open bars) human peripheral blood lymphocytes harvested 24 hours after irradiation. Results are from 4-8 independent donors. Error bars are standard deviations.

244386; 1486083; 194395; 191826; 230100; 310406; 377314; 487172; 491763; 241097; 269815; 49389; 511091; 626716; 154472; 753104; 205633; 810711; 77577; 130826; 769603; 884425; 811015; 1475730; 826254; 80649; 82556; 825080; 213136; 898221; 273546; 701112; 843312; 128126; 415899; 146605; 823665; 745019; 1391644; 461759; 810017; 591653; 713193; 687054; 70692; 126466; 242790;

The alteration in gene expression following γ-irradiation was examined in PBLs for five genes identified as being differentially expressed in response to irradiation (Table 14). As shown in FIG. 10, the expression of DDB2, CIP/WAF1, XPC, cyclin G1 and PCNA genes in response to irradiation was induced 3-6 fold over non-irradiated PBLs. These results demonstrate that the present invention can be used to determine if a subject has been exposed to ionizing radiation by testing PBLs, which are sensitive to the effects of irradiation. Genes which are identified as being differentially expressed in response to irradiation (for example Table 14) are incorporated into a probe set, which is exposed to the labeled nucleic acid of a test cell (such as PBLs) using a microarray.

Figure 11:
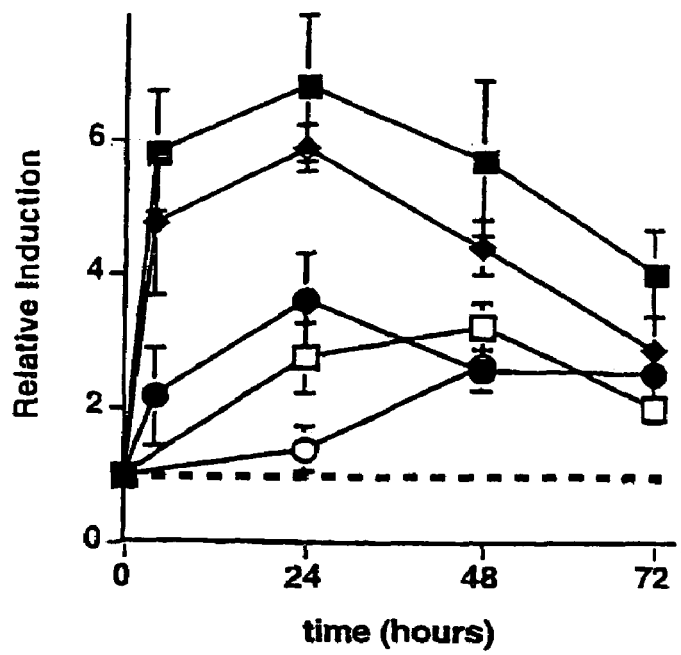
FIG. 11 is a graphical representation showing a timecourse of marker levels following 2 Gy gamma-rays delivered ex vivo. Each point is the mean of relative induction above background in 3-4 independent donors for DDB2 (■), CIP1/WAF1 (♦), XP-C (●), PCNA (□) and IFNγp10 (○). RNA was harvested from lymphocytes following one, two, or three days of incubation. Error bars are standard errors of the mean. The dashed line shows the basal level of expression in untreated PBLs.
Figure 12A:
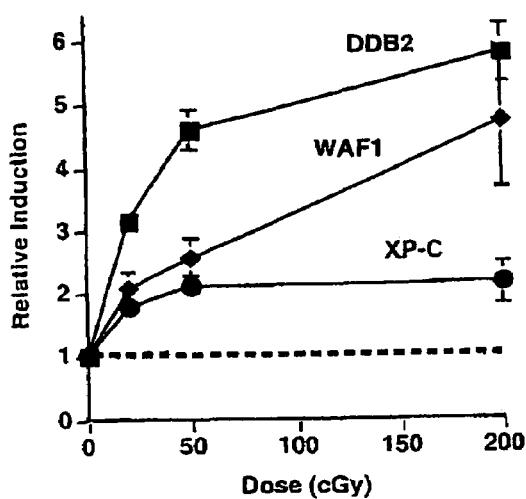
FIGS. 12A-D are graphical representations showing the dose-response relationship for the induction of DDB2 (■), CIP1/WAF1 (♦), and XP-C (●) in human PBL. PBL were irradiated ex vivo with graded doses of γ-rays and RNA was harvested after (A) 4 hours, (B) 24 hours or (C) 48 hours (D) 72 hours of incubation. Points are the mean of relative expression in three or more independent donors, and error bars are standard errors of the mean. The dashed lines indicate the level of expression in un-irradiated control cultures.
Figure 12B:
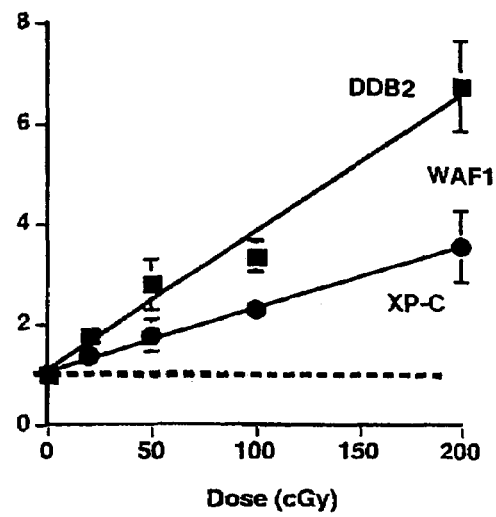
Figure 12C:
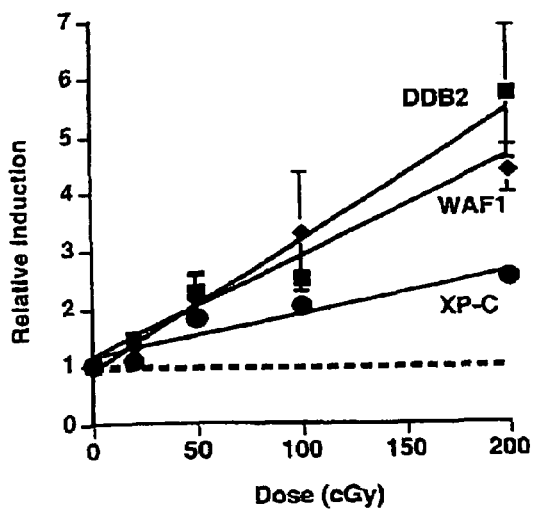
Figure 12D:
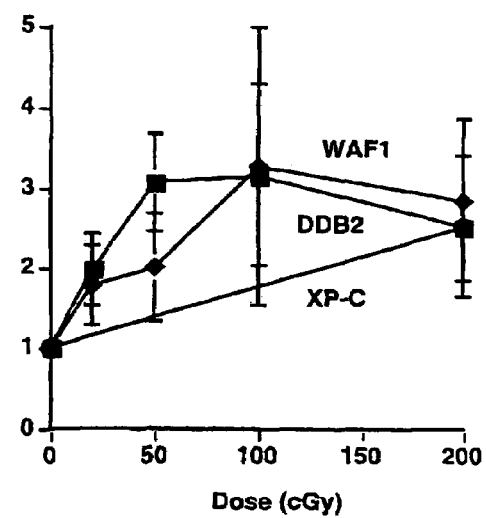

A timecourse of induction following 2 Gy γ-rays delivered ex vivo to PBLs was also examined as described in EXAMPLE 3. RNA was harvested from lymphocytes following one, two, or three days of incubation. Following irradiation, the DDB2, CIP1/WAF1, and XP-C genes reached maximal induction 24 hours after irradiation, then declined (FIG. 11). The induction of PCNA and IFNγp10 reached maximal levels 48 hours after induction (FIG. 11). These results demonstrate that the identification of which genes are differentially expressed in a biological specimen, can be correlated with the approximate time of irradiation. For example, a probe set which contains the DDB2, CIP1/WAF1, and XP-C genes would be useful for determining if a subject has been exposed within the past 24 hours, and a probe set which contains the PCNA and IFNγp10 gene would be useful for determining if a subject has been exposed within the past 48 hours.

The relative induction of expression was correlated to dosage, as shown in FIGS. 12A-12D for several genes. PBL were irradiated ex vivo with graded doses of γ-rays and RNA was harvested after four hours (FIG. 12A), 24 hours (FIG. 12B), 48 hours (FIG. 12C), or 72 hours (FIG. 12D) of incubation. These results demonstrate that the measured relative induction of expression of genes that are differentially expressed in response to irradiation, can be used to interpret the results. For example, by determining the relative induction of the radiosensitive genes DDB2 or WAF-1 in a particular cell type, that relative induction is correlated to the dosage of irradiation received by a subject, such as a plant, animal, or microbial subject.

In conclusion, this example demonstrates that biological specimens can be used to determine if a cell has been exposed to a biologically significant amount of ionizing radiation, and approximately how much time has elapsed since the cell was exposed. In addition, the relative induction of radiosensitive genes can be correlated to the dosage of irradiation received by the cell.

EXAMPLE 10

Analysis of In Vivo Irradiated Organisms

This example describes methods which can be used to analyze organisms which have been, or may have been, exposed to ionizing radiation.

Analysis of Irradiated Animals

The analysis of animals which have potentially been exposed to, or are known to have been exposed to, ionizing irradiation can be performed. As test subjects, rodents such as mice or rats are whole body irradiated, for example using a Mark I-68 $^{137}$Cs source (JL Shepherd and Associates, San Fernando, Calif.) to deliver total doses between 2 and 500 cGy as described in the above examples. Following irradiation, biological samples are harvested from the animals. Examples of biological samples include, but are not limited to, those listed above in EXAMPLE 9. Tissues are flash frozen in GTC (guanidine thiocyanate solution, used above), and the RNA is isolated and reverse transcribed incorporating a label, as described above. The labeled nucleic acids are then exposed to an array, for example using mouse equivalents of the genes shown in any of Tables 9-13. A test array can be generated, by selecting for probe sets as described herein, for example probe sets designed to detect radiation exposure in a specimen that is to be tested, such as peripheral blood cells for example leukocytes. Patterns or hybridization to the array can then be observed to determine the likelihood of exposure, and/or a dose of exposure in subsequent test subjects.

Analysis of Subjects Undergoing Radiation Therapy

The disclosed arrays can also be used to evaluate and/or select patients who are undergoing (or are candidates for) radiation therapy, for the treatment of cancer or a tumor. For example, subjects can be monitored during radiotherapy to detect gene expression induced by irradiation. Differential gene expression provides diagnostic or prognostic information, for example, it may indicate whether sufficient doses of radiation are being administered to cause regression of the cancer. An indication that a sufficient dose of radiation has been used may be a pattern of differential gene expression associated with a successful outcome of treatment of tumors of a particular type. In addition, subjects can be monitored to determine if the dose of radiation is causing harmful effects, for example iatrogenic carcinogenesis or suppression of the immune system by determining whether a pattern of differential expression has occurred that is associated with either of these outcomes.

The RNA from subjects is isolated, reverse-transcribed, and labeled as described above in EXAMPLE 2. The labeled nucleic acids are then exposed to an array, for example an array which contains a probe set which has been selected for genes which are differentially expressed at the radiation dose which the subject is being treated with. For example, the array may include genes which have been shown using the methods described in the above examples to be differentially expressed at 2 Gy, a typical daily dose which a subject might receive in radiotherapy. In addition, an array can be selected based on the tumor which is being treated. For example, the array can include or consist of genes which have been shown (using the methods described in the above examples) to be differentially expressed at the dose which the subject is receiving, in the type of tumor the subject suffers from. Such specific probe sets provide useful diagnostic information regarding the subject's progress in the radiotherapy.

Analysis of Irradiated Plants or Microbes

In addition to humans and other animals, plants or microbes which have been, or may have been, exposed to radiation can be analyzed using the present invention. In one example, following a nuclear accident, if there are no animals present to examine to determine the amount of exposure, the plant or microbial flora present in the area can be analyzed. Nucleic acids, for example RNA is isolated using standard methods. Nucleic acids are isolated from any part of the plant, for example roots, stems, leaves or flowers. The RNA is isolated, reverse-transcribed, and labeled as described above. The labeled plant nucleic acids can then be exposed to an array, for example using plant equivalents of the genes shown in Tables 9-13, or other plant genes that are found to be differentially expressed following radiation exposure.

Having illustrated and described the principles of assessing whether an organism has been exposed to biologically significant levels of ionizing radiation by detecting differential cellular expression of genes that are differentially expressed following such exposure, it should be apparent to one skilled in the art that the invention can be modified in arrangement and detail without departing from such principles. In view of the many possible embodiments to which the principles of our invention may be applied, it should be recognized that the illustrated embodiments are only examples of the invention and should not be taken as a limitation on the scope of the invention. Rather, the scope of the invention is in accord with the following claims. We therefore claim as our invention all that comes within the scope and spirit of these claims.

We claim:

1. A method of identifying cells that have been exposed to radiation induced biological stress, comprising:
    exposing a probe set comprising nucleic acid molecules representing genes that are differentially expressed in cells that have been exposed to an amount of ionizing radiation sufficient to cause differential expression of genes in the cell to a labeled nucleic acid composition from a test cell which specifically hybridizes to members of the probe set when the test cell has been exposed to an amount of ionizing radiation sufficient to cause differential expression of stress genes in the test cell, wherein at least one nucleic acid molecule of the probe set comprises SEQ ID NO: 14; and
    determining whether the probe set hybridizes to the nucleic acid composition.

2. The method of claim 1, wherein the probe set is bound in an array to a surface.

3. The method of claim 2, wherein the probe set comprises oligonucleotides that specifically hybridize to sequences in the nucleic acid composition.

4. The method of claim 3, wherein the nucleic acid composition comprises cDNA reverse transcribed from mRNA in the test cell.

5. The method of claim 1, wherein the labeled nucleic acid is labeled with a fluorophore.

6. The method of claim 1, further comprising exposing the probe set to a labeled nucleic acid composition from a control cell, such that the labeled nucleic acid composition from the control cell specifically hybridizes to members of the probe set.

7. The method of claim 1, further comprising determining a probable time of radiation exposure, wherein the probe set comprises probes that specifically hybridize to the labeled nucleic acid composition, when the nucleic acid composition has been obtained more than four hours after exposure to the biologically significant amount of ionizing radiation, and wherein hybridization to the probe set indicates that the cells have been exposed to the biologically significant amount of ionizing radiation at least four hours previously.

8. The method of claim 1, further comprising determining a probable time of radiation exposure, wherein the probe set comprises probes that specifically hybridize to the labeled nucleic acid composition, when the nucleic acid composition has been obtained more than 24 hours after exposure to the biologically significant amount of ionizing radiation, and wherein hybridization to the probe set indicates that the cells have been exposed to the biologically significant amount of ionizing radiation at least 24 hours previously.

9. The method of claim 1, further comprising determining a probable time of radiation exposure, wherein the probe set comprises probes that specifically hybridize to the labeled nucleic acid composition, when the nucleic acid composition has been obtained more than 48 hours after exposure to the biologically significant amount of ionizing radiation, and wherein hybridization to the probe set indicates that the cells have been exposed to the biologically significant amount of ionizing radiation at least 48 hours previously.

10. The method of claim 1, wherein the probe set comprises probes that specifically hybridize to the labeled nucleic acid composition, when the nucleic acid composition has been exposed to less than about 25 cGy of ionizing radiation.

11. The method of claim 1, wherein the probe set comprises genes that are differentially expressed by at least 1.5 fold following exposure to a biologically significant amount of ionizing radiation.

12. The method of claim 11, wherein the genes are differentially expressed by at least 2-fold following exposure to a biologically significant amount of ionizing radiation.

13. The method of claim 1, wherein the probe set comprises:
    (a) at least 10% of the probes identified in Tables 13 wherein the at least 10% of the probes comprises SEQ ID NO: 14; or (b) at least 10 of the probes identified in Table 13 wherein the at least one of the 10 probes comprises SEQ ID NO: 14; or (b) at least 20 of the probes identified in Table 13 wherein the at least one of the 20 probes comprises SEQ ID NO: 14.

14. A method of identifying cells that have been exposed to radiation induced biological stress, comprising:
providing a plurality of probe elements bound to a surface, each probe element comprising a nucleic acid that is differentially expressed by a cell following ionizing radiation induced biological stress, wherein at least one probe element comprises SEO ID NO: 14;
contacting the plurality of probe elements with a plurality of test nucleic acid sequences obtained from a test cell, under conditions that allow the test nucleic acid sequences to specifically hybridize to one or more of the probe elements, and provide a signal which indicates differential expression of one or more genes if the cell has been exposed to an amount of ionizing radiation sufficient to cause differential expression of stress genes in the cell; and
detecting the presence or absence of the signal.

15. The method of claim 14, wherein the plurality of probe elements is a selected set of nucleic acids from a set of nucleic acids that hybridize to nucleic acids obtained from cells exposed to ionizing radiation.

16. The method of claim 14, wherein the probe elements are nucleic acid sequences that are differentially expressed by a cell more than four hours after exposure to the ionizing radiation.

17. The method of claim 16, wherein the probe elements are nucleic acid sequences that are differentially expressed at a time at least 24 hours after exposure to the ionizing radiation.

18. The method of claim 16, wherein the probe elements are nucleic acid sequences that are differentially expressed more than 48 hours after exposure to the ionizing radiation.

19. The method of claim 16, wherein the probe elements comprise nucleic acid sequences that are differentially expressed by at least 1.5-fold following exposure to a biologically significant amount of ionizing radiation.

20. The method of claim 19, wherein the nucleic acid sequences are differentially expressed by at least 2-fold following exposure to a biologically significant amount of ionizing radiation.

21. The method of claim 1, wherein the probe set comprises nucleic acid molecules identified by Image ID number: 203132, 251591, 489805, 753447, or 1493160.

22. The method of claim 1, wherein the probe set is DNA.

23. The method of claim 22, wherein the probe set is cDNA.

24. The method of claim 23, wherein the labeled nucleic acid composition is cDNA obtained from mRNA expressed by the test cell.

25. The method of claim 1, wherein the probe set nucleic acids are about 10 to about 1,000,000 nucleotides in length.

26. The method of claim 1, further comprising contacting the probe set with a plurality of control nucleic acids obtained from mRNA of a control cell that has not been exposed to a biologically significant amount of ionizing radiation; and
determining whether the nucleic acids from mRNA of the control cells hybridize differentially to the probe set than the nucleic acid composition from the test cell.

27. The method of claim 14, wherein the test nucleic acid sequences are labeled with a fluorophore that detects hybridization of the test nucleic acid sequences to the probe elements.

28. The method of claim 27, wherein the test nucleic acid sequences are labeled with a first label that detects hybridization of the test nucleic acids to the probe elements, and a plurality of control nucleic acids are labeled with a second label that detects hybridization of the plurality of control nucleic acids to the probe elements, and the first and second labels interact to indicate whether expression of a nucleic acid in the test cell has increased or decreased, relative to expression of the control nucleic acids.

29. The method of claim 28, wherein the first and second labels are fluorophores of different colors.

30. The method of claim 14, wherein the cells are animal cells, microbial cells, or plant cells.

31. The method of claim 30, wherein the animal cells are human cells.

32. The method of claim 30, wherein the animal cells are peripheral blood cells.

33. The method of claim 32, wherein the peripheral blood cells are peripheral blood mononuclear cells.

34. The method of claim 33, wherein the peripheral blood mononuclear cells are lymphocytes.

35. A method of making a microarray for identifying cells that have actually or potentially been exposed to an amount of ionizing radiation sufficient to cause differential expression of stress genes in the cell, comprising:
identifying genes that are differentially expressed by a cell following exposure to the ionizing radiation; and
providing a plurality of probe elements bound to a substrate surface, the probe elements comprising probe nucleic acids from genes that are identified as differentially expressed by a cell following ionizing radiation induced biological stress, wherein at least one probe element comprises SEQ ID NO: 14, and wherein the probe nucleic acid is capable of hybridizing to a nucleic acid differentially expressed by the cell following exposure of the cell to the ionizing radiation.

36. The method of claim 35, wherein identifying genes that are differentially expressed by a cell following exposure to biologically significant amounts of ionizing radiation comprises exposing the cell to a biologically significant amount of ionizing radiation, obtaining mRNA expressed by the cell, reverse transcribing the mRNA into cDNA, labeling the cDNA, and hybridizing the labeled cDNA to a probe set and identifying members of the probe set that hybridize with the labeled cDNA.

37. The method of claim 36, where in the genes comprise p53 regulated genes.

38. The method of claim 35, further comprising determining a dose response relationship between radiation exposure and differential expression of one or more genes.

39. A method of diagnosing ionizing radiation exposure in a subject, comprising:
obtaining a biological sample from the subject;
synthesizing cDNA from mRNA expressed in one or more cells of the biological sample, and labeling the cDNA with a detectable label;
exposing the labeled cDNA to a probe set which represents genes that are differentially expressed in the biological sample following exposure to ionizing radiation, and determining if the labeled cDNA selectively hybridizes to one or more probes of the probe set that are associated with the radiation exposure, wherein the probe set comprises SEQ ID NO: 14.

40. The method of claim 39, wherein the probe set comprises one or more of the probes identified in Table 13.

41. The method of claim 35, wherein identifying genes that are differentially expressed comprises identifying genes that are differentially expressed in a cell type that is to be obtained from a subject for testing.

42. The method of claim 39, further comprising detecting patterns of differential expression associated with biologically significant radiation exposure.

43. A method for measuring a biological response to in a subject comprising:
- obtaining a biological sample from the subject;
- synthesizing cDNA from mRNA expressed in one or more cells of the biological sample;
- labeling the cDNA with a detectable label;
- exposing the labeled cDNA to a probe set comprising nucleic acid molecules representing genes that are differentially expressed in cells that have been exposed to an amount of ionizing radiation sufficient to cause differential expression of genes in the cell, wherein at least one nucleic acid molecule of the probe set comprises SEQ ID NO: 14; and
- determining if the labeled cDNA selectively hybridizes to one or more probes of the probe set differentially expressed following exposure to ionizing radiation.

44. The method of claim 43 wherein the subject is undergoing radiotherapy for the treatment of cancer and the probe set is used to monitor the subject's biological response to the radiotherapy.

45. The method of claim 43 wherein the biological response is a biological response to potential radiation exposure in the subject.

46. The method of claim 45, wherein the biological response is measured in a cell type.

47. The method of claim 46, wherein the cell type is a peripheral blood cell obtained from the subject.

48. The method of claim 43, further comprising determining a relationship between radiation exposure and differential expression of one or more genes to determine a probable radiation dose in cells that have actually or potentially been exposed to the ionizing radiation.

49. The method of claim 1, wherein at least 50% of the nucleic acid sequences of the probe set are differentially expressed following exposure to the ionizing radiation.

50. The method of claim 1, wherein the probe set comprises:
- (a) at least 10% of the probes identified in any one of Tables 9, 10, 11, 12, or 14 wherein the at least 10% of the probes comprises SEQ ID NO: 14; or
- (b) at least 10 of the probes identified in any one of Tables 9, 10, 11, 12, or 14 wherein the at least one of the 10 probes comprises SEQ ID NO: 14; or
- (c) at least 20 of the probes identified in any one of Tables 9, 10, 11, 12, or 14 wherein the at least one of the 20 probes comprises SEQ ID NO: 14.

51. The method of claim 1, wherein the probe set comprises nucleic acid molecules identified by Image ID number: 268652, 34396, 35318, 50615, 110589, 247483, 360778, 415817, 469954, 489805, or 884719.

52. The method of claim 39, wherein the probe set comprises one or more of the probes identified in any one of Tables 9, 10, 11, 12, or 14.

* * * * *